US012723089B2

(12) United States Patent
Greenberg

(10) Patent No.: US 12,723,089 B2
(45) Date of Patent: Sep. 1, 2026

(54) KLRB1 BINDING AGENTS AND METHODS OF USE THEREOF

(71) Applicant: The Brigham and Women's Hospital, Inc., Boston, MA (US)

(72) Inventor: Steven A. Greenberg, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 19/259,821

(22) Filed: Jul. 3, 2025

(65) Prior Publication Data

US 2026/0070990 A1 Mar. 12, 2026

Related U.S. Application Data

(63) Continuation of application No. PCT/US2024/056624, filed on Nov. 20, 2024.

(60) Provisional application No. 63/601,664, filed on Nov. 21, 2023.

(51) Int. Cl.
*C07K 16/28* (2006.01)

(52) U.S. Cl.
CPC ...... *C07K 16/2851* (2013.01); *C07K 2317/24* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 12,018,080 | B2 | 6/2024 | Suva et al. |
| 2017/0088605 | A1 | 3/2017 | Abend et al. |
| 2017/0260290 | A1 | 9/2017 | Shionogi et al. |
| 2019/0194333 | A1 | 6/2019 | Greenberg et al. |
| 2021/0122826 | A1 | 4/2021 | Wittrup et al. |
| 2025/0270328 | A1 | 8/2025 | Greenberg |
| 2025/0333516 | A1 | 10/2025 | Greenberg |
| 2026/0008855 | A1 | 1/2026 | Greenberg |

FOREIGN PATENT DOCUMENTS

| | | | |
|---|---|---|---|
| WO | WO 2000/002583 | A1 | 1/2000 |
| WO | WO 2013/126746 | A2 | 8/2013 |
| WO | WO 2014/179664 | A2 | 11/2014 |
| WO | WO 2017/019846 | A1 | 2/2017 |
| WO | WO 2017/046676 | A1 | 3/2017 |
| WO | WO 2020/055975 | A1 | 3/2020 |
| WO | WO 2020/223573 | A2 | 11/2020 |
| WO | WO 2020/257760 | A1 | 12/2020 |
| WO | WO 2021/155380 | A1 | 8/2021 |
| WO | WO 2022/093640 | A1 | 5/2022 |
| WO | WO 2023/028501 | A1 | 3/2023 |
| WO | WO 2023/225197 | A2 | 11/2023 |
| WO | WO 2024/091919 | A2 | 5/2024 |
| WO | WO 2024/229461 | A2 | 11/2024 |

OTHER PUBLICATIONS

PCT/US2025/025311, Apr. 18, 2025, Greenberg.
U.S. Appl. No. 19/123,478, filed Apr. 23, 2025, Greenberg.
U.S. Appl. No. 19/259,911, filed Jul. 3, 2025, Greenberg.
U.S. Appl. No. 19/259,995, filed Jul. 3, 2025, Greenberg.
[No Author Listed] [online], "Adtralza," Summary of opinion, Committee for Medicinal Products for Human Use (CHMP), European Medicines Agency,. EMA/CHMP/202204/2021, Apr. 22, 2021, retrieved on Jul. 23, 2025, retrieved from URL <https://www.ema.europa.eu/en/documents/smop-initial/chmp-summary-positive-opinion-adtralza_en.pdf>, 1 page.
[No Author Listed] [online], "Drug Trials Snapshots: Dupixent," U.S. Food & Drug Administration, Jul. 7, 2020, via Internet Archive: Wayback Machine URL <https://web.archive.org/web/20201222050432/https://www.fda.gov/drugs/drug-approvals-and-databases/drug-trials-snapshots-dupixent>, retrieved on Jul. 23, 2025, retrieved from URL <https://www.fda.gov/drugs/drug-approvals-and-databases/drug-trials-snapshots-dupixent>, 7 pages.
[No Author Listed] [online], "Dupixent," Summary of opinion, Committee for Medicinal Products for Human Use (CHMP), European Medicines Agency, EMA/CHMP/453766/2017, Jul. 20, 2017, retrieved on Jul. 23, 2025, retrieved from URL <https://www.ema.europa.eu/en/documents/smop-initial/chmp-summary-positive-opinion-dupixent_en.pdf>, 1 page.
Abrahamsson et al., "Non-myeloablative autologous haematopoietic stem cell transplantation expands regulatory cells and depletes IL-17 producing mucosal-associated invariant T cells in multiple sclerosis," Brain, Jul. 2013, 136(9):2888-2903.
Acquaviva et al., "Loss of Circulating CD8+ CD161high T Cells in Primary Progressive Multiple Sclerosis," Frontiers in Immunology, Aug. 2019, 10:1922, 6 pages.
Aldemir et al., "Cutting edge: lectin-like transcript 1 is a ligand for the CD161 receptor," The Journal of Immunology, Dec. 2005, 175(12):7791-5.
Almagro et al., "Humanization of antibodies, Frontiers in Bioscience," Jan. 2008, 13(1):1619-33.
Annibali et al., "CD161highCD8+ T cells bear pathogenetic potential in multiple sclerosis," Brain, Jan. 2011, 134(2):542-554.
Annunziato et al., "Reasons for rarity of Th17 cells in inflammatory sites of human disorders," Seminars in Immunology, Nov. 2013, 25(4):299-304.

(Continued)

*Primary Examiner* — Marianne P Allen
(74) *Attorney, Agent, or Firm* — Fish & Richardson P.C.

(57) ABSTRACT

KLRB1 binding agents (in particular anti-KLRB1-antibodies and antigen binding portion thereof) with increased humanness and compositions thereof, as well as therapeutic methods of using the agents, e.g., for depleting cells or inhibiting cells or activating cells, (in particular, Th17, Th17.1, ex-Th17, Tc17, MAIT, INKT, peTh2, ILC2, ILC3, NK cells, and/or neoplastic T or NK cells in vivo), for the treatment of autoimmune disease, allergic diseases, transplant rejection, hematologic malignancies, and cancer.

16 Claims, 26 Drawing Sheets

Specification includes a Sequence Listing.

(56) References Cited

OTHER PUBLICATIONS

Assa'ad et al., "An Antibody Against IL-5 Reduces Nos. of Esophageal Intraepithelial Eosinophils in Children With Eosinophilic Esophagitis," Gastroenterology, Nov. 2011, 141(5):1593-1604.
Bailey et al., "Th17 cells in cancer: the ultimate identity crisis," Frontiers in Immunology, Jun. 2014, 5:276, 13 pages.
Bangert et al., "Persistence of mature dendritic cells, TH2A, and Tc2 cells characterize clinically resolved atopic dermatitis under IL-4Rα blockade," Science Immunology, Jan. 2021, 6(55):eabe2749, 16 pages.
Basdeo et al., "Ex-Th17 (nonclassical Th1) cells are functionally distinct from classical Th1 and Th17 cells and are not constrained by regulatory T cells, " The Journal of Immunology, Mar. 2017, 198(6):2249-59.
Basdeo et al., "Polyfunctional, Pathogenic CD161+ Th17 Lineage Cells Are Resistant to Regulatory T Cell-Mediated Suppression in the Context of Autoimmunity," The Journal of Immunology, Jul. 2015, 195(2):528-540.
Bieber, "Atopic dermatitis: an expanding therapeutic pipeline for a complex disease," Nature Reviews Drug discovery, Jan. 2022, 21(1):21-40.
Bittner et al., "Death receptor 3 signaling enhances proliferation of human regulatory T cells," FEBS Letters, Apr. 2017, 591(8):1187-1195.
Brandt et al., "Th2 Cytokines and Atopic Dermatitis," Journal of Clinical & Cellular Immunology, Aug. 2011, 2(3):110, 13 pages.
Brunner et al., "Early-onset pediatric atopic dermatitis is characterized by TH2/TH17/TH22-centered inflammation and lipid alterations," Journal of Allergy and Clinical Immunology, Jun. 2018, 141(6):2094-2106.
Buscarinu et al., "Intestinal permeability and circulating CD161+ CCR6+ CD8+ T cells in patients with relapsing-remitting multiple sclerosis treated with dimethylfumarate," Frontiers in Neurology, Aug. 2021, 12:683398, 8 pages.
Calise et al., "Distinct trajectories distinguish antigen-specific T cells in peanut-allergic individuals undergoing oral immunotherapy," Journal of Allergy and Clinical Immunology, Jul. 2023, 152(1):155-166.
Camelo et al., "IL-33, IL-25, and TSLP induce a distinct phenotypic and activation profile in human type 2 innate lymphoid cells," Blood Advances, Apr. 2017, 1(10):577-589.
Chen et al., "CXCL12-CXCR4-mediated chemotaxis supports accumulation of mucosal-associated invariant T cells into the liver of patients with PBC," Frontiers in Immunology, Mar. 2021, 12:578548, 10 pages.
Chen et al., "Inebilizumab, a B Cell-Depleting Anti-CD19 Antibody for the Treatment of Autoimmune Neurological Diseases: Insights from Preclinical Studies," Journal of Clinical Medicine, Nov. 2016, 5(12):107, 12 pages.
Cheuk et al., "Epidermal Th22 and Tc17 Cells Form a Localized Disease Memory in Clinically Healed Psoriasis," The Journal of Immunology, Apr. 2014, 192(7):3111-3120.
Choy et al., "TH2 and TH17 inflammatory pathways are reciprocally regulated in asthma," Science Translational Medicine, Aug. 2015, 7(301):301ra129, 10 pages.
Christophersen et al., "Distinct phenotype of CD4+ T cells driving celiac disease identified in multiple autoimmune conditions," Nature Medicine, Mar. 2019, 25(5):734-737.
ClinicalTrials.gov [online], "ADCC Mediated B-Cell dEpletion and BAFF-R Blockade (AMBER)," Novartis Clinical study, NCT03217422, last updated Jul. 2, 2025, retrieved on Jul. 23, 2025, retrieved from URL <https://clinicaltrials.gov/study/NCT03217422> 12 pages.
ClinicalTrials.gov [online], "Dose Ranging Study of RPC4046 in Eosinophilic Esophagitis," NCT02098473, last updated May 9, 2017, retrieved on Jul. 23, 2025, retrieved from URL <https://clinicaltrials.gov/study/NCT02098473>, 11 pages.
ClinicalTrials.gov [online], "Study of Dupilumab in Adult Participants With Active Eosinophilic Esophagitis (EoE)," NCT02379052, last updated Feb. 28, 2020, retrieved on Jul. 23, 2025, retrieved from URL <https://clinicaltrials.gov/study/NCT02379052>, 19 pages.
ClinicalTrials.gov [online], "Study to Determine the Efficacy and Safety of Dupilumab in Adult and Adolescent Patients With Eosinophilic Esophagitis (EoE)," NCT03633617, last updated Jun. 28, 2023, retrieved on Jul. 23, 2025, retrieved from URL <https://clinicaltrials.gov/study/NCT03633617>, 28 pages.
Cohavy et al., "Cd161 defines effector T cells that express light and respond to Tl1a-Dr3 signaling," European Journal of Microbiology and Immunology, Mar. 2011, 1(1):70-79.
Cosmi et al., "Evidence of the Transient Nature of the Th17 Phenotype of CD4+CD161+ T Cells in the Synovial Fluid of Patients With Juvenile Idiopathic Arthritis," Arthritis & Rheumatism, Aug. 2011, 63(8):2504-2515.
Cosmi et al., "Human interleukin 17-producing cells originate from a CD161+CD4+ T cell precursor," The Journal of Experimental Medicine, Aug. 2008, 205(8):1903-1916.
Cosmi et al., "Identification of a novel subset of human circulating memory CD4+ T cells that produce both IL-17A and IL-4," Journal of Allergy and Clinical Immunology, Jan. 2010, 125(1):222-230.
Cross et al., "Anti-CD8 monoclonal antibody-mediated depletion alters the phenotype and behavior of surviving CD8+ T cells," PLoS One, Feb. 2019, 14(2):e0211446, 24 pages.
D'Amico et al., "Immunological Subsets Characterization in Newly Diagnosed Relapsing-Remitting Multiple Sclerosis," Frontiers in Immunology, Feb. 2022, 13:819136, 9 pages.
Dobreanu et al., "Treatment With Cladribine Selects IFNγ+ IL17+ T Cells in RRMS Patients—an In Vitro Study," Frontiers in Immunology, Dec. 2021, 12:743010, 19 pages.
Doherty et al., "Airway innate lymphoid cells in the induction and regulation of allergy," Allergology International, Jan. 2019, 68(1):9, 18 pages.
Esaki et al., "Early-onset pediatric atopic dermatitis is TH2 but also TH17 polarized in skin," Journal of Allergy and Clinical Immunology, Dec. 2016, 138(6):1639-1651.
Falk, "Eosinophilic Esophagitis," Gastroenterology Clinics of North America, Jun. 2014, 43(2):xiii, 1 page.
Fergusson et al., "CD161 defines a transcriptional and functional phenotype across distinct human T cell lineages," Cell Reports, Nov. 2014, 9(3): 1075, 12 pages.
Ferreira et al., "RORα is a critical checkpoint for T cell and ILC2 commitment in the embryonic thymus," Nature Immunology, Feb. 2021, 22(2): 166, 38 pages.
Fort et al., "A Role for NK Cells as Regulators of CD4+ T Cells in a Transfer Model of Colitis," The Journal of Immunology, Oct. 1998, 161(7):3256-3261.
French et al., "Natural killer cells and autoimmunity," Arthritis Research & Therapy, Dec. 2003, 6(1):8-14.
Frenzel et al., "Expression of recombinant antibodies," Frontiers in Immunology, Jul. 2013, 4:217, 20 pages.
Fukasawa et al., "Interleukin-17 pathway inhibition with brodalumab in early systemic sclerosis: Analysis of a single-arm, open-label, phase 1 trial," Journal of the American Academy of Dermatology, Aug. 2023, 89(2):366-369.
Fusco et al., "1332 Anti-CD161 antibody IMT-009 is a novel immunotherapeutic agent that reinvigorates T and NK cell function and anti-tumor efficacy through blocking interaction of CD161 with its ligand CLEC2D," Journal for ImmunoTherapy of Cancer, Nov. 2022, 10(Suppl 2):A1-A1603, 1 page.
Gentles et al., "The prognostic landscape of genes and infiltrating immune cells across human cancers," Nature Medicine, Jul. 2015, 21(8):938, 28 pages.
Geremia et al., "IL-23-responsive innate lymphoid cells are increased in inflammatory bowel disease," Journal of Experimental Medicine, Jun. 2011, 208(6):1127-1133.
Ghesquiere et al., "Mucosal-associated invariant T cells in Giant Cell Arteritis," Journal of Autoimmunity, Jul. 2021, 121:102652, 23 pages (Open manuscript).
Ginaldi et al., "Levels of expression of CD52 in normal and leukemic B and T cells: correlation with in vivo therapeutic responses to Campath-1H," Leukemia Research, Feb. 1998, 22(2):185-191.
Giudici et al., "Perianal Crohn's disease and hidradenitis suppurativa: a possible common immunological scenario," Clinical and Molecular Allergy, Jul. 2015, 13(1):12, 6 pages.

(56) References Cited

OTHER PUBLICATIONS

Glatt et al., "Efficacy and Safety of Bimekizumab in Moderate to Severe Hidradenitis Suppurativa A Phase 2, Double-blind, Placebo-Controlled Randomized Clinical Trial," JAMA Dermatology, Nov. 2021, 157(11):1279-1288.
Goel et al., "Selective Depletion of KLRG1+ T cells in a First-in-Human Clinical Trial of ABC008 in Inclusion Body Myositis (IBM)," Poster, Presented at the 4th Global Conference on Myositis (GCOM), Prague, Czech Republic, Jun. 6-9, 2022, 1 page.
Gronbaek et al., "Autoimmune hepatitis in Denmark: incidence, prevalence, prognosis, and causes of death. A nationwide registry-based cohort study," Journal of Hepatology, Mar. 2014, 60(3):612-617.
Gur et al., "LGR5 expressing skin fibroblasts define a major cellular hub perturbed in scleroderma," Cell, Apr. 2022, 185(8):1373-1388.e20.
Guttman-Yassky et al., "An anti-OX40 antibody to treat moderate-to-severe atopic dermatitis: a multicentre, double-blind, placebo-controlled phase 2b study," The Lancet, Jan. 2023, 401(10372):204-214.
Haberger et al., "Assessment of chemical modifications of sitesin the CDRs of recombinant antibodies Susceptibility vs. functionality of critical quality attributes," mAbs, Mar. 2014, 6(2):327-339.
Haga et al., "MAIT cells are activated and accumulated in the inflamed mucosa of ulcerative colitis," Journal of Gastroenterology and Hepatology, May 2016, 31(5):965-972.
Hamilton et al., "Asthma Phenotypes as a Guide for Current and Future Biologic Therapies," Clinical Reviews in Allergy & Immunology, Jul. 2019, 59(2): 160-174.
Heremans et al., "Essential role for natural killer cells in the lethal lipopolysaccharide-induced Shwartzman-like reaction in mice," European Journal of Immunology, May 1994, 24(5):1155-1160.
Hirano et al., "Efficacy of Dupilumab in a Phase 2 Randomized Trial of Adults With Active Eosinophilic Esophagitis," Gastroenterology, Jan. 2020, 158(1):111-122.e10.
Hirano et al., "RPC4046, a Monoclonal Antibody Against IL13, Reduces Histologic and Endoscopic Activity in Patients With Eosinophilic Esophagitis," Gastroenterology, Feb. 2019, 156(3):592-603.e10.
Hjelmervik et al., "Gene Expression Profiling of Minor Salivary Glands Clearly Distinguishes Primary Sjogren's Syndrome Patients From Healthy Control Subjects," Arthritis & Rheumatism, May 2005, 52(5):1534-1544.
Holmkvist et al., "A major population of mucosal memory CD4+ T cells, coexpressing IL-18Rα and DR3, display innate lymphocyte functionality," Mucosal Immunology, May 2015, 8(3):545-558.
Huang et al., "Th2A cells: The pathogenic players in allergic diseases," Frontiers in Immunology, Aug. 2022, 13:916778, 10 pages.
Ichiki et al., "T cell immunity in autoimmune hepatitis," Autoimmunity Reviews, Jun. 2005, 4(5):315-321.
Irvin et al., "Increased frequency of dual-positive TH2/TH17 cells in bronchoalveolar lavage fluid characterizes a population of patients with severe asthma, " Journal of Allergy and Clinical Immunology, Nov. 2014, 134(5):1175-1186.e7.
Jeffery et al., "Changes in Natural Killer Cells and Exhausted Memory Regulatory T Cells With Corticosteroid Therapy in Acute Autoimmune Hepatitis," Hepatology Communications, Apr. 2018, 2(4):421-436.
Jin et al., "TL1A/TNFSF15 directly induces proinflammatory cytokines, including TNFα, from CD3+CD161+ T cells to exacerbate gut inflammation," Mucosal Immunology, Sep. 2013, 6(5):886-899.
Kang et al., "Boosting therapeutic potency of antibodies by taming Fc domain functions," Experimental & Molecular Medicine, Nov. 2019, 51:138, 9 pages.
Kaufmann, et al., "Identifying CNS-colonizing T cells as potential therapeutic targets to prevent progression of multiple sclerosis, " Med, Mar. 2021, 2(3):296-312.e8.
Kharawala et al., "The clinical, humanistic, and economic burden of palmoplantar pustulosis: a structured review," Expert Review of Clinical Immunology, Feb. 2020, 16(3):253-266.
Kim et al., "Single-cell transcriptomics suggest distinct upstream drivers of IL-17A/F in hidradenitis versus psoriasis," Journal of Allergy and Clinical Immunology, Sep. 2023, 152(3):656-666.
Kitaichi et al., "Diminution of experimental autoimmune uveoretinitis (EAU) in mice depleted of NK cells," Journal of Leukocyte Biology, Dec. 2002, 72(6): 1117-1121.
Klapa et al., "Expansion of CD161 expressing CD8+ single-positive and CD4+CD8+ double-positive PR3-specific T-cells in granulomatosis with polyangiitis," Clinical and Experimental Rheumatology, Mar. 2021, 39(2): S182-S183.
Kleinschek et al., "Circulating and gut-resident human Th17 cells express CD161 and promote intestinal inflammation," The Journal of Experimental Medicine, Mar. 2009, 206(3):525-534.
Konduri et al., "CD8+CD161+ T-Cells: Cytotoxic Memory Cells With High Therapeutic Potential," Frontiers in Immunology, Feb. 2021, 11:613204, 10 pages.
Kurioka et al., "CD161 Defines a Functionally Distinct Subset of Pro-Inflammatory Natural Killer Cells," Frontiers in Immunology, Apr. 2018, 9:486, 14 pages.
Lanier et al., "Human NKR-P1A. A disulfide-linked homodimer of the C-type lectin superfamily expressed by a subset of NK and T lymphocytes," The Journal of Immunology, Sep. 1994, 153(6):2417-28.
Laskay et al., "Natural killer cells participate in the early defense against Leishmania major infection in mice," European Journal of Immunology, Sep. 1993, 23(9):2237-2241.
Lee et al., "Eosinophilic allergic rhinitis is strongly associated with the CD45RBlo subset of CD161+ Th2 cells that secretes IL-2, IL-3, IL-4, IL-5, IL-9, and IL-13," Allergy, Oct. 2023, 78(10):2794-2798.
Leng et al., "TCR and Inflammatory Signals Tune Human MAIT Cells to Exert Specific Tissue Repair and Effector Functions," Cell Reports, Sep. 2019, 28(12):3077-3091.e5.
Liu et al., "Transcriptomic Profiling of Plaque Psoriasis and Cutaneous T-Cell Subsets during Treatment with Secukinumab," JID Innovations, Dec. 2021, 2(3):100094, 13 pages.
Lobner et al., "Engineered IgG1-Fc—one fragment to bind them all, " Immunological Reviews, Mar. 2016, 270(1):113-131.
Lu et al., "Deamidation and isomerization liability analysis of 131 clinical-stage antibodies," mAbs, Jan. 2019, 11(1):45-57.
Lustig et al., "Antibody-mediated cell cytotoxicity in a defined system: regulation by antigen, antibody, and complement," The Journal of Immunology, Jan. 1976, 116(1):253-260.
Lynch et al., "Th2/Th17 reciprocal regulation: twists and turns in the complexity of asthma phenotypes," Annals of Translational Medicine, Oct. 2016, 4(Suppl 1):S59, 4 pages.
MacDonald et al., "Prevention of acute lethal graft-versus-host disease in F1 hybrid mice by pretreatment of the graft with anti-NK-1.1 and complement," Transplantation, Jul. 1992, 54(1):147-151.
Maggi et al., "CD161 is a marker of all human IL-17-producing T-cell subsets and is induced by RORC," European Journal of Immunology, Aug. 2010, 40(8):2174-81.
Maggi et al., "CD4+CD161+ T Lymphocytes Infiltrate Crohn's Disease-Associated Perianal Fistulas and Are Reduced by Anti-TNF-α Local Therapy," International Archives of Allergy and Immunology, Apr. 2013, 161(1):81-86.
Maggi et al., "Th17 and Th1 Lymphocytes in Oligoarticular Juvenile Idiopathic Arthritis," Frontiers in Immunology, Mar. 2019, 10:450, 8 pages.
Makiya et al., "Distinct CRTH2+CD161+ (peTh2) memory CD4+ T-cell cytokine profiles in food allergy and eosinophilic gastrointestinal disorders," Clinical & Experimental Allergy, Oct. 2023, 53(10):1031-1040.
Malik-Chaudhry et al., "TNB-486 induces potent tumor cell cytotoxicity coupled with low cytokine release in preclinical models of B-NHL," mAbs, Jan. 2021, 13(1):e1890411, 16 pages.
Manns et al., "Budesonide Induces Remission More Effectively Than Prednisone in a Controlled Trial of Patients With Autoimmune Hepatitis," Gastroenterology, Oct. 2010, 139(4):1198-1206.

(56) References Cited

OTHER PUBLICATIONS

Manns et al., “Diagnosis and Management of Autoimmune Hepatitis,” Hepatology, Jun. 2010, 51(6):2193-2213.
Mariottini et al., “Antibody-mediated cell depletion therapies in multiple sclerosis,” Frontiers in Immunology, Sep. 2022, 13:953649, 23 pages.
Martin et al., “Manipulating T cell-mediated pathology: targets and functions of monoclonal antibody immunotherapy,” Clinical Immunology, Apr. 2013, 148(1):136-147.
Mathewson et al., “Inhibitory CD161 receptor identified in glioma-infiltrating T cells by single-cell analysis,” Cell, Mar. 2021, 184(5):1281, 45 pages.
Matos et al., “Clinically resolved psoriatic lesions contain psoriasis-specific IL-17- producing aß T cell clones,” The Journal of Clinical Investigation, Nov. 2017, 127(11):4031-4041.
Mccluskey et al., “Single-cell analysis implicates TH17-to-TH2 cell plasticity in the pathogenesis of palmoplantar pustulosis,” Journal of Allergy and Clinical Immunology, Oct. 2022, 150(4):882-893.
Meca-Lallana et al., “Expert-Agreed Practical Recommendations on the Use of Cladribine,” Neurology and Therapy, Sep. 2022, 11(4):1475-1488.
Menon et al., “Interleukin-17+CD8+ T Cells Are Enriched in the Joints of Patients With Psoriatic Arthritis and Correlate With Disease Activity and Joint Damage Progression,” Arthritis & Rheumatology, May 2014, 66(5):1272-1281.
Meuer, “CD2, Role of CD2”, Encyclopedia of Immunology (Second Edition), Jan. 1998, 463.
Miao et al., “Circulating Th17 and Th1 cells expressing CD161 are associated with disease activity in rheumatoid arthritis,” Scandinavian Journal of Rheumatology, Jan. 2014, 43(3): 194-201.
Miao et al., “Percentages of CD4+CD161+ and CD4-CD8-CD161+ T cells in the Synovial Fluid are Correlated with Disease Activity in Rheumatoid Arthritis,” Mediators of Inflammation, Jan. 2015, 2015:563713, 7 pages.
Mieli-Vergani et al., “Autoimmune hepatitis,” Nature Reviews Disease Primers, Apr. 2018, 4:18017, 21 pages.
Mikhael et al., “A dose-finding Phase 2 study of single agent isatuximab (anti-CD38 mAb) in relapsed/refractory multiple myeloma,” Leukemia, May 2020, 34(12):3298-3309.
Mitsialis et al., “Single-Cell Analyses of Colon and Blood Reveal Distinct Immune Cell Signatures of Ulcerative Colitis and Crohn’s Disease,” Gastroenterology, Aug. 2020, 159(2):591-608.e10.
Mitson-Salazar et al., “Hematopoietic prostaglandin D synthase defines a proeosinophilic pathogenic effector human TH2 cell subpopulation with enhanced function,” Journal of Allergy and Clinical Immunology, Mar. 2016, 137(3):907-918.e9.
Mitson-Salazar et al., “Pathogenic Effector Th2 Cells in Allergic Eosinophilic Inflammatory Disease,” Frontiers in Medicine, Oct. 2017, 4:165, 8 pages.
Mjosberg et al., “Human IL-25- and IL-33-responsive type 2 innate lymphoid cells are defined by expression of CRTH2 and CD161,” Nature Immunology, Sep. 2011, 12(11):1055-1062.
Moran et al., “Hidradenitis Suppurativa Is Characterized by Dysregulation of the Th17: Treg Cell Axis, Which Is Corrected by Anti-TNF Therapy,” Journal of Investigative Dermatology, Jun. 2017, 137(11):2389-2395.
Morgan et al., “Clonally expanded, GPR15-expressing pathogenic effector TH2 cells are associated with eosinophilic esophagitis,” Science Immunology, Aug. 2021, 6(62):eabi5586, 28 pages (Author manuscript).
Morille et al., “Multiple Sclerosis CSF Is Enriched With Follicular T Cells Displaying a Th1/Eomes Signature,” Neurology: Neuroimmunology & Neuroinflammation, Nov. 2022, 9(6):e200033, 14 pages.
Moser et al., “Long-term peripheral immune cell profiling reveals further targets of oral cladribine in MS,” Annals of Clinical and Translational Neurology, Nov. 2020, 7(11):2199-2212.
Mrowietz et al., “Secukinumab for moderate-to-severe palmoplantar pustular psoriasis: Results of the 2PRECISE study,” Journal of the American Academy of Dermatology, May 2019, 80(5):1344-1352.
Mrowietz et al., “Spesolimab, an Anti-Interleukin-36 Receptor Antibody, in Patients with Palmoplantar Pustulosis: Results of a Phase IIa, Multicenter, Double-Blind, Randomized, Placebo-Controlled Pilot Study,” Dermatology and Therapy (Heidelb), Mar. 2021, 11(2):571-585.
Needleman et al., “A General Method Applicable to the Search for Similarities in the Amino Acid Sequence of Two Proteins,” Journal of Molecular Biology, Mar. 1970, 48:443-453.
Ngu et al., “Population-based epidemiology study of autoimmune hepatitis: a disease of older women?,” Journal of Gastroenterology and Hepatology, Oct. 2010, 25(10):1681-1686.
Nicol et al., “An intermediate level of CD161 expression defines a novel activated, inflammatory, and pathogenic subset of CD8+ T cells involved in multiple sclerosis,” Journal of Autoimmunity, Oct. 2017, 88:61-74.
Niwa et al., “Enhanced Natural Killer Cell Binding and Activation by Low-Fucose IgG1 Antibody Results in Potent Antibody-Dependent Cellular Cytotoxicity Induction at Lower Antigen Density,” Clinical Cancer Research, Mar. 2005, 11(6):2327-2336.
Noda et al., “The Asian atopic dermatitis phenotype combines features of atopic dermatitis and psoriasis with increased TH17 polarization,” Journal of Allergy and Clinical Immunology, Nov. 2015, 136(5):1254-1264.
Novartis.com [online], “Novartis Cosentyx® shows clinically meaningful symptom improvements in patients with hidradenitis suppurativa in pivotal Phase III trials,” Sep. 10, 2022, retrieved on Jul. 23, 2025, retrieved from URL <https://www.novartis.com/news/media-releases/novartis-cosentyx-shows-clinically-meaningful-symptom-improvements-patients-hidradenitis-suppurativa-pivotal-phase-iii-trials>, 9 pages.
PCT International Preliminary Report on Patentability in International Appln. No. PCT/US2023/022735, mailed on Nov. 28, 2024, 10 pages.
PCT International Preliminary Report on Patentability in International Appln. No. PCT/US2023/077607, mailed on May 8, 2025, 12 pages.
PCT International Search Report and Written Opinion in International Appln. No. PCT/US2023/022735, mailed on Jan. 24, 2024, 20 pages.
PCT International Search Report and Written Opinion in International Appln. No. PCT/US2023/077607, mailed on May 15, 2024, 17 pages.
PCT International Search Report and Written Opinion in International Appln. No. PCT/US2024/056624, mailed on Apr. 23, 2025, 15 pages.
Peng et al., “Clinical features in different age groups of patients with autoimmune hepatitis,” Experimental and Therapeutic Medicine, Jan. 2014, 7(1):145-148.
Pesenacker et al., “CD161 defines the subset of FoxP3+ T cells capable of producing proinflammatory cytokines,” Blood, The Journal of the American Society of Hematology, Apr. 2013, 121(14):2647-58.
Poch et al., “Single-cell atlas of hepatic T cells reveals expansion of liver-resident naive-like CD4+ T cells in primary sclerosing cholangitis,” Journal of Hepatology, Mar. 2021, 75(2):414-423.
Pope et al., “7-Ally1-8-oxoguanosine (loxoribine) inhibits the metastasis of B16 melanoma cells and has adjuvant activity in mice immunized with a B16 tumor vaccine,” Cancer Immunology Immunotherapy, Feb. 1994, 38(2):83-91.
Posna.org [online], “Juvenile Idiopathic Arthritis,” Study Guide, Physical Education, Pediatric Orthopaedic Society of North America (POSNA), retrieved on Jul. 23, 2025, retrieved from URL <https://posna.org/physician-education/study-guide/juvenile-idiopathic-arthritis>, 8 pages.
Prihoda et al., “BioPhi: A platform for antibody design, humanization, and humanness evaluation based on natural antibody repertoires and deep learning,” mAbs, Feb. 2022, 14(1):e2020203, 16 pages.
Rafei-Shamsabadi et al., “Context Dependent Role of Type 2 Innate Lymphoid Cells in Allergic Skin Inflammation,” Frontiers in Immunology, Nov. 2019, 10:2591, 14 pages.

(56) References Cited

OTHER PUBLICATIONS

Ramesh et al., "Pro-inflammatory human Th17 cells selectively express P-glycoprotein and are refractory to glucocorticoids," The Journal of Experimental Medicine, Jan. 2014, 211(1):89-104.
Renand et al., "Immune Alterations in Patients With Type 1 Autoimmune Hepatitis Persist Upon Standard Immunosuppressive Treatment," Hepatology Communications, Aug. 2018, 2(8):972-985.
RheumatoidArthritis.net [online], "Statistics: Who Gets Rheumatoid Arthritis?," last updated Oct. 2024, retrieved on Jul. 23, 2025, retrieved from URL <https://rheumatoidarthritis.net/what-is-ra/ra-statistics>, 4 pages.
Robak et al., "Serum concentrations of IL-17A, IL-17B, IL-17E and IL-17F in patients with systemic sclerosis," Archives of Medical Science, May 2019, 15(3):706-712.
Rosati et al., "A novel unconventional T cell population enriched in Crohn's disease," Gut, Mar. 2022, 71(11):2194-2204.
Salimi et al., "A role for IL-25 and IL-33-driven type-2 innate lymphoid cells in atopic dermatitis," The Journal of Experimental Medicine, Dec. 2013, 210(13):2939-2950.
Samson et al., "Th1 and Th17 Lymphocytes Expressing CD161 Are Implicated in Giant Cell Arteritis and Polymyalgia Rheumatica Pathogenesis," Arthritis & Rheumatism, Nov. 2012, 64(11):3788-3798.
Satoh et al., "Non-fucosylated therapeutic antibodies as next-generation therapeutic antibodies," Expert Opinion on Biological Therapy, Oct. 2006, 6(11):1161-1173.
Schirmer et al., "Enriched CD161high CCR6+ γδ T Cells in the Cerebrospinal Fluid of Patients With Multiple Sclerosis," JAMA Neurology, Mar. 2013, 70(3):345-351.
Sebode et al., "Inflammatory Phenotype of Intrahepatic Sulfatide-Reactive Type II NKT Cells in Humans With Autoimmune Hepatitis," Frontiers in Immunology, May 2019, 10:1065, 14 pages.
Serriari et al., "Innate mucosal-associated invariant T (MAIT) cells are activated in inflammatory bowel diseases," Clinical & Experimental Immunology, May 2014, 176(2):266-274.
Setiady et al., "Requirements of NK Cells and Proinflammatory Cytokines in T Cell-Dependent Neonatal Autoimmune Ovarian Disease Triggered by Immune Complex," The Journal of Immunology, Jul. 2004, 173(2): 1051-1058.
Shields et al., "Lack of Fucose on Human IgG1 N-Linked Oligosaccharide Improves Binding to Human FcγRIII and Antibody-dependent Cellular Toxicity," The Journal of Biological Chemistry, Jul. 2002, 277(30):26733-26740.
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, Jan. 2003, 278(5):3466-3473.
Silverberg et al., "Two Phase 3 Trials of Lebrikizumab for Moderate-to-Severe Atopic Dermatitis," The New England Journal of Medicine, Mar. 2023, 388(12):1080-1091.
Simpson et al., "Two Phase 3 Trials of Dupilumab versus Placebo in Atopic Dermatitis," The New England Journal of Medicine, Dec. 2016, 375(24):2335-2348.
Smith et al., "Increased Nos. of activated group 2 innate lymphoid cells in the airways of patients with severe asthma and persistent airway eosinophilia," Journal of Allergy and Clinical Immunology, Jan. 2016, 137(1):75-86.e8.
Sondergaard et al., "Alterations in KLRB1 gene expression and a Scandinavian multiple sclerosis association study of the KLRB1 SNP rs4763655," European Journal of Human Genetics, May 2011, 19(10):1100-1103.
Spergel et al., "Reslizumab in children and adolescents with eosinophilic esophagitis: results of a double-blind, randomized, placebo-controlled trial," Journal of Allergy and Clinical Immunology, Feb. 2012, 129(2):456-463.e3.
Stein et al., "Anti-IL-5 (mepolizumab) therapy for eosinophilic esophagitis," Journal of Allergy and Clinical Immunology, Dec. 2006, 118(6):1312-1319.
Steinman, "Capturing pathogenic immune cells before they home to brain," Med, Mar. 2021, 2(3):214-216.
Stewart et al., "The role of Fc gamma receptors in the activity of immunomodulatory antibodies for cancer," Journal for ImmunoTherapy of Cancer, Aug. 2014, 2:29, 10 pages.
Straumann et al., "Anti-interleukin-5 antibody treatment (mepolizumab) in active eosinophilic oesophagitis: a randomised, placebo-controlled, double-blind trial," Gut, Oct. 2009, 59(1):21-30.
Straumann et al., "Idiopathic eosinophilic esophagitis is associated with a T(H)2-type allergic inflammatory response," Journal of Allergy and Clinical Immunology, Dec. 2001, 108(6):954-961.
Suarez-Farinas et al., "Intrinsic atopic dermatitis shows similar TH2 and higher TH17 immune activation compared with extrinsic atopic dermatitis," Journal of Allergy and Clinical Immunology, Aug. 2013, 132(2):361-370.
Sun et al., "Single-cell landscape of the ecosystem in early-relapse hepatocellular carcinoma," Cell, Jan. 2021, 184(2):404-421.e16.
Takahashi et al., "Expression of CD161 (NKR-P1A) Defines Subsets of Human CD4 and CD8 T Cells with Different Functional Activities," The Journal of Immunology, Jan. 2006, 176(1):211-216.
Tarazona et al., "Increased expression of NK cell markers on T lymphocytes in aging and chronic activation of the immune system reflects the accumulation of effector/senescent T cells," Mechanisms of Ageing and Development, Dec. 2000, 121(1-3):77-88.
Terao et al., "The Opposite Effect of Tumor-Infiltrating Natural Killer Cells on In Vivo Priming of Tumor-Specific CD8+ T Cells and CD4+ T Cells," Immunobiology, Jul. 1996, 195(2):172-186.
Terui et al., "Efficacy and Safety of Guselkumab in Japanese Patients With Palmoplantar Pustulosis: A Phase 3 Randomized Clinical Trial," JAMA Dermatology, Oct. 2019, 155(10):1153-1161.
Tominaga et al., "IL-12 synergizes with IL-18 or IL-1β for IFN-γ production from human T cells," International Immunology, Feb. 2000, 12(2):151-160.
Tominaga et al., "Possible involvement of mucosal-associated invariant T cells in the progression of inflammatory bowel diseases," Biomedical Research (Tokyo), Apr. 2017, 38(2):111-121.
Truchetet et al., "Increased frequency of circulating Th22 in addition to Th17 and Th2 lymphocytes in systemic sclerosis: association with interstitial lung disease," Arthritis Research & Therapy, Oct. 2011, 13(5):R166, 9 pages.
Truong et al., "Killer-like receptors and GPR56 progressive expression defines cytokine production of human CD4+ memory T cells," Nature Communications, May 2019, 10(1):2263, 15 pages.
Tsoi et al., "Atopic Dermatitis Is an IL-13-Dominant Disease with Greater Molecular Heterogeneity Compared to Psoriasis," Journal of Investigative Dermatology, Jan. 2019, 139(7):1480-1489.
Tunio et al., "Epidemiology of Autoimmune Hepatitis (AIH) in the United States Between 2014 and 2019: A Population-based National Study," Journal of Clinical Gastroenterology, Nov. 2021, 55(10), 21 pages (Author manuscript).
Valatas et al., "TL1A (TNFSF15) and DR3 (TNFRSF25): A Co-stimulatory System of Cytokines With Diverse Functions in Gut Mucosal Immunity," Frontiers in Immunology, Mar. 2019, 10:583, 14 pages.
Van der Waart et al., "Targeting the IL17 pathway for the prevention of graft-versus-host disease," Biology of Blood and Marrow Transplantation, Jun. 2014, 20(6):752-9.
Van Langelaar et al., "T helper 17.1 cells associate with multiple sclerosis disease activity: perspectives for early intervention," Brain, Apr. 2018, 141(5):1334-1349.
Velders et al., "The impact of antigen density and antibody affinity on antibody-dependent cellular cytotoxicity: relevance for immunotherapy of carcinomas," British Journal of Cancer, Aug. 1998, 78(4):478-483.
Victorino et al., "Tissue-Resident NK Cells Mediate Ischemic Kidney Injury and Are Not Depleted by Anti-Asialo-GM1 Antibody," The Journal of Immunology, Nov. 2015, 195(10), 26 pages (Author manuscript).
Wade et al., "Association of synovial tissue polyfunctional T-cells with DAPSA in psoriatic arthritis," Annals of the Rheumatic Diseases, Jan. 2019, 78(3):350-354.
Wallace et al., "Role of Fcγ receptors in cancer and infectious disease, " Journal of Leukocyte Biology, Jun. 1994, 55(6):816-826.

(56) References Cited

OTHER PUBLICATIONS

Wambre et al., "A phenotypically and functionally distinct human TH2 cell subpopulation is associated with allergic disorders," Science Translational Medicine, Aug. 2017, 9(401):eaam9171, 21 pages (Author manuscript).
Wang et al., "Optimization of therapeutic antibodies," Antibody Therapeutics, Feb. 2021, 4(1):45-54.
Wen et al., "Single-cell RNA sequencing identifies inflammatory tissue T cells in eosinophilic esophagitis," The Journal of Clinical Investigation, Apr. 2019, 129(5):2014-2028.
White et al., "Long-term safety profile of siplizumab, a humanized anti-CD2 monoclonal antibody, in subjects with chronic plaque psoriasis," The Internet Journal of Dermatology, Jun. 2008, 7(2), 7 pages.
Winthrop et al., "The unmet need in rheumatology: reports from the Targeted Therapies meeting 2016," Clinical and Experimental Rheumatology, Jul. 2016, 34(Suppl. 98):S69-S76.
Wollenberg et al., "Tralokinumab for moderate-to-severe atopic dermatitis: results from two 52-week, randomized, double-blind, multicentre, placebo-controlled phase III trials (ECZTRA 1 and ECZTRA 2)," British Journal of Dermatology, Mar. 2021, 184(3):437-449.
Worm et al., "Efficacy and Safety of Multiple Dupilumab Dose Regimens After Initial Successful Treatment in Patients With Atopic Dermatitis A Randomized Clinical Trial," JAMA Dermatology, Feb. 2020, 156(2):131-143.
Woynarowski et al., "Budesonide versus prednisone with azathioprine for the treatment of autoimmune hepatitis in children and adolescents," The Journal of Pediatrics, Nov. 2013, 163(5):1347-53.e1.
Wyrozemski et al., "Immunobiology and conflicting roles of the human CD161 receptor in T cells," Scandinavian Journal of Immunology, Sep. 2021, 94(3):e13090, 8 pages.
Xu et al., "Mechanism of natural killer (NK) cell regulatory role in experimental autoimmune encephalomyelitis," Journal of Neuroimmunology, Jun. 2005, 163(1-2):24-30.
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotechnology and Bioengineering, Sep. 2004, 87(5):614-622.
Yamane-Ohnuki et al., "Production of therapeutic antibodies with controlled fucosylation," mAbs, May 2009, 1(3):230-236.
Yang et al., "Targeting Th17 cells in autoimmune diseases," Trends in Pharmacological Sciences, Oct. 2014, 35(10):493-500.
Yi et al., "Depleting Anti-CD4 Monoclonal Antibody (GK1.5) Treatment: Influence on Regulatory CD4+CD25+Foxp3+ T cells in Mice," Transplantation, Apr. 2008, 85(8):1167-1174.
Yokoi et al., "Identification of a unique subset of tissue-resident memory CD4+ T cells in Crohn's disease," Proceedings of the National Academy of Sciences U. S. A., Dec. 2022, 120(1):e2204269120, 12 pages.
Yoshizawa et al., "Incidence and prevalence of autoimmune hepatitis in the Ueda area, Japan," Hepatology Research, Aug. 2016, 46(9):878-883.
Zhang et al., "B cell depletion therapies in autoimmune diseases: Monoclonal antibodies or chimeric antigen receptor-based therapy?," Frontiers in Immunology, Feb. 2023, 14:1126421, 9 pages.
Zhang et al., "Mouse Nkrp1-Clr Gene Cluster Sequence and Expression Analyses Reveal Conservation of Tissue-Specific MHC Independent Immunosurveillance," PLoS One, Dec. 2012, 7(12):e50561, 19 pages.
Zhang et al., "Regulation of Experimental Autoimmune Encephalomyelitis by Natural Killer (NK) Cells," The Journal of Experimental Medicine, Nov. 1997, 186(10):1677-1687.
Zhang et al., "Single-cell transcriptomic architecture and intercellular crosstalk of human intrahepatic cholangiocarcinoma," Journal of Hepatology, Nov. 2020, 73(5):1118-1130.
Zhao et al., "Clinical relevance of RORγ positive and negative subsets of CD161+CD4+ T cells in primary Sjogren's syndrome," Rheumatology, Feb. 2017, 56(2):303-312.
Zhao et al., "Interleukin-17 Contributes to the Pathogenesis of Autoimmune Hepatitis through Inducing Hepatic Interleukin-6 Expression," PLoS One, Apr. 2011, 6(4):e18909, 8 pages.
Zheng et al., "Landscape of Infiltrating T Cells in Liver Cancer Revealed by Single-Cell Sequencing," Cell, Jun. 2017, 169(7):1342-1356.e16.
Zhou et al., "The elevated expression of Th17-related cytokines and receptors is associated with skin lesion severity in early systemic sclerosis," Human Immunology, Jan. 2015, 76(1):22-29.
Zhu et al., "Isatuximab Acts Through Fc-Dependent, Independent, and Direct Pathways to Kill Multiple Myeloma Cells," Frontiers in Immunology, Aug. 2020, 11:1771, 19 pages.
PCT International Search Report and Written Opinion in International Appln. No. PCT/US2025/025311, mailed on Dec. 30, 2025, 13 pages.

| | 13.2 | 12.0 | 10A3D6hum2.2 | 10A3D6hum1.2 |
|---|---|---|---|---|
| EC50 | 8.319 | 5.447 | 4.783 | 5.830 |
| Span | 77.78 | 80.82 | 74.19 | 74.95 |

SEQUENCE LISTING

```
Sequence total quantity: 137
SEQ ID NO: 1            moltype = AA  length = 225
FEATURE                 Location/Qualifiers
source                  1..225
                        mol_type = protein
                        organism = Homo sapiens
SEQUENCE: 1
MDQQAIYAEL NLPTDSGPES SSPSSLPRDV CQGSPWHQFA LKLSCAGIIL LVLVVTGLSV  60
SVTSLIQKSS IEKCSVDIQQ SRNKTTERPG LLNCPIYWQQ LREKCLLFSH TVNPWNNSLA  120
DCSTKESSLL LIRDKDELIH TQNLIRDKAI LFWIGLNFSL SEKNWKWING SFLNSNDLEI  180
RGDAKENSCI SISQTSVYSE YCSTEIRWIC QKELTPVRNK VYPDS                  225

SEQ ID NO: 2            moltype = AA  length = 227
FEATURE                 Location/Qualifiers
source                  1..227
                        mol_type = protein
                        note = Simiiformes catarrhini
                        organism = unidentified
SEQUENCE: 2
MDQQMMYAEL TLPKDSGPES SSPSSLPRDV CQGSPWHQFA LKLSCAGIIL LVLVVTGLSL  60
SVASLLQKPS IGKCSVDIQQ NRTKTTERPD LLNCPIYWQQ VQEKCLLFSH TVNPWNNSLA  120
DCSTKESSLL LIQDKDELTR TQNLIHDKAI SFWIGLNFSL SEKNWKWING SFLSSNDLKI  180
TGDAKENSCV YISQTSVYSE YCSTEMKWIC QKELTLVRNK VSPDSWL                227
```

```
SEQ ID NO: 3            moltype = AA  length = 227
FEATURE                 Location/Qualifiers
source                  1..227
                        mol_type = protein
                        note = Simiiformes catarrhini
                        organism = unidentified
SEQUENCE: 3
MDQQMMYAEL TLPKDSGPES SSPSSLPRDV CQGSPWHQFA LKLSCAGIIL LVLVVTGLSL  60
SVASLLQKPS IGKCSVDIQQ NRTKTTERPD LLNCPIYWKQ VQEKCLLFSH TVNPWNNSLA  120
DCSTKESSLL LIQDKDELTR TQNLIHDKAI SFWIGLNFSL SEKNWKWING SFLSSNDLKI  180
TGDAKENSCV YISQTSVYSE YCSTEMKWIC QKELTLVRNK VSPDSWL              227

SEQ ID NO: 4            moltype = AA  length = 330
FEATURE                 Location/Qualifiers
source                  1..330
                        mol_type = protein
                        organism = Homo sapiens
SEQUENCE: 4
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 5            moltype = AA  length = 330
FEATURE                 Location/Qualifiers
source                  1..330
                        mol_type = protein
                        organism = Homo sapiens
SEQUENCE: 5
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 6            moltype = AA  length = 213
FEATURE                 Location/Qualifiers
source                  1..213
                        mol_type = protein
                        organism = Homo sapiens
SEQUENCE: 6
LGGPSVFLFP PKPKDTLMIS RTPEVTCVVV DVSHEDPEVK FNWYVDGVEV HNAKTKPREE  60
QYNSTYRVVS VLTVLHQDWL NGKEYKCKVS NKALPAPIEK TISKAKGQPR EPQVYTLPPS  120
RDELTKNQVS LTCLVKGFYP SDIAVEWESN GQPENNYKTT PPVLDSDGSF FLYSKLTVDK  180
SRWQQGNVFS CSVMHEALHN HYTQKSLSLS PGK                              213

SEQ ID NO: 7            moltype = AA  length = 107
FEATURE                 Location/Qualifiers
source                  1..107
                        mol_type = protein
                        organism = Homo sapiens
SEQUENCE: 7
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 8            moltype = AA  length = 324
FEATURE                 Location/Qualifiers
source                  1..324
                        mol_type = protein
                        organism = Mus musculus
SEQUENCE: 8
AKTTPPSVYP LAPGSAAQTN SMVTLGCLVK GYFPEPVTVT WNSGSLSSGV HTFPAVLQSD  60
LYTLSSSVTV PSSPRPSETV TCNVAHPASS TKVDKKIVPR DCGCKPCICT VPEVSSVFIF  120
PPKPKDVLTI TLTPKVTCVV VDISKDDPEV QFSWFVDDVE VHTAQTQPRE EQFNSTFRSV  180
SELPIMHQDW LNGKEFKCRV NSAAFPAPIE KTISKTKGRP KAPQVYTIPP PKEQMAKDKV  240
SLTCMITDFF PEDITVEWQW NGQPAENYKN TQPIMNTNGS YFVYSKLNVQ KSNWEAGNTF  300
TCSVLHEGLH NHHTEKSLSH SPGK                                        324

SEQ ID NO: 9            moltype = AA  length = 330
FEATURE                 Location/Qualifiers
source                  1..330
                        mol_type = protein
                        organism = Mus musculus
SEQUENCE: 9
AKTTAPSVYP LAPVCGDTTG SSVTLGCLVK GYFPEPVTLT WNSGSLSSGV HTFPAVLQSD  60
LYTLSSSVTV TSSTWPSQSI TCNVAHPASS TKVDKKIEPR GPTIKPCPPC KCPAPNLLGG  120
```

-continued

```
PSVFIFPPKI KDVLMISLSP IVTCVVVDVS EDDPDVQISW FVNNVEVHTA QTQTHREDYN  180
STLRVVSALP IQHQDWMSGK EFKCKVNNKD LPAPIERTIS KPKGSVRAPQ VYVLPPPEEE  240
MTKKQVTLTC MVTDFMPEDI YVEWTNNGKT ELNYKNTEPV LDSDGSYFMY SKLRVEKKNW  300
VERNSYSCSV VHEGLHNHHT TKSFSRTPGK                                  330

SEQ ID NO: 10          moltype = AA  length = 404
FEATURE                Location/Qualifiers
source                 1..404
                       mol_type = protein
                       organism = Mus musculus
SEQUENCE: 10
KTTPPSVYPL APGCGDTTGS SVTLGCLVKG YFPESVTVTW NSGSLSSSVH TFPALLQSGL  60
YTMSSSVTVP SSTWPSQTVT CSVAHPASST TVDKKLEPSG PISTINPCPP CKECHKCPAP  120
NLEGGPSVFI FPPNIKDVLM ISLTPKVTCV VVDVSEDDPD VQISWFVNNV EVHTAQTQTH  180
REDYNSTIRV VSTLPIQHQD WMSGKEFKCK VNNKDLPSPI ERTISKIKGL VRAPQVYILP  240
PPAEQLSRKD VSLTCLVVGF NPGDISVEWT SNGHTEENYK DTAPVLDSDG SYFIYSKLNM  300
KTSKWEKTDS FSCNVRHEGL KNYYLKKTIS RSPGLDLDDI CAEAKDGELD GLWTTITIFI  360
SLFLLSVCYS ASVTLFKVKW IFSSVVELKQ KISPDYRNMI GQGA                  404

SEQ ID NO: 11          moltype = AA  length = 107
FEATURE                Location/Qualifiers
source                 1..107
                       mol_type = protein
                       organism = Mus musculus
SEQUENCE: 11
RADAAPTVSI FPPSSEQLTS GGASVVCFLN NFYPKDINVK WKIDGSERQN GVLNSWTDQD  60
SKDSTYSMSS TLTLTKDEYE RHNSYTCEAT HKTSTSPIVK SFNRNEC                107

SEQ ID NO: 12          moltype = AA  length = 7
FEATURE                Location/Qualifiers
source                 1..7
                       mol_type = protein
                       organism = synthetic construct
SEQUENCE: 12
GYSFTGY                                                           7

SEQ ID NO: 13          moltype = AA  length = 10
FEATURE                Location/Qualifiers
source                 1..10
                       mol_type = protein
                       organism = synthetic construct
SEQUENCE: 13
GYSFTGYTMN                                                        10

SEQ ID NO: 14          moltype = AA  length = 5
FEATURE                Location/Qualifiers
source                 1..5
                       mol_type = protein
                       organism = synthetic construct
SEQUENCE: 14
GYTMN                                                             5

SEQ ID NO: 15          moltype = AA  length = 6
FEATURE                Location/Qualifiers
source                 1..6
                       mol_type = protein
                       organism = synthetic construct
SEQUENCE: 15
TGYTMN                                                            6

SEQ ID NO: 16          moltype = AA  length = 8
FEATURE                Location/Qualifiers
source                 1..8
                       mol_type = protein
                       organism = synthetic construct
SEQUENCE: 16
GYSFTGYT                                                          8

SEQ ID NO: 17          moltype = AA  length = 6
FEATURE                Location/Qualifiers
source                 1..6
                       mol_type = protein
                       organism = synthetic construct
SEQUENCE: 17
NPNTGG                                                            6

SEQ ID NO: 18          moltype = AA  length = 10
FEATURE                Location/Qualifiers
source                 1..10
```

```
                      mol_type = protein
                      organism = synthetic construct
SEQUENCE: 18
LINPNTGGTY                                                        10

SEQ ID NO: 19         moltype = AA  length = 17
FEATURE               Location/Qualifiers
source                1..17
                      mol_type = protein
                      organism = synthetic construct
SEQUENCE: 19
LINPNTGGTY YNQKFKD                                                17

SEQ ID NO: 20         moltype = AA  length = 13
FEATURE               Location/Qualifiers
source                1..13
                      mol_type = protein
                      organism = synthetic construct
SEQUENCE: 20
WMGLINPNTG GTY                                                    13

SEQ ID NO: 21         moltype = AA  length = 8
FEATURE               Location/Qualifiers
source                1..8
                      mol_type = protein
                      organism = synthetic construct
SEQUENCE: 21
INPNTGGT                                                          8

SEQ ID NO: 22         moltype = AA  length = 11
FEATURE               Location/Qualifiers
source                1..11
                      mol_type = protein
                      organism = synthetic construct
SEQUENCE: 22
LGDNYRGYFD Y                                                      11

SEQ ID NO: 23         moltype = AA  length = 12
FEATURE               Location/Qualifiers
source                1..12
                      mol_type = protein
                      organism = synthetic construct
SEQUENCE: 23
ARLGDNYRGY FD                                                     12

SEQ ID NO: 24         moltype = AA  length = 13
FEATURE               Location/Qualifiers
source                1..13
                      mol_type = protein
                      organism = synthetic construct
SEQUENCE: 24
ARLGDNYRGY FDY                                                    13

SEQ ID NO: 25         moltype = AA  length = 11
FEATURE               Location/Qualifiers
source                1..11
                      mol_type = protein
                      organism = synthetic construct
SEQUENCE: 25
KASQDVGTAV V                                                      11

SEQ ID NO: 26         moltype = AA  length = 7
FEATURE               Location/Qualifiers
source                1..7
                      mol_type = protein
                      organism = synthetic construct
SEQUENCE: 26
GTAVVWY                                                           7

SEQ ID NO: 27         moltype = AA  length = 6
FEATURE               Location/Qualifiers
source                1..6
                      mol_type = protein
                      organism = synthetic construct
SEQUENCE: 27
QDVGTA                                                            6

SEQ ID NO: 28         moltype = AA  length = 7
FEATURE               Location/Qualifiers
```

```
source                  1..7
                        mol_type = protein
                        organism = synthetic construct
SEQUENCE: 28
WASIRHT                                                                   7

SEQ ID NO: 29           moltype = AA  length = 10
FEATURE                 Location/Qualifiers
source                  1..10
                        mol_type = protein
                        organism = synthetic construct
SEQUENCE: 29
LLIDWASIRH                                                                10

SEQ ID NO: 30           moltype =   length =
SEQUENCE: 30
000

SEQ ID NO: 31           moltype = AA  length = 9
FEATURE                 Location/Qualifiers
source                  1..9
                        mol_type = protein
                        organism = synthetic construct
SEQUENCE: 31
QQYSTYLYT                                                                 9

SEQ ID NO: 32           moltype = AA  length = 8
FEATURE                 Location/Qualifiers
source                  1..8
                        mol_type = protein
                        organism = synthetic construct
SEQUENCE: 32
QQYSTYLY                                                                  8

SEQ ID NO: 33           moltype = AA  length = 120
FEATURE                 Location/Qualifiers
source                  1..120
                        mol_type = protein
                        organism = synthetic construct
SEQUENCE: 33
QVQLVQSGAE VKKPGASVKV SCKASGYSFT GYTMNWVRQA PGQGLEWMGL INPNTGGTYY  60
NQKFKDRVTM TRDTSISTAY MELSRLRSDD TAVYYCARLG DNYRGYFDYW GQGTTVTVSS  120

SEQ ID NO: 34           moltype = AA  length = 107
FEATURE                 Location/Qualifiers
source                  1..107
                        mol_type = protein
                        organism = synthetic construct
SEQUENCE: 34
DIQLTQSPSF LSASVGDRVT ITCKASQDVG TAVVWYQQKP GKAPKLLIDW ASIRHTGVPS  60
RFSGSGSGTE FTLTISSLQP EDFADYFCQQ YSTYLYTFGG GTKLEIK                107

SEQ ID NO: 35           moltype = AA  length = 6
FEATURE                 Location/Qualifiers
source                  1..6
                        mol_type = protein
                        organism = synthetic construct
SEQUENCE: 35
NPSTGG                                                                    6

SEQ ID NO: 36           moltype = AA  length = 10
FEATURE                 Location/Qualifiers
source                  1..10
                        mol_type = protein
                        organism = synthetic construct
SEQUENCE: 36
LINPSTGGTY                                                                10

SEQ ID NO: 37           moltype = AA  length = 17
FEATURE                 Location/Qualifiers
source                  1..17
                        mol_type = protein
                        organism = synthetic construct
SEQUENCE: 37
LINPSTGGTY YNQKFKD                                                        17

SEQ ID NO: 38           moltype = AA  length = 13
FEATURE                 Location/Qualifiers
source                  1..13
```

```
                      mol_type = protein
                      organism = synthetic construct
SEQUENCE: 38
WMGLINPSTG GTY                                                    13

SEQ ID NO: 39         moltype = AA  length = 8
FEATURE               Location/Qualifiers
source                1..8
                      mol_type = protein
                      organism = synthetic construct
SEQUENCE: 39
INPSTGGT                                                          8

SEQ ID NO: 40         moltype = AA  length = 11
FEATURE               Location/Qualifiers
source                1..11
                      mol_type = protein
                      organism = synthetic construct
SEQUENCE: 40
LGDNYRGYFD S                                                      11

SEQ ID NO: 41         moltype = AA  length = 13
FEATURE               Location/Qualifiers
source                1..13
                      mol_type = protein
                      organism = synthetic construct
SEQUENCE: 41
ARLGDNYRGY FDS                                                    13

SEQ ID NO: 42         moltype = AA  length = 120
FEATURE               Location/Qualifiers
source                1..120
                      mol_type = protein
                      organism = synthetic construct
SEQUENCE: 42
QVQLVQSGAE VKKPGASVKV SCKASGYSFT GYTMNWVRQA PGQGLEWMGL INPSTGGTYY  60
NQKFKDRVTM TRDTSISTAY MELSRLRSDD TAVYYCARLG DNYRGYFDSW GQGTTVTVSS  120

SEQ ID NO: 43         moltype = AA  length = 6
FEATURE               Location/Qualifiers
source                1..6
                      mol_type = protein
                      organism = synthetic construct
SEQUENCE: 43
NPSSGG                                                            6

SEQ ID NO: 44         moltype = AA  length = 10
FEATURE               Location/Qualifiers
source                1..10
                      mol_type = protein
                      organism = synthetic construct
SEQUENCE: 44
LINPSSGGTY                                                        10

SEQ ID NO: 45         moltype = AA  length = 17
FEATURE               Location/Qualifiers
source                1..17
                      mol_type = protein
                      organism = synthetic construct
SEQUENCE: 45
LINPSSGGTY YNQKFKD                                                17

SEQ ID NO: 46         moltype = AA  length = 13
FEATURE               Location/Qualifiers
source                1..13
                      mol_type = protein
                      organism = synthetic construct
SEQUENCE: 46
WMGLINPSSG GTY                                                    13

SEQ ID NO: 47         moltype = AA  length = 8
FEATURE               Location/Qualifiers
source                1..8
                      mol_type = protein
                      organism = synthetic construct
SEQUENCE: 47
INPSSGGT                                                          8

SEQ ID NO: 48         moltype = AA  length = 120
```

```
FEATURE                Location/Qualifiers
source                 1..120
                       mol_type = protein
                       organism = synthetic construct
SEQUENCE: 48
QVQLVQSGAE VKKPGASVKV SCKASGYSFT GYTMNWVRQA PGQGLEWMGL INPSSGGTYY  60
NQKFKDRVTM TRDTSISTAY MELSRLRSDD TAVYYCARLG DNYRGYFDSW GQGTTVTVSS  120

SEQ ID NO: 49          moltype = AA  length = 11
FEATURE                Location/Qualifiers
source                 1..11
                       mol_type = protein
                       organism = synthetic construct
SEQUENCE: 49
LGDNYRGYFD V                                                        11

SEQ ID NO: 50          moltype = AA  length = 13
FEATURE                Location/Qualifiers
source                 1..13
                       mol_type = protein
                       organism = synthetic construct
SEQUENCE: 50
ARLGDNYRGY FDV                                                      13

SEQ ID NO: 51          moltype = AA  length = 120
FEATURE                Location/Qualifiers
source                 1..120
                       mol_type = protein
                       organism = synthetic construct
SEQUENCE: 51
QVQLVQSGAE VKKPGASVKV SCKASGYSFT GYTMNWVRQA PGQGLEWMGL INPSTGGTYY  60
NQKFKDRVTM TRDTSISTAY MELSRLRSDD TAVYYCARLG DNYRGYFDVW GQGTTVTVSS  120

SEQ ID NO: 52          moltype = AA  length = 107
FEATURE                Location/Qualifiers
source                 1..107
                       mol_type = protein
                       organism = synthetic construct
SEQUENCE: 52
DIQLTQSPSF LSASVGDRVT ITCKASQDVG TAVVWYQQKP GKAPKLLIDW ASIRHTGVPS  60
RFSGSGSGTE FTLTISSLQP EDFATYYCQQ YSTYLYTFGG GTKLEIK                107

SEQ ID NO: 53          moltype = AA  length = 120
FEATURE                Location/Qualifiers
source                 1..120
                       mol_type = protein
                       organism = synthetic construct
SEQUENCE: 53
QVQLVQSGAE VKKPGASVKV SCKASGYSFT GYTMNWVRQA PGQGLEWMGL INPSSGGTYY  60
NQKFKDRVTM TRDTSISTAY MELSRLRSDD TAVYYCARLG DNYRGYFDVW GQGTTVTVSS  120

SEQ ID NO: 54          moltype = AA  length = 7
FEATURE                Location/Qualifiers
source                 1..7
                       mol_type = protein
                       organism = synthetic construct
SEQUENCE: 54
GYTFTGY                                                             7

SEQ ID NO: 55          moltype = AA  length = 10
FEATURE                Location/Qualifiers
source                 1..10
                       mol_type = protein
                       organism = synthetic construct
SEQUENCE: 55
GYTFTGYTMN                                                          10

SEQ ID NO: 56          moltype = AA  length = 8
FEATURE                Location/Qualifiers
source                 1..8
                       mol_type = protein
                       organism = synthetic construct
SEQUENCE: 56
GYTFTGYT                                                            8

SEQ ID NO: 57          moltype = AA  length = 120
FEATURE                Location/Qualifiers
source                 1..120
                       mol_type = protein
```

```
                         organism = synthetic construct
SEQUENCE: 57
QVQLVQSGAE VKKPGASVKV SCKASGYTFT GYTMNWVRQA PGQGLEWMGL INPSSGGTYY  60
NQKFKDRVTM TRDTSISTAY MELSRLRSDD TAVYYCARLG DNYRGYFDYW GQGTTVTVSS  120

SEQ ID NO: 58            moltype = AA  length = 11
FEATURE                  Location/Qualifiers
source                   1..11
                         mol_type = protein
                         organism = synthetic construct
SEQUENCE: 58
KASQDVGSAV V                                                       11

SEQ ID NO: 59            moltype = AA  length = 7
FEATURE                  Location/Qualifiers
source                   1..7
                         mol_type = protein
                         organism = synthetic construct
SEQUENCE: 59
GSAVVWY                                                            7

SEQ ID NO: 60            moltype = AA  length = 6
FEATURE                  Location/Qualifiers
source                   1..6
                         mol_type = protein
                         organism = synthetic construct
SEQUENCE: 60
QDVGSA                                                             6

SEQ ID NO: 61            moltype = AA  length = 7
FEATURE                  Location/Qualifiers
source                   1..7
                         mol_type = protein
                         organism = synthetic construct
SEQUENCE: 61
WASIRHS                                                            7

SEQ ID NO: 62            moltype = AA  length = 120
FEATURE                  Location/Qualifiers
source                   1..120
                         mol_type = protein
                         organism = synthetic construct
SEQUENCE: 62
QVQLVQSGAE VKKPGASVKV SCKASGYSFT GYTMNWVRQA PGQGLEWMGL INPSSGGTYY  60
NQKFKDRVTM TRDTSISTAY MELSRLRSDD TAVYYCARLG DNYRGYFDYW GQGTTVTVSS  120

SEQ ID NO: 63            moltype = AA  length = 107
FEATURE                  Location/Qualifiers
source                   1..107
                         mol_type = protein
                         organism = synthetic construct
SEQUENCE: 63
DIQLTQSPSF LSASVGDRVT ITCKASQDVG SAVVWYQQKP GKAPKLLIDW ASIRHSGVPS  60
RFSGSGSGTE FTLTISSLQP EDFATYYCQQ YSTYLYTFGG GTKLEIK                107

SEQ ID NO: 64            moltype = AA  length = 11
FEATURE                  Location/Qualifiers
source                   1..11
                         mol_type = protein
                         organism = synthetic construct
SEQUENCE: 64
RASQDVGTAV V                                                       11

SEQ ID NO: 65            moltype = AA  length = 107
FEATURE                  Location/Qualifiers
source                   1..107
                         mol_type = protein
                         organism = synthetic construct
SEQUENCE: 65
DIQLTQSPSF LSASVGDRVT ITCRASQDVG TAVVWYQQKP GKAPKLLIDW ASIRHTGVPS  60
RFSGSGSGTE FTLTISSLQP EDFATYYCQQ YSTYLYTFGG GTKLEIK                107

SEQ ID NO: 66            moltype = AA  length = 11
FEATURE                  Location/Qualifiers
source                   1..11
                         mol_type = protein
                         organism = synthetic construct
SEQUENCE: 66
RASQDVGSAV V                                                       11
```

```
SEQ ID NO: 67          moltype = AA  length = 107
FEATURE                Location/Qualifiers
source                 1..107
                       mol_type = protein
                       organism = synthetic construct
SEQUENCE: 67
DIQLTQSPSF LSASVGDRVT ITCRASQDVG SAVVWYQQKP GKAPKLLIDW ASIRHSGVPS  60
RFSGSGSGTE FTLTISSLQP EDFATYYCQQ YSTYLYTFGG GTKLEIK                107

SEQ ID NO: 68          moltype = AA  length = 120
FEATURE                Location/Qualifiers
source                 1..120
                       mol_type = protein
                       organism = synthetic construct
SEQUENCE: 68
QVQLVQSGAE VKKPGASVKV SCKASGYTFT GYTMNWVRQA PGQGLEWMGL INPSTGGTYY  60
NQKFKDRVTM TRDTSISTAY MELSRLRSDD TAVYYCARLG DNYRGYFDYW GQGTTVTVSS  120

SEQ ID NO: 69          moltype = AA  length = 11
FEATURE                Location/Qualifiers
source                 1..11
                       mol_type = protein
                       organism = synthetic construct
SEQUENCE: 69
RASQGIGSAV V                                                       11

SEQ ID NO: 70          moltype = AA  length = 6
FEATURE                Location/Qualifiers
source                 1..6
                       mol_type = protein
                       organism = synthetic construct
SEQUENCE: 70
QGIGSA                                                             6

SEQ ID NO: 71          moltype = AA  length = 107
FEATURE                Location/Qualifiers
source                 1..107
                       mol_type = protein
                       organism = synthetic construct
SEQUENCE: 71
DIQLTQSPSF LSASVGDRVT ITCRASQGIG SAVVWYQQKP GKAPKLLIDW ASIRHTGVPS  60
RFSGSGSGTE FTLTISSLQP EDFATYYCQQ YSTYLYTFGG GTKLEIK                107

SEQ ID NO: 72          moltype = AA  length = 11
FEATURE                Location/Qualifiers
source                 1..11
                       mol_type = protein
                       organism = synthetic construct
SEQUENCE: 72
RASQGISSYL A                                                       11

SEQ ID NO: 73          moltype = AA  length = 7
FEATURE                Location/Qualifiers
source                 1..7
                       mol_type = protein
                       organism = synthetic construct
SEQUENCE: 73
SSYLAWY                                                            7

SEQ ID NO: 74          moltype = AA  length = 6
FEATURE                Location/Qualifiers
source                 1..6
                       mol_type = protein
                       organism = synthetic construct
SEQUENCE: 74
QGISSY                                                             6

SEQ ID NO: 75          moltype = AA  length = 107
FEATURE                Location/Qualifiers
source                 1..107
                       mol_type = protein
                       organism = synthetic construct
SEQUENCE: 75
DIQLTQSPSF LSASVGDRVT ITCRASQGIS SYLAWYQQKP GKAPKLLIDW ASIRHTGVPS  60
RFSGSGSGTE FTLTISSLQP EDFATYYCQQ YSTYLYTFGG GTKLEIK                107

SEQ ID NO: 76          moltype = AA  length = 10
FEATURE                Location/Qualifiers
```

```
source                  1..10
                        mol_type = protein
                        organism = synthetic construct
SEQUENCE: 76
LLIYWASIRH                                                   10

SEQ ID NO: 77           moltype = AA  length = 9
FEATURE                 Location/Qualifiers
source                  1..9
                        mol_type = protein
                        organism = synthetic construct
SEQUENCE: 77
QQLSTYPYT                                                    9

SEQ ID NO: 78           moltype = AA  length = 8
FEATURE                 Location/Qualifiers
source                  1..8
                        mol_type = protein
                        organism = synthetic construct
SEQUENCE: 78
QQLSTYPY                                                     8

SEQ ID NO: 79           moltype = AA  length = 107
FEATURE                 Location/Qualifiers
source                  1..107
                        mol_type = protein
                        organism = synthetic construct
SEQUENCE: 79
DIQLTQSPSF LSASVGDRVT ITCRASQGIS SYLAWYQQKP GKAPKLLIYW ASIRHTGVPS  60
RFSGSGSGTE FTLTISSLQP EDFATYYCQQ LSTYPYTFGG GTKLEIK             107

SEQ ID NO: 80           moltype = AA  length = 107
FEATURE                 Location/Qualifiers
source                  1..107
                        mol_type = protein
                        organism = synthetic construct
SEQUENCE: 80
EIVMTQSPAT LSVSPGERAT LSCRASQDVG TAVVWYQQKP GQAPRLLIDW ASIRHTGIPA  60
RFSGSGSGTE FTLTISSLQS EDFAVYYCQQ YSTYLYTFGG GTKVEIK             107

SEQ ID NO: 81           moltype = AA  length = 9
FEATURE                 Location/Qualifiers
source                  1..9
                        mol_type = protein
                        organism = synthetic construct
SEQUENCE: 81
QQYSTWPLT                                                    9

SEQ ID NO: 82           moltype = AA  length = 8
FEATURE                 Location/Qualifiers
source                  1..8
                        mol_type = protein
                        organism = synthetic construct
SEQUENCE: 82
QQYSTWPL                                                     8

SEQ ID NO: 83           moltype = AA  length = 107
FEATURE                 Location/Qualifiers
source                  1..107
                        mol_type = protein
                        organism = synthetic construct
SEQUENCE: 83
EIVMTQSPAT LSVSPGERAT LSCRASQDVG TAVVWYQQKP GQAPRLLIDW ASIRHTGIPA  60
RFSGSGSGTE FTLTISSLQS EDFAVYYCQQ YSTWPLTFGG GTKVEIK             107

SEQ ID NO: 84           moltype = AA  length = 11
FEATURE                 Location/Qualifiers
source                  1..11
                        mol_type = protein
                        organism = synthetic construct
SEQUENCE: 84
RASQSVGTAV V                                                 11

SEQ ID NO: 85           moltype = AA  length = 6
FEATURE                 Location/Qualifiers
source                  1..6
                        mol_type = protein
                        organism = synthetic construct
SEQUENCE: 85
```

```
QSVGTA                                                             6

SEQ ID NO: 86           moltype = AA  length = 107
FEATURE                 Location/Qualifiers
source                  1..107
                        mol_type = protein
                        organism = synthetic construct
SEQUENCE: 86
EIVMTQSPAT LSVSPGERAT LSCRASQSVG TAVVWYQQKP GQAPRLLIDW ASIRHTGIPA  60
RFSGSGSGTE FTLTISSLQS EDFAVYYCQQ YSTWPLTFGG GTKVEIK                107

SEQ ID NO: 87           moltype = AA  length = 11
FEATURE                 Location/Qualifiers
source                  1..11
                        mol_type = protein
                        organism = synthetic construct
SEQUENCE: 87
RASQSVGTNL A                                                       11

SEQ ID NO: 88           moltype = AA  length = 7
FEATURE                 Location/Qualifiers
source                  1..7
                        mol_type = protein
                        organism = synthetic construct
SEQUENCE: 88
GTNLAWY                                                            7

SEQ ID NO: 89           moltype = AA  length = 6
FEATURE                 Location/Qualifiers
source                  1..6
                        mol_type = protein
                        organism = synthetic construct
SEQUENCE: 89
QSVGTN                                                             6

SEQ ID NO: 90           moltype = AA  length = 107
FEATURE                 Location/Qualifiers
source                  1..107
                        mol_type = protein
                        organism = synthetic construct
SEQUENCE: 90
EIVMTQSPAT LSVSPGERAT LSCRASQSVG TNLAWYQQKP GQAPRLLIDW ASIRHTGIPA  60
RFSGSGSGTE FTLTISSLQS EDFAVYYCQQ YSTWPLTFGG GTKVEIK                107

SEQ ID NO: 91           moltype = AA  length = 450
FEATURE                 Location/Qualifiers
source                  1..450
                        mol_type = protein
                        organism = synthetic construct
SEQUENCE: 91
QVQLVQSGAE VKKPGASVKV SCKASGYSFT GYTMNWVRQA PGQGLEWMGL INPNTGGTYY  60
NQKFKDRVTM TRDTSISTAY MELSRLRSDD TAVYYCARLG DNYRGYFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 92           moltype = AA  length = 450
FEATURE                 Location/Qualifiers
source                  1..450
                        mol_type = protein
                        organism = synthetic construct
SEQUENCE: 92
QVQLVQSGAE VKKPGASVKV SCKASGYSFT GYTMNWVRQA PGQGLEWMGL INPSTGGTYY  60
NQKFKDRVTM TRDTSISTAY MELSRLRSDD TAVYYCARLG DNYRGYFDSW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 93           moltype = AA  length = 450
FEATURE                 Location/Qualifiers
source                  1..450
                        mol_type = protein
                        organism = synthetic construct
```

```
SEQUENCE: 93
QVQLVQSGAE VKKPGASVKV SCKASGYSFT GYTMNWVRQA PGQGLEWMGL INPSSGGTYY  60
NQKFKDRVTM TRDTSISTAY MELSRLRSDD TAVYYCARLG DNYRGYFDSW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 94          moltype = AA  length = 450
FEATURE                Location/Qualifiers
source                 1..450
                       mol_type = protein
                       organism = synthetic construct
SEQUENCE: 94
QVQLVQSGAE VKKPGASVKV SCKASGYSFT GYTMNWVRQA PGQGLEWMGL INPSTGGTYY  60
NQKFKDRVTM TRDTSISTAY MELSRLRSDD TAVYYCARLG DNYRGYFDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 95          moltype = AA  length = 450
FEATURE                Location/Qualifiers
source                 1..450
                       mol_type = protein
                       organism = synthetic construct
SEQUENCE: 95
QVQLVQSGAE VKKPGASVKV SCKASGYSFT GYTMNWVRQA PGQGLEWMGL INPSSGGTYY  60
NQKFKDRVTM TRDTSISTAY MELSRLRSDD TAVYYCARLG DNYRGYFDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 96          moltype = AA  length = 450
FEATURE                Location/Qualifiers
source                 1..450
                       mol_type = protein
                       organism = synthetic construct
SEQUENCE: 96
QVQLVQSGAE VKKPGASVKV SCKASGYTFT GYTMNWVRQA PGQGLEWMGL INPSSGGTYY  60
NQKFKDRVTM TRDTSISTAY MELSRLRSDD TAVYYCARLG DNYRGYFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 97          moltype = AA  length = 450
FEATURE                Location/Qualifiers
source                 1..450
                       mol_type = protein
                       organism = synthetic construct
SEQUENCE: 97
QVQLVQSGAE VKKPGASVKV SCKASGYSFT GYTMNWVRQA PGQGLEWMGL INPSSGGTYY  60
NQKFKDRVTM TRDTSISTAY MELSRLRSDD TAVYYCARLG DNYRGYFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 98          moltype = AA  length = 450
FEATURE                Location/Qualifiers
source                 1..450
                       mol_type = protein
                       organism = synthetic construct
SEQUENCE: 98
QVQLVQSGAE VKKPGASVKV SCKASGYTFT GYTMNWVRQA PGQGLEWMGL INPSTGGTYY  60
NQKFKDRVTM TRDTSISTAY MELSRLRSDD TAVYYCARLG DNYRGYFDYW GQGTTVTVSS  120
ASTKGPSVFP LAPSSKSTSG GTAALGCLVK DYFPEPVTVS WNSGALTSGV HTFPAVLQSS  180
```

```
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 99          moltype = AA  length = 214
FEATURE                Location/Qualifiers
source                 1..214
                       mol_type = protein
                       organism = synthetic construct
SEQUENCE: 99
DIQLTQSPSF LSASVGDRVT ITCKASQDVG TAVVWYQQKP GKAPKLLIDW ASIRHTGVPS  60
RFSGSGSGTE FTLTISSLQP EDFADYFCQQ YSTYLYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 100         moltype = AA  length = 214
FEATURE                Location/Qualifiers
source                 1..214
                       mol_type = protein
                       organism = synthetic construct
SEQUENCE: 100
DIQLTQSPSF LSASVGDRVT ITCKASQDVG TAVVWYQQKP GKAPKLLIDW ASIRHTGVPS  60
RFSGSGSGTE FTLTISSLQP EDFATYYCQQ YSTYLYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 101         moltype = AA  length = 214
FEATURE                Location/Qualifiers
source                 1..214
                       mol_type = protein
                       organism = synthetic construct
SEQUENCE: 101
DIQLTQSPSF LSASVGDRVT ITCKASQDVG SAVVWYQQKP GKAPKLLIDW ASIRHSGVPS  60
RFSGSGSGTE FTLTISSLQP EDFATYYCQQ YSTYLYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 102         moltype = AA  length = 214
FEATURE                Location/Qualifiers
source                 1..214
                       mol_type = protein
                       organism = synthetic construct
SEQUENCE: 102
DIQLTQSPSF LSASVGDRVT ITCRASQDVG TAVVWYQQKP GKAPKLLIDW ASIRHTGVPS  60
RFSGSGSGTE FTLTISSLQP EDFATYYCQQ YSTYLYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 103         moltype = AA  length = 214
FEATURE                Location/Qualifiers
source                 1..214
                       mol_type = protein
                       organism = synthetic construct
SEQUENCE: 103
DIQLTQSPSF LSASVGDRVT ITCRASQDVG SAVVWYQQKP GKAPKLLIDW ASIRHSGVPS  60
RFSGSGSGTE FTLTISSLQP EDFATYYCQQ YSTYLYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 104         moltype = AA  length = 214
FEATURE                Location/Qualifiers
source                 1..214
                       mol_type = protein
                       organism = synthetic construct
SEQUENCE: 104
DIQLTQSPSF LSASVGDRVT ITCRASQGIG SAVVWYQQKP GKAPKLLIDW ASIRHTGVPS  60
RFSGSGSGTE FTLTISSLQP EDFATYYCQQ YSTYLYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 105         moltype = AA  length = 214
FEATURE                Location/Qualifiers
source                 1..214
                       mol_type = protein
                       organism = synthetic construct
SEQUENCE: 105
DIQLTQSPSF LSASVGDRVT ITCRASQGIS SYLAWYQQKP GKAPKLLIDW ASIRHTGVPS  60
```

```
RFSGSGSGTE FTLTISSLQP EDFATYYCQQ YSTYLYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 106          moltype = AA  length = 214
FEATURE                 Location/Qualifiers
source                  1..214
                        mol_type = protein
                        organism = synthetic construct
SEQUENCE: 106
DIQLTQSPSF LSASVGDRVT ITCRASQGIS SYLAWYQQKP GKAPKLLIYW ASIRHTGVPS  60
RFSGSGSGTE FTLTISSLQP EDFATYYCQQ LSTYPYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 107          moltype = AA  length = 214
FEATURE                 Location/Qualifiers
source                  1..214
                        mol_type = protein
                        organism = synthetic construct
SEQUENCE: 107
EIVMTQSPAT LSVSPGERAT LSCRASQDVG TAVVWYQQKP GQAPRLLIDW ASIRHTGIPA  60
RFSGSGSGTE FTLTISSLQS EDFAVYYCQQ YSTYLYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 108          moltype = AA  length = 214
FEATURE                 Location/Qualifiers
source                  1..214
                        mol_type = protein
                        organism = synthetic construct
SEQUENCE: 108
EIVMTQSPAT LSVSPGERAT LSCRASQDVG TAVVWYQQKP GQAPRLLIDW ASIRHTGIPA  60
RFSGSGSGTE FTLTISSLQS EDFAVYYCQQ YSTWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 109          moltype = AA  length = 214
FEATURE                 Location/Qualifiers
source                  1..214
                        mol_type = protein
                        organism = synthetic construct
SEQUENCE: 109
EIVMTQSPAT LSVSPGERAT LSCRASQSVG TAVVWYQQKP GQAPRLLIDW ASIRHTGIPA  60
RFSGSGSGTE FTLTISSLQS EDFAVYYCQQ YSTWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 110          moltype = AA  length = 214
FEATURE                 Location/Qualifiers
source                  1..214
                        mol_type = protein
                        organism = synthetic construct
SEQUENCE: 110
EIVMTQSPAT LSVSPGERAT LSCRASQSVG TNLAWYQQKP GQAPRLLIDW ASIRHTGIPA  60
RFSGSGSGTE FTLTISSLQS EDFAVYYCQQ YSTWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 111          moltype = AA  length = 120
FEATURE                 Location/Qualifiers
source                  1..120
                        mol_type = protein
                        organism = synthetic construct
SEQUENCE: 111
QVQLVQSGAE VKKPGASVKV SCKASGYSFT GYTMNWVRQA PGQNLEWIGL INPNTGGTYY  60
NQKFKDRVTL TVDTSISTAY MELSRLRSDD TAVYYCARLG DNYRGYFDSW GQGTTVTVSS  120

SEQ ID NO: 112          moltype = AA  length = 120
FEATURE                 Location/Qualifiers
source                  1..120
                        mol_type = protein
                        organism = synthetic construct
SEQUENCE: 112
QVQLVQSGAE VKKPGASVKV SCKASGYSFT GYTMNWVRQA PGQNLEWIGL INPATGGTYY  60
NQKFKDRVTL TVDTSISTAY MELSRLRSDD TAVYYCARLG DNYRGYFDVW GQGTTVTVSS  120

SEQ ID NO: 113          moltype = AA  length = 120
FEATURE                 Location/Qualifiers
```

```
source                  1..120
                        mol_type = protein
                        organism = synthetic construct
SEQUENCE: 113
QVQLVQSGAE VKKPGASVKV SCKASGYSFT GYTMNWVRQA PGQGLEWMGL INPNTGGTYY  60
NQKFKDRVTM TRDTSISTAY MELSRLRSDD TAVYYCARLG DNYRGYFDSW GQGTTVTVSS  120

SEQ ID NO: 114          moltype = AA  length = 107
FEATURE                 Location/Qualifiers
source                  1..107
                        mol_type = protein
                        organism = synthetic construct
SEQUENCE: 114
DIQLTQSPSF LSASVGDRVT ITCKASQDVG TAVVWYQQKP GKAPKLLIDW ASIRHTGVPS  60
RFSGSGSGTE FTLTISSLQP EDFADYFCQQ YSTYLYTFGG GTKLEIK                 107

SEQ ID NO: 115          moltype = AA  length = 107
FEATURE                 Location/Qualifiers
source                  1..107
                        mol_type = protein
                        organism = synthetic construct
SEQUENCE: 115
EIVMTQSPAT LSVSPGERAT LSCKASQDVG TAVVWYQQKP GQAPRLLIDW ASIRHTGIPA  60
RFSGSGSGTE FTLTISSLQS EDFAVYYCQQ YSTYLYTFGG GTKVEIK                 107

SEQ ID NO: 116          moltype = AA  length = 5
FEATURE                 Location/Qualifiers
source                  1..5
                        mol_type = protein
                        organism = synthetic construct
SEQUENCE: 116
GGGGS                                                               5

SEQ ID NO: 117          moltype = AA  length = 5
FEATURE                 Location/Qualifiers
source                  1..5
                        mol_type = protein
                        organism = synthetic construct
SEQUENCE: 117
GGGGS                                                               5

SEQ ID NO: 118          moltype = AA  length = 10
FEATURE                 Location/Qualifiers
source                  1..10
                        mol_type = protein
                        organism = synthetic construct
SEQUENCE: 118
GGGGSGGGGS                                                          10

SEQ ID NO: 119          moltype = AA  length = 15
FEATURE                 Location/Qualifiers
source                  1..15
                        mol_type = protein
                        organism = synthetic construct
SEQUENCE: 119
GGGGSGGGGS GGGGS                                                    15

SEQ ID NO: 120          moltype = AA  length = 20
FEATURE                 Location/Qualifiers
source                  1..20
                        mol_type = protein
                        organism = synthetic construct
SEQUENCE: 120
GGGGSGGGGS GGGGSGGGGS                                               20

SEQ ID NO: 121          moltype = AA  length = 5
FEATURE                 Location/Qualifiers
source                  1..5
                        mol_type = protein
                        organism = synthetic construct
SEQUENCE: 121
GGGGA                                                               5

SEQ ID NO: 122          moltype = AA  length = 449
FEATURE                 Location/Qualifiers
source                  1..449
                        mol_type = protein
                        organism = synthetic construct
SEQUENCE: 122
```

-continued

```
QVQLVQSGAE VKKPGASVKV SCKASGYSFT GYWMHWVRQA PGQGLEWMGM IHPSDSETRL  60
NQKFKDRVTM TRDTSTSTVY MELSSLRSED TAVYYCASEG LRRGSFAYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 123         moltype = AA  length = 449
FEATURE                Location/Qualifiers
source                 1..449
                       mol_type = protein
                       organism = synthetic construct
SEQUENCE: 123
QVQLVQSGAE VKKPGASVKV SCKASGYSFT GYWMHWVRQA PGQGLEWMGM IHPSDSETRL  60
NQKFKDRVTM TVDTSTSTVY MELSSLRSED TAVYYCASEG LRRGSFAYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 124         moltype = AA  length = 449
FEATURE                Location/Qualifiers
source                 1..449
                       mol_type = protein
                       organism = synthetic construct
SEQUENCE: 124
QVQLVQSGAE VKKPGASVKV SCKASGYSFT GYWMHWVRQA PGQGLEWMGM IHPSDSETRL  60
NQKFKDRVTM TVDKSTSTVY MELSSLRSED TAVYYCASEG LRRGSFAYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 125         moltype = AA  length = 449
FEATURE                Location/Qualifiers
source                 1..449
                       mol_type = protein
                       organism = synthetic construct
SEQUENCE: 125
QVQLVQSGAE VKKPGASVKV SCKGSGYSFT GYWMHWVRQA PGQGLEWMGM IHPSDSETRL  60
NQKFKDKVTM TVDKSTSTVY MELSSLRSED TAVYYCASEG LRRGSFAYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 126         moltype = AA  length = 450
FEATURE                Location/Qualifiers
source                 1..450
                       mol_type = protein
                       organism = synthetic construct
SEQUENCE: 126
QVQLVQSGAE VKKPGASVKV SCKASGYTFI DYYINWVRQA PGQGLEWMGW IFPGSGHTKY  60
NENFKGRVTM TRDTSTSTVY MELSSLRSED TAVYYCARGD RSALGYFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGA  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 127         moltype = AA  length = 450
FEATURE                Location/Qualifiers
source                 1..450
                       mol_type = protein
                       organism = synthetic construct
SEQUENCE: 127
QVQLVQSGAE VKKPGASVKV SCKASGYTFI DYYINWVRQA PGQGLEWMGW IFPGSGHTKY  60
NENFKGKVTM TVDTSTSTVY MELSSLRSED TAVYYCARGD RSALGYFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGA  240
```

```
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 128          moltype = AA  length = 450
FEATURE                 Location/Qualifiers
source                  1..450
                        mol_type = protein
                        organism = synthetic construct
SEQUENCE: 128
QVQLVQSGAE VKKPGASVKV SCKASGYTFI DYYINWVRQA PGQGLEWMGW IFPGSGHTKY  60
NENFKGKVTL TVDTSTSTVY MELSSLRSED TAVYYCARGD RSALGYFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGA  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 129          moltype = AA  length = 450
FEATURE                 Location/Qualifiers
source                  1..450
                        mol_type = protein
                        organism = synthetic construct
SEQUENCE: 129
QVQLVQSGAE VKKPGASVKV SCKASGYTFI DYYINWVRQA PGQGLEWIGW IFPGSGHTKY  60
NENFKGKVTL TVDTSTSTVY MELSSLRSED TAVYFCARGD RSALGYFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGA  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 130          moltype = AA  length = 218
FEATURE                 Location/Qualifiers
source                  1..218
                        mol_type = protein
                        organism = synthetic construct
SEQUENCE: 130
DIVMTQSPDS LAVSLGERAT INCRASESVD NYGMTFMSWY QQKPGQPPKL LIYAASNQGS  60
GVPDRFSGSG SGTDFTLTIS SLQAEDVAVY YCQQSKEVPY TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 131          moltype = AA  length = 218
FEATURE                 Location/Qualifiers
source                  1..218
                        mol_type = protein
                        organism = synthetic construct
SEQUENCE: 131
DIVLTQSPDS LAVSLGERAT INCRASESVD NYGMTFMSWY QQKPGQPPKL LIYAASNQGS  60
GVPDRFSGSG SGTDFTLTIS SLQAEDVAVY YCQQSKEVPY TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 132          moltype = AA  length = 218
FEATURE                 Location/Qualifiers
source                  1..218
                        mol_type = protein
                        organism = synthetic construct
SEQUENCE: 132
DIVLTQSPDS LAVSLGERAT INCRASESVD NYGMTFMSWF QQKPGQPPKL LIYAASNQGS  60
GVPDRFSGSG SGTDFTLTIS SLQAEDVAVY YCQQSKEVPY TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 133          moltype = AA  length = 218
FEATURE                 Location/Qualifiers
source                  1..218
                        mol_type = protein
                        organism = synthetic construct
SEQUENCE: 133
EIVLTQSPAT LSLSPGERAT LSCRASESVD NYGMTFMSWY QQKPGQAPRL LIYAASNQGS  60
GIPARFSGSG SGTDFTLTIS SLEPEDFAVY YCQQSKEVPY TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218
```

```
SEQ ID NO: 134          moltype = AA  length = 215
FEATURE                 Location/Qualifiers
source                  1..215
                        mol_type = protein
                        organism = synthetic construct
SEQUENCE: 134
DIQMTQSPSS LSASVGDRVT ITCTASSSVS STYLHWYQQK PGKAPKLLIY STSNLASGVP  60
SRFSGSGSGT DFTLTISSLQ PEDFATYYCH QYHRSPLTFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 135          moltype = AA  length = 215
FEATURE                 Location/Qualifiers
source                  1..215
                        mol_type = protein
                        organism = synthetic construct
SEQUENCE: 135
DIQMTQSPSS LSASVGDRVT ITCTASSSVS STYLHWYQQK PGKAPKLLIY STSNLASGVP  60
SRFSGSGSGT DYTLTISSLQ PEDFATYYCH QYHRSPLTFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 136          moltype = AA  length = 215
FEATURE                 Location/Qualifiers
source                  1..215
                        mol_type = protein
                        organism = synthetic construct
SEQUENCE: 136
DIQLTQSPSS LSASVGDRVT ITCTASSSVS STYLHWYQQK PGKSPKLLIY STSNLASGVP  60
SRFSGSGSGT DYTLTISSLQ PEDFATYYCH QYHRSPLTFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 137          moltype = AA  length = 215
FEATURE                 Location/Qualifiers
source                  1..215
                        mol_type = protein
                        organism = synthetic construct
SEQUENCE: 137
DIQLTQSPSS LSASVGDRVT ITCTASSSVS STYLHWYQQK PGKSPKLLIY STSNLASGVP  60
SRFSGSGSGT DYTLTISSLQ PEDAATYYCH QYHRSPLTFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215
```

KLRB1 BINDING AGENTS AND METHODS OF USE THEREOF

CLAIM OF PRIORITY

This application is a continuation of PCT/US2024/056624, filed on Nov. 20, 2024, which claims the benefit of U.S. Provisional Patent Application Ser. No. 63/601,664, filed on Nov. 21, 2023. The entire contents of the foregoing are hereby incorporated by reference.

STATEMENT REGARDING FEDERALLY SPONSORED RESEARCH

This invention was made with government support under HL119145 awarded by the National Institutes of Health. The government has certain rights in the invention.

SEQUENCE LISTING

This application contains a Sequence Listing that has been submitted electronically as an XML file named "40175-0484001 ST26_SL.XML." The XML file, created on Jul. 3, 2025, is 135,943 bytes in size. The material in the XML file is hereby incorporated by reference in its entirety.

TECHNICAL FIELD

This disclosure generally relates to KLRB1 binding agents, in particular anti-KLRB1-antibodies as well as therapeutic methods of using the agents for autoimmune disease, allergic diseases, transplant rejection, hematologic malignancies, and cancer.

BACKGROUND

The expression of killer cell lectin-like receptor subfamily B, member 1 (KLRB1; also known as CD161) defines a unique population of immune cells implicated in a variety of autoimmune and allergic diseases. For example, T-helper IL-17 secreting (Th17) cells express KLRB1 (Maggi et al. 2010). Th17 cells, and the cytokine IL-17 they produce, are implicated in psoriasis, psoriatic arthritis, ankylosing spondylitis, and inflammatory bowel disease (Yang et al. 2014), among other autoimmune diseases. Monoclonal antibody therapeutics targeting IL-17, or the upstream cytokine IL-23 that stimulates IL-17 producing cells, are FDA approved and marketed for use in psoriasis (e.g., secukinumab and ixekizumab) and ankylosing spondylitis (e.g., secukinumab). However, therapeutic developments based upon targeting these molecules remain limited and there remains a need for new therapeutics utilizing these targets for various indications including autoimmune disease, allergic disease, inflammatory diseases, and cancer.

SUMMARY OF THE DISCLOSURE

Described herein are KLRB1-binding antibodies (and antigen-binding fragments thereof) with increased humanness and/or with decreased potential deamidation and/or isomerization sites that have numerous uses, including therapeutic and diagnostic uses. For example, the antibodies can be used for treating, and in some cases preventing, various diseases associated with KLRB1 expressing cells (i.e., by depleting the KLRB1 expressing cells), e.g., for treating, and in some cases preventing (i.e., reducing the risk of developing), autoimmune diseases including psoriasis, psoriatic arthritis, ankylosing spondylitis, palmoplantar pustulosis, hidradenitis suppurativa, and inflammatory bowel disease; allergic diseases including asthma and atopic dermatitis; transplant rejection; hematologic malignancies, and cancer.

Provided herein are antibodies or antigen binding portions thereof that specifically bind to killer cell lectin-like receptor subfamily B, member 1, (KLRB1; optionally SEQ ID NO: 1, SEQ ID NO: 2, or SEQ ID NO: 3), wherein the antibody or antigen binding portion thereof comprises or consists of at least one of (a) a heavy chain variable region (VH) comprising a VH complementarity determining region (CDR) 1 comprising a sequence that is at least 95% identical to a VH CDR1 amino acid sequence set forth in one of Table 1 to 17, preferably Table 10, 14, or 4; a VH CDR2 comprising a sequence that is at least 95% identical to a VH CDR2 amino acid sequence set forth in one of Table 1 to 17, preferably Table 10, 14, or 4, and a VH CDR3 comprising a sequence that is at least 95% identical to a VH CDR3 amino acid sequence set forth in one of Table 1 to 17, preferably Table 10, 14, or 4; and (b) a light chain variable region (VL) comprising a VL CDR1 comprising a sequence that is at least 95% identical to a VL CDR1 amino acid sequence set forth in one of Table 1 to 17, preferably Table 10, 14, or 4, a VL CDR2 comprising a sequence that is at least 95% identical to a VL CDR2 amino acid sequence set forth in one of Table 1 to 17, preferably Table 10, 14, or 4, and a VL CDR3 comprising a sequence that is at least 95% identical to a VL CDR3 amino acid sequence set forth in one of Table 1 to 17, preferably Table 10, 14, or 4.

In some embodiments, described herein are antibodies or antigen-binding fragments thereof that specifically binds to killer cell lectin-like receptor subfamily B, member 1 (KLRB1), comprising:

a. a heavy chain variable region (VH) comprising three VH complementarity determining regions (CDR-H1, CDR-H2 and CDR-H3); and
b. a light chain variable region (VL) comprising three VL complementarity determining regions (CDR-L1, CDR-L2 and CDR-L3), wherein the CDR-H1, CDR-H2, CDR-H3, CDR-L1, CDR-L2 and CDR-L3 are selected from one of the following:

i. CDR-H1 has the amino acid sequence of any one of SEQ ID NOs: 14, 15, 54, 55, and 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 26, 27, and 64; CDR-L2 has the amino acid sequence of any one of SEQ ID NOs: 28-29, or WA; and CDR-L3 has the amino acid sequence of SEQ ID NOs: 31 or 32; or
ii. CDR-H1 has the amino acid sequence of any one of SEQ ID NOs: 12-16; CDR-H2 has the amino acid sequence of any one of SEQ ID NOs: 17-21; CDR-H3 has the amino acid sequence of any one of SEQ ID NOs: 22-24; CDR-L1 has the amino acid sequence of any one of SEQ ID NOs: 25-27; CDR-L2 has the amino acid sequence of any one of SEQ ID NOs: 28-29, or WA; and CDR-L3 has the amino acid sequence of SEQ ID NOs: 31 or 32; or
iii. CDR-H1 has the amino acid sequence of any one of SEQ ID NOs: 12-16; CDR-H2 has the amino acid sequence of any one of SEQ ID NOs: 35-39; CDR-H3 has the amino acid sequence of any one of SEQ ID NOs: 23, 40, or 41; CDR-L1 has the amino acid sequence of any one of SEQ ID NOs: 25-27; CDR-L2 has the amino acid sequence of any one of SEQ ID NOs: 28-29, or WA; and CDR-L3 has the amino acid sequence of SEQ ID NOs: 31 or 32; or iv. CDR-H1 has the amino acid sequence of any one of SEQ ID NOs: 12-16; CDR-H2 has the amino acid sequence of any one of SEQ ID NOs: 43-47; CDR-H3 has the amino acid sequence of any one of SEQ ID NOs: 23, 40, or 41; CDR-L1 has the amino acid sequence of any one of SEQ ID NOs: 25-27; CDR-L2 has the amino acid sequence of any one of SEQ ID NOs: 28-29, or WA; and CDR-L3 has the amino acid sequence of SEQ ID NOs: 31 or 32; or v. CDR-H1 has the amino acid sequence of any one of SEQ ID NOs: 12-16; CDR-H2 has the amino acid sequence of any one of SEQ ID NOs: 35-39; CDR-H3 has the amino acid sequence of any one of SEQ ID NOs: 23, 49, or 50; CDR-L1 has the amino acid sequence of any one of SEQ ID NOs: 25-27; CDR-L2 has the amino acid sequence of any one of SEQ ID NOs: 28-29, or WA; and CDR-L3 has the amino acid sequence of SEQ ID NOs: 31 or 32; or vi. CDR-H1 has the amino acid sequence of any one of SEQ ID NOs: 12-16; CDR-H2 has the amino acid sequence of any one of SEQ ID NOs: 43-47; CDR-H3 has the amino acid sequence of any one of SEQ ID NOs: 23, 49, or 50; CDR-L1 has the amino acid sequence of any one of SEQ ID NOs: 25-27; CDR-L2 has the amino acid sequence of any one of SEQ ID NOs: 28-29, or WA; and CDR-L3 has the amino acid sequence of SEQ ID NOs: 31 or 32; or vii. CDR-H1 has the amino acid sequence of any one of SEQ ID NOs: 14, 15, 54, 55, or 56; CDR-H2 has the amino acid sequence of any one of SEQ ID NOs: 43-47; CDR-H3 has the amino acid sequence of any one of SEQ ID NOs: 22-24; CDR-L1 has the amino acid sequence of any one of SEQ ID NOs: 25-27; CDR-L2 has the amino acid sequence of any one of SEQ ID NOs: 28-29, or WA; and CDR-L3 has the amino acid sequence of SEQ ID NOs: 31 or 32; or viii. CDR-H1 has the amino acid sequence of any one of SEQ ID NOs: 12-16; CDR-H2 has the amino acid sequence of any one of SEQ ID NOs: 43-47; CDR-H3 has the amino acid sequence of any one of SEQ ID NOs: 22-24; CDR-L1 has the amino acid sequence of any one of SEQ ID NOs: 58-60; CDR-L2 has the amino acid sequence of any one of SEQ ID NO:29, SEQ ID NO:61 or WA; and CDR-L3 has the amino acid sequence of SEQ ID NOs: 31 or 32; or ix. CDR-H1 has the amino acid sequence of any one of SEQ ID NOs: 12-16; CDR-H2 has the amino acid sequence of any one of SEQ ID NOs: 43-47; CDR-H3 has the amino acid sequence of any one of SEQ ID NOs: 22-24; CDR-L1 has the amino acid sequence of any one of SEQ ID NOs: 26, 27, or 64; CDR-L2 has the amino acid sequence of any one of SEQ ID NOs: 28-29, or WA; and CDR-L3 has the amino acid sequence of SEQ ID NOs: 31 or 32; or x. CDR-H1 has the amino acid sequence of any one of SEQ ID NOs: 14, 15, 54, 55, or 56; CDR-H2 has the amino acid sequence of any one of SEQ ID NOs: 43-47; CDR-H3 has the amino acid sequence of any one of SEQ ID NOs: 22-24; CDR-L1 has the amino acid sequence of any one of SEQ ID NOs: 59, 60, or 66; CDR-L2 has the amino acid sequence of any one of SEQ ID NO:29, SEQ ID NO:61 or WA; and CDR-L3 has the amino acid sequence of SEQ ID NOs: 31 or 32; or xi. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 59, 69, or 70; CDR-L2 has the amino acid sequence of any one of SEQ ID NOs: 28-29, or WA; and CDR-L3 has the amino acid sequence of SEQ ID NOs: 31 or 32; or xii. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 72-74; CDR-L2 has the amino acid sequence of any one of SEQ ID NOs: 28-29, or WA; and CDR-L3 has the amino acid sequence of SEQ ID NOs: 31 or 32; or xiii. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 72-74; CDR-L2 has the amino acid sequence of any one of SEQ ID NO:28, SEQ ID NO:76 or WA; and CDR-L3 has the amino acid sequence of SEQ ID NOs: 77 or 78; or xiv. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 26, 27, or 64; CDR-L2 has the amino acid sequence of any one of SEQ ID NOs: 28-29 or WA; and CDR-L3 has the amino acid sequence of SEQ ID NOs: 31 or 32; or xv. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 26, 27, or 64; CDR-L2 has the amino acid sequence of any one of SEQ ID NOs: 28-29 or WA; and CDR-L3 has the amino acid sequence of SEQ ID NOs: 81 or 82; or xvi. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 26, 84, or 85; CDR-L2 has the amino acid sequence of any one of SEQ ID NOs: 28-29 or WA; and CDR-L3 has the amino acid sequence of SEQ ID NOs: 81 or 82; or xvii. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 87-89; CDR-L2 has the amino acid sequence of any one of SEQ ID NOs: 28-29 or WA; and CDR-L3 has the amino acid sequence of SEQ ID NOs: 81 or 82.

In some embodiments, the amino acid sequence of each grouping of CDR-H1, CDR-H2, CDR-H3, CDR-L1, CDR-L2 and CDR-L3 is selected from the same antibody numbering convention. In some embodiments, the amino acid sequence of each grouping of CDR-H1, CDR-H2, CDR-H3, CDR-L1, CDR-L2 and CDR-L3 is selected from the Kabat antibody numbering convention.

In some embodiments, the CDR-H1 has the amino acid sequence of SEQ ID NO: 14, CDR-H2 has the amino acid sequence of SEQ ID NO: 37, CDR-H3 has the amino acid sequence of SEQ ID NO: 22, CDR-L1 has the amino acid sequence of SEQ ID NO: 64, CDR-L2 has the amino acid sequence of SEQ ID NO: 28, and CDR-L3 has the amino acid sequence of SEQ ID NO: 31.

In some embodiments, the VH has the amino acid sequence of any one of SEQ ID NOs: 33, 42, 48, 51, 53, 57, 62, or 68, or an amino acid sequence having at least 90% sequence identity to any one of SEQ ID NOs: 33, 42, 48, 51, 53, 57, 62, or 68 and having the CDR-H1, CDR-H2, CDR-H3 amino acid sequences set forth herein (e.g., above in i-xvii). In some embodiments, the VH comprises the amino acid sequence of any one of SEQ ID NOs: 33, 42, 48, 51, 53, 57, 62, or 68. In some embodiments, the VH comprises the amino acid sequence of SEQ ID NO: 68.

In some embodiments, the VL comprises the amino acid sequence of any one of SEQ ID NOs: 34, 52, 63, 65, 67, 71, 75, 79, 80, 83, 86, or 90, or an amino acid sequence having at least 90% sequence identity to any one of SEQ ID NOs: 34, 52, 63, 65, 67, 71, 75, 79, 80, 83, 86, or 90 and having the CDR-L1, CDR-L2, CDR-L3 amino acid sequences set forth herein (e.g., above in i-xvii). In some embodiments, the VL comprises the amino acid sequence of any one of SEQ ID NOs: 34, 52, 63, 65, 67, 71, 75, 79, 80, 83, 86, or 90. In some embodiments, the VL comprises the amino acid sequence of SEQ ID NO:65.

In some embodiments, the VL and VH are selected from one of the following:

a. the VH comprises SEQ ID NO: 68; and the VL comprises any one of SEQ ID NOs: 65, 71, 75, 79, 80, 83, 86, or 90;
b. the VH comprises any one of SEQ ID NOs: 33, 42, or 48; and the VL comprises SEQ ID NO: 34;
c. the VH comprises any one of SEQ ID NO: 51, 53, or 57; and the VL comprises SEQ ID NO: 52;
d. the VH comprises SEQ ID NO: 62; and the VL comprises SEQ ID NO: 63, or SEQ ID NO: 65; or
e. the VH comprises SEQ ID NO: 57; and the VL comprises SEQ ID NO: 67

In some embodiments, the VH comprises SEQ ID NO:68; and the VL comprises SEQ ID NO: 65. In some embodiments, the VL is part of a light chain, wherein the light chain comprises the amino acid sequence of any one of SEQ ID NOs: 99-110, or an amino acid sequence having at least 90% sequence identity to any one of SEQ ID NOs: 99-110. In some embodiments, the light chain comprises the amino acid sequence of any one of SEQ ID NOs: 99-110. In some embodiments, the light chain comprises the amino acid sequence of SEQ ID NO: 102.

In some embodiments, disclosed herein are antibodies or antibody fragments thereof that comprises an Fc region that binds to Fc gamma receptors (FcγRs) and induces antibody dependent cell-mediated cytotoxicity (ADCC) to deplete cells expressing KLRB1, or that binds to C1q and induces complement dependent cytotoxicity (CDC). In some embodiments, the Fc region is afucosylated. In some embodiments, the antibody is an immunoglobulin G (IgG) subtype IgG1 antibody, an IgG2 antibody, or an IgG4 antibody.

In some embodiments, the VH is part of a heavy chain, wherein the heavy chain comprises the amino acid sequence of any one of SEQ ID NOs: 91-98, or an amino acid sequence having at least 90% sequence identity to any one of SEQ ID NOs: 91-98. In some embodiments, the heavy chain comprises the amino acid sequence of any one of SEQ ID NOs: 91-98. In some embodiments, the heavy chain comprises the amino acid sequence of SEQ ID NO: 98.

In some embodiments, the heavy chain (HC) and the light chain (LC) selected from the one of the following:

a. the HC comprises SEQ ID NO: 98; and the LC comprises any one of SEQ ID NOs: 102, or 104-110;
b. the HC comprises any one of SEQ ID NOs: 91-93; and the LC comprises SEQ ID NO: 99;
c. the HC comprises any one of SEQ ID NOs: 94-96; and the LC comprises SEQ ID NO: 100;
d. the HC comprises SEQ ID NO: 97; and the LC comprises SEQ ID NO: 101, or SEQ ID NO: 102; or
e. the HC comprises SEQ ID NO: 96; and the LC comprises SEQ ID NO: 103.

In some embodiments, the HC comprises SEQ ID NO:98 and the LC comprises SEQ ID NO: 102.

In some embodiments, the antibodies or antibody fragments thereof are conjugated to a cytotoxic agent.

Also disclosed herein are sets of polynucleotides comprising:

a. a first nucleic acid sequence encoding a VH or a heavy chain of an antibody or antigen binding portion thereof as disclosed herein (e.g., any of the above embodiments); and
b. a second nucleic acid sequence encoding a VL or a light chain of an antibody or antigen binding portion thereof as described herein (e.g., any of the above embodiments).

In some embodiments, each of the first and second nucleic acid sequences is operably linked to a promoter. Also disclosed herein are vectors comprising the set of polynucleotides on the same vector. Also disclosed herein are sets of vectors comprising:

a. a first vector comprising the first nucleic acid sequence encoding a VH or a heavy chain of an antibody or antigen binding portion thereof as disclosed herein (e.g., any of the above embodiments); and
b. a second vector comprising the second nucleic acid sequence encoding a VL or a light chain of an antibody or antigen binding portion thereof as described herein (e.g., any of the above embodiments).

Also described herein are host cells comprising a set of polynucleotides described herein, or a vector described herein, or a set of vectors described herein, and optionally expressing an antibody or antigen binding portion thereof described herein.

Also described herein are methods of making any of the antibodies or antigen binding portions thereof described herein, comprising:

a. culturing a host cell described herein under conditions sufficient to express the antibody or antigen binding portion thereof; and
b. isolating the antibody or antigen binding portion thereof.

In some embodiments, the methods further comprise formulating the antibody as a pharmaceutical composition. In some embodiments, the VH comprises or consists of an VH amino acid sequence set forth in Table 10, 14, or 4. In some embodiments, the VL comprises or consists of an VL amino acid sequence set forth in Table 10, 14, or 4. In some embodiments, the VH comprises or consists of the VH amino acid sequence set forth in Table 14, and the VL comprises or consists of the VH amino acid sequence set forth in Table 14. In some embodiments, the VH comprises or consists of the VH amino acid sequence set forth in Table 10, and the VL comprises or consists of the VH amino acid sequence set forth in Table 10. In some embodiments, the VH comprises or consists of the VH amino acid sequence set forth in Table 4, and the VL comprises or consists of the VH amino acid sequence set forth in Table 4. In some embodiments, the VH comprises or consists of an amino acid sequence having at least 95% sequence identity to the VH amino acid sequence set forth in Table C, and the VL comprises or consists of an amino acid sequence having at least 95% sequence identity to the VL amino acid sequence set forth in Table C. In some embodiments, the VH comprises or consists of an amino acid sequence having at least 95% sequence identity to the VH amino acid sequence set forth in one of Tables 10, 14, or 4, and the VL comprises or consists of an amino acid sequence having at least 95% sequence identity to the amino acid sequence set forth in one of Tables 10, 14, or 4, preferably wherein the VH and VL are from the same Table.

In some embodiments, the antibodies or antigen binding portions thereof comprise a constant region heavy chain and light chain, wherein the constant region heavy chain and/or light chain comprises or consists of an amino acid sequence set forth in one of Table A.

In some embodiments, the antibodies or antigen binding portions thereof comprise a constant region heavy chain and light chain, wherein the constant region heavy chain and/or light chain comprises or consists of an amino acid sequence set forth in one of Table D.

Additionally, provided herein are antibodies or antigen binding portions thereof that specifically bind to human killer cell lectin-like receptor subfamily B, member 1, (KLRB1; e.g., SEQ ID NO: 1), comprising or consisting of a variable region heavy chain consisting of the VH amino acid sequence set forth in Table 14, and a variable region light chain consisting of the VL amino acid sequence set forth in Table 14, and optionally a constant region, optionally comprising a sequence that is at least 95% identical to a sequence set forth in Table A.

Further, provided herein are antibodies or antigen binding portions thereof that specifically bind to human killer cell lectin-like receptor subfamily B, member 1, (KLRB1; e.g., SEQ ID NO: 1), comprising or consisting of a variable region heavy chain consisting of the VH amino acid sequence set forth in Table 10, and a variable region light chain consisting of the VL amino acid sequence set forth in Table 10, and optionally a constant region, optionally comprising a sequence that is at least 95% identical to a sequence set forth in Table A.

Further, provided herein are antibodies or antigen binding portions thereof that specifically bind to human killer cell lectin-like receptor subfamily B, member 1, (KLRB1; e.g., SEQ ID NO: 1), comprising or consisting of a variable region heavy chain consisting of the VH amino acid sequence set forth in Table 4, and a variable region light chain consisting of the VL amino acid sequence set forth in Table 4, and optionally a constant region, optionally comprising a sequence that is at least 95% identical to a sequence set forth in Table A.

In some embodiments, the constant region comprises or consists of a sequence as set forth in Table A.

In some embodiments, the antibodies comprise or consist of a heavy chain variable and/or light chain variable sequence that is at least 95% identical to a sequence set forth in Table B.

In some embodiments, the antibodies comprise or consist of a complete heavy chain and/or light chain sequence that is at least 95% identical to a sequence set forth in Table C.

Also provided herein are antibodies or antigen binding portions thereof that specifically bind to human KLRB1, comprising CDRs from different tables herein, or heavy/light chain pairs from different tables herein. In some embodiments, the antibodies or antigen binding portions thereof comprise a heavy chain constant region hinge region and Fc domain.

In some embodiments, the antibody or antigen binding portion thereof is an antibody that comprises a heavy chain constant region comprising an amino acid sequence having at least 80%, 90%, 95%, or 97% sequence identity to a heavy chain constant region amino acid sequence set forth in Table A.

In some embodiments, the antibody or antigen binding portion thereof is a monoclonal antibody.

In some embodiments, the antibody or antigen binding portion thereof is a chimeric, humanized, or human antibody, and/or comprises one or more mutations (e.g., in a CDR) that remove Asn (N)-glycosylation sites or remove Cys, Asp, Met, Trp or Lys.

In some embodiments, the antibody or antigen binding portion thereof is an immunoglobulin G (IgG) subtype IgG1 antibody, an IgG2 antibody, or an IgG4 antibody.

In some embodiments, the antibody or antigen binding portion thereof is an antibody that comprises an Fc region, preferably human IgG1, that binds to Fc gamma receptors (FcγRs) and induces antibody dependent cell-mediated cytotoxicity (ADCC) to deplete cells expressing KLRB1, or that binds to C1q and induce complement dependent cytotoxicity (CDC).

In some embodiments, the antibody or antigen binding portion thereof is conjugated to a cytotoxic agent.

In some embodiments, the antibody or antigen binding portion thereof comprises an Fc region that is afucosylated.

As CD161 is an inhibitory receptor when bound to ligand CLEC2D (LLT1), modulation of this interaction can therefore affect immune cell activity. Thus, inhibiting the CD161/CLEC2D interaction could enhance T cell function, a typical mechanism of action of the class of immuno-oncology therapeutics, while augmenting the CD161/CLEC2D interaction could act as immunosuppression for autoimmune and allergic diseases. In some embodiments, antibodies disclosed herein block CD161/CLEC2D interaction thereby activating T or NK cells to attack tumor cells in a variety of cancers, typical of an immuno-oncology checkpoint inhibition mechanism.

In some embodiments, antibodies disclosed herein augment (e.g., increase) CD161/CLEC2D interaction thereby suppressing T or NK cells providing immunosuppression applicable for treating a variety of autoimmune, allergic, and inflammatory diseases.

In some embodiments, a KLRB1-binding antibody disclosed herein achieves better immune cell activation, for example demonstrates improvements in any one or more of the activities of activating T cells to produce cytokines, activating T cells to kill tumor cells, activating NK cells (e.g., increased expression of CD107a), activating NK cells to produce cytokines or cytotoxic molecules such as granzymes, and activating NK cells to kill tumor cells when compared to the immune cell activation of one or more of prior antibodies (e.g., B199.2, HP-3G10, OTI1D8, 14F1F11, 702228, B-D51, 2F3, EP7169, DX1, DX12, 191B8, Ab9, KW1.2.1, KW7.3.7, or JNH25G2G22).

In some embodiments, an antibody disclosed herein that has an N-terminal glutamine or glutamate may be post-translationally modified at such N-terminus to form a pyroglutamate (or pyrrolidone carboxylic acid).

Also provided herein are polynucleotides comprising a nucleic acid sequence encoding an antibody or antigen binding portion thereof as described herein. In some embodiments, the nucleic acid sequence is operably linked to a promoter.

Additionally provided are vectors comprising the polynucleotides described herein, as well as host cells comprising the polynucleotides or the vectors, and optionally expressing an antibody or antigen binding portion thereof as described herein. Also provided herein are methods for making the antibodies or antigen binding portions thereof as described herein. The methods can include culturing the host cells under conditions sufficient to express the antibody or antigen binding portion thereof and isolating the antibody or antigen binding portion thereof. In some embodiments, the methods include formulating the antibody as a pharmaceutical composition.

Further, provided herein are pharmaceutical compositions that comprise an antibody or antigen binding portion thereof of as described herein (e.g., comprises or consists of the antibody or antigen binding portion thereof as an active agent), and a pharmaceutically acceptable carrier or diluent.

In some embodiments, the antibody or antigen binding portion thereof is not B199.2 (Invitrogen), HP-3G10 (Invitrogen), OTI1D8 (OriGene), 14F1F11 (OriGene), 702228 (R&D Systems), B-D51 (Cell Sciences), 2F3 (Novus Biologics), EP7169 (Abcam), DX1 (Thermo Fisher), DX12 (BD Biosciences), 191B8 (Miltenyi Biotec), Ab9 (PCT publication WO2023028501A1), KW1.2.1 (United States patent publication US20210122826A1), KW7.3.7 (United States patent publication US20210122826A1), or JNH25G2G22 (Creative Diagnostics).

Also provided herein are methods for treating one or more of an autoimmune disease, an allergic disease, a transplant rejection, and a hematologic malignancy in a subject in need thereof, the method comprising administering to the subject an effective amount of an antibody or antigen binding portion thereof that binds KLRB1, preferably an antibody or antigen binding portion thereof, polynucleotide, vector, pharmaceutical composition, or host cell that expresses the antibody or antigen binding portion thereof, as described herein. Also provided are an antibody that binds KLRB1, preferably an antibody or antigen binding portion thereof, polynucleotide, vector, pharmaceutical composition, or host cell that expresses the antibody or antigen binding portion thereof, as described herein, for use in a method of treating one or more of an autoimmune disease, an allergic disease, a transplant rejection, and a hematologic malignancy in a subject in need thereof. In some embodiments, the autoimmune disease is rheumatoid arthritis, Sjogren's syndrome, inclusion body myositis (IBM), discoid lupus, psoriasis, idiopathic pulmonary fibrosis, diabetes, alopecia universalis, primary biliary cholangitis, multiple sclerosis, lymphocytic colitis, palmoplantar pustulosis, or hidradenitis suppurativa. In some embodiments, the allergic disease is asthma, allergic eosinophilic asthma, allergy, atopic dermatitis, nasal polyposis, eosinophilic gastrointestinal disorder, or hypereosinophilic syndrome. In some embodiments, the transplant rejection can be a rejection of a kidney, lung, heart, liver, limb, skin, or multi-organ transplant. In some embodiments, the hematological malignancy is a leukemia, e.g., T cell leukemia, NK cell leukemia, T cell prolymphocytic leukemia (T-PLL), or large granular lymphocytic leukemia (LGLL). In some embodiments, the hematological malignancy is a lymphoma, e.g., hepatosplenic T cell lymphoma, NK/T cell lymphoma, mycosis fungoides, Sezary syndrome, peripheral T cell lymphoma, angioimmunoblastic T cell lymphoma (AITL), or peripheral T cell lymphoma not otherwise specified (PTCL-NOS).

In some embodiments, the antibody or antigen binding portion thereof, the polynucleotide, the vector, the antibody binds to and depletes Th17, Th17.1, ex-Th17, Tc17, mucosal-associated invariant T cells (MAIT), invariant NK-T cells (INKT), innate lymphoid cells types 2 and 3 (ILC2, and ILC3), pathogenic effector Th2 (peTh2) cells, and/or NK cells expressing KLRB1.

In some embodiments of each of the aforementioned aspects and embodiments, as well as other aspects and embodiments described herein, the subject is human.

Without wishing to be being bound by theory, Applicant believes that the antibodies disclosed herein will demonstrate superiority to previously described antibodies, e.g., commercially available antibodies, in one or more of the following activities:

- increased binding potency (lower binding $EC_{50}$ to cell expressed KLRB1 or to soluble KLRB1 extracellular domain);
- increased ADCC mediated depletion potency (lower EC50 for depletion of CHO-KLRB1+ cells or lower $EC_{50}$ for reporter cell line ADCC assay);
- increased binding affinity kinetics (lower KD or lower $K_{off}$);
- increased blocking potency (lower $IC_{50}$ for inhibition of CLEC2D binding to cell expressed KLRB1); and/or
- increased augmentation potency (lower $EC_{50}$ for augmenting (increasing) CLEC2D binding to cell expressed KLRB1).

In some embodiments, the antibodies disclosed herein have a higher production yield, lower immunogenicity (due to the presence of humanized variable regions and/or human Fc sequences), and/or improved biophysical parameters (e.g., higher melting temperature, greater freeze-thaw stability, lower isomerization, reduced or absence of deamidation, and/or less susceptibility to oxidation) when compared to previously described antibodies, e.g., commercially available antibodies. Examples of previously described antibodies include B199.2, HP-3G10, OTI1D8, 14F1F11, 702228, B-D51, 2F3, EP7169, DX1, DX12, 191B8, Ab9, KW1.2.1, KW7.3.7, or JNH25G2G22.

Where aspects or embodiments of the disclosure are described in terms of a Markush group or other grouping of alternatives, the present disclosure encompasses not only the entire group listed as a whole, but also each member of the group individually and all possible subgroups of the main group, and also the main group absent one or more of the group members. The present disclosure also envisages the explicit exclusion of one or more of any of the group members in the claimed disclosure.

These and other advantages of the present technology will be apparent when reference is made to the accompanying drawings and the following description.

BRIEF DESCRIPTION OF THE DRAWINGS

FIG. 22A shows increased expression of KLRB1 in tumor cells from 4/4 patients with hepatosplenic T cell lymphoma (HSTCL), 7/19 patients with NK/T cell lymphoma (NKTCL), and 2/2 patients with mycosis fungoides. FIG. 22B shows expression of KLRB1 in various forms of peripheral T cell lymphoma (PTCL) including angioimmunoblastic T cell lymphoma (AITL), anaplastic large cell lymphoma (ALCL; both ALK-positive and ALK-negative), NK/T cell lymphoma (NKTCL), peripheral T cell lymphoma not otherwise specified (PTCL-NOS), and T cell prolymphocytic leukemia (T-PLL). FIG. 22C shows KLRB1 increased expression in spleen tumor cells compared to healthy spleen and from tumor cells compared to healthy CD4 T cells in 4 patients each with HSTCL. FIG. 22D shows increased expression of KLRB1 an HSTCL cell line (DERL-2) and from aggressive NK cell leukemia (ANKL) cell lines (KHYG-1 and NKL).

DETAILED DESCRIPTION

Figure 1:
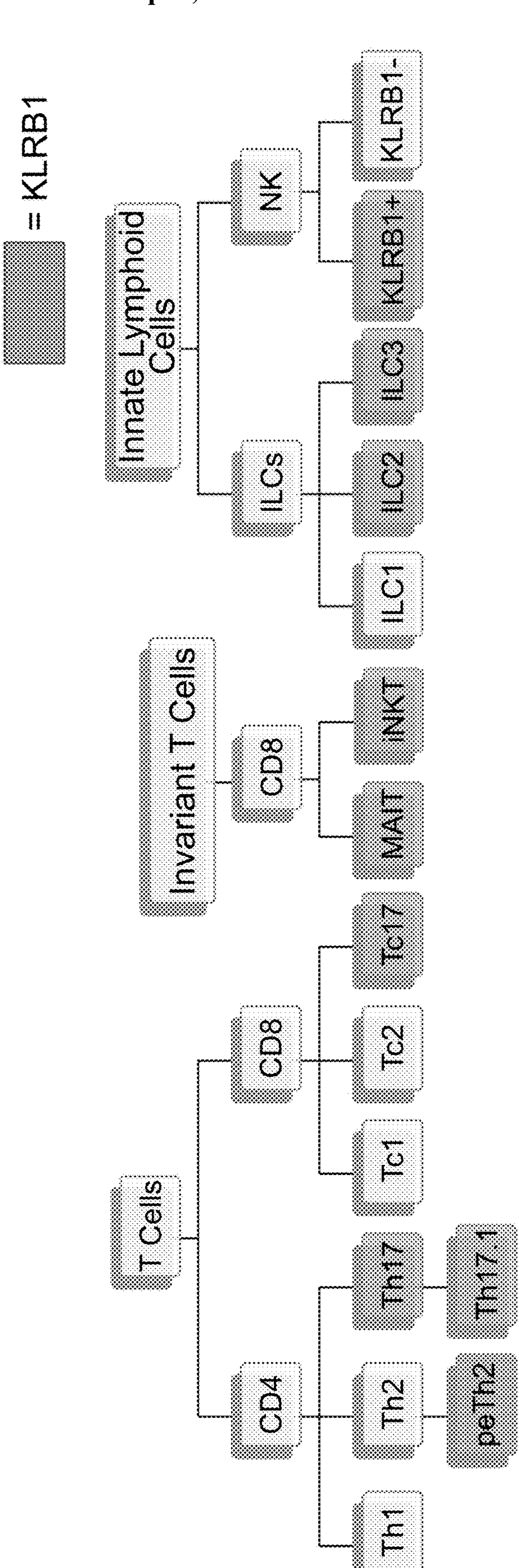
FIG. 1 shows KLRB1 expression marks Th17, Th17.1, ex-Th17, Tc17, iNKTs, IL2, ILC3, peTh2, and a subset of NK cells.

KLRB1 expression marks a unique set of immune system cells implicated in a variety of autoimmune diseases. These include Th17, Th17.1, ex-Th17, Tc17, MAIT, INKT, ILC2, ILC3, peTh2, and/or NK cells.

KLRB1 is also expressed by neoplastic cells present in a number of T and NK cell malignancies. These include various peripheral T cell and NK cell lymphomas and leukemias.

The KLRB1-binding antibodies described herein can be used to preferentially target Th17, Th17.1, ex-Th17, Tc17, MAIT, INKT, ILC2, ILC3, peTh2, NK cells, and/or neoplastic T or NK cells for depletion. The population of KLRB1 expressing immune cells more abundantly expresses IL-17 than the population of total CD4 or CD8 T cells, and are more specific to Th17 and Tc17 T cells than CD4 or CD8, respectively. Thus described herein are methods for treating a subject by administering to a subject in need thereof an effective amount of a killer cell lectin-like receptor B1 (KLRB1) binding agent with cell depleting activity, thereby depleting Th17, Th17.1, ex-Th17, Tc17, MAIT, INKT, ILC2, ILC3, peTh2, NK cells, and/or neoplastic T or NK cells in vivo. These methods can be used to treat an autoimmune disease, allergic disease, transplant rejection, or hematologic malignancies, e.g., as described herein.

Additionally, because modulating KLRB1 has inhibitory or stimulatory effects on T and NK cells, thus described herein are methods for treating a subject by administering to a subject in need thereof an effective amount of a killer cell lectin-like receptor B1 (KLRB1) binding agent with KLRB1 receptor blocking activity (in which blocking of binding of CLEC2D (LLT1) to KLRB1 is achieved), thereby activating or inhibiting Th17, Th17.1, ex-Th17, Tc17, MAIT, INKT, ILC2, ILC3, and/or peTh2 in vivo. These methods can be used to activate T and/or NK cells to enhance their activity against tumor cells to be used to treat cancer.

In some embodiments, the antibodies have antibody dependent cellular cytotoxicity (ADCC) effector activity or complement dependent cytotoxicity (CDC) effector activity. Administering to a subject in need thereof an effective amount of an anti-KLRB1 antibody that has ADCC or CDC effector function, or that is linked to a cytotoxic agent, can be used to eliminate or reduce the number of Th17, Th17.1, ex-Th17, Tc17, MAIT, INKT, ILC2, ILC3, peTh2, NK cells, and/or neoplastic T or NK cells. In some embodiments, the disclosure provides a killer cell lectin-like receptor B1 (KLRB1) binding agent as described herein that has ADCC or CDC activity or is conjugated to a cytotoxic agent. In various aspects, the disclosure provides an mRNA or cDNA encoding the binding agent. In various aspects, the disclosure provides a pharmaceutical composition comprising an effective amount of the binding agent.

Various features of the disclosure, including KLRB1 and its ligands, anti-KLRB1 antibodies or antigen-binding portions thereof, pharmaceutical compositions, treatment and administration, and illustrative examples are discussed, in turn, below. The following sections contain definitions of terms used in this disclosure. Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

Killer Cell Lectin-Like Receptor B1 (KLRB1)

Killer cell lectin-like receptor B1 (KLRB1), also known as CD161, is a type II transmembrane protein. It is a receptor modulating the activity of T and NK cells and can act as either a stimulatory (Fergusson et al. 2014) or inhibitory (Aldemir et al. 2005, Mathewson et al. 2021) receptor for different types of T and NK cells. It is present on the surface of a variety of immune cells. The ligand for KLRB1 is LLT1 (also called CLEC2D) (Aldemir et al. 2005).

KLRB1 expression among T cells is limited to those with an ability to respond to IL-12 and IL-18 (Fergusson et al. 2014). Among CD4+T helper cells, KLRB1 expression uniquely marks Th17, Th17.1, and ex-Th17 cells (cells that no longer produce IL-17 but produce IFN-γ). KLRB1 expression distinguishes Th1 IFNG producing cells (which are KLRB1-negative) from ex-Th17 IFNG producing cells (which are KLRB1+) (Basdeo et al. 2017). Among CD8+T cytotoxic cells, KLRB1 expression uniquely marks Tc17 cells. Thus, KLRB1 marks T cells with capacity for IL-17 production or, in the case of ex-Th17 cells, interferon-gamma (IFNG) production. This cytokine production is undesired in the case of autoimmune disease.

Described herein are antibodies and antigen-binding fragments thereof that bind to KLRB1, preferably human KLRB1. An exemplary sequence of human KLRB1 is provided as SEQ ID NO: 1:

```
MDQQAIYAELNLPTDSGPESSSPSSLPRDVCQGSPWHQFALKLSC
AGIILLVLVVTGLSVSVTSLIQKSSIEKCSVDIQQSRNKTTERPG
LLNCPIYWQQLREKCLLFSHTVNPWNNSLADCSTKESSLLLIRDK
DELIHTQNLIRDKAILFWIGLNFSLSEKNWKWINGSFLNSNDLEI
RGDAKENSCISISQTSVYSEYCSTEIR WICQKELTPVRNKVYPD
S.
```

In some embodiments, the KLRB1 is cynomolgus KLRB1 (e.g., AOA2K5WYI1 from UniParc UPI0003ABB264); an exemplary sequence is provided as SEQ ID NO: 2:

```
MDQQMMYAELTLPKDSGPESSSPSSLPRDVCQGSPWHQFALKLSC
AGIILLVLVVTGLSLSVASLLQKPSIGKCSVDIQQNRTKTTERPD
LLNCPIYWQQVQEKCLLFSHTVNPWNNSLADCSTKESSLLLIQDK
DELTRTQNLIHDKAISFWIGLNFSLSEKNWKWINGSFLSSNDLKI
TGDAKENSCVYISQTSVYSEYCSTEMKWICQKELTLVRNKVSPDS
WL.
```

In some embodiments, the KLRB1 is cynomolgus KLRB1 (e.g., UniProt A0A7N9D796); an exemplary sequence is provided as SEQ ID NO: 3:

```
MDQQMMYAELTLPKDSGPESSSPSSLPRDVCQGSPWHQFALKLSC
AGIILLVLVVTGLSLSVASLLQKPSIGKCSVDIQQNRTKTTERPD
LLNCPIYWKQVQEKCLLFSHTVNPWNNSLADCSTKESSLLLIQDK
DELTRTQNLIHDKAISFWIGLNFSLSEKNWKWINGSFLSSNDLKI
TGDAKENSCVYISQTSVYSEYCSTEMKWICQKELTLVRNKVSPDS
WL.
```

KLRB1-Binding Antibodies

Described herein are antibodies and antigen binding fragments thereof that bind to KLRB1. The term "antibody" refers to an immunoglobulin molecule or immunologically active portion thereof, i.e., an antigen-binding portion.

The term "monoclonal antibody" as used herein refers to an antibody obtained from a population of substantially homogeneous antibodies, e.g., the individual antibodies comprising the population are identical except for possible naturally-occurring mutations that may be present in minor amounts. An antibody can be monoclonal. An antibody can be a human or humanized antibody. The term "monoclonal antibody" encompasses intact and full-length monoclonal antibodies as well as antibody fragments (e.g., Fab, Fab', $F(ab')_2$, Fv), single chain antibodies (e.g., scFv), fusion proteins comprising an antibody fragment, and any other modified immunoglobulin molecule comprising at least one antigen-binding site. Furthermore, "monoclonal antibody" refers to such antibodies made by any number of techniques, including but not limited to, hybridoma production, phage library display, recombinant expression, and transgenic animals.

The term "chimeric antibody" refers to an antibody in which a portion of the heavy and/or light chain is derived from a first source or species, while the remainder of the heavy and/or light chain is derived from a different source or species.

The term "humanized antibody" as used herein refers to an antibody that comprises a human heavy chain variable region and a light chain variable region wherein the native CDR residues are replaced by residues from corresponding CDRs from a nonhuman antibody (e.g., mouse, rat, rabbit, or nonhuman primate), wherein the nonhuman antibody has the desired specificity, affinity, and/or activity. In some embodiments, one or more framework region residues of the human heavy chain or light chain variable regions are replaced by corresponding residues from nonhuman antibody. Furthermore, humanized antibodies can comprise residues that are not found in the human antibody or in the nonhuman antibody. In some embodiments, these modifications are made to further refine and/or optimize antibody characteristics. In some embodiments, the humanized antibody comprises at least a portion of an immunoglobulin constant region (e.g., CH1, CH2, CH3, Fc), typically that of a human immunoglobulin. Exemplary constant regions include those shown in Table A.

TABLE A

Sequences of Exemplary Constant Regions

| Antibody Fragment | Sequence |
|---|---|
| Human IgG1 Constant (IGHG1)/ G1m(z) allele (K214/D356/L358) | ASTKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCPAPELLGGPSVFLFPPK PKDTLMISRTPEVTCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSRDELTKNQVSLTCLVKG FYPSDIAVEWESNGQPENNYKTTPPVLDSDGSFFLYSKLTVDKSRWQQGNVFSCSVMHEALHN HYTQKSLSLSPGK (SEQ ID NO: 4) |
| Human IgG1 Constant (IGHG1) LALAGA/G1m(z) allele with L234A/L235A/G237 A | ASTKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCPAPEAAGAPSVFLFPPK PKDTLMISRTPEVTCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSRDELTKNQVSLTCLVKG FYPSDIAVEWESNGQPENNYKTTPPVLDSDGSFFLYSKLTVDKSRWQQGNVFSCSVMHEALHN HYTQKSLSLSPGK (SEQ ID NO: 5) |
| Human IgG1 Fc region/WT | LGGPSVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDELTK NQVSLTCLVKGFYPSDIAVEWESNGQPENNYKTTPPVLDSDGSFFLYSKLTVDKSRW QQGNVFSCSVMHEALHNHYTQKSLSLSPGK (SEQ ID NO: 6) |
| Human IgK Constant (IGKC)/Uniprot P01834 | RTVAAPSVFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC (SEQ ID NO: 7) |
| Mouse IgG1 Constant (IGHG1 Mouse)/Uniprot P01868 | AKTTPPSVYPLAPGSAAQTNSMVTLGCLVKGYFPEPVTVTWNSGSLSSGVHTFPAVLQSDLYT LSSSVTVPSSPRPSETVTCNVAHPASSTKVDKKIVPRDCGCKPCICTVPEVSSVFIFPPKPKD VLTITLTPKVTCVVVDISKDDPEVQFSWFVDDVEVHTAQTQPREEQFNSTFRSVSELPIMHQD WLNGKEFKCRVNSAAFPAPIEKTISKTKGRPKAPQVYTIPPPKEQMAKDKVSLTCMITDFFPE DITVEWQWNGQPAENYKNTQPIMNTNGSYFVYSKLNVQKSNWEAGNTFTCSVLHEGLHNHHTE KSLSHSPGK (SEQ ID NO: 8) |
| Mouse IgG2a Constant (IGHG Mouse)/Uniprot P01863 | AKTTAPSVYPLAPVCGDTTGSSVTLGCLVKGYFPEPVTLTWNSGSLSSGVHTFPAVLQSDLYTL SSSVTVTSSTWPSQSITCNVAHPASSTKVDKKIEPRGPTIKPCPPCKCPAPNLLGGPSVFIFPP KIKDVLMISLSPIVTCVVVDVSEDDPDVQISWFVNNVEVHTAQTQTHREDYNSTLRVVSALPIQ HQDWMSGKEFKCKVNNKDLPAPIERTISKPKGSVRAPQVYVLPPPEEEMTKKQVTLTCMVTDFM PEDIYVEWTNNGKTELNYKNTEPVLDSDGSYFMYSKLRVEKKNWVERNSYSCSVVHEGLHNHH TTKSFSRTPGK (SEQ ID NO: 9) |
| Mouse IgG2b Constant (IGG2B Mouse)/Uniprot P01867 | KTTPPSVYPLAPGCGDTTGSSVTLGCLVKGYFPESVTVTWNSGSLSSSVHTFPALLQSGLYTMSS SVTVPSSTWPSQTVTCSVAHPASSTTVDKKLEPSGPISTINPCPPCKECHKCPAPNLEGGPSVFI FPPNIKDVLMISLTPKVTCVVVDVSEDDPDVQISWFVNNVEVHTAQTQTHREDYNSTIRVVSTLP IQHQDWMSGKEFKCKVNNKDLPSPIERTISKIKGLVRAPQVYILPPPAEQLSRKDVSLTCLVVGF NPGDISVEWTSNGHTEENYKDTAPVLDSDGSYFIYSKLNMKTSKWEKTDSFSCNVRHEGLKNYYL KKTISRSPGLDLDDICAEAKDGELDGLWTTITIFISLFLLSVCYSASVTLFKVKWIFSSVVELK QKISPDYRNMIGQGA (SEQ ID NO: 10) |
| Mouse IgK Constant (IGKC Mouse)/ Uniprot P01837 | RADAAPTVSIFPPSSEQLTSGGASVVCFLNNFYPKDINVKWKIDGSERQNGVLNSWTDQDSKDS TYSMSSTLTLTKDEYERHNSYTCEATHKTSTSPIVKSFNRNEC (SEQ ID NO: 11) |

The term "human antibody" as used herein refers to an antibody that possesses an amino acid sequence that corresponds to an antibody produced by a human and/or an antibody that has been made using any of the techniques that are known to those of skill in the art for making human antibodies. These techniques include, but not limited to, phage display libraries, yeast display libraries, transgenic animals, recombinant protein production, and B-cell hybridoma technology.

"Antibody fragments" can include a portion of an intact antibody, preferably the antigen binding or variable region of the intact antibody. Examples of antibody fragments include Fab, Fab', F(ab')2, and Fv fragments; diabodies; linear antibodies; single-chain antibody molecules; and multispecific antibodies formed from antibody fragments.

The terms "epitope" and "antigenic determinant" are used interchangeably herein and refer to that portion of an antigen or target capable of being recognized and bound by a particular antibody. When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation. Epitopes can be predicted using any one of a large number of software bioinformatic tools available on the internet. X-ray crystallography may be used to characterize an epitope on a target protein by analyzing the amino acid residue interactions of an antigen/antibody complex.

"Fv" includes the minimum antibody fragment which contains a complete antigen-recognition and binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgB1, IgG2, IgG3, IgG4, IgA, and IgA2. “Single-chain Fv” or “sFv” antibody fragments comprise the VH and VL domains of antibody, wherein these domains are present in a single polypeptide chain. Preferably, the Fv polypeptide further comprises a polypeptide linker between the VH and VL domains which enables the sFv to form the desired structure for antigen binding.

In various embodiments, the antibody or antigen binding fragment thereof comprises a human or humanized antibody. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. Methods for humanizing non-human antibodies are well known in the art.

The KLRB1 antibodies described herein can be affinity matured, for example using selection and/or mutagenesis methods known in the art. In general, an “affinity matured” antibody is one with one or more alterations in one or more hyper variable regions thereof which result in an improvement in the affinity of the antibody for antigen, compared to a parent antibody which does not possess those alteration(s). In one embodiment, an affinity matured antibody has nanomolar or even picomolar affinities for the target antigen. Preferred affinity matured antibodies have an affinity that is five times, more preferably 10 times, even more preferably 20 or 30 times greater than the starting antibody (generally murine, humanized or human) from which the matured antibody is prepared.

An antibody that “binds to,” “specifically binds to,” or is “specific for” a particular polypeptide or an epitope on a particular polypeptide is one that binds to that particular polypeptide or epitope on a particular polypeptide without substantially binding to any other polypeptide or polypeptide epitope. The term “specifically binds” as used herein refers to a KLRB1 agent (e.g., an anti-KLRB1 antibody) that interacts more frequently, more rapidly, with greater duration, with greater affinity, or with some combination of the above to a particular antigen, epitope, protein, or target molecule than with alternative substances. A binding agent (e.g. antibody) that specifically binds an antigen can be identified, for example, by immunoassays, ELISAs, Surface Plasmon Resonance (SPR) assays (e.g., Biacore), or other techniques known to those of skill in the art. As such, described herein are functional equivalents to the specific anti-KLRB1 antibodies described. In some cases, the KLRB1 antibody may be cross reactive with various similar KLRB1 proteins (e.g., with highest affinity for one, such as human KLRB1, and lower affinity for others, such as mouse KLRB1). A binding agent that specifically binds an antigen binds the target antigen with a higher affinity than its affinity for a different antigen. The different antigen can be a related antigen. In some embodiments, a binding agent that specifically binds an antigen binds the target antigen with an affinity that is at least 20 times greater than its affinity for a different antigen, e.g., at least 30 times greater, at least 40 times greater, at least 50 times greater, at least 60 times greater, at least 70 times greater, at least 80 times greater, at least 90 times greater, or at least 100 times greater, than its affinity for a different antigen. In some embodiments, a binding agent that specifically binds a particular antigen binds a different antigen at such a low affinity that binding cannot be detected using an assay described herein or otherwise known in the art. In some embodiments, affinity is measured using SPR technology, e.g., in a Biacore system or other system known to those of skill in the art.

The terms “identical” or “percent identity” in the context of two or more polypeptides (e.g., two anti-KLRB1 antibodies), refer to two or more sequences or subsequences that are the same or have a specified percentage of amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm. Such homology is well-represented in the art via local alignment tools and/or algorithms, and may include pairwise alignment, multiple sequence alignment methods, structural alignment methods, and/or phylogenetic analysis methods. Where sequences differ in conservative substitutions, the percent sequence identity may be, but not necessarily is, adjusted upwards to correct for the conservative nature of the substitution. Means for making this adjustment are well known to those of skill in the art. Typically, but not necessarily, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1.

In some embodiments, two polypeptides (e.g., antibodies or antibody domains (e.g., VL, CL, VH, CH1, CH2, CH3 domains) thereof) of the disclosure are substantially identical, meaning they have at least 70%, at least 75%, at least 80%, at least 85%, at least 90%, and in some embodiments at least 95%, 96%, 97%, 98%, 99% amino acid residue identity, when compared and aligned for maximum correspondence, as measured using a sequence comparison algorithm or by visual inspection. In some embodiments, percent identity exists over a region of the sequences that is at least about 10, at least about 20, at least about 20-40, at least about 40-60 amino acid residues, at least about 60-80 nucleotides or amino acid residues in length or any integral value there between. In some embodiments, percent identity exists over a longer region than 60-80 amino acid residues, such as at least about 80-100 amino acid residues, and in some embodiments the sequences are substantially identical over the full length of the sequences being compared, for example, an amino acid sequence.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can determined using the Needleman and Wunsch ((1970) *J. Mol. Biol.* 48:444-453) algorithm which has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5.

The terms "conservative sequence modifications" or "conservative substitutions" as used herein may refer to amino acid modifications to a target epitope or antibodies and antigen-binding portions thereof of the disclosure that does not significantly affect or alter the binding characteristics of the anti-KLRB1 antibodies. "Conservative substitution" as used herein refers to a substitution in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is considered to be a conservative substitution. Methods of identifying amino acid conservative substitutions that do not eliminate binding are well-known in the art.

In various embodiments, the antibody is a blocking or antagonist binding agent. "Blocking" or "antagonist" means the agent (e.g., antibody or binding fragment thereof) is one that inhibits or reduces biological activity of the antigen it binds. Certain blocking agents or antagonist agents substantially or completely inhibit the biological activity of the antigen. For example, a KLRB1 binding agent can block KLRB1 signaling (e.g., thereby disrupting KLRB1 signaling and modulating Th17, Th17.1, ex-Th17, Tc17, MAIT, INKT, ILC2, ILC3, peTh2, NK cells, and/or neoplastic T or NK cells cells).

In some embodiments, the KLRB1 binding agent is an antibody that comprises: a. a full length antibody that binds KLRB1 and comprises an Fc domain that can bind Fcgamma receptors with effector function to trigger antibody-dependent cell-mediated cytotoxicity (ADCC); b. an antibody that binds KLRB1 and comprises an Fc domain that can bind complement protein 1q (C1q) with effector function to trigger complement dependent cytotoxicity (CDC); c. an antibody conjugate that binds KLRB1 and comprises a cytotoxic agent, e.g., antibody-drug conjugate (ADC); or d. a multispecific antibody (e.g., a bispecific or trispecific antibody), wherein the antibody binds to KLRB1 and another antigen.

In some embodiments, the KLRB1 antibodies described herein bind to the extracellular domain of human KLRB1; in some embodiments, the antibody cross-reacts with (binds to both of) the extracellular domains of human and cynomolgus KLRB1. In some embodiments, the antibody binds to an epitope of the extracellular domain of KLRB1, wherein the epitope is at least 90% identical in human and cynomolgus.

In some embodiments, the antibody binds to KLRB1 and is not a mouse antibody.

In some embodiments, the antibody described herein is not B199.2 (Invitrogen), HP-3G10 (Invitrogen), OTI1D8 (OriGene), 14F1F11 (OriGene), 702228 (R&D Systems), B-D51 (Cell Sciences), 2F3 (Novus Biologics), EP7169 (Abcam), 191B8 (Miltenyi), DX12 (BD Biosciences), or JNH25G2G22 (Creative Diagnostics).

In some embodiments, a KLRB1-binding agent is an antibody, e.g., a full length antibody comprising an Fc domain including at least one heavy chain. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgA, IgD, IgE, IgG, or IgM antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody.

In some embodiments, the antibody is an antibody fragment comprising an antigen-binding site. In some embodiments, the antibody is a scFv. In some embodiments, the antibody is a disulfide-linked scFv. In some embodiments, the antibody is a bispecific antibody or a multispecific antibody. In some embodiments, the antibody is a monovalent antibody. In some embodiments, the antibody is a monospecific antibody. In some embodiments, the antibody is a bivalent antibody. In some embodiments, the antibody is isolated. In some embodiments, the antibody is substantially pure. In some embodiments, a KLRB1-binding agent is a polyclonal antibody. Polyclonal antibodies can be prepared by any method known to those of skill in the art. In some embodiments, polyclonal antibodies are produced by immunizing an animal (e.g., a rabbit, rat, mouse, goat, donkey) with an antigen of interest (e.g., a purified peptide fragment, a recombinant protein, or a fusion protein) using multiple subcutaneous or intraperitoneal injections. In some embodiments, the antigen is conjugated to a carrier such as keyhole limpet hemocyanin (KLH), serum albumin, bovine thyroglobulin, or soybean trypsin inhibitor. The antigen (with or without a carrier protein) is diluted in sterile saline and usually combined with an adjuvant (e.g., Complete or Incomplete Freund's Adjuvant) to form a stable emulsion. After a period of time, polyclonal antibodies are recovered from the immunized animal (e.g., from blood or ascites). In some embodiments, the polyclonal antibodies are purified from serum or ascites according to standard methods in the art including, but not limited to, affinity chromatography, ion-exchange chromatography, gel electrophoresis, and/or dialysis.

In some embodiments, a KLRB1-binding agent is a monoclonal antibody. Monoclonal antibodies can be prepared by any method known to those of skill in the art. In some embodiments, monoclonal antibodies are prepared using hybridoma methods known to one of skill in the art. For example, using a hybridoma method, a mouse, rat, rabbit, hamster, or other appropriate host animal, is immunized as described above. In some embodiments, lymphocytes are immunized in vitro. In some embodiments, the immunizing antigen is a human protein or a fragment thereof. In some embodiments, the immunizing antigen is a mouse protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen can be identified by a variety of methods including, but not limited to, immunoprecipitation, immunoblotting, and in vitro binding assays (e.g., flow cytometry, FACS, ELISA, SPR (e.g., Biacore), and radioimmunoassay). Once hybridoma cells that produce antibodies of the desired specificity, affinity, and/or activity are identified, the clones may be subcloned by limiting dilution techniques. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding an antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin proteins.

In some embodiments, recombinant monoclonal antibodies are isolated from phage display libraries expressing variable domains or CDRs of a desired species. Screening of phage libraries can be accomplished by various techniques known in the art.

In some embodiments, a monoclonal antibody is modified by using recombinant DNA technology to generate alternative antibodies. In some embodiments, the constant domains of the light chain and heavy chain of a mouse monoclonal antibody are substituted for constant regions of a human antibody to generate a chimeric antibody. In some embodiments, the constant regions are truncated or removed to generate a desired antibody fragment of a monoclonal antibody. In some embodiments, site-directed or high-density mutagenesis of the variable region(s) is used to optimize specificity and affinity of a monoclonal antibody.

In some embodiments, a KLRB1-binding agent is a humanized antibody. Various methods for generating humanized antibodies are known in the art. In some embodiments, a humanized antibody comprises one or more amino acid residues that have been introduced into it from a source that is non-human. In some embodiments, humanization is performed by substituting one or more non-human CDR sequences for the corresponding CDR sequences of a human antibody. In some embodiments, the humanized antibodies are constructed by substituting all six CDRs of a non-human antibody (e.g., a mouse antibody) for the corresponding CDRs of a human antibody.

The choice of which human heavy chain variable region and/or light chain variable region is used for generating humanized antibodies can be made based on a variety of factors and by a variety of methods known in the art. In some embodiments, the "best-fit" method is used where the sequence of the variable region of a non-human (e.g., rodent) antibody is screened against the entire library of known human variable region sequences. The human sequence that is most similar to that of the non-human (e.g., rodent) sequence is selected as the human variable region framework for the humanized antibody. In some embodiments, a particular variable region framework derived from a consensus sequence of all human antibodies of a particular subgroup of light or heavy chains is selected as the variable region framework. In some embodiments, the variable region framework sequence is derived from the consensus sequences of the most abundant human subclasses. In some embodiments, human germline genes are used as the source of the variable region framework sequences.

Other methods for humanization include, but are not limited to, a method called "superhumanization" which is described as the direct transfer of CDRs to a human germline framework, a method termed Human String Content (HSC) which is based on a metric of "antibody humanness", methods based on generation of large libraries of humanized variants (including phage, ribosomal, and yeast display libraries), and methods based on framework region shuffling.

Humanness can be defined by the OASis score calculated as part of the BioPhi platform. Biophi is an open-source platform featuring novel methods for humanization (*Sapiens*) and humanness evaluation (OASis). *Sapiens* is a deep learning humanization method trained on the Observed Antibody Space (OAS) using language modeling. Based on an in silico humanization benchmark of 177 antibodies, *Sapiens* produced sequences at scale while achieving results comparable to that of human experts. OASis is a granular, interpretable and diverse humanness score based on 9-mer peptide search in the OAS. OASis separated human and non-human sequences with high accuracy, and correlated with clinical immunogenicity (Prihoda D et al. 2022). Humanness evaluation settings can be chosen such as Kabat numbering, Kabat CDR definition, and relaxed OASis prevalence threshold.

In some embodiments, a KLRB1-binding agent is a human antibody. Human antibodies can be prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, from immunoglobulin variable region gene repertoires from unimmunized donors. Techniques for the generation and use of antibody phage libraries are well known in the art. Once antibodies are identified, affinity maturation strategies known in the art, including but not limited to, chain shuffling and site-directed mutagenesis, may be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

In some embodiments, a KLRB1-binding agent is a scFv antibody. ScFvs are molecules that comprise a variable heavy chain region and a variable light chain region linked to form a single polypeptide. ScFvs can be produced using recombinant technologies known in the art. In some embodiments, a scFv comprises a polypeptide linker between the heavy chain variable region and the light chain variable region. In some embodiments, the scFv comprises an orientation of (from N- to C-terminus) (i) heavy chain variable region, (ii) linker, and (iii) light chain variable region. In some embodiments, the scFv comprises an orientation (from N- to C-terminus) of (i) light chain variable region, (ii) linker, and (iii) heavy chain variable region. In some embodiments, the scFv is a disulfide-linked scFv (dsscFv), which is a scFv comprising an engineered disulfide bond between the light chain variable region and heavy chain variable region of the scFv. In some embodiments, the scFv (e.g., dsscFv) is attached (either directly or indirectly) to a half-life extending moiety such as, e.g., an Fc molecule, a CH3 domain of an immunoglobulin (e.g., CH3 of IgG1), polyethylene glycol (PEG) or a PEG mimetic, XTEN, serum albumin (e.g., human serum albumin), polysicalic acid, N-(2-hydroxypropyl) methacrylamide, or dextran, or is modified by, e.g., hyperglycosylation, to extend the half-life of the scFv (e.g., dsscFv).

A variety of suitable linkers are known to those of skill in the art and are not limited by any specific sequences disclosed herein. In some embodiments, the polypeptide linker is comprised of naturally, or non-naturally, occurring amino acids. In some embodiments, the linker comprises amino acids that allow for flexibility. In some embodiments, the linker comprises amino acids that allow for suitable solubility. In some embodiments, the linker comprises glycine amino acids. In some embodiments, the linker comprises glycine and serine amino acids. In certain embodiments, the linker comprises one or more sets of glycine/serine repeats. In some embodiments, the polypeptide linker is selected from the group consisting of: (GGGGS)n wherein n=1-4 (SEQ ID NO: 116), GGGGS (SEQ ID NO: 117), GGGGSGGGGS (SEQ ID NO: 118), GGGGSGGGGSGGGGS (SEQ ID NO: 119), GGGGSGGGGSGGGGSGGGGS (SEQ ID NO: 120), and (GGGGA)n wherein n=1-4 (SEQ ID NO: 121). In some embodiments, the linker comprises GGGGSGGGGSGGGGS (SEQ ID NO: 119).

In some embodiments, a KLRB1-binding agent is a Fv. A Fv comprises a heavy chain variable region and a light chain variable region. In some embodiments, the Fv is attached (either directly or indirectly) to a half-life extending moiety such as, e.g., an Fc molecule, a CH3 domain of an IgG (e.g., CH3 of IgG1), PEG or a PEG mimetic, XTEN, serum albumin (e.g., human serum albumin), polysicalic acid, N-(2-hydroxypropyl) methacrylamide, or dextran, or is modified, e.g., by hyperglycosylation, to extend the half-life of the Fv.

In some embodiments, a KLRB1-binding agent is a Fab. A Fab is one of the molecules that result from digestion of an immunoglobulin antibody with papain. Fabs are monovalent molecules that comprise a light chain, a heavy chain variable region, a CH1 region, and, optionally, a heavy chain constant region hinge region or a portion thereof. Fabs can be produced using recombinant technologies known in the art. In some embodiments, a Fab comprises a polypeptide linker between the light chain constant region and the heavy chain variable region. In some embodiments, a Fab comprises a polypeptide linker between the heavy chain constant region and the light chain variable region. A variety of suitable linkers are known to those of skill in the art and are not limited by any specific sequences disclosed herein. In certain embodiments, the linker is a linker described herein. In some embodiments, the Fab is attached (either directly or indirectly) to a half-life extending moiety such as, e.g., an Fc molecule, a CH3 domain of an IgG (e.g., CH3 of IgG1), PEG or a PEG mimetic, XTEN, serum albumin (e.g., human serum albumin), polysicalic acid, N-(2-hydroxypropyl) methacrylamide, or dextran, or is modified, e.g., by hyperglycosylation, to extend the half-life of the Fab.

In some embodiments, a Fab comprises a disulfide bond formed between the heavy chain variable region and the light chain variable region. In some embodiments, a Fab comprises a disulfide bond that increases stability of the Fab molecule. In some embodiments, a Fab comprises a disulfide bond that increases thermostability of the Fab molecule.

In some embodiments, a KLRB1-binding agent is a $F(ab')_2$. A $F(ab')_2$ is one of the molecules that results from digestion of an immunoglobulin antibody with pepsin. A $F(ab')_2$ is a divalent molecule that comprises a first light chain in association with a first polypeptide comprising a first heavy chain variable region, a first CH1, and a first hinge region, and a second light chain in association with a second polypeptide comprising a second heavy chain variable region, a second CH1, and a second hinge region, wherein the first hinge region is linked to the second hinge region via at least one disulfide bond. $F(ab')_2$s can be produced using recombinant technologies known in the art. In some embodiments, the $F(ab')_2$ is attached (either directly or indirectly) to a half-life extending moiety such as, e.g., a CH3 domain of an IgG (e.g., CH3 of IgG1), PEG or a PEG mimetic, XTEN, serum albumin (e.g., human serum albumin), polysicalic acid, N-(2-hydroxypropyl) methacrylamide, or dextran, or is modified, e.g., by hyperglycosylation, to extend the half-life of the $F(ab')_2$.

In some embodiments, a $F(ab')_2$ comprises a disulfide bond formed between the heavy chain variable region and the light chain variable region. In some embodiments, a $F(ab')_2$ comprises a disulfide bond that increases stability of the $F(ab')_2$ molecule. In some embodiments, a $F(ab')_2$ comprises a disulfide bond that increases thermostability of the $F(ab')_2$ molecule.

In some embodiments, a KLRB1-binding agent is a F(ab'). A F(ab') is a molecule that results from treatment of a $F(ab')_2$ with beta-mercaptoethanol. A F(ab') is a monovalent molecule that comprises a light chain in association with a polypeptide comprising a heavy chain variable region, a CH1, and a hinge region. In some embodiments, the F(ab') is attached (either directly or indirectly) to a half-life extending moiety such as, e.g., an Fc molecule, a CH3 domain of an IgG (e.g., CH3 of IgG1), PEG or a PEG mimetic, XTEN, serum albumin (e.g., human serum albumin), polysicalic acid, N-(2-hydroxypropyl) methacrylamide, or dextran, or is modified, e.g., by hyperglycosylation, to extend the half-life of the F(ab').

In some embodiments, a F(ab') comprises a disulfide bond formed between the heavy chain variable region and the light chain variable region. In some embodiments, a F(ab') comprises a disulfide bond that increases stability of the F(ab') molecule. In some embodiments, a F(ab') comprises a disulfide bond that increases thermostability of the F(ab') molecule.

In some embodiments, a KLRB1-binding agent is a bispecific antibody. Bispecific antibodies are capable of recognizing and binding at least two different antigens or epitopes. The different epitopes can either be within the same molecule (e.g., two epitopes on KLRB1) or on different molecules (e.g., one epitope on KLRB1 and one epitope on a different target). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two agents in a common area (e.g., tissue) in a subject (e.g., a human). In some embodiments, a bispecific antibody has the ability to concentrate the actions of two agents to a common target (e.g., a specific cell type). In some embodiments, a bispecific antibody has the ability to target the actions of two agents to more than one biological pathway or function. In some embodiments, a bispecific antibody has the ability to target two different cells and bring them closer together.

In some embodiments, a bispecific antibody has decreased toxicity and/or side effects. In some embodiments, a bispecific antibody has decreased toxicity and/or side effects as compared to a mixture of the two individual antibodies or the antibodies as single agents. In some embodiments, a bispecific antibody has an increased therapeutic index. In some embodiments, a bispecific antibody has an increased therapeutic index as compared to a mixture of the two individual antibodies or the antibodies as single agents.

Several techniques for making bispecific antibodies are known by those skilled in the art. In some embodiments, the bispecific antibodies comprise heavy chain constant regions with modifications in the amino acids that are part of the interface between the two heavy chains. These modifications are made to enhance heterodimer formation and generally reduce or eliminate homodimer formation. In some embodiments, the bispecific antibodies are generated using a knobs-into-holes (KIH) strategy. In some embodiments, the bispecific antibodies comprise variant hinge regions incapable of forming disulfide linkages between identical heavy chains (e.g., reduce homodimer formation). In some embodiments, the bispecific antibodies comprise heavy chains with changes in amino acids that result in altered electrostatic interactions. In some embodiments, the bispecific antibodies comprise heavy chains with changes in amino acids that result in altered hydrophobic/hydrophilic interactions.

Bispecific antibodies can be intact antibodies or antibody fragments comprising antigen-binding sites.

KLRB1-binding agents with more than two valencies are also contemplated. In some embodiments, trispecific or tetraspecific antibodies are generated.

In some embodiments, a KLRB1-binding agent is an anti-KLRB1 antibody that comprises one, two, three, four, five, and/or six CDRs of any one of the antibodies described herein. In some embodiments, an anti-KLRB1 antibody comprises (i) one, two, and/or three heavy chain CDRs from antibody 11.12, e.g., as shown in Table 1 and/or (ii) one, two, and/or three light chain CDRs from antibody 11.12, e.g., as shown in Table 1. In some embodiments, an anti-KLRB1 antibody comprises (i) three heavy chain CDRs from antibody 11.12, e.g., as shown in Table 1 (i.e., a CDR1, a CDR2, and a CDR3), and (ii) three light chain CDRs from antibody 11.12, e.g., as shown in Table 1. In some embodiments, an anti-KLRB1 antibody comprises (i) one, two, and/or three heavy chain CDRs from antibody 11.27, e.g., as shown in Table 2, and/or (ii) one, two, and/or three light chain CDRs from antibody 11.27, e.g., as shown in Table 2. In some embodiments, an anti-KLRB1 antibody comprises (i) three heavy chain CDRs from antibody 11.27, e.g., as shown in Table 2 (i.e., a CDR1, a CDR2, and a CDR3), and (ii) three light chain CDRs from antibody 11.27, e.g., as shown in Table 2. In some embodiments, an anti-KLRB1 antibody comprises (i) one, two, and/or three heavy chain CDRs from antibody 11.29, e.g., as shown in Table 3, and/or (ii) one, two, and/or three light chain CDRs from antibody 11.29, e.g., as shown in Table 3. In some embodiments, an anti-KLRB1 antibody comprises (i) three heavy chain CDRs from antibody 11.29, e.g., as shown in Table 3 (i.e., a CDR1, a CDR2, and a CDR3), and (ii) three light chain CDRs from antibody 11.29, e.g., as shown in Table 3. In some embodiments, an anti-KLRB1 antibody comprises (i) one, two, and/or three heavy chain CDRs from antibody 11.41.1, e.g., as shown in Table 4, and/or (ii) one, two, and/or three light chain CDRs from antibody 11.41.1, e.g., as shown in Table 4. In some embodiments, an anti-KLRB1 antibody comprises (i) three heavy chain CDRs from antibody 11.41.1, e.g., as shown in Table 4 (i.e., a CDR1, a CDR2, and a CDR3), and (ii) three light chain CDRs from antibody 11.41.1, e.g., as shown in Table 4. In some embodiments, an anti-KLRB1 antibody comprises (i) one, two, and/or three heavy chain CDRs from antibody 11.44.1, e.g., as shown in Table 5 and/or (ii) one, two, and/or three light chain CDRs from antibody 11.44.1, e.g., as shown in Table 5. In some embodiments, an anti-KLRB1 antibody comprises (i) three heavy chain CDRs from antibody 11.44.1, e.g., as shown in Table 5 (i.e., a CDR1, a CDR2, and a CDR3), and (ii) three light chain CDRs from antibody 11.44.1, e.g., as shown in Table 5. In some embodiments, an anti-KLRB1 antibody comprises (i) one, two, and/or three heavy chain CDRs from antibody 11.45, e.g., as shown in Table 6 and/or (ii) one, two, and/or three light chain CDRs from antibody 11.45, e.g., as shown in Table 6. In some embodiments, an anti-KLRB1 antibody comprises (i) three heavy chain CDRs from antibody 11.45, e.g., as shown in Table 6 (i.e., a CDR1, a CDR2, and a CDR3), and (ii) three light chain CDRs from antibody 11.45, e.g., as shown in Table 6. In some embodiments, an anti-KLRB1 antibody comprises (i) one, two, and/or three heavy chain CDRs from antibody 11.54, e.g., as shown in Table 7 and/or (ii) one, two, and/or three light chain CDRs from antibody 11.54, e.g., as shown in Table 7. In some embodiments, an anti-KLRB1 antibody comprises (i) three heavy chain CDRs from antibody 11.54, e.g., as shown in Table 7 (i.e., a CDR1, a CDR2, and a CDR3), and (ii) three light chain CDRs from antibody 11.54, e.g., as shown in Table 7. In some embodiments, an anti-KLRB1 antibody comprises (i) one, two, and/or three heavy chain CDRs from antibody 11.55, e.g., as shown in Table 8 and/or (ii) one, two, and/or three light chain CDRs from antibody 11.55, e.g., as shown in Table 8. In some embodiments, an anti-KLRB1 antibody comprises (i) three heavy chain CDRs from antibody 11.55, e.g., as shown in Table 8 (i.e., a CDR1, a CDR2, and a CDR3), and (ii) three light chain CDRs from antibody 11.55, e.g., as shown in Table 8. In some embodiments, an anti-KLRB1 antibody comprises (i) one, two, and/or three heavy chain CDRs from antibody 11.57, e.g., as shown in Table 9 and/or (ii) one, two, and/or three light chain CDRs from antibody 11.57, e.g., as shown in Table 9. In some embodiments, an anti-KLRB1 antibody comprises (i) three heavy chain CDRs from antibody 11.57, e.g., as shown in Table 9 (i.e., a CDR1, a CDR2, and a CDR3), and (ii) three light chain CDRs from antibody 11.57, e.g., as shown in Table 9. In some embodiments, an anti-KLRB1 antibody comprises (i) one, two, and/or three heavy chain CDRs from antibody 12.0, e.g., as shown in Table 10 and/or (ii) one, two, and/or three light chain CDRs from antibody 12.0, e.g., as shown in Table 10. In some embodiments, an anti-KLRB1 antibody comprises (i) three heavy chain CDRs from antibody 12.0, e.g., as shown in Table 10 (i.e., a CDR1, a CDR2, and a CDR3), and (ii) three light chain CDRs from antibody 12.0, e.g., as shown in Table 10. In some embodiments, an anti-KLRB1 antibody comprises (i) one, two, and/or three heavy chain CDRs from antibody 12.1.3, e.g., as shown in Table 11 and/or (ii) one, two, and/or three light chain CDRs from antibody 12.1.3, e.g., as shown in Table 11. In some embodiments, an anti-KLRB1 antibody comprises (i) three heavy chain CDRs from antibody 12.1.3, e.g., as shown in Table 11 (i.e., a CDR1, a CDR2, and a CDR3), and (ii) three light chain CDRs from antibody 12.1.3, e.g., as shown in Table 11. In some embodiments, an anti-KLRB1 antibody comprises (i) one, two, and/or three heavy chain CDRs from antibody 12.2, e.g., as shown in Table 12 and/or (ii) one, two, and/or three light chain CDRs from antibody 12.2, e.g., as shown in Table 12. In some embodiments, an anti-KLRB1 antibody comprises (i) three heavy chain CDRs from antibody 12.2, e.g., as shown in Table 12 (i.e., a CDR1, a CDR2, and a CDR3), and (ii) three light chain CDRs from antibody 12.2, e.g., as shown in Table 12. In some embodiments, an anti-KLRB1 antibody comprises (i) one, two, and/or three heavy chain CDRs from antibody 12.3, e.g., as shown in Table 13 and/or (ii) one, two, and/or three light chain CDRs from antibody 12.3, e.g., as shown in Table 13. In some embodiments, an anti-KLRB1 antibody comprises (i) three heavy chain CDRs from antibody 12.3, e.g., as shown in Table 13 (i.e., a CDR1, a CDR2, and a CDR3), and (ii) three light chain CDRs from antibody 12.3 e.g., as shown in Table 13. In some embodiments, an anti-KLRB1 antibody comprises (i) one, two, and/or three heavy chain CDRs from antibody 13.2, e.g., as shown in Table 14 and/or (ii) one, two, and/or three light chain CDRs from antibody 13.2, e.g., as shown in Table 14. In some embodiments, an anti-KLRB1 antibody comprises (i) three heavy chain CDRs from antibody 13.2, e.g., as shown in Table 14 (i.e., a CDR1, a CDR2, and a CDR3), and (ii) three light chain CDRs from antibody 13.2, e.g., as shown in Table 14. In some embodiments, an anti-KLRB1 antibody comprises (i) one, two, and/or three heavy chain CDRs from antibody 13.4, e.g., as shown in Table 15 and/or (ii) one, two, and/or three light chain CDRs from antibody 13.4, e.g., as shown in Table 15. In some embodiments, an anti-KLRB1 antibody comprises (i) three heavy chain CDRs from antibody 13.4, e.g., as shown in Table 15 (i.e., a CDR1, a CDR2, and a CDR3), and (ii) three light chain CDRs from antibody 13.4, e.g., as shown in Table 15. In some embodiments, an anti-KLRB1 antibody comprises (i) one, two, and/or three heavy chain CDRs from antibody 13.5, e.g., as shown in Table 16 and/or (ii) one, two, and/or three light chain CDRs from antibody 13.5, e.g., as shown in Table 16. In some embodiments, an anti-KLRB1 antibody comprises (i) three heavy chain CDRs from antibody 13.5, e.g., as shown in Table 16 (i.e., a CDR1, a CDR2, and a CDR3), and (ii) three light chain CDRs from antibody 13.5, e.g., as shown in Table 16. In some embodiments, an anti-KLRB1 antibody comprises (i) one, two, and/or three heavy chain CDRs from antibody 13.6, e.g., as shown in Table 17 and/or (ii) one, two, and/or three light chain CDRs from antibody 13.6, e.g., as shown in Table 17. In some embodiments, an anti-KLRB1 antibody comprises (i) three heavy chain CDRs from antibody 13.6, e.g., as shown in Table 17 (i.e., a CDR1, a CDR2, and a CDR3), and (ii) three light chain CDRs from antibody 13.6, e.g., as shown in Table 17.

In some embodiments, a KLRB1-binding agent is a humanized version of an anti-KLRB1 antibody that comprises (i) one, two, and/or three heavy chain CDRs, and/or (ii) one, two, and/or three light chain CDRs from any one of Tables 1-17. In some embodiments, a KLRB1-binding agent is a humanized version of an anti-KLRB1 antibody that comprises (i) three heavy chain CDRs (i.e., a CDR1, a CDR2, and a CDR3) and (ii) three light chain CDRs from any one of Tables 1-17, i.e., wherein the heavy chain CDRs and light chain CDRs are from the same table.

TABLE 1

| Antibody 11.12 Sequences | | | | | |
|---|---|---|---|---|---|
| 11.12 | Chothia | AbM | Kabat | Contact | IMGT |
| CDRH1 | GYSFTGY (SEQ ID NO: 12) | GYSFTGYTMN (SEQ ID NO: 13) | GYTMN (SEQ ID NO: 14) | TGYTMN (SEQ ID NO: 15) | GYSFTGYT (SEQ ID NO: 16) |
| CDRH2 | NPNTGG (SEQ ID NO: 17) | LINPNTGGTY (SEQ ID NO: 18) | LINPNTGGTYYNQKF KD (SEQ ID NO: 19) | WMGLINPNTGG TY (SEQ ID NO: 20) | INPNTGGT (SEQ ID NO: 21) |
| CDRH3 | LGDNYRGYF DY (SEQ ID NO: 22) | LGDNYRGYF DY (SEQ ID NO: 22) | LGDNYRGYFDY (SEQ ID NO: 22) | ARLGDNYRGYF D (SEQ ID NO: 23) | ARLGDNYRGYF DY (SEQ ID NO: 24) |
| CDRL1 | KASQDVGTA VV (SEQ ID NO: 25) | KASQDVGTA VV (SEQ ID NO: 25) | KASQDVGTAVV (SEQ ID NO: 25) | GTAVVWY (SEQ ID NO: 26) | QDVGTA (SEQ ID NO: 27) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

11.12-VH
QVQLVQSGAEVKKPGASVKVSCKASGYSFTGYTMNWVRQAPGQGLEWMGLINPNTGGTYYNQKFKDRVTMTR
DTSISTAYMELSRLRSDDTAVYYCARLGDNYRGYFDYWGQGTTVTVSS (SEQ ID NO: 33)

11.12-VL
DIQLTQSPSFLSASVGDRVTITCKASQDVGTAVVWYQQKPGKAPKLLIDWASIRHTGVPSRFSGSGSGTEFTLTISS
LQPEDFADYFCQQYSTYLYTFGGGTKLEIK (SEQ ID NO: 34)

TABLE 2

| Antibody 11.27 Sequences | | | | | |
|---|---|---|---|---|---|
| 11.27 | Chothia | AbM | Kabat | Contact | IMGT |
| CDRH1 | GYSFTGY (SEQ ID NO: 12) | GYSFTGYTMN (SEQ ID NO: 13) | GYTMN (SEQ ID NO: 14) | TGYTMN (SEQ ID NO: 15) | GYSFTGYT (SEQ ID NO: 16) |
| CDRH2 | NPSTGG (SEQ ID NO: 35) | LINPSTGGTY (SEQ ID NO: 36) | LINPSTGGTYYNQKF KD (SEQ ID NO: 37) | WMGLINPSTGG TY (SEQ ID NO: 38) | INPSTGGT (SEQ ID NO: 39) |
| CDRH3 | LGDNYRGYFD S (SEQ ID NO: 40 | LGDNYRGYFD S (SEQ ID NO: 40) | LGDNYRGYFDS (SEQ ID NO: 40) | ARLGDNYRGYF D (SEQ ID NO: 23) | ARLGDNYRGYF DS (SEQ ID NO: 41) |
| CDRL1 | KASQDVGTA VV (SEQ ID NO: 25) | KASQDVGTA VV (SEQ ID NO: 25) | KASQDVGTAVV (SEQ ID NO: 25) | GTAVVWY (SEQ ID NO: 26) | QDVGTA (SEQ ID NO: 27) |
| CDRL2 | WASIRHT (SEQ ID NO: 28 | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

11.27-VH
QVQLVQSGAEVKKPGASVKVSCKASGYSFTGYTMNWVRQAPGQGLEWMGLINPSTGGTYYNQKFKDRVTMTR
DTSISTAYMELSRLRSDDTAVYYCARLGDNYRGYFDSWGQGTTVTVSS (SEQ ID NO: 42)

11.27-VL
DIQLTQSPSFLSASVGDRVTITCKASQDVGTAVVWYQQKPGKAPKLLIDWASIRHTGVPSRFSGSGSGTEFTLTISS
LQPEDFADYFCQQYSTYLYTFGGGTKLEIK (SEQ ID NO: 34)

TABLE 3

| Antibody 11.29 Sequences | | | | | |
|---|---|---|---|---|---|
| 11.29 | Chothia | AbM | Kabat | Contact | IMGT |
| CDRH1 | GYSFTGY (SEQ ID NO: 12) | GYSFTGYTMN (SEQ ID NO: 13) | GYTMN (SEQ ID NO: 14) | TGYTMN (SEQ ID NO: 15) | GYSFTGYT (SEQ ID NO: 16) |
| CDRH2 | NPSSGG (SEQ ID NO: 43) | LINPSSGGTY (SEQ ID NO: 44) | LINPSSGGTYYNQKF KD (SEQ ID NO: 45) | WMGLINPSSGG TY (SEQ ID NO: 46) | INPSSGGT (SEQ ID NO: 47) |
| CDRH3 | LGDNYRGYFD S (SEQ ID NO: 40) | LGDNYRGYFD S (SEQ ID NO: 40) | LGDNYRGYFDS (SEQ ID NO: 40) | ARLGDNYRGY FD (SEQ ID NO: 23) | ARLGDNYRGYF DS (SEQ ID NO: 41) |
| CDRL1 | KASQDVGTAV V (SEQ ID NO: 25) | KASQDVGTAV V (SEQ ID NO: 25) | KASQDVGTAVV (SEQ ID NO: 25) | GTAVVWY (SEQ ID NO: 26) | QDVGTA (SEQ ID NO: 27) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

11.29-VH
QVQLVQSGAEVKKPGASVKVSCKASGYSFTGYTMNWVRQAPGQGLEWMGLINPSSGGTYYNQKFKDRVTMTR DTSISTAYMELSRLRSDDTAVYYCARLGDNYRGYFDSWGQGTTVTVSS (SEQ ID NO: 48)

11.29-VL
DIQLTQSPSFLSASVGDRVTITCKASQDVGTAVVWYQQKPGKAPKLLIDWASIRHTGVPSRFSGSGSGTEFTLTISS LQPEDFADYFCQQYSTYLYTFGGGTKLEIK (SEQ ID NO: 34)

TABLE 4

| Antibody 11.41.1 Sequences | | | | | |
|---|---|---|---|---|---|
| 11.41.1 | Chothia | AbM | Kabat | Contact | IMGT |
| CDRH1 | GYSFTGY (SEQ ID NO: 12) | GYSFTGYTMN (SEQ ID NO: 13) | GYTMN (SEQ ID NO: 14) | TGYTMN (SEQ ID NO: 15) | GYSFTGYT (SEQ ID NO: 16) |
| CDRH2 | NPSTGG (SEQ ID NO: 35) | LINPSTGGTY (SEQ ID NO: 36) | LINPSTGGTYYNQKF KD (SEQ ID NO: 37) | WMGLINPSTGG TY (SEQ ID NO: 38) | INPSTGGT (SEQ ID NO: 39) |
| CDRH3 | LGDNYRGYFD V (SEQ ID NO: 49) | LGDNYRGYFD V (SEQ ID NO: 49) | LGDNYRGYFDV (SEQ ID NO: 49) | ARLGDNYRGY FD (SEQ ID NO: 23) | ARLGDNYRGYF DV (SEQ ID NO: 50) |
| CDRL1 | KASQDVGTAV V (SEQ ID NO: 25 | KASQDVGTAV V (SEQ ID NO: 25) | KASQDVGTAVV (SEQ ID NO: 25) | GTAVVWY (SEQ ID NO: 26) | QDVGTA (SEQ ID NO: 27) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

11.41.1-VH
QVQLVQSGAEVKKPGASVKVSCKASGYSFTGYTMNWVRQAPGQGLEWMGLINPSTGGTYYNQKFKDRVTMTR DTSISTAYMELSRLRSDDTAVYYCARLGDNYRGYFDVWGQGTTVTVSS (SEQ ID NO: 51)

11.41.1-VL
DIQLTQSPSFLSASVGDRVTITCKASQDVGTAVVWYQQKPGKAPKLLIDWASIRHTGVPSRFSGSGSGTEFTLTISS LQPEDFATYYCQQYSTYLYTFGGGTKLEIK (SEQ ID NO: 52)

TABLE 5

| Antibody 11.44.1 Sequences | | | | | |
|---|---|---|---|---|---|
| 11.44.1 | Chothia | AbM | Kabat | Contact | IMGT |
| CDRH1 | GYSFTGY (SEQ ID NO: 12) | GYSFTGYTMN (SEQ ID NO: 13) | GYTMN (SEQ ID NO: 14) | TGYTMN (SEQ ID NO: 15) | GYSFTGYT (SEQ ID NO: 16) |
| CDRH2 | NPSSGG (SEQ ID NO: 43) | LINPSSGGTY (SEQ ID NO: 44) | LINPSSGGTYYNQKF KD (SEQ ID NO: 45) | WMGLINPSSGG TY (SEQ ID NO: 46) | INPSSGGT (SEQ ID NO: 47) |
| CDRH3 | LGDNYRGYFD V (SEQ ID NO: 49) | LGDNYRGYFD V (SEQ ID NO: 49) | LGDNYRGYFDV (SEQ ID NO: 49) | ARLGDNYRGY FD (SEQ ID NO: 23) | ARLGDNYRGYF DV (SEQ ID NO: 50) |
| CDRL1 | KASQDVGTAV V (SEQ ID NO: 25 | KASQDVGTAV V (SEQ ID NO: 25) | KASQDVGTAVV (SEQ ID NO: 25) | GTAVVWY (SEQ ID NO: 26) | QDVGTA (SEQ ID NO: 27) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

11.44.1-VH
QVQLVQSGAEVKKPGASVKVSCKASGYSFTGYTMNWVRQAPGQGLEWMGLINPSSGGTYYNQKFKDRVTMTR
DTSISTAYMELSRLRSDDTAVYYCARLGDNYRGYFDVWGQGTTVTVSS (SEQ ID NO: 53)

11.44.1-VL
DIQLTQSPSFLSASVGDRVTITCKASQDVGTAVVWYQQKPGKAPKLLIDWASIRHTGVPSRFSGSGSGTEFTLTISS
LQPEDFATYYCQQYSTYLYTFGGGTKLEIK (SEQ ID NO: 52)

TABLE 6

| Antibody 11.45 Sequences | | | | | |
|---|---|---|---|---|---|
| 11.45 | Chothia | AbM | Kabat | Contact | IMGT |
| CDRH1 | GYTFTGY (SEQ ID NO: 54) | GYTFTGYTMN (SEQ ID NO: 55) | GYTMN (SEQ ID NO: 14) | TGYTMN (SEQ ID NO: 15) | GYTFTGYT (SEQ ID NO: 56) |
| CDRH2 | NPSSGG (SEQ ID NO: 43) | LINPSSGGTY (SEQ ID NO: 44) | LINPSSGGTYYNQKF KD (SEQ ID NO: 45) | WMGLINPSSGG TY (SEQ ID NO: 46) | INPSSGGT (SEQ ID NO: 47) |
| CDRH3 | LGDNYRGYFD Y (SEQ ID NO: 22) | LGDNYRGYFD Y (SEQ ID NO: 22) | LGDNYRGYFDY (SEQ ID NO: 22) | ARLGDNYRGYF D (SEQ ID NO: 23) | ARLGDNYRGYF DY (SEQ ID NO: 24) |
| CDRL1 | KASQDVGTA VV (SEQ ID NO: 25) | KASQDVGTA VV (SEQ ID NO: 25) | KASQDVGTAVV (SEQ ID NO: 25) | GTAVVWY (SEQ ID NO: 26) | QDVGTA (SEQ ID NO: 27) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

11.45-VL
DIQLTQSPSFLSASVGDRVTITCKASQDVGTAVVWYQQKPGKAPKLLIDWASIRHTGVPSRFSGSGSGTEFTLTISS
LQPEDFATYYCQQYSTYLYTFGGGTKLEIK (SEQ ID NO: 52)

11.45-VH
QVQLVQSGAEVKKPGASVKVSCKASGYTFTGYTMNWVRQAPGQGLEWMGLINPSSGGTYYNQKFKDRVTMTR
DTSISTAYMELSRLRSDDTAVYYCARLGDNYRGYFDYWGQGTTVTVSS (SEQ ID NO: 57)

TABLE 7

| Antibody 11.54 Sequences | | | | | |
|---|---|---|---|---|---|
| 11.54 | Chothia | AbM | Kabat | Contact | IMGT |
| CDRH1 | GYSFTGY (SEQ ID NO: 12) | GYSFTGYTMN (SEQ ID NO: 13) | GYTMN (SEQ ID NO: 14) | TGYTMN (SEQ ID NO: 15) | GYSFTGYT (SEQ ID NO: 16) |
| CDRH2 | NPSSGG (SEQ ID NO: 43) | LINPSSGGTY (SEQ ID NO: 44) | LINPSSGGTYYNQKF KD (SEQ ID NO: 45) | WMGLINPSSGG TY (SEQ ID NO: 46) | INPSSGGT (SEQ ID NO: 47) |
| CDRH3 | LGDNYRGYF DY (SEQ ID NO: 22) | LGDNYRGYF DY (SEQ ID NO: 22) | LGDNYRGYFDY (SEQ ID NO: 22) | ARLGDNYRGYF D (SEQ ID NO: 23) | ARLGDNYRGYF DY (SEQ ID NO: 24) |
| CDRL1 | KASQDVGSA VV (SEQ ID NO: 58) | KASQDVGSA VV (SEQ ID NO: 58) | KASQDVGSAVV (SEQ ID NO: 58) | GSAVVWY (SEQ ID NO: 59) | QDVGSA (SEQ ID NO: 60) |
| CDRL2 | WASIRHS (SEQ ID NO: 61) | WASIRHS (SEQ ID NO: 61) | WASIRHS (SEQ ID NO: 61) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

11.54-VH
QVQLVQSGAEVKKPGASVKVSCKASGYSFTGYTMNWVRQAPGQGLEWMGLINPSSGGTYYNQKFKDRVTMTR
DTSISTAYMELSRLRSDDTAVYYCARLGDNYRGYFDYWGQGTTVTVSS (SEQ ID NO: 62)

11.54-VL
DIQLTQSPSFLSASVGDRVTITCKASQDVGSAVVWYQQKPGKAPKLLIDWASIRHSGVPSRFSGSGSGTEFTLTISS
LQPEDFATYYCQQYSTYLYTFGGGTKLEIK (SEQ ID NO: 63)

TABLE 8

| Antibody 11.55 Sequences | | | | | |
|---|---|---|---|---|---|
| 11.55 | Chothia | AbM | Kabat | Contact | IMGT |
| CDRH1 | GYSFTGY (SEQ ID NO: 12) | GYSFTGYTMN (SEQ ID NO: 13) | GYTMN (SEQ ID NO: 14) | TGYTMN (SEQ ID NO: 15) | GYSFTGYT (SEQ ID NO: 16) |
| CDRH2 | NPSSGG (SEQ ID NO: 43) | LINPSSGGTY (SEQ ID NO: 44 | LINPSSGGTYYNQKF KD (SEQ ID NO: 45) | WMGLINPSSGG TY (SEQ ID NO: 46) | INPSSGGT (SEQ ID NO: 47) |
| CDRH3 | LGDNYRGYF DY (SEQ ID NO: 22) | LGDNYRGYF DY (SEQ ID NO: 22) | LGDNYRGYFDY (SEQ ID NO: 22) | ARLGDNYRGYF D (SEQ ID NO: 23) | ARLGDNYRGYF DY (SEQ ID NO: 24) |
| CDRL1 | RASQDVGTA VV (SEQ ID NO: 64) | RASQDVGTA VV (SEQ ID NO: 64) | RASQDVGTAVV (SEQ ID NO: 64) | GTAVVWY (SEQ ID NO: 26) | QDVGTA (SEQ ID NO: 27) |
| CDRL2 | WASIRHT (SEQ ID NO: 28) | WASIRHT (SEQ ID NO: 28 | WASIRHT (SEQ ID NO: 28) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

11.55-VH
QVQLVQSGAEVKKPGASVKVSCKASGYSFTGYTMNWVRQAPGQGLEWMGLINPSSGGTYYNQKFKDRVTMTR
DTSISTAYMELSRLRSDDTAVYYCARLGDNYRGYFDYWGQGTTVTVSS (SEQ ID NO: 62)

11.55-VL
DIQLTQSPSFLSASVGDRVTITCRASQDVGTAVVWYQQKPGKAPKLLIDWASIRHTGVPSRFSGSGSGTEFTLTISS
LQPEDFATYYCQQYSTYLYTFGGGTKLEIK (SEQ ID NO: 65)

TABLE 9

| Antibody 11.57 Sequences | | | | | |
|---|---|---|---|---|---|
| 11.57 | Chothia | AbM | Kabat | Contact | IMGT |
| CDRH1 | GYTFTGY (SEQ ID NO: 54) | GYTFTGYTMN (SEQ ID NO: 55) | GYTMN (SEQ ID NO: 14) | TGYTMN (SEQ ID NO: 15) | GYTFTGYT (SEQ ID NO: 56) |
| CDRH2 | NPSSGG (SEQ ID NO: 43) | LINPSSGGTY (SEQ ID NO: 44) | LINPSSGGTYYNQKFKD (SEQ ID NO: 45) | WMGLINPSSGGTY (SEQ ID NO: 46) | INPSSGGT (SEQ ID NO: 47) |
| CDRH3 | LGDNYRGYFDY (SEQ ID NO: 22) | LGDNYRGYFDY (SEQ ID NO: 22) | LGDNYRGYFDY (SEQ ID NO: 22) | ARLGDNYRGYFD (SEQ ID NO: 23) | ARLGDNYRGYFDY (SEQ ID NO: 24) |
| CDRL1 | RASQDVGSAVV (SEQ ID NO: 66) | RASQDVGSAVV (SEQ ID NO: 66) | RASQDVGSAVV (SEQ ID NO: 66) | GSAVVWY (SEQ ID NO: 59) | QDVGSA (SEQ ID NO: 60) |
| CDRL2 | WASIRHS (SEQ ID NO: 61) | WASIRHS (SEQ ID NO: 61) | WASIRHS (SEQ ID NO: 61) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

11.57-VH
QVQLVQSGAEVKKPGASVKVSCKASGYTFTGYTMNWVRQAPGQGLEWMGLINPSSGGTYYNQKFKDRVTMTR DTSISTAYMELSRLRSDDTAVYYCARLGDNYRGYFDYWGQGTTVTVSS (SEQ ID NO: 57)

11.57-VL
DIQLTQSPSFLSASVGDRVTITCRASQDVGSAVVWYQQKPGKAPKLLIDWASIRHSGVPSRFSGSGSGTEFTLTISS LQPEDFATYYCQQYSTYLYTFGGGTKLEIK (SEQ ID NO: 67)

TABLE 10

| Antibody 12.0 Sequences | | | | | |
|---|---|---|---|---|---|
| 12.0 | Chothia | AbM | Kabat | Contact | IMGT |
| CDRH1 | GYTFTGY (SEQ ID NO: 54) | GYTFTGYTMN (SEQ ID NO: 55) | GYTMN (SEQ ID NO: 14) | TGYTMN (SEQ ID NO: 15) | GYTFTGYT (SEQ ID NO: 56) |
| CDRH2 | NPSTGG (SEQ ID NO: 35) | LINPSTGGTY (SEQ ID NO: 36) | LINPSTGGTYYNQKFKD (SEQ ID NO: 37) | WMGLINPSTGGTY (SEQ ID NO: 38) | INPSTGGT (SEQ ID NO: 39) |
| CDRH3 | LGDNYRGYFDY (SEQ ID NO: 22) | LGDNYRGYFDY (SEQ ID NO: 22) | LGDNYRGYFDY (SEQ ID NO: 22) | ARLGDNYRGYFD (SEQ ID NO: 23) | ARLGDNYRGYFDY (SEQ ID NO: 24) |
| CDRL1 | RASQDVGTAVV (SEQ ID NO: 64) | RASQDVGTAVV (SEQ ID NO: 64) | RASQDVGTAVV (SEQ ID NO: 64) | GTAVVWY (SEQ ID NO: 26) | QDVGTA (SEQ ID NO: 27) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

12.0-VH
QVQLVQSGAEVKKPGASVKVSCKASGYTFTGYTMNWVRQAPGQGLEWMGLINPSTGGTYYNQKFKDRVTMTR DTSISTAYMELSRLRSDDTAVYYCARLGDNYRGYFDYWGQGTTVTVSS (SEQ ID NO: 68)

12.0-VL
DIQLTQSPSFLSASVGDRVTITCRASQDVGTAVVWYQQKPGKAPKLLIDWASIRHTGVPSRFSGSGSGTEFTLTISS LQPEDFATYYCQQYSTYLYTFGGGTKLEIK (SEQ ID NO: 65)

TABLE 11

| Antibody 12.1.3 Sequences | | | | | |
|---|---|---|---|---|---|
| 12.1.3 | Chothia | AbM | Kabat | Contact | IMGT |
| CDRH1 | GYTFTGY (SEQ ID NO: 54) | GYTFTGYTM N (SEQ ID NO: 55) | GYTMN (SEQ ID NO: 14) | TGYTMN (SEQ ID NO: 15) | GYTFTGYT (SEQ ID NO: 56) |
| CDRH2 | NPSTGG (SEQ ID NO: 35) | LINPSTGGTY (SEQ ID NO: 36) | LINPSTGGTYYNQKF KD (SEQ ID NO: 37) | WMGLINPSTGG TY (SEQ ID NO: 38) | INPSTGGT (SEQ ID NO: 39) |
| CDRH3 | LGDNYRGYF DY (SEQ ID NO: 22) | LGDNYRGYF DY (SEQ ID NO: 22) | LGDNYRGYFDY (SEQ ID NO: 22) | ARLGDNYRGYF D (SEQ ID NO: 23) | ARLGDNYRGYF DY (SEQ ID NO: 24) |
| CDRL1 | RASQGIGSAV V (SEQ ID NO: 69) | RASQGIGSAV V (SEQ ID NO: 69) | RASQGIGSAVV (SEQ ID NO: 69) | GSAVVWY (SEQ ID NO: 59) | QGIGSA (SEQ ID NO: 70) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

12.1.3-VH
QVQLVQSGAEVKKPGASVKVSCKASGYTFTGYTMNWVRQAPGQGLEWMGLINPSTGGTYYNQKFKDRVTMTR DTSISTAYMELSRLRSDDTAVYYCARLGDNYRGYFDYWGQGTTVTVSS (SEQ ID NO: 68)

12.1.3-VL
DIQLTQSPSFLSASVGDRVTITCRASQGIGSAVVWYQQKPGKAPKLLIDWASIRHTGVPSRFSGSGSGTEFTLTISSL QPEDFATYYCQQYSTYLYTFGGGTKLEIK (SEQ ID NO: 71)

TABLE 12

| Antibody 12.2 Sequences | | | | | |
|---|---|---|---|---|---|
| 12.2 | Chothia | AbM | Kabat | Contact | IMGT |
| CDRH1 | GYTFTGY (SEQ ID NO: 54) | GYTFTGYTM N (SEQ ID NO: 55) | GYTMN (SEQ ID NO: 14) | TGYTMN (SEQ ID NO: 15) | GYTFTGYT (SEQ ID NO: 56) |
| CDRH2 | NPSTGG (SEQ ID NO: 35) | LINPSTGGTY (SEQ ID NO: 36) | LINPSTGGTYYNQKF KD (SEQ ID NO: 37) | WMGLINPSTGG TY (SEQ ID NO: 38) | INPSTGGT (SEQ ID NO: 39) |
| CDRH3 | LGDNYRGYF DY (SEQ ID NO: 22) | LGDNYRGYF DY (SEQ ID NO: 22) | LGDNYRGYFDY (SEQ ID NO: 22) | ARLGDNYRGYF D (SEQ ID NO: 23) | ARLGDNYRGYF DY (SEQ ID NO: 24) |
| CDRL1 | RASQGISSYL A (SEQ ID NO: 72) | RASQGISSYL A (SEQ ID NO: 72) | RASQGISSYLA (SEQ ID NO: 72) | SSYLAWY (SEQ ID NO: 73) | QGISSY (SEQ ID NO: 74) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

12.2-VH
QVQLVQSGAEVKKPGASVKVSCKASGYTFTGYTMNWVRQAPGQGLEWMGLINPSTGGTYYNQKFKDRVTMTR DTSISTAYMELSRLRSDDTAVYYCARLGDNYRGYFDYWGQGTTVTVSS (SEQ ID NO: 68)

12.2-VL
DIQLTQSPSFLSASVGDRVTITCRASQGISSYLAWYQQKPGKAPKLLIDWASIRHTGVPSRFSGSGSGTEFTLTISSL QPEDFATYYCQQYSTYLYTFGGGTKLEIK (SEQ ID NO: 75)

TABLE 13

| Antibody 12.3 Sequences | | | | | |
|---|---|---|---|---|---|
| 12.3 | Chothia | AbM | Kabat | Contact | IMGT |
| CDRH1 | GYTFTGY (SEQ ID NO: 54) | GYTFTGYTMN (SEQ ID NO: 55) | GYTMN (SEQ ID NO: 14) | TGYTMN (SEQ ID NO: 15) | GYTFTGYT (SEQ ID NO: 56) |
| CDRH2 | NPSTGG (SEQ ID NO: 35) | LINPSTGGTY (SEQ ID NO: 36) | LINPSTGGTYYNQKFKD (SEQ ID NO: 37) | WMGLINPSTGGTY (SEQ ID NO: 38) | INPSTGGT (SEQ ID NO: 39) |
| CDRH3 | LGDNYRGYFDY (SEQ ID NO: 22) | LGDNYRGYFDY (SEQ ID NO: 22) | LGDNYRGYFDY (SEQ ID NO: 22) | ARLGDNYRGYFD (SEQ ID NO: 23) | ARLGDNYRGYFDY (SEQ ID NO: 24 |
| CDRL1 | RASQGISSYLA (SEQ ID NO: 72) | RASQGISSYLA (SEQ ID NO: 72) | RASQGISSYLA (SEQ ID NO: 72) | SSYLAWY (SEQ ID NO: 73) | QGISSY (SEQ ID NO: 74) |
| CDRL2 | WASIRHT (SEQ ID NO: 28) | WASIRHT (SEQ ID NO: 28) | WASIRHT (SEQ ID NO: 28) | LLIYWASIRH (SEQ ID NO: 76) | WA (SEQ ID NO: 30) |
| CDRL3 | QQLSTYPYT (SEQ ID NO: 77) | QQLSTYPYT (SEQ ID NO: 77) | QQLSTYPYT (SEQ ID NO: 77) | QQLSTYPY (SEQ ID NO: 78) | QQLSTYPYT (SEQ ID NO: 77) |

12.3-VH
QVQLVQSGAEVKKPGASVKVSCKASGYTFTGYTMNWVRQAPGQGLEWMGLINPSTGGTYYNQKFKDRVTMTR
DTSISTAYMELSRLRSDDTAVYYCARLGDNYRGYFDYWGQGTTVTVSS (SEQ ID NO: 68)

12.3-VL
DIQLTQSPSFLSASVGDRVTITCRASQGISSYLAWYQQKPGKAPKLLIYWASIRHTGVPSRFSGSGSGTEFTLTISSL
QPEDFATYYCQQLSTYPYTFGGGTKLEIK (SEQ ID NO: 79)

TABLE 14

| Antibody 13.2 Sequences | | | | | |
|---|---|---|---|---|---|
| 13.2 | Chothia | AbM | Kabat | Contact | IMGT |
| CDRH1 | GYTFTGY (SEQ ID NO: 54) | GYTFTGYTMN (SEQ ID NO: 55) | GYTMN (SEQ ID NO: 14) | TGYTMN (SEQ ID NO: 15) | GYTFTGYT (SEQ ID NO: 56) |
| CDRH2 | NPSTGG (SEQ ID NO: 35) | LINPSTGGTY (SEQ ID NO: 36) | LINPSTGGTYYNQKFKD (SEQ ID NO: 37) | WMGLINPSTGGTY (SEQ ID NO: 38) | INPSTGGT (SEQ ID NO: 39) |
| CDRH3 | LGDNYRGYFDY (SEQ ID NO: 22) | LGDNYRGYFDY (SEQ ID NO: 22) | LGDNYRGYFDY (SEQ ID NO: 22) | ARLGDNYRGYFD (SEQ ID NO: 23) | ARLGDNYRGYFDY (SEQ ID NO: 24) |
| CDRL1 | RASQDVGTAVV (SEQ ID NO: 64) | RASQDVGTAVV (SEQ ID NO: 64) | RASQDVGTAVV (SEQ ID NO: 64) | GTAVVWY (SEQ ID NO: 26) | QDVGTA (SEQ ID NO: 27) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTYLYT (SEQ ID NO: 31) | QQYSTYLYT (SEQ ID NO: 31) | QQYSTYLYT (SEQ ID NO: 31) | QQYSTYLY (SEQ ID NO: 32) | QQYSTYLYT (SEQ ID NO: 31) |

13.2-VH
QVQLVQSGAEVKKPGASVKVSCKASGYTFTGYTMNWVRQAPGQGLEWMGLINPSTGGTYYNQKFKDRVTMTR
DTSISTAYMELSRLRSDDTAVYYCARLGDNYRGYFDYWGQGTTVTVSS (SEQ ID NO: 68)

13.2-VL
EIVMTQSPATLSVSPGERATLSCRASQDVGTAVVWYQQKPGQAPRLLIDWASIRHTGIPARFSGSGSGTEFTLTISS
LQSEDFAVYYCQQYSTYLYTFGGGTKVEIK (SEQ ID NO: 80)

TABLE 15

| Antibody 13.4 Sequences | | | | | |
|---|---|---|---|---|---|
| 13.4 | Chothia | AbM | Kabat | Contact | IMGT |
| CDRH1 | GYTFTGY (SEQ ID NO: 54) | GYTFTGYTMN (SEQ ID NO: 55) | GYTMN (SEQ ID NO: 14) | TGYTMN (SEQ ID NO: 15) | GYTFTGYT (SEQ ID NO: 56) |
| CDRH2 | NPSTGG (SEQ ID NO: 35) | LINPSTGGTY (SEQ ID NO: 36) | LINPSTGGTYYNQKF KD (SEQ ID NO: 37) | WMGLINPSTGG TY (SEQ ID NO: 38) | INPSTGGT (SEQ ID NO: 39) |
| CDRH3 | LGDNYRGYFD Y (SEQ ID NO: 22) | LGDNYRGYFD Y (SEQ ID NO: 22) | LGDNYRGYFDY (SEQ ID NO: 22) | ARLGDNYRGY FD (SEQ ID NO: 23) | ARLGDNYRGYF DY (SEQ ID NO: 24) |
| CDRL1 | RASQDVGTAV V (SEQ ID NO: 64) | RASQDVGTAV V (SEQ ID NO: 64) | RASQDVGTAVV (SEQ ID NO: 64) | GTAVVWY (SEQ ID NO: 26) | QDVGTA (SEQ ID NO: 27) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTWPLT (SEQ ID NO: 81) | QQYSTWPLT (SEQ ID NO: 81) | QQYSTWPLT (SEQ ID NO: 81) | QQYSTWPL (SEQ ID NO: 82) | QQYSTWPLT (SEQ ID NO: 81) |

13.4-VH
QVQLVQSGAEVKKPGASVKVSCKASGYTFTGYTMNWVRQAPGQGLEWMGLINPSTGGTYYNQKFKDRVTMTR DTSISTAYMELSRLRSDDTAVYYCARLGDNYRGYFDYWGQGTTVTVSS (SEQ ID NO: 68)

13.4-VL
EIVMTQSPATLSVSPGERATLSCRASQDVGTAVVWYQQKPGQAPRLLIDWASIRHTGIPARFSGSGSGTEFTLTISS LQSEDFAVYYCQQYSTWPLTFGGGTKVEIK (SEQ ID NO: 83)

TABLE 16

| Antibody 13.5 Sequences | | | | | |
|---|---|---|---|---|---|
| 13.5 | Chothia | AbM | Kabat | Contact | IMGT |
| CDRH1 | GYTFTGY (SEQ ID NO: 54) | GYTFTGYTM N (SEQ ID NO: 55) | GYTMN (SEQ ID NO: 14) | TGYTMN (SEQ ID NO: 15) | GYTFTGYT (SEQ ID NO: 56) |
| CDRH2 | NPSTGG (SEQ ID NO: 35) | LINPSTGGTY (SEQ ID NO: 36) | LINPSTGGTYYNQKF KD (SEQ ID NO: 37) | WMGLINPSTGG TY (SEQ ID NO: 38) | INPSTGGT (SEQ ID NO: 39) |
| CDRH3 | LGDNYRGYF DY (SEQ ID NO: 22) | LGDNYRGYF DY (SEQ ID NO: 22) | LGDNYRGYFDY (SEQ ID NO: 22) | ARLGDNYRGYF D (SEQ ID NO: 23) | ARLGDNYRGYF DY (SEQ ID NO: 24) |
| CDRL1 | RASQSVGTAV V (SEQ ID NO: 84) | RASQSVGTAV V (SEQ ID NO: 84) | RASQSVGTAVV (SEQ ID NO: 84) | GTAVVWY (SEQ ID NO: 26) | QSVGTA (SEQ ID NO: 85) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTWPLT (SEQ ID NO: 81) | QQYSTWPLT (SEQ ID NO: 81) | QQYSTWPLT (SEQ ID NO: 81) | QQYSTWPL (SEQ ID NO: 82) | QQYSTWPLT (SEQ ID NO: 81) |

13.5-VH
QVQLVQSGAEVKKPGASVKVSCKASGYTFTGYTMNWVRQAPGQGLEWMGLINPSTGGTYYNQKFKDRVTMTR DTSISTAYMELSRLRSDDTAVYYCARLGDNYRGYFDYWGQGTTVTVSS (SEQ ID NO: 68)

13.5-VL
EIVMTQSPATLSVSPGERATLSCRASQSVGTAVVWYQQKPGQAPRLLIDWASIRHTGIPARFSGSGSGTEFTLTISS LQSEDFAVYYCQQYSTWPLTFGGGTKVEIK (SEQ ID NO: 86)

TABLE 17

| Antibody 13.6 Sequences | | | | | |
|---|---|---|---|---|---|
| 13.6 | Chothia | AbM | Kabat | Contact | IMGT |
| CDRH1 | GYTFTGY (SEQ ID NO: 54) | GYTFTGYTMN (SEQ ID NO: 55) | GYTMN (SEQ ID NO: 14) | TGYTMN (SEQ ID NO: 15) | GYTFTGYT (SEQ ID NO: 56) |
| CDRH2 | NPSTGG (SEQ ID NO: 35) | LINPSTGGTY (SEQ ID NO: 36) | LINPSTGGTYYNQKFKD (SEQ ID NO: 37) | WMGLINPSTGGTY (SEQ ID NO: 38) | INPSTGGT (SEQ ID NO: 39) |
| CDRH3 | LGDNYRGYFDY (SEQ ID NO: 22) | LGDNYRGYFDY (SEQ ID NO: 22) | LGDNYRGYFDY (SEQ ID NO: 22) | ARLGDNYRGYFD (SEQ ID NO: 23) | ARLGDNYRGYFDY (SEQ ID NO: 24) |
| CDRL1 | RASQSVGTNLA (SEQ ID NO: 87) | RASQSVGTNLA (SEQ ID NO: 87) | RASQSVGTNLA (SEQ ID NO: 87) | GTNLAWY (SEQ ID NO: 88) | QSVGTN (SEQ ID NO: 89) |
| CDRL2 | WASIRHT (SEQ ID NO: 28) | WASIRHT (SEQ ID NO: 28) | WASIRHT (SEQ ID NO: 28) | LLIDWASIRH (SEQ ID NO: 29) | WA (SEQ ID NO: 30) |
| CDRL3 | QQYSTWPLT (SEQ ID NO: 81) | QQYSTWPLT (SEQ ID NO: 81) | QQYSTWPLT (SEQ ID NO: 81) | QQYSTWPL (SEQ ID NO: 82) | QQYSTWPLT (SEQ ID NO: 81) |

13.6-VL
EIVMTQSPATLSVSPGERATLSCRASQSVGTNLAWYQQKPGQAPRLLIDWASIRHTGIPARFSGSGSGTEFTLTISS
LQSEDFAVYYCQQYSTWPLTFGGGTKVEIK (SEQ ID NO: 90)

13.6-VH
QVQLVQSGAEVKKPGASVKVSCKASGYTFTGYTMNWVRQAPGQGLEWMGLINPSTGGTYYNQKFKDRVTMT
RDTSISTAYMELSRLRSDDTAVYYCARLGDNYRGYFDYWGQGTTVTVSS (SEQ ID NO: 68)

In some embodiments, a KLRB1-binding agent comprises a heavy chain CDR1, CDR2, and CDR3 and/or a light chain CDR1, CDR2, CDR3 from an antibody described herein. In some embodiments, a KLRB1-binding agent comprises a humanized version or humanized variant of an antibody described herein. In some embodiments, a KLRB1-binding agent comprises a heavy chain CDR1, CDR2, and CDR3 and/or a light chain CDR1, CDR2, CDR3 from antibody 11.12 (Table 1) or a humanized version thereof. In some embodiments, a KLRB1-binding agent comprises a heavy chain CDR1, CDR2, and CDR3 and/or a light chain CDR1, CDR2, CDR3 from antibody 11.27 (Table 2) or a humanized version thereof. In some embodiments, a KLRB1-binding agent comprises a heavy chain CDR1, CDR2, and CDR3 and/or a light chain CDR1, CDR2, CDR3 from antibody 11.29 (Table 3) or a humanized version thereof. In some embodiments, a KLRB1-binding agent comprises a heavy chain CDR1, CDR2, and CDR3 and/or a light chain CDR1, CDR2, CDR3 from antibody 11.41.1 (Table 4) or a humanized version thereof. In some embodiments, a KLRB1-binding agent comprises a heavy chain CDR1, CDR2, and CDR3 and/or a light chain CDR1, CDR2, CDR3 from antibody 11.44.1 (Table 5) or a humanized version thereof. In some embodiments, a KLRB1-binding agent comprises a heavy chain CDR1, CDR2, and CDR3 and/or a light chain CDR1, CDR2, CDR3 from antibody 11.45 (Table 6) or a humanized version thereof. In some embodiments, a KLRB1-binding agent comprises a heavy chain CDR1, CDR2, and CDR3 and/or a light chain CDR1, CDR2, CDR3 from antibody 11.54 (Table 7) or a humanized version thereof. In some embodiments, a KLRB1-binding agent comprises a heavy chain CDR1, CDR2, and CDR3 and/or a light chain CDR1, CDR2, CDR3 from antibody 11.55 (Table 8) or a humanized version thereof. In some embodiments, a KLRB1-binding agent comprises a heavy chain CDR1, CDR2, and CDR3 and/or a light chain CDR1, CDR2, CDR3 from antibody 11.57 (Table 9) or a humanized version thereof. In some embodiments, a KLRB1-binding agent comprises a heavy chain CDR1, CDR2, and CDR3 and/or a light chain CDR1, CDR2, CDR3 from antibody 12.0 (Table 10) or a humanized version thereof. In some embodiments, a KLRB1-binding agent comprises a heavy chain CDR1, CDR2, and CDR3 and/or a light chain CDR1, CDR2, CDR3 from antibody 12.1.3 (Table 11) or a humanized version thereof. In some embodiments, a KLRB1-binding agent comprises a heavy chain CDR1, CDR2, and CDR3 and/or a light chain CDR1, CDR2, CDR3 from antibody 12.2 (Table 12) or a humanized version thereof. In some embodiments, a KLRB1-binding agent comprises a heavy chain CDR1, CDR2, and CDR3 and/or a light chain CDR1, CDR2, CDR3 from antibody 12.3 (Table 13) or a humanized version thereof. In some embodiments, a KLRB1-binding agent comprises a heavy chain CDR1, CDR2, and CDR3 and/or a light chain CDR1, CDR2, CDR3 from antibody 13.2 (Table 14) or a humanized version thereof. In some embodiments, a KLRB1-binding agent comprises a heavy chain CDR1, CDR2, and CDR3 and/or a light chain CDR1, CDR2, CDR3 from antibody 13.4 (Table 15) or a humanized version thereof. In some embodiments, a KLRB1-binding agent comprises a heavy chain CDR1, CDR2, and CDR3 and/or a light chain CDR1, CDR2, CDR3 from antibody 13.5 (Table 16) or a humanized version thereof. In some embodiments, a KLRB1-binding agent comprises a heavy chain CDR1, CDR2, and CDR3 and/or a light chain CDR1, CDR2, CDR3 from antibody 13.6 (Table 17) or a humanized version thereof.

In some embodiments, a KLRB1-binding agent comprises a more humanized version or humanized variant of an antibody described herein. In some embodiments, a KLRB1-binding agent comprises a heavy chain CDR1, CDR2, and CDR3 and/or a light chain CDR1, CDR2, CDR3 shown in Tables 1-17 or a more humanized version thereof.

CDRs are defined by a variety of methods/systems by those skilled in the art. These systems and/or definitions have been developed and refined over a number of years and include Kabat, Chothia, IMGT, AbM, and Contact. The Kabat definition is based on sequence variability and generally is the most commonly used. The Chothia definition is based on the location of the structural loop regions. The IMGT system is based on sequence variability and location within the structure of the variable domain. The AbM definition is a compromise between Kabat and Chothia. The Contact definition is based on analyses of the available antibody crystal structures. An Exemplary system is a combination of Kabat and Chothia. Software programs (e.g., abYsis (bioinf.org.uk/abysis/sequence_input/key_annotation/key_annotation.cgi)) are available and known to those of skill in the art for analysis of antibody sequences and determination of CDRs.

The specific CDR sequences defined herein are generally based on Kabat definitions. However, it will be understood that reference to a heavy chain CDR or CDRs and/or a light chain CDR or CDRs of a specific antibody will encompass all CDR definitions as known to those of skill in the art, e.g., as shown in the Tables herein. In some embodiments, CDR sequences used will all be identified using the same definitions, i.e., will all be Chothia, all Kabat, all IMGT, and so on. The term "antibody numbering conventions" is defined as the various conventions of Kabat, Chothia, AbM, Contact, and IMGT for defining CDR regions.

In some embodiments, a KLRB1-binding agent is a variant of an agent described herein. In some embodiments, a KLRB1-binding agent (e.g., an antibody) comprises (a) a heavy chain CDR1, CDR2, CDR3 from a VH sequence presented herein (e.g., in Tables 1-17, Table B, or Table C), or a variant thereof comprising 1, 2, 3, or 4 amino acid substitutions; and/or a light chain CDR1, CDR2, and/or CDR3 from a VL sequence presented herein (e.g., in Tables 1-17, Table B, or Table C), or a variant thereof comprising 1, 2, 3, or 4 amino acid substitutions. In some embodiments, the amino acid substitutions are conservative substitutions. In some embodiments, a CDR comprises one conservative amino acid substitution. In some embodiments, a CDR comprises two conservative amino acid substitutions. In some embodiments, a CDR comprises three conservative amino acid substitutions. In some embodiments, a CDR comprises four conservative amino acid substitutions. In some embodiments, the CDR is a heavy chain CDR1. In some embodiments, the CDR is a heavy chain CDR2. In some embodiments, the CDR is a heavy chain CDR3. In some embodiments, the CDR is a light chain CDR1. In some embodiments, the CDR is a light chain CDR2. In some embodiments, the CDR is a light chain CDR3. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

In some embodiments, a KLRB1-binding agent (e.g., an antibody) comprises one or more heavy chain or light chain CDRs that have been modified, e.g., to reduce deamidation within the CDR sequence, to remove Asn (N)-glycosylation sites, to remove cysteines, or to remove Asp to reduce isomerization sites, to remove Met/Trp or Lys, e.g., to reduce the likelihood within a CDR sequence of asparagine (N)-glycosylation, cysteinylation, asparagine (Asn) deamidation, aspartate (Asp) isomerization, methionine/tryptophan (Met/Trp) oxidation, and non-enzymatic lysine (Lys) glycation (see, e.g., Haberger et al., MAbs. 2014 Mar. 1; 6(2): 327-339; Lu et al., MAbs. 2019 January; 11(1): 45-57). Deamidation is a chemical reaction in which an amide functional group in the side chain of the amino acids asparagine (N) or glutamine (Q) is removed or converted to another functional group. Generally, asparagine is converted to aspartic acid or isoaspartic acid and glutamine is converted to glutamic acid or polyglutamic acid. In some situations, deamidation may change the structure, function, and/or stability of a polypeptide, potentially resulting in decreased biological activity.

Exemplary human heavy chain variable region and light chain variable region sequences are provided in Table B.

TABLE B

Sequences of Exemplary Antibody Variable Sequences

| Name | Heavy Chain Variable Sequence | Light Chain Variable Sequence |
|---|---|---|
| 11.12 | QVQLVQSGAEVKKPGASVKVSCKASGYSFT GYTMNWVRQAPGQGLEWMGLINPNTGGTY YNQKFKDRVTMTRDTSISTAYMELSRLRSDD TAVYYCARLGDNYRGYFDYWGQGTTVTVSS (SEQ ID NO: 33) | DIQLTQSPSFLSASVGDRVTITCKASQDVGTAVV WYQQKPGKAPKLLIDWASIRHTGVPSRFSGSGSG TEFTLTISSLQPEDFADYFCQQYSTYLYTFGGGTK LEIK (SEQ ID NO: 34) |
| 11.27 | QVQLVQSGAEVKKPGASVKVSCKASGYSFT GYTMNWVRQAPGQGLEWMGLINPSTGGTY YNQKFKDRVTMTRDTSISTAYMELSRLRSDD TAVYYCARLGDNYRGYFDSWGQGTTVTVSS (SEQ ID NO: 42) | DIQLTQSPSFLSASVGDRVTITCKASQDVGTAVV WYQQKPGKAPKLLIDWASIRHTGVPSRFSGSGSG TEFTLTISSLQPEDFADYFCQQYSTYLYTFGGGTK LEIK (SEQ ID NO: 34) |
| 11.29 | QVQLVQSGAEVKKPGASVKVSCKASGYSFT GYTMNWVRQAPGQGLEWMGLINPSSGGTYY NQKFKDRVTMTRDTSISTAYMELSRLRSDDT AVYYCARLGDNYRGYFDSWGQGTTVTVSS (SEQ ID NO: 48) | DIQLTQSPSFLSASVGDRVTITCKASQDVGTAVV WYQQKPGKAPKLLIDWASIRHTGVPSRFSGSGSG TEFTLTISSLQPEDFADYFCQQYSTYLYTFGGGTK LEIK (SEQ ID NO: 34) |
| 11.41.1 | QVQLVQSGAEVKKPGASVKVSCKASGYSFT GYTMNWVRQAPGQGLEWMGLINPSTGGTY YNQKFKDRVTMTRDTSISTAYMELSRLRSDD TAVYYCARLGDNYRGYFDVWGQGTTVTVSS (SEQ ID NO: 51) | DIQLTQSPSFLSASVGDRVTITCKASQDVGTAVV WYQQKPGKAPKLLIDWASIRHTGVPSRFSGSGSG TEFTLTISSLQPEDFATYYCQQYSTYLYTFGGGT KLEIK (SEQ ID NO: 52) |

TABLE B-continued

| Sequences of Exemplary Antibody Variable Sequences | | |
|---|---|---|
| Name | Heavy Chain Variable Sequence | Light Chain Variable Sequence |
| 11.44.1 | QVQLVQSGAEVKKPGASVKVSCKASGYSFT GYTMNWVRQAPGQGLEWMGLINPSSGGTYY NQKFKDRVTMTRDTSISTAYMELSRLRSDDT AVYYCARLGDNYRGYFDVWGQGTTVTVSS (SEQ ID NO: 53) | DIQLTQSPSFLSASVGDRVTITCKASQDVGTAVV WYQQKPGKAPKLLIDWASIRHTGVPSRFSGSGSG TEFTLTISSLQPEDFATYYCQQYSTYLYTFGGGT KLEIK (SEQ ID NO: 52) |
| 11.45 | QVQLVQSGAEVKKPGASVKVSCKASGYTFT GYTMNWVRQAPGQGLEWMGLINPSSGGTYY NQKFKDRVTMTRDTSISTAYMELSRLRSDDT AVYYCARLGDNYRGYFDYWGQGTTVTVSS (SEQ ID NO: 57) | DIQLTQSPSFLSASVGDRVTITCKASQDVGTAVV WYQQKPGKAPKLLIDWASIRHTGVPSRFSGSGSG TEFTLTISSLQPEDFATYYCQQYSTYLYTFGGGT KLEIK (SEQ ID NO: 52) |
| 11.54 | QVQLVQSGAEVKKPGASVKVSCKASGYSFT GYTMNWVRQAPGQGLEWMGLINPSSGGTYY NQKFKDRVTMTRDTSISTAYMELSRLRSDDT AVYYCARLGDNYRGYFDYWGQGTTVTVSS (SEQ ID NO: 62) | DIQLTQSPSFLSASVGDRVTITCKASQDVGSAVV WYQQKPGKAPKLLIDWASIRHSGVPSRFSGSGSG TEFTLTISSLQPEDFATYYCQQYSTYLYTFGGGT KLEIK (SEQ ID NO: 63) |
| 11.55 | QVQLVQSGAEVKKPGASVKVSCKASGYSFT GYTMNWVRQAPGQGLEWMGLINPSSGGTYY NQKFKDRVTMTRDTSISTAYMELSRLRSDDT AVYYCARLGDNYRGYFDYWGQGTTVTVSS (SEQ ID NO: 62) | DIQLTQSPSFLSASVGDRVTITCRASQDVGTAVV WYQQKPGKAPKLLIDWASIRHTGVPSRFSGSGSG TEFTLTISSLQPEDFATYYCQQYSTYLYTFGGGT KLEIK (SEQ ID NO: 65) |
| 11.57 | QVQLVQSGAEVKKPGASVKVSCKASGYTFT GYTMNWVRQAPGQGLEWMGLINPSSGGTYY NQKFKDRVTMTRDTSISTAYMELSRLRSDDT AVYYCARLGDNYRGYFDYWGQGTTVTVSS (SEQ ID NO: 57) | DIQLTQSPSFLSASVGDRVTITCRASQDVGSAVV WYQQKPGKAPKLLIDWASIRHSGVPSRFSGSGSG TEFTLTISSLQPEDFATYYCQQYSTYLYTFGGGT KLEIK (SEQ ID NO: 67) |
| 12.0 | QVQLVQSGAEVKKPGASVKVSCKASGYTFT GYTMNWVRQAPGQGLEWMGLINPSTGGTY YNQKFKDRVTMTRDTSISTAYMELSRLRSDD TAVYYCARLGDNYRGYFDYWGQGTTVTVSS (SEQ ID NO: 68) | DIQLTQSPSFLSASVGDRVTITCRASQDVGTAVV WYQQKPGKAPKLLIDWASIRHTGVPSRFSGSGSG TEFTLTISSLQPEDFATYYCQQYSTYLYTFGGGT KLEIK (SEQ ID NO: 65) |
| 12.1.3 | QVQLVQSGAEVKKPGASVKVSCKASGYTFT GYTMNWVRQAPGQGLEWMGLINPSTGGTY YNQKFKDRVTMTRDTSISTAYMELSRLRSDD TAVYYCARLGDNYRGYFDYWGQGTTVTVSS (SEQ ID NO: 68) | DIQLTQSPSFLSASVGDRVTITCRASQGIGSAVVW YQQKPGKAPKLLIDWASIRHTGVPSRFSGSGSGT EFTLTISSLQPEDFATYYCQQYSTYLYTFGGGTK LEIK (SEQ ID NO: 71) |
| 12.2 | QVQLVQSGAEVKKPGASVKVSCKASGYTFT GYTMNWVRQAPGQGLEWMGLINPSTGGTY YNQKFKDRVTMTRDTSISTAYMELSRLRSDD TAVYYCARLGDNYRGYFDYWGQGTTVTVSS (SEQ ID NO: 68) | DIQLTQSPSFLSASVGDRVTITCRASQGISSYLAW YQQKPGKAPKLLIDWASIRHTGVPSRFSGSGSGT EFTLTISSLQPEDFATYYCQQYSTYLYTFGGGTK LEIK (SEQ ID NO: 75) |
| 12.3 | QVQLVQSGAEVKKPGASVKVSCKASGYTFT GYTMNWVRQAPGQGLEWMGLINPSTGGTY YNQKFKDRVTMTRDTSISTAYMELSRLRSDD TAVYYCARLGDNYRGYFDYWGQGTTVTVSS (SEQ ID NO: 68) | DIQLTQSPSFLSASVGDRVTITCRASQGISSYLAW YQQKPGKAPKLLIYWASIRHTGVPSRFSGSGSGT EFTLTISSLQPEDFATYYCQQLSTYPYTFGGGTKL EIK (SEQ ID NO: 79) |
| 13.2 | QVQLVQSGAEVKKPGASVKVSCKASGYTFT GYTMNWVRQAPGQGLEWMGLINPSTGGTY YNQKFKDRVTMTRDTSISTAYMELSRLRSDD TAVYYCARLGDNYRGYFDYWGQGTTVTVSS (SEQ ID NO: 68) | EIVMTQSPATLSVSPGERATLSCRASQDVGTAVV WYQQKPGQAPRLLIDWASIRHTGIPARFSGSGSG TEFTLTISSLQSEDFAVYYCQQYSTYLYTFGGGT KVEIK (SEQ ID NO: 80) |
| 13.4 | QVQLVQSGAEVKKPGASVKVSCKASGYTFT GYTMNWVRQAPGQGLEWMGLINPSTGGTY YNQKFKDRVTMTRDTSISTAYMELSRLRSDD TAVYYCARLGDNYRGYFDYWGQGTTVTVSS (SEQ ID NO: 68) | EIVMTQSPATLSVSPGERATLSCRASQDVGTAVV WYQQKPGQAPRLLIDWASIRHTGIPARFSGSGSG TEFTLTISSLQSEDFAVYYCQQYSTWPLTFGGGT KVEIK (SEQ ID NO: 83) |
| 13.5 | QVQLVQSGAEVKKPGASVKVSCKASGYTFT GYTMNWVRQAPGQGLEWMGLINPSTGGTY YNQKFKDRVTMTRDTSISTAYMELSRLRSDD TAVYYCARLGDNYRGYFDYWGQGTTVTVSS (SEQ ID NO: 68) | EIVMTQSPATLSVSPGERATLSCRASQSVGTAVV WYQQKPGQAPRLLIDWASIRHTGIPARFSGSGSG TEFTLTISSLQSEDFAVYYCQQYSTWPLTFGGGT KVEIK (SEQ ID NO: 86) |

TABLE B-continued

Sequences of Exemplary Antibody Variable Sequences

| Name | Heavy Chain Variable Sequence | Light Chain Variable Sequence |
|---|---|---|
| 13.6 | QVQLVQSGAEVKKPGASVKVSCKASGYTFT GYTMNWVRQAPGQGLEWMGLINPSTGGTY YNQKFKDRVTMTRDTSISTAYMELSRLRSDD TAVYYCARLGDNYRGYFDYWGQGTTVTVSS (SEQ ID NO: 68) | EIVMTQSPATLSVSPGERATLSCRASQSVGTNLA WYQQKPGQAPRLLIDWASIRHTGIPARFSGSGSG TEFTLTISSLQSEDFAVYYCQQYSTWPLTFGGGT KVEIK (SEQ ID NO: 90) |

In certain embodiments, a KLRB1-binding agent comprises a heavy chain variable region comprising heavy chain CDRs 1, 2, and 3, and a light chain variable region comprising light chain CDRs 1, 2, and 3 as shown in Tables 1-17, Table B, or Table C.

In some embodiments, a KLRB1-binding agent (e.g., an antibody) comprises a heavy chain variable region or sequence having at least about 80% (e.g., at least 90%, 95%, 97%, 99%, or 100%) sequence identity to a heavy chain variable region sequence presented herein (e.g., in Tables 1-17, Table B, or Table C), and/or a light chain variable region having at least 80% (e.g., at least 90%, 95%, 97%, 99%, or 100%) sequence identity to a light chain variable region sequence presented herein (e.g., in Tables 1-17, Table B, or Table C). The term "consensus sequence," as used herein with respect to light chain (VL) and heavy chain (VH) variable regions, refers to a composite or genericized VL or VH sequence defined based on information as to which amino acid residues within the VL or VH chain are amenable to modification without detriment to antigen binding. Thus, in a "consensus sequence" for a VL or VH chain, certain amino acid positions are occupied by one of multiple possible amino acid residues at that position. For example, if an arginine (R) or a serine(S) occur at a particular position, then that particular position within the consensus sequence can be either arginine or serine (R or S). Consensus sequences for VH and VL chain can be defined, for example, by in vitro affinity maturation (e.g., randomizing every amino acid position in a certain CDR using degenerate coding primers), by scanning mutagenesis (e.g., alanine scanning mutagenesis) of amino acid residues within the antibody CDRs, or any other methods known in the art, followed by evaluation of the binding of the mutants to the antigen to determine whether the mutated amino acid position affects antigen binding. In some aspects, mutations are introduced in the CDR regions. In other aspects, mutations are introduced in framework regions. In some other aspects, mutations are introduced in CDR and framework regions. Consensus sequences can be determined by software such as the EMBOSS Cons available at: ebi.ac.uk/Tools/msa/emboss cons/.

In some embodiments, a KLRB1-binding agent described herein (e.g., an antibody) comprises one or more constant heavy domains (e.g., CH1, CH2 and/or CH3 regions). In some embodiments, the KLRB1-binding agent comprises a constant heavy domain 1 (CH1) having an amino acid sequence set forth herein, e.g., in Tables B or C. In some embodiments, the KLRB1-binding agent comprises a constant heavy domain 2 ($CH_2$) comprising an amino acid sequence set forth herein, e.g., in Tables B or C. In some embodiments, the KLRB1-binding agent comprises a constant heavy domain 3 (CH3) comprising an amino acid sequence set forth herein, e.g., in Tables B or C. In some embodiments, the KLRB1-binding agent comprises a heavy chain constant region comprising an amino acid sequence having at least 80, 85%, 90%, 95%, 97%, or 99% sequence identity to an amino acid sequence set forth herein, e.g., in Tables B or C. In some embodiments, the one or more constant regions of the KLRB1-binding agent has/have been modified. In some embodiments, the antibodies may comprise modifications to one or more of the three heavy chain constant regions (CH1, CH2 or CH3) and/or to the light chain constant region (CL). In some embodiments, the heavy chain constant region of the modified antibodies comprises at least one human constant region. In some embodiments, the heavy chain constant region of the modified antibodies comprises more than one human constant region. In some embodiments, modifications to the constant region comprise additions, deletions, or substitutions of one or more amino acids in one or more regions. In some embodiments, one or more regions are partially or entirely deleted from the constant regions of the modified antibodies. In some embodiments, the entire CH2 domain has been removed from an antibody (ΔCH2 constructs). In some embodiments, a deleted constant region is replaced by a short amino acid spacer that provides some of the molecular flexibility typically imparted by the absent constant region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

It is known in the art that the constant region(s) of an antibody mediates several effector functions and these effector functions can vary depending on the isotype of the antibody. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), cell-mediated cytotoxicity (ADCC), antibody-dependent cellular phagocytosis (ADCP), complement-dependent cytotoxicity (CDC), release of inflammatory mediators, placental transfer, and control of immunoglobulin production. In some embodiments, an antibody comprises a variant Fc region. The amino acid sequences of the Fc region of human IgG1, IgG2, IgG3, and IgG4 are known to those of ordinary skill in the art (e.g., a representative human IgG1 Fc region is shown in Lobner et al., Immunol Rev. 2016 March; 270(1): 113-131; see, e.g., Table A, Table C). In some cases, Fc regions with amino acid variations have been identified in native antibodies. In some embodiments, a variant Fc region is engineered with substitutions at specific amino acid positions as compared to a native Fc region. In some embodiments, the Fc region is mutated to alter (reduce) antibody dependent cell-mediated cytotoxicity (ADCC), antibody induced complement dependent cytotoxicity (CDC), and/or antibody dependent cell-mediated phagocytosis (ADCP) (see, e.g., Kang and Jung, Experimental & Molecular Medicine. 2019. 51:1-9; Wang et al., Antibody Therapeutics, January 2021. 4 (1): 45-54; Lobner et al., Immunol Rev. 2016 March; 270(1): 113-131). In some embodiments, the Fc region is afucosylated (see, e.g., Yamane-Ohnuki and Satoh, MAbs. 2009 May-June; 1(3): 230-236, which describes methods for production of therapeutic antibodies with controlled levels of fucosylation of Fc region N-glycans).

In some embodiments, the modified antibodies (e.g., modified Fc region) provide for altered effector functions that, in turn, affect the biological profile of the antibody. For example, in some embodiments, the deletion or inactivation (through point mutations or other means) of a constant region enhances Fc receptor binding of the modified antibody as it circulates. In some embodiments, the constant region modifications increase the serum half-life of the antibody. In some embodiments, the constant region modifications reduce the serum half-life of the antibody. In some embodiments, the constant region modifications increase or enhance ADCC and/or complement dependent cytotoxicity (CDC) of the antibody. In some embodiments, the constant region is modified to eliminate disulfide linkages or oligosaccharide moieties. In some embodiments, the constant region is modified to add/substitute one or more amino acids to provide one or more cytotoxin, oligosaccharide, or carbohydrate attachment sites.

Modifications to the constant region of antibodies described herein may be made using well known biochemical or molecular engineering techniques. In some embodiments, antibody variants are prepared by introducing appropriate nucleotide changes into the encoding DNA, and/or by synthesis of the desired antibody or polypeptide. Using these antibody variants, it may be possible to enhance the activity or effector function provided by a specific sequence or region while substantially maintaining the structure, binding activity, and other desired characteristics of the modified antibody.

Exemplary complete full Heavy Chain (HC) and Light Chain (LC) sequences are provided in Table C.

TABLE C

Sequences of Exemplary Complete Heavy Chain (HC) and Light Chain (LC) Regions

| Name | Heavy Chain Sequence | Light Chain Sequence |
|---|---|---|
| 11.12 | QVQLVQSGAEVKKPGASVKVSCKASGYSFTGYTMNW<br>VRQAPGQGLEWMGLINPNTGGTYYNQKFKDRVTMTR<br>DTSISTAYMELSRLRSDDTAVYYCARLGDNYRGYFDY<br>WGQGTTVTVSSASTKGPSVFPLAPSSKSTSGGTAALGC<br>LVKDYFPEPVTVSWNSGALTSGVHTFPAVLQSSGLYS<br>LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV<br>KGFYPSDIAVEWESNGQPENNYKTTPPVLDSDGSFFLY<br>SKLTVDKSRWQQGNVFSCSVMHEALHNHYTQKSLSL<br>SPGK (SEQ ID NO: 91) | DIQLTQSPSFLSASVGDRVTITCKASQ<br>DVGTAVVWYQQKPGKAPKLLIDWAS<br>IRHTGVPSRFSGSGSGTEFTLTISSLQP<br>EDFADYFCQQYSTYLYTFGGGTKLEI<br>KRTVAAPSVFIFPPSDEQLKSGTASVV<br>CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 99) |
| 11.27 | QVQLVQSGAEVKKPGASVKVSCKASGYSFTGYTMNW<br>VRQAPGOGLEWMGLINPSTGGTYYNQKFKDRVTMTR<br>DTSISTAYMELSRLRSDDTAVYYCARLGDNYRGYFDS<br>WGQGTTVTVSSASTKGPSVFPLAPSSKSTSGGTAALGC<br>LVKDYFPEPVTVSWNSGALTSGVHTFPAVLQSSGLYS<br>LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV<br>KGFYPSDIAVEWESNGQPENNYKTTPPVLDSDGSFFLY<br>SKLTVDKSRWQQGNVFSCSVMHEALHNHYTQKSLSL<br>SPGK (SEQ ID NO: 92) | DIQLTQSPSFLSASVGDRVTITCKASQ<br>DVGTAVVWYQQKPGKAPKLLIDWAS<br>IRHTGVPSRFSGSGSGTEFTLTISSLQP<br>EDFADYFCQQYSTYLYTFGGGTKLEI<br>KRTVAAPSVFIFPPSDEQLKSGTASVV<br>CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 99) |
| 11.29 | QVQLVQSGAEVKKPGASVKVSCKASGYSFTGYTMNW<br>VRQAPGQGLEWMGLINPSSGGTYYNQKFKDRVTMTR<br>DTSISTAYMELSRLRSDDTAVYYCARLGDNYRGYFDS<br>WGQGTTVTVSSASTKGPSVFPLAPSSKSTSGGTAALGC<br>LVKDYFPEPVTVSWNSGALTSGVHTFPAVLQSSGLYS<br>LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV<br>KGFYPSDIAVEWESNGQPENNYKTTPPVLDSDGSFFLY<br>SKLTVDKSRWQQGNVFSCSVMHEALHNHYTQKSLSL<br>SPGK (SEQ ID NO: 93) | DIQLTQSPSFLSASVGDRVTITCKASQ<br>DVGTAVVWYQQKPGKAPKLLIDWAS<br>IRHTGVPSRFSGSGSGTEFTLTISSLQP<br>EDFADYFCQQYSTYLYTFGGGTKLEI<br>KRTVAAPSVFIFPPSDEQLKSGTASVV<br>CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 99) |
| 11.41.1 | QVQLVQSGAEVKKPGASVKVSCKASGYSFTGYTMNW<br>VRQAPGOGLEWMGLINPSTGGTYYNQKFKDRVTMTR<br>DTSISTAYMELSRLRSDDTAVYYCARLGDNYRGYFDV<br>WGQGTTVTVSSASTKGPSVFPLAPSSKSTSGGTAALGC<br>LVKDYFPEPVTVSWNSGALTSGVHTFPAVLQSSGLYS | DIQLTQSPSFLSASVGDRVTITCKASQ<br>DVGTAVVWYQQKPGKAPKLLIDWAS<br>IRHTGVPSRFSGSGSGTEFTLTISSLQP<br>EDFATYYCQQYSTYLYTFGGGTKLEI<br>KRTVAAPSVFIFPPSDEQLKSGTASVV |

TABLE C-continued

| Sequences of Exemplary Complete Heavy Chain (HC) and Light Chain (LC) Regions | | |
|---|---|---|
| Name | Heavy Chain Sequence | Light Chain Sequence |
| | LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV<br>KGFYPSDIAVEWESNGQPENNYKTTPPVLDSDGSFFLY<br>SKLTVDKSRWQQGNVFSCSVMHEALHNHYTQKSLSL<br>SPGK (SEQ ID NO: 94) | CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 100) |
| 11.44.1 | QVQLVQSGAEVKKPGASVKVSCKASGYSFTGYTMNW<br>VRQAPGQGLEWMGLINPSSGGTYYNQKFKDRVTMTR<br>DTSISTAYMELSRLRSDDTAVYYCARLGDNYRGYFDV<br>WGQGTTVTVSSASTKGPSVFPLAPSSKSTSGGTAALGC<br>LVKDYFPEPVTVSWNSGALTSGVHTFPAVLQSSGLYS<br>LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV<br>KGFYPSDIAVEWESNGQPENNYKTTPPVLDSDGSFFLY<br>SKLTVDKSRWQQGNVFSCSVMHEALHNHYTQKSLSL<br>SPGK (SEQ ID NO: 95) | DIQLTQSPSFLSASVGDRVTITCKASQ<br>DVGTAVVWYQQKPGKAPKLLIDWAS<br>IRHTGVPSRFSGSGSGTEFTLTISSLQP<br>EDFATYYCQQYSTYLYTFGGGTKLEI<br>KRTVAAPSVFIFPPSDEQLKSGTASVV<br>CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 100) |
| 11.45 | QVQLVQSGAEVKKPGASVKVSCKASGYTFTGYTMNW<br>VRQAPGQGLEWMGLINPSSGGTYYNQKFKDRVTMTR<br>DTSISTAYMELSRLRSDDTAVYYCARLGDNYRGYFDY<br>WGQGTTVTVSSASTKGPSVFPLAPSSKSTSGGTAALGC<br>LVKDYFPEPVTVSWNSGALTSGVHTFPAVLQSSGLYS<br>LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV<br>KGFYPSDIAVEWESNGQPENNYKTTPPVLDSDGSFFLY<br>SKLTVDKSRWQQGNVFSCSVMHEALHNHYTQKSLSL<br>SPGK (SEQ ID NO: 96) | DIQLTQSPSFLSASVGDRVTITCKASQ<br>DVGTAVVWYQQKPGKAPKLLIDWAS<br>IRHTGVPSRFSGSGSGTEFTLTISSLQP<br>EDFATYYCQQYSTYLYTFGGGTKLEI<br>KRTVAAPSVFIFPPSDEQLKSGTASVV<br>CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 100) |
| 11.54 | QVQLVQSGAEVKKPGASVKVSCKASGYSFTGYTMNW<br>VRQAPGQGLEWMGLINPSSGGTYYNQKFKDRVTMTR<br>DTSISTAYMELSRLRSDDTAVYYCARLGDNYRGYFDY<br>WGQGTTVTVSSASTKGPSVFPLAPSSKSTSGGTAALGC<br>LVKDYFPEPVTVSWNSGALTSGVHTFPAVLQSSGLYS<br>LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV<br>KGFYPSDIAVEWESNGQPENNYKTTPPVLDSDGSFFLY<br>SKLTVDKSRWQQGNVFSCSVMHEALHNHYTQKSLSL<br>SPGK (SEQ ID NO: 97) | DIQLTQSPSFLSASVGDRVTITCKASQ<br>DVGSAVVWYQQKPGKAPKLLIDWAS<br>IRHSGVPSRFSGSGSGTEFTLTISSLQP<br>EDFATYYCQQYSTYLYTFGGGTKLEI<br>KRTVAAPSVFIFPPSDEQLKSGTASVV<br>CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 101) |
| 11.55 | QVQLVQSGAEVKKPGASVKVSCKASGYSFTGYTMNW<br>VRQAPGOGLEWMGLINPSSGGTYYNQKFKDRVTMTR<br>DTSISTAYMELSRLRSDDTAVYYCARLGDNYRGYFDY<br>WGQGTTVTVSSASTKGPSVFPLAPSSKSTSGGTAALGC<br>LVKDYFPEPVTVSWNSGALTSGVHTFPAVLQSSGLYS<br>LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV<br>KGFYPSDIAVEWESNGQPENNYKTTPPVLDSDGSFFLY<br>SKLTVDKSRWQQGNVFSCSVMHEALHNHYTQKSLSL<br>SPGK (SEQ ID NO: 97) | DIQLTQSPSFLSASVGDRVTITCRASQ<br>DVGTAVVWYQQKPGKAPKLLIDWAS<br>IRHTGVPSRFSGSGSGTEFTLTISSLQP<br>EDFATYYCQQYSTYLYTFGGGTKLEI<br>KRTVAAPSVFIFPPSDEQLKSGTASVV<br>CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 102) |
| 11.57 | QVQLVQSGAEVKKPGASVKVSCKASGYTFTGYTMNW<br>VRQAPGQGLEWMGLINPSSGGTYYNQKFKDRVTMTR<br>DTSISTAYMELSRLRSDDTAVYYCARLGDNYRGYFDY<br>WGQGTTVTVSSASTKGPSVFPLAPSSKSTSGGTAALGC<br>LVKDYFPEPVTVSWNSGALTSGVHTFPAVLQSSGLYS<br>LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV | DIQLTQSPSFLSASVGDRVTITCRASQ<br>DVGSAVVWYQQKPGKAPKLLIDWAS<br>IRHSGVPSRFSGSGSGTEFTLTISSLQP<br>EDFATYYCQQYSTYLYTFGGGTKLEI<br>KRTVAAPSVFIFPPSDEQLKSGTASVV<br>CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 103) |

TABLE C-continued

Sequences of Exemplary Complete Heavy Chain (HC) and Light Chain (LC) Regions

| Name | Heavy Chain Sequence | Light Chain Sequence |
|---|---|---|
| | KGFYPSDIAVEWESNGQPENNYKTTPPVLDSDGSFFLY SKLTVDKSRWQQGNVFSCSVMHEALHNHYTQKSLSL SPGK (SEQ ID NO: 96) | |
| 12.0 | QVQLVQSGAEVKKPGASVKVSCKASGYTFTGYTMNW VRQAPGQGLEWMGLINPSTGGTYYNQKFKDRVTMTR DTSISTAYMELSRLRSDDTAVYYCARLGDNYRGYFDY WGQGTTVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKKVEPKS CDKTHTCPPCPAPELLGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALPA PIEKTISKAKGQPREPQVYTLPPSRDELTKNQVSLTCLV KGFYPSDIAVEWESNGQPENNYKTTPPVLDSDGSFFLY SKLTVDKSRWQQGNVFSCSVMHEALHNHYTQKSLSL SPGK (SEQ ID NO: 98) | DIQLTQSPSFLSASVGDRVTITCRASQ DVGTAVVWYQQKPGKAPKLLIDWAS IRHTGVPSRFSGSGSGTEFTLTISSLQP EDFATYYCQQYSTYLYTFGGGTKLEI KRTVAAPSVFIFPPSDEQLKSGTASVV CLLNNFYPREAKVQWKVDNALQSGN SQESVTEQDSKDSTYSLSSTLTLSKAD YEKHKVYACEVTHQGLSSPVTKSFNR GEC (SEQ ID NO: 102) |
| 12.1.3 | QVQLVQSGAEVKKPGASVKVSCKASGYTFTGYTMNW VRQAPGQGLEWMGLINPSTGGTYYNQKFKDRVTMTR DTSISTAYMELSRLRSDDTAVYYCARLGDNYRGYFDY WGQGTTVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKKVEPKS CDKTHTCPPCPAPELLGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALPA PIEKTISKAKGQPREPQVYTLPPSRDELTKNQVSLTCLV KGFYPSDIAVEWESNGQPENNYKTTPPVLDSDGSFFLY SKLTVDKSRWQQGNVFSCSVMHEALHNHYTQKSLSL SPGK (SEQ ID NO: 98) | DIQLTQSPSFLSASVGDRVTITCRASQ GIGSAVVWYQQKPGKAPKLLIDWASI RHTGVPSRFSGSGSGTEFTLTISSLQPE DFATYYCQQYSTYLYTFGGGTKLEIK RTVAAPSVFIFPPSDEQLKSGTASVVC LLNNFYPREAKVQWKVDNALQSGNS QESVTEQDSKDSTYSLSSTLTLSKAD YEKHKVYACEVTHQGLSSPVTKSFNR GEC (SEQ ID NO: 104) |
| 12.2 | QVQLVQSGAEVKKPGASVKVSCKASGYTFTGYTMNW VRQAPGQGLEWMGLINPSTGGTYYNQKFKDRVTMTR DTSISTAYMELSRLRSDDTAVYYCARLGDNYRGYFDY WGQGTTVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKKVEPKS CDKTHTCPPCPAPELLGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALPA PIEKTISKAKGQPREPQVYTLPPSRDELTKNQVSLTCLV KGFYPSDIAVEWESNGQPENNYKTTPPVLDSDGSFFLY SKLTVDKSRWQQGNVFSCSVMHEALHNHYTQKSLSL SPGK (SEQ ID NO: 98) | DIQLTQSPSFLSASVGDRVTITCRASQ GISSYLAWYQQKPGKAPKLLIDWASI RHTGVPSRFSGSGSGTEFTLTISSLQPE DFATYYCQQYSTYLYTFGGGTKLEIK RTVAAPSVFIFPPSDEQLKSGTASVVC LLNNFYPREAKVQWKVDNALQSGNS QESVTEQDSKDSTYSLSSTLTLSKAD YEKHKVYACEVTHQGLSSPVTKSFNR GEC (SEQ ID NO: 105) |
| 12.3 | QVQLVQSGAEVKKPGASVKVSCKASGYTFTGYTMNW VRQAPGQGLEWMGLINPSTGGTYYNQKFKDRVTMTR DTSISTAYMELSRLRSDDTAVYYCARLGDNYRGYFDY WGQGTTVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKKVEPKS CDKTHTCPPCPAPELLGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALPA PIEKTISKAKGQPREPQVYTLPPSRDELTKNQVSLTCLV KGFYPSDIAVEWESNGQPENNYKTTPPVLDSDGSFFLY SKLTVDKSRWQQGNVFSCSVMHEALHNHYTQKSLSL SPGK (SEQ ID NO: 98) | DIQLTQSPSFLSASVGDRVTITCRASQ GISSYLAWYQQKPGKAPKLLIYWASI RHTGVPSRFSGSGSGTEFTLTISSLQPE DFATYYCQQLSTYPYTFGGGTKLEIK RTVAAPSVFIFPPSDEQLKSGTASVVC LLNNFYPREAKVQWKVDNALQSGNS QESVTEQDSKDSTYSLSSTLTLSKAD YEKHKVYACEVTHQGLSSPVTKSFNR GEC (SEQ ID NO: 106) |
| 13.2 | QVQLVQSGAEVKKPGASVKVSCKASGYTFTGYTMNW VRQAPGQGLEWMGLINPSTGGTYYNQKFKDRVTMTR DTSISTAYMELSRLRSDDTAVYYCARLGDNYRGYFDY WGQGTTVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKKVEPKS CDKTHTCPPCPAPELLGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALPA PIEKTISKAKGQPREPQVYTLPPSRDELTKNQVSLTCLV KGFYPSDIAVEWESNGQPENNYKTTPPVLDSDGSFFLY SKLTVDKSRWQQGNVFSCSVMHEALHNHYTQKSLSL SPGK (SEQ ID NO: 98) | EIVMTQSPATLSVSPGERATLSCRASQ DVGTAVVWYQQKPGQAPRLLIDWAS IRHTGIPARFSGSGSGTEFTLTISSLQSE DFAVYYCQQYSTYLYTFGGGTKVEIK RTVAAPSVFIFPPSDEQLKSGTASVVC LLNNFYPREAKVQWKVDNALQSGNS QESVTEQDSKDSTYSLSSTLTLSKAD YEKHKVYACEVTHQGLSSPVTKSFNR GEC (SEQ ID NO: 107) |

TABLE C-continued

Sequences of Exemplary Complete Heavy Chain (HC) and Light Chain (LC) Regions

| Name | Heavy Chain Sequence | Light Chain Sequence |
| --- | --- | --- |
| 13.4 | QVQLVQSGAEVKKPGASVKVSCKASGYTFTGYTMNW<br>VRQAPGQGLEWMGLINPSTGGTYYNQKFKDRVTMTR<br>DTSISTAYMELSRLRSDDTAVYYCARLGDNYRGYFDY<br>WGQGTTVTVSSASTKGPSVFPLAPSSKSTSGGTAALGC<br>LVKDYFPEPVTVSWNSGALTSGVHTFPAVLQSSGLYS<br>LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV<br>KGFYPSDIAVEWESNGQPENNYKTTPPVLDSDGSFFLY<br>SKLTVDKSRWQQGNVFSCSVMHEALHNHYTQKSLSL<br>SPGK (SEQ ID NO: 98) | EIVMTQSPATLSVSPGERATLSCRASQ<br>DVGTAVVWYQQKPGQAPRLLIDWAS<br>IRHTGIPARFSGSGSGTEFTLTISSLQSE<br>DFAVYYCQQYSTWPLTFGGGTKVEI<br>KRTVAAPSVFIFPPSDEQLKSGTASVV<br>CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 108) |
| 13.5 | QVQLVQSGAEVKKPGASVKVSCKASGYTFTGYTMNW<br>VRQAPGOGLEWMGLINPSTGGTYYNQKFKDRVTMTR<br>DTSISTAYMELSRLRSDDTAVYYCARLGDNYRGYFDY<br>WGQGTTVTVSSASTKGPSVFPLAPSSKSTSGGTAALGC<br>LVKDYFPEPVTVSWNSGALTSGVHTFPAVLQSSGLYS<br>LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV<br>KGFYPSDIAVEWESNGQPENNYKTTPPVLDSDGSFFLY<br>SKLTVDKSRWQQGNVFSCSVMHEALHNHYTQKSLSL<br>SPGK (SEQ ID NO: 98) | EIVMTQSPATLSVSPGERATLSCRASQ<br>SVGTAVVWYQQKPGQAPRLLIDWAS<br>IRHTGIPARFSGSGSGTEFTLTISSLQSE<br>DFAVYYCQQYSTWPLTFGGGTKVEI<br>KRTVAAPSVFIFPPSDEQLKSGTASVV<br>CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 109) |
| 13.6 | QVQLVQSGAEVKKPGASVKVSCKASGYTFTGYTMNW<br>VRQAPGQGLEWMGLINPSTGGTYYNQKFKDRVTMTR<br>DTSISTAYMELSRLRSDDTAVYYCARLGDNYRGYFDY<br>WGQGTTVTVSSASTKGPSVFPLAPSSKSTSGGTAALGC<br>LVKDYFPEPVTVSWNSGALTSGVHTFPAVLQSSGLYS<br>LSSVVTVPSSSLGTQTYICNVNHKPSNTKVDKKVEPKS<br>CDKTHTCPPCPAPELLGGPSVFLFPPKPKDTLMISRTPE<br>VTCVVVDVSHEDPEVKFNWYVDGVEVHNAKTKPREE<br>QYNSTYRVVSVLTVLHQDWLNGKEYKCKVSNKALPA<br>PIEKTISKAKGQPREPQVYTLPPSRDELTKNQVSLTCLV<br>KGFYPSDIAVEWESNGQPENNYKTTPPVLDSDGSFFLY<br>SKLTVDKSRWQQGNVFSCSVMHEALHNHYTQKSLSL<br>SPGK (SEQ ID NO: 98) | EIVMTQSPATLSVSPGERATLSCRASQ<br>SVGTNLAWYQQKPGQAPRLLIDWASI<br>RHTGIPARFSGSGSGTEFTLTISSLQSE<br>DFAVYYCQQYSTWPLTFGGGTKVEI<br>KRTVAAPSVFIFPPSDEQLKSGTASVV<br>CLLNNFYPREAKVQWKVDNALQSGN<br>SQESVTEQDSKDSTYSLSSTLTLSKAD<br>YEKHKVYACEVTHQGLSSPVTKSFNR<br>GEC (SEQ ID NO: 110) |

In some embodiments, a KLRB1-binding agent (e.g., an antibody) as described herein comprises a heavy chain region having at least about 80% (e.g., at least 90%, 95%, 97%, 99%, or 100%) sequence identity to a HC sequence set forth in Table C, and/or a light chain region having at least about 80% (e.g., at least 90%, 95%, 97%, 99%, or 100%) sequence identity to a LC sequence set forth in Table C. In some embodiments, the VH comprises or consists of an amino acid sequence having at least 95% sequence identity to the VH amino acid sequence set forth in Table C, and the VL comprises or consists of an amino acid sequence having at least 95% sequence identity to the VL amino acid sequence set forth in Table C.

The present disclosure further embraces additional variants and equivalents that are substantially homologous to the recombinant, monoclonal, chimeric, humanized, and human antibodies, or antibody fragments thereof, described herein. In some embodiments, it is desirable to improve the binding affinity of the antibody. In some embodiments, it is desirable to modulate biological properties of the antibody, including but not limited to, specificity, thermostability, expression level, effector function(s), glycosylation, immunogenicity, or solubility. Those skilled in the art will appreciate that amino acid changes may alter post-translational processes of an antibody, such as changing the number or position of glycosylation sites or altering membrane anchoring characteristics.

Variations may be a substitution, deletion, or insertion of one or more nucleotides encoding the antibody or polypeptide that results in a change in the amino acid sequence as compared with the native antibody or polypeptide sequence. In some embodiments, amino acid substitutions are the result of replacing one amino acid with another amino acid having similar structural and/or chemical properties, such as the replacement of a leucine with a serine, e.g., conservative amino acid replacements. Insertions or deletions may optionally be in the range of about 1 to 5 amino acids. In some embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. In some embodiments, variations in the amino acid sequence that are biologically useful and/or relevant are determined by systematically making insertions, deletions, or substitutions in the sequence and testing the resulting variant proteins for activity as compared to the parental antibody.

In some embodiments, variants may include addition of amino acid residues at the amino- and/or carboxyl-terminal end of the antibody or polypeptide. The length of additional amino acids residues may range from one residue to a hundred or more residues. In some embodiments, a variant comprises an N-terminal methionyl residue. In some embodiments, the variant comprises an additional polypeptide/protein, i.e., a fusion protein. In some embodiments, a variant is engineered to be detectable and may comprise a detectable label and/or protein (e.g., an enzyme).

In some embodiments, a cysteine residue not involved in maintaining the proper conformation of an antibody may be substituted or deleted to modulate the antibody's characteristics, for example, to improve oxidative stability and/or prevent aberrant disulfide crosslinking. Conversely, in some embodiments, one or more cysteine residues may be added to create disulfide bond(s) to improve stability.

The variant antibodies or polypeptides described herein may be generated using methods known in the art, including but not limited to, site-directed mutagenesis, alanine scanning mutagenesis, and PCR mutagenesis.

In some embodiments, KLRB1-binding agents described herein are chemically modified. In some embodiments, the KLRB1-binding agents are anti-KLRB1 antibodies that have been chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications may be carried out by known techniques.

The present disclosure encompasses KLRB1-binding agents built upon non-immunoglobulin backbones, wherein the agents bind to the same epitope or essentially the same epitope as an anti-KLRB1 antibody disclosed herein. In some embodiments, a non-immunoglobulin-based binding agent is an agent that competes with an anti-KLRB1 antibody described herein in a competitive binding assay. In some embodiments, alternative KLRB1-binding agents comprise a scaffold protein. Generally, scaffold proteins can be assigned to one of three groups based on the architecture of their backbone (1) scaffolds consisting of α-helices; (2) small scaffolds with few secondary structures or an irregular architecture of α-helices and β-sheets; and (3) scaffolds consisting of predominantly β-sheets. Scaffold proteins include, but are not limited to, anticalins, which are based upon the lipocalin scaffold; adnectins, which are based on the 10th domain of human fibronectin type 3; affibodies, which are based on the B-domain in the Ig-binding region of *Staphylococcus aureus* protein A; darpins, which are based on ankyrin repeat domain proteins; fynomers, which are based on the SH3 domain of the human Fyn protein kinase; affitins, which are based on Sac7d from *Sulfolobus acidocaldarius*; affilins, which are based on human γ-B-crystallin or human ubiquitin; avimers, which are based on the A-domains of membrane receptor proteins; knottins (cysteine knot miniproteins), which are based upon a stable 30-amino acid anti-parallel β-strand protein fold; and Kunitz domain inhibitor scaffolds, which are based upon a structure that contains three disulfide bonds and three loops. In some embodiments, a KLRB1-binding agent comprises an engineered scaffold protein comprising a heavy chain CDR1, CDR2, and CDR3 and a light chain CDR1, CDR2, and CDR3 shown in any one of Table 1 to 17, e.g., in Table 14, 4, or 10.

In general, antigen-antibody interactions are non-covalent and reversible, formed by a combination of hydrogen bonds, hydrophobic interactions, electrostatic and van der Waals forces. When describing the strength of an antigen-antibody complex, the terms affinity and/or avidity are commonly used mentioned. The binding of an antibody to its antigen is a reversible process, and the affinity of the binding is typically reported as an equilibrium dissociation constant ($K_D$). $K_D$ is the ratio of an antibody dissociation rate ($k_{off}$) (how quickly it dissociates from its antigen) to the antibody association rate ($k_{on}$) (how quickly it binds to its antigen). In some embodiments, $K_D$ values are determined by measuring the $k_{on}$ and $k_{off}$ rates of a specific antibody/antigen interaction and then using a ratio of these values to calculate the $K_D$ value. $K_D$ values may be used to evaluate and rank order the strength of individual antibody/antigen interactions. The lower the $K_D$ of an antibody, the higher the affinity of the antibody for its target. In some embodiments, affinity is measured using SPR technology in a Biacore system. Avidity gives a measure of the overall strength of an antibody-antigen complex. It is dependent on three major parameters: (i) affinity of the antibody for the target, (ii) valency of both the antibody and antigen, and (iii) structural arrangement of the parts that interact.

In some embodiments, a KLRB1-binding agent (e.g., an antibody) binds KLRB1 (e.g., human KLRB1) with a dissociation constant ($K_D$) of about 1 μM or less, about 100 nM or less, about 40 nM or less, about 20 nM or less, about 10 nM or less, about 1 nM or less, about 0.1 nM or less, 50 pM or less, 10 pM or less, or 1 pM or less. In some embodiments, a KLRB1-binding agent binds KLRB1 (e.g., human KLRB1) with a $K_D$ of about 20 nM or less. In some embodiments, a KLRB1-binding agent binds KLRB1 (e.g., human KLRB1) with a $K_D$ of about 10 nM or less. In some embodiments, a KLRB1-binding agent binds KLRB1 (e.g., human KLRB1) with a $K_D$ of about 1 nM or less. In some embodiments, a KLRB1-binding agent binds KLRB1 (e.g., human KLRB1) with a $K_D$ of about 0.5 nM or less. In some embodiments, a KLRB1-binding agent binds KLRB1 (e.g., human KLRB1) with a $K_D$ of about 0.1 nM or less. In some embodiments, a KLRB1-binding agent binds KLRB1 (e.g., human KLRB1) with a $K_D$ of about 50 pM or less. In some embodiments, a KLRB1-binding agent binds KLRB1 (e.g., human KLRB1) with a $K_D$ of about 25 pM or less. In some embodiments, a KLRB1-binding agent binds KLRB1 (e.g., human KLRB1) with a $K_D$ of about 10 pM or less. In some embodiments, a KLRB1-binding agent binds KLRB1 (e.g., human KLRB1) with a $K_D$ of about 1 pM or less. In some embodiments, the dissociation constant of the binding agent (e.g., an antibody) for KLRB1 is the dissociation constant determined using a KLRB1 protein immobilized on a Biacore chip and the binding agent flowed over the chip. In some embodiments, the dissociation constant of the binding agent (e.g., an antibody) for KLRB1 is the dissociation constant determined using the binding agent captured by an anti-human IgG antibody on a Biacore chip and soluble KLRB1 flowed over the chip.

In some embodiments, a KLRB1-binding agent (e.g., an antibody) binds KLRB1 (e.g., human KLRB1) with a half maximal effective concentration (EC50) of about 1 μM or less, about 100 nM or less, about 40 nM or less, about 20 nM or less, about 10 nM or less, about 1 nM or less, or about 0.1 nM or less. In some embodiments, a KLRB1-binding agent binds to human KLRB1 with an EC50 of about 1 μM or less, about 100 nM or less, about 40 nM or less, about 20 nM or less, about 10 nM or less, about 1 nM or less, or about 0.1 nM or less. In some embodiments, a KLRB1-binding agent binds cyno KLRB1 and/or human KLRB1 with an EC50 Of about 40 nM or less, about 20 nM or less, about 10 nM or less, about 1 nM or less or about 0.1 nM or less.

The KLRB1-binding agents (e.g., antibodies) described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof. In some embodiments, a DNA sequence encoding a polypeptide of interest is constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In some embodiments, recombinant expression vectors are used to amplify and express DNA encoding antibodies, or fragments thereof, against human KLRB1. For example, recombinant expression vectors can be replicable DNA constructs which have synthetic or cDNA-derived DNA fragments encoding a polypeptide chain of a KLRB1-binding agent, such as an anti-KLRB1 antibody, or antigen-binding fragment thereof, operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide may include an N-terminal methionine residue. This residue can optionally be subsequently cleaved from the expressed recombinant protein to provide a final product.

The choice of an expression control sequence and an expression vector generally depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

The KLRB1-binding agents (e.g., antibodies) of the present disclosure can be expressed from one or more vectors. For example, in some embodiments, a heavy chain polypeptide is expressed by one vector and a light chain polypeptide is expressed by a second vector. In some embodiments, a heavy chain polypeptide and a light chain polypeptide are expressed by one vector.

Suitable host cells for expression of a KLRB1-binding agent (e.g., an antibody) or a KLRB1 protein or fragment thereof to use as an antigen or immunogen include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described herein. Cell-free translation systems may also be employed. Appropriate cloning and expression vectors for use with bacterial, fungal, yeast, and mammalian cellular hosts, as well as methods of protein production, including antibody production are well known in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art. Thus, the present disclosure provides cells comprising the KLRB1-binding agents described herein. In some embodiments, the cells produce the KLRB1-binding agents described herein. In some embodiments, the cells produce an antibody. In some embodiments, the cells produce an antibody that binds human KLRB1. In some embodiments, the cells produce an antibody that binds cyno KLRB1. In some embodiments, the cells produce an antibody that binds human KLRB1 and cyno KLRB1. In some embodiments, the cells produce an antibody designated 11.12, 11.27, 11.29, 11.41.1, 11.44.1, 11.45, 11.54, 11.55, 11.57, 12.0, 12.1.3, 12.2, 12.3, 13.2, 13.4, 13.5, 13.6, or variants thereof. In some embodiments, the cells produce a scFv version of antibody 11.12, 11.27, 11.29, 11.41.1, 11.44.1, 11.45, 11.54, 11.55, 11.57, 12.0, 12.1.3, 12.2, 12.3, 13.2, 13.4, 13.5, or 13.6. In some embodiments, the cell is a prokaryotic cell (e.g., *E. coli*). In some embodiments, the cell is an eukaryotic cell. In some embodiments, the cell is a mammalian cell. In some embodiments, the cell is a hybridoma cell. Proteins produced by a host cell can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column. Affinity chromatography used for purifying immunoglobulins can include Protein A, Protein G, and Protein L chromatography. Isolated proteins can be physically characterized using such techniques as proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF). In some embodiments, supernatants from expression systems which secrete recombinant protein into culture media are first concentrated using a commercially available protein concentration filter, for example, an Amicon® or Millipore Pellicon® ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT). In some embodiments, one or more reverse-phase HPLC steps employing hydrophobic RP-HPLC media, e.g., silica gel having pendant methyl or other aliphatic groups, are employed to further purify a recombinant protein. In some embodiments, hydrophobic interaction chromatography (HIC) is used to separate recombinant proteins based on their hydrophobicity. HIC is a useful separation technique for purifying proteins while maintaining biological activity due to the use of conditions and matrices that operate under less denaturing conditions than some other techniques. Some or all of the foregoing purification steps, in various combinations, can be employed to provide a homogeneous recombinant protein.

Anti-KLRB1 antibodies of the present disclosure may be analyzed for their physical/chemical properties and/or biological activities by various assays known in the art. In some embodiments, an anti-KLRB1 antibody is tested for its ability to bind KLRB1 (e.g., human KLRB1 and/or cyno KLRB1). Binding assays include, but are not limited to, SPR (e.g., Biacore), ELISA, and FACS. In some embodiments, an anti-KLRB1 antibody is tested for its ability to induce ADCC, ADCP, and/or CDC, as well as the ability of the antibody to kill KLRB1 target cells (cell depletion). Assays include, but are not limited to, ADCC cell lysis assays, e.g., that use LDH release and detection of formazan salt. In addition, antibodies may be evaluated for solubility, stability, thermostability, viscosity, expression levels, expression quality, and/or purification efficiency.

In some embodiments, purified anti-KLRB1 antibodies are characterized by assays including, but not limited to, N-terminal sequencing, amino acid analysis, high pressure liquid chromatography (HPLC), mass spectrometry, ion exchange chromatography, and papain digestion.

Antibody Conjugates

The present disclosure also provides conjugates comprising an anti-KLRB1 antibody or antigen-binding fragment thereof described herein. In some embodiments, the antibody or antigen-binding fragment thereof is attached to a second molecule. In some embodiments, the antibody or antigen-binding fragment thereof is conjugated to a cytotoxic agent or moiety. In some embodiments, the antibody or antigen-binding fragment thereof is conjugated to a cytotoxic agent to form an ADC (antibody-drug conjugate). In some embodiments, the cytotoxic agent is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic agent is a microtubule inhibitor including, but not limited to, auristatins, maytansinoids (e.g., DM1 and DM4), and tubulysins. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, an antibody is conjugated to one or more small molecule toxins, such as calicheamicins, maytansinoids, trichothenes, and CC1065. A derivative of any one of these toxins may be used as long as the derivative retains the cytotoxic activity of the parent molecule.

Conjugates comprising an anti-KLRB1 antibody or antigen-binding fragment thereof described herein can be made using any suitable method known in the art. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, an anti-KLRB1 antibody or antigen-binding fragment thereof described herein is conjugated to a detectable substance or molecule that allows the antibody to be used for diagnosis and/or detection. A detectable substance can include but is not limited to, enzymes, such as horseradish peroxidase, alkaline phosphatase, beta-galactosidase, and acetylcholinesterase; prosthetic groups, such as biotin and flavine(s); fluorescent materials, such as, umbelliferone, fluorescein, fluorescein isothiocyanate (FITC), rhodamine, tetramethylrhodamine isothiocyanate (TRITC), dichlorotriazinylamine fluorescein, dansyl chloride, cyanine (Cy3), and phycoerythrin; bioluminescent materials, such as luciferase; radioactive materials, such as $^{212}$Bi, $^{14}$C, $^{57}$Co, $^{51}$Cr, $^{67}$Cu, $^{18}$F, $^{68}$Ga, $^{67}$Ga, $^{153}$Gd, $^{159}$Gd, $^{68}$Ge, $^{3}$H, $^{166}$Ho, $^{131}$I, $^{125}$I, $^{123}$I, $^{121}$I, $^{115}$In, $^{113}$In, $^{112}$In, $^{111}$In, $^{140}$La, $^{177}$Lu, $^{54}$Mn, $^{99}$Mo, $^{32}$P, $^{103}$Pd, $^{149}$Pm, $^{142}$Pr, $^{186}$Re, $^{188}$Re, $^{105}$Rh, $^{97}$Ru, $^{35}$S, $^{47}$Sc, $^{75}$Se, $^{153}$Sm, $^{113}$Sn, $^{117}$Sn, $^{85}$Sr, $^{99m}$Tc, $^{201}$Ti, $^{133}$Xe, $^{90}$Y, $^{69}$Yb, $^{175}$Yb, $^{65}$Zn; positron emitting metals; and magnetic metal ions.

An anti-KLRB1 antibody or antigen-binding fragment thereof described herein can also be conjugated to a second antibody to form an antibody heteroconjugate.

An anti-KLRB1 antibody or antigen-binding fragment thereof as described herein may be attached to a solid support. Such solid supports include, but are not limited to, glass, cellulose, polyacrylamide, nylon, polystyrene, polyvinyl chloride, or polypropylene. In some embodiments, immobilized anti-KLRB1 antibodies are used in immunoassays. In some embodiments, immobilized anti-KLRB1 antibodies are used in purification of the target antigen.

Polynucleotides/Methods of Making Binding Agents

Also provided herein are nucleic acids encoding a polypeptide described herein and vectors, preferably expression vectors, containing the nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein that encode a KLRB1 binding agent as described herein.

The recombinant expression vectors of the invention can be designed for expression of KLRB1 binding agent proteins in prokaryotic cells. Preferably, the KLRB1 binding agents can be expressed in mammalian cells, preferably human cells. See, e.g., Frenzel et al., Front Immunol. 2013; 4:217. When used in mammalian cells, the expression vector's control functions are often provided by viral regulatory elements. For example, commonly used promoters are derived from polyoma, Adenovirus 2, cytomegalovirus and Simian Virus 40.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell can be used to produce (i.e., express) a KLRB1 binding agent protein. Accordingly, the invention further provides methods for producing a KLRB1 binding agent protein using the host cells of the invention. In one embodiment, the method includes culturing the host cell of the invention (into which a recombinant expression vector encoding a KLRB1 binding agent protein has been introduced) in a suitable medium such that a KLRB1 binding agent protein is produced. In another embodiment, the method further includes isolating a KLRB1 binding agent protein from the medium or the host cell. In some embodiments, the Fc region is afucosylated (see, e.g., Yamane-Ohnuki and Satoh, MAbs. 2009 May-June; 1(3): 230-236, which describes methods for production of therapeutic antibodies with controlled levels of fucosylation of Fc region N-glycans).

Pharmaceutical Compositions

Also provided herein are pharmaceutical compositions comprising a KLRB1-binding agent as described herein as an active ingredient. In various embodiments, the KLRB1 binding agent is prepared as a pharmaceutical composition, for example as a pharmaceutical composition for use as a medicament. In various embodiments, the pharmaceutical composition is for use as a medicament for treating a disease as described herein, optionally an autoimmune disease, an allergic disease, a transplant rejection, or a hematologic malignancy, in a subject in need thereof. In some embodiments, the autoimmune disease is rheumatoid arthritis, Sjögren's syndrome, inclusion body myositis (IBM), discoid lupus, psoriasis, idiopathic pulmonary fibrosis, diabetes, alopecia universalis, primary biliary cholangitis, multiple sclerosis, lymphocytic colitis, palmoplantar pustulosis, hidradenitis suppurativa, Crohn's disease, ulcerative colitis, or celiac disease. In some embodiments, the allergic disease is asthma, allergic eosinophilic asthma, allergy, atopic dermatitis, nasal polyposis, eosinophilic gastrointestinal disorder, or hypereosinophilic syndrome. In some embodiments, the transplant rejection can be a rejection of a kidney, lung, heart, liver, limb, skin, or multi-organ transplant. In some embodiments, the hematological malignancy is a leukemia, e.g., T cell leukemia, NK cell leukemia, T cell lymphoma, or large granular lymphocytic leukemia (LGLL). In some embodiments, the lymphoma is hepatosplenic T cell lymphoma (HSTCL), NK/T cell lymphomas (NKTCL), extranodal NK/T cell lymphomas (ENKL), aggressive NK cell leukemia (ANKL), mycosis fungoides, Sezary syndrome, peripheral T cell lymphoma, angioimmunoblastic T cell lymphoma (AITL), and peripheral T cell lymphoma not otherwise specified (PTCL-NOS). In some embodiments, the leukemia is aggressive NK cell leukemia or T cell prolymphocytic leukemia.

One skilled in the art can formulate the KLRB1-binding agent as a pharmaceutical composition according to known methods.

Pharmaceutical compositions can include a carrier. "Carriers" as used herein can include pharmaceutically acceptable carriers, excipients, or stabilizers that are nontoxic (or relatively non-toxic) to the cell or subject being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

In various embodiments, the KLRB1 binding agent is comprised in an injectable formulation, for example, a subcutaneous, intravenous, intramuscular, intrathecal or intraperitoneal injection formulation. Injectable formulations can be aqueous solutions, for example in physiologically compatible buffers such as Hanks' solution, Ringer's solution, or physiological saline buffer. The injectable formulation can contain formulatory agents such as suspending, stabilizing and/or dispersing agents. Alternatively, the KLRB1 binding agent can be in a dried or powder form for constitution with a suitable vehicle, e.g., sterile pyrogen-free water, before use.

The binding agents of the present disclosure can be formulated in any suitable form for delivery to a target cell/tissue. In some embodiments, a KLRB1-binding agent can be formulated as a liposome, microparticle, microcapsule, albumin microsphere, microemulsion, nano-particle, nanocapsule, or macroemulsion. In some embodiments, the pharmaceutical formulation includes an agent of the present disclosure complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE).

In some embodiments, a KLRB1-binding agent is formulated as a sustained-release preparation. Suitable examples of sustained-release preparations include semi-permeable matrices of solid hydrophobic polymers containing an agent, where the matrices are in the form of shaped articles (e.g., films or microcapsules). Sustained-release matrices include but are not limited to polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

Treatment and Administration

The disclosure provides methods comprising administering a KLRB1 binding agent as described herein, or a pharmaceutical composition comprising a KLRB1 binding agent as described herein, to a subject in need thereof. In some embodiments, the subject is a human. In some embodiments, the methods are carried out in vivo (e.g., as opposed to ex vivo). As used herein, "treatment" refers to therapeutic treatment (treating a subject who has a disease); the methods can also be used for prophylactic or preventative measures, wherein the object is to prevent or slow down (lessen) the targeted pathologic condition or disorder, in a subject who does not have the disease. Those in need of treatment can include those already with the disorder, those prone to have the disorder, or those in whom the disorder is to be prevented (as used herein, "prevent" means to reduce the risk of developing).

In various aspects and embodiments, the disclosure provides methods for treating an autoimmune disease, an allergic disease, a transplant rejection, or a hematologic malignancy, in a subject in need thereof. As described herein, KLRB1 expressing cells are implicated in the pathogenesis of these diseases. In accordance with the present disclosure, depletion of such KLRB1 expressing cells provides a therapeutic benefit. In some embodiments, the autoimmune disease is rheumatoid arthritis, Sjögren's syndrome, inclusion body myositis (IBM), discoid lupus, psoriasis, idiopathic pulmonary fibrosis, diabetes, alopecia universalis, primary biliary cholangitis, multiple sclerosis, lymphocytic colitis, palmoplantar pustulosis, hidradenitis suppurativa, Crohn's disease, ulcerative colitis, or celiac disease. In some embodiments, the allergic disease is asthma, allergic eosinophilic asthma, allergy, atopic dermatitis, nasal polyposis, eosinophilic gastrointestinal disorder, or hypereosinophilic syndrome. In some embodiments, the transplant rejection can be a rejection of a kidney, lung, heart, liver, limb, skin, or multi-organ transplant. In some embodiments, the hematological malignancy is a leukemia, e.g., T cell leukemia, NK cell leukemia, T cell lymphoma, T cell prolymphocytic leukemia (T-PLL), or large granular lymphocytic leukemia (LGLL). In some embodiments, the lymphoma is hepatosplenic T cell lymphoma (HSTCL), NK/T cell lymphomas (NKTCL), extranodal NK/T cell lymphomas (ENKL), aggressive NK cell leukemia (ANKL), mycosis fungoides, Sezary syndrome, peripheral T cell lymphoma, angioimmunoblastic T cell lymphoma (AITL), and peripheral T cell lymphoma not otherwise specified (PTCL-NOS). In some embodiments, the leukemia is aggressive NK cell leukemia or T cell prolymphocytic leukemia.

In various aspects and embodiments, the disclosure provides methods for treating or preventing transplant rejection. The transplant rejection can be, for example, kidney rejection.

"Administration" and "treatment," as it applies to an animal, human, experimental subject, cell, tissue, organ, or biological fluid, can include contacting an exogenous pharmaceutical, therapeutic agent, diagnostic agent, or composition to the animal, human, subject, cell, tissue, organ, or biological fluid. "Administration" and "treatment" include in vivo, as well as in some embodiments in vitro or ex vivo treatments.

Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom can vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom.

As such, in various embodiments, the term "effective amount" or therapeutically effective amount" is a concentration or amount of the KLRB1 binding agent that results in achieving a particular stated purpose, e.g., reduction in one or more symptoms of a disease described herein. An "effective amount" of a KLRB1 binding agent can be determined empirically. Furthermore, a "therapeutically effective amount" is a concentration or amount of a KLRB1 binding agent which is effective for achieving a stated therapeutic effect. This amount can also be determined empirically.

In some embodiments, treatment with the KLRB1-binding agents of the disclosure can kill at least about 20%, e.g., at least about 30%, 40%, 50%, 60%, 70%, or 80% of the KLRB1 expressing cells that are implicated in the pathogenesis of the diseases disclosed herein.

The term “subject” refers to any animal (e.g., a mammal), including, but not limited to, humans and non-human veterinary subjects including non-human primates.

As used herein, reference to “about” or “approximately” a value or parameter includes (and describes) embodiments that are directed to that value or parameter. For example, a description referring to “about X” includes description of “X”. “About” as used herein means plus or minus 10 percent.

As used in the present disclosure and claims, the singular forms “a”, “an” and “the” include plural forms unless the context clearly dictates otherwise.

It is understood that wherever embodiments are described herein with the term “comprising” otherwise analogous embodiments described in terms of “consisting of” and/or “consisting essentially of” are also provided. It is also understood that wherever embodiments are described herein with the phrase “consisting essentially of” otherwise analogous embodiments described in terms of “consisting of” are also provided.

The term “and/or” as used in a phrase such as “A and/or B” herein is intended to include both A and B; A or B; A (alone); and B (alone). Likewise, the term “and/or” as used in a phrase such as “A, B, and/or C” is intended to encompass each of the following embodiments: A, B, and C; A, B, or C; A or C; A or B; B or C; A and C; A and B; B and C; A (alone); B (alone); and C (alone).

In various embodiments, the KLRB1 binding agent can be administered by providing an mRNA encoding the binding agent to the subject.

The following examples are illustrative and not restrictive. Many variations of the technology will become apparent to those of skill in the art upon review of this disclosure. The scope of the technology should, therefore, be determined not with reference to the examples, but instead should be determined with reference to the appended claims along with their full scope of equivalents.

EXAMPLES

Example 1: Gene Expression of KLRB1 Marks a Unique Collection of Immune Cells, and is Limited to Immune Cells KLRB1 expression cuts across traditional lymphocyte classification and marks Th17, Th17.1, ex-Th17, Tc17, iNKTs, ILC2, ILC3, peTh2, and a subset of NK cells (FIG. 1).

Figure 2:
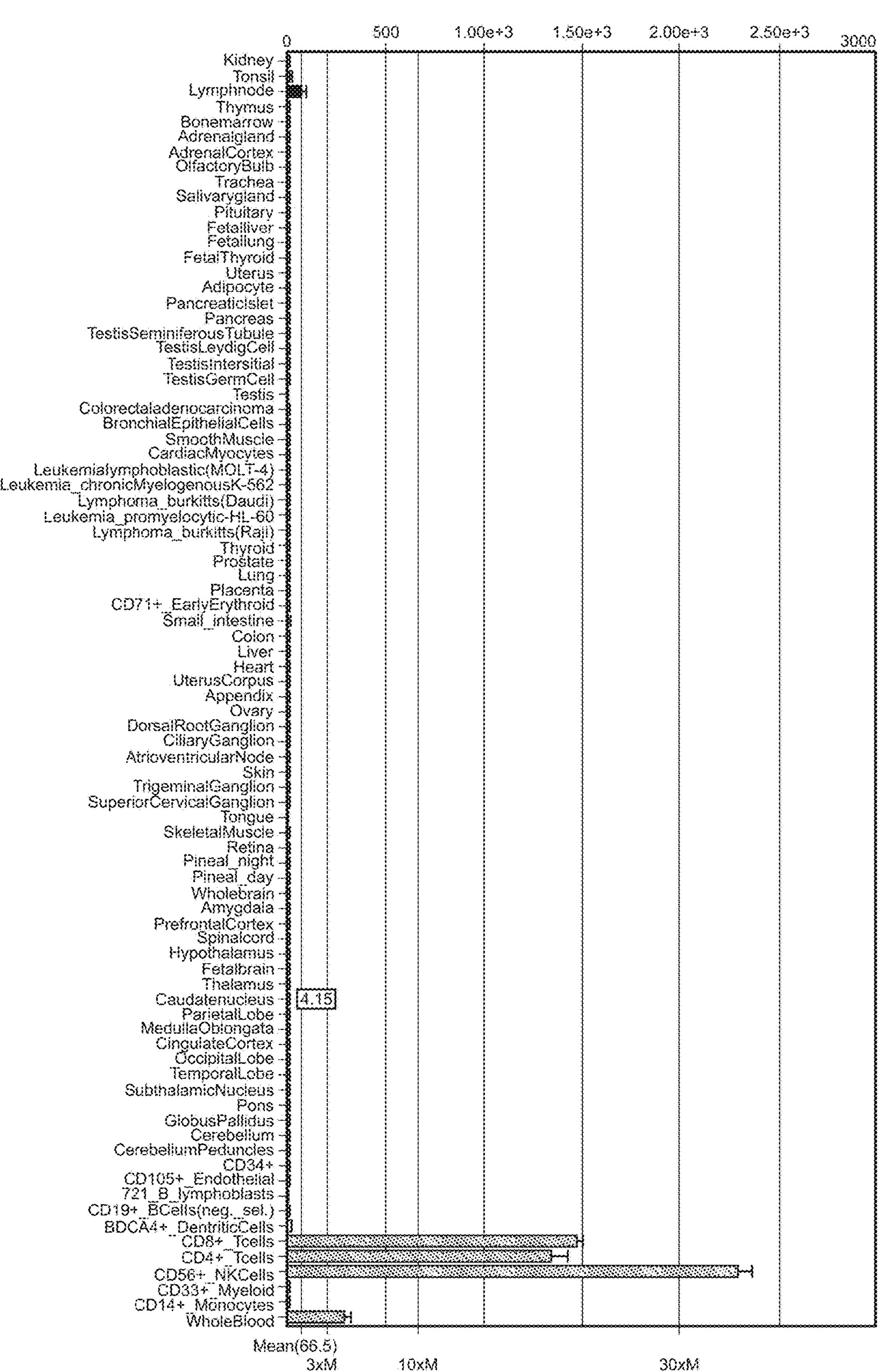
FIG. 2 shows body-wide KLRB1 expression profiling data indicating that KLRB1 has no significant expression on any cell type other than immune cells

Body-wide KLRB1 expression profiling data indicates KLRB1 has no significant expression on any cell type other than immune cells (FIG. 2).

Example 2: KLRB1 Expression is Enhanced in Various Immune Conditions

Figure 3:
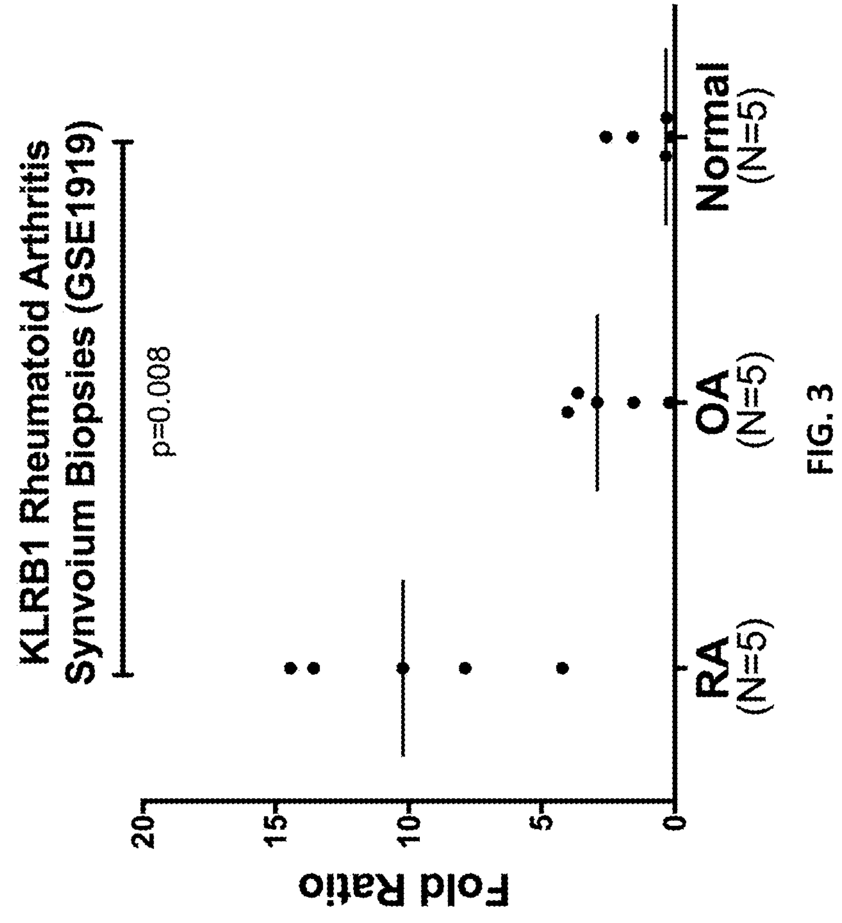
FIG. 3 shows KLRB1 is overexpressed in rheumatoid arthritis synovium compared to osteoarthritis and normal synovium.

Rheumatoid arthritis: Analysis of expression data (GSE1919) from synovium biopsies from patients with rheumatoid arthritis compared to normal patients shows increased expression of KLRB1 (10 fold ratio) (FIG. 3). Accordingly, rheumatoid arthritis is a particularly attractive target for therapies according to the present disclosure.

Figure 4:
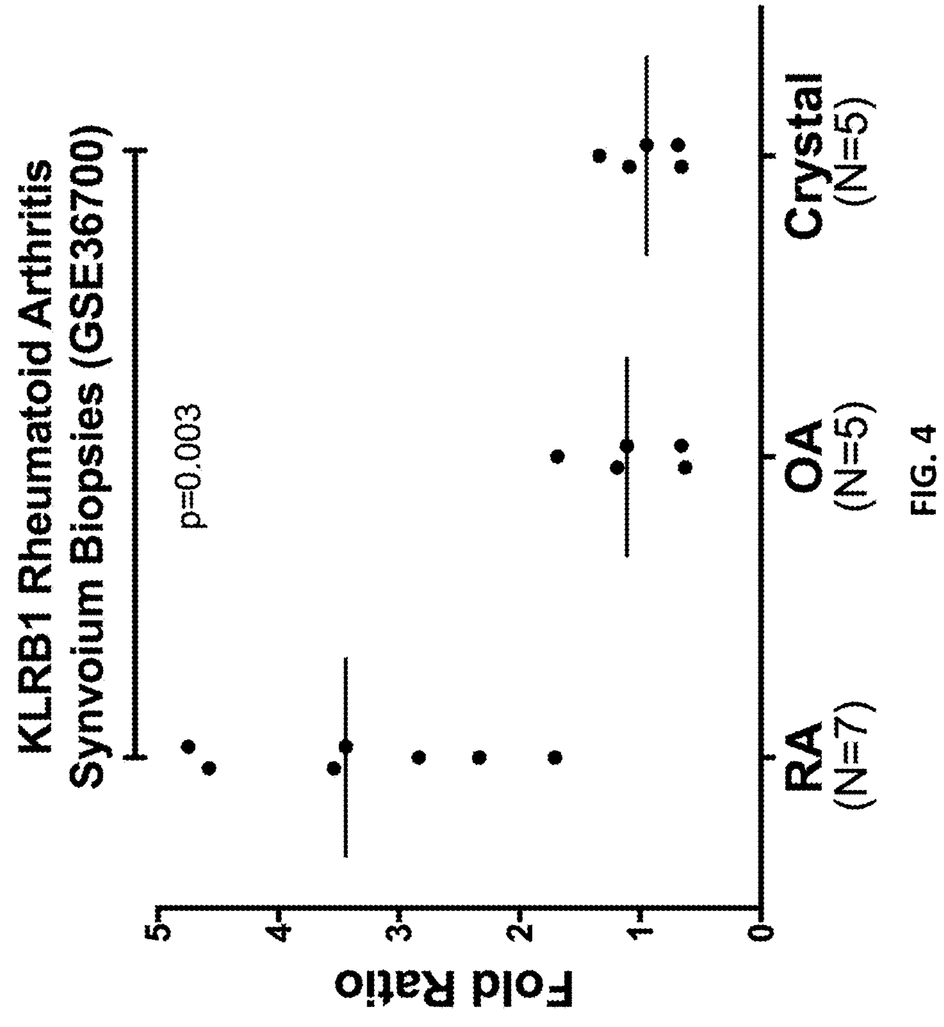
FIG. 4 shows KLRB1 is overexpressed in rheumatoid arthritis synovium compared to osteoarthritis and crystal-induced arthritis synovium.

Analysis of expression data (GSE36700) from synovium biopsies from patients with rheumatoid arthritis compared to crystal-induced arthritis patients shows increased expression of KLRB1 (3.3 fold ratio) (FIG. 4). Accordingly, rheumatoid arthritis is a particularly attractive target for therapies according to the present disclosure.

Figure 5:
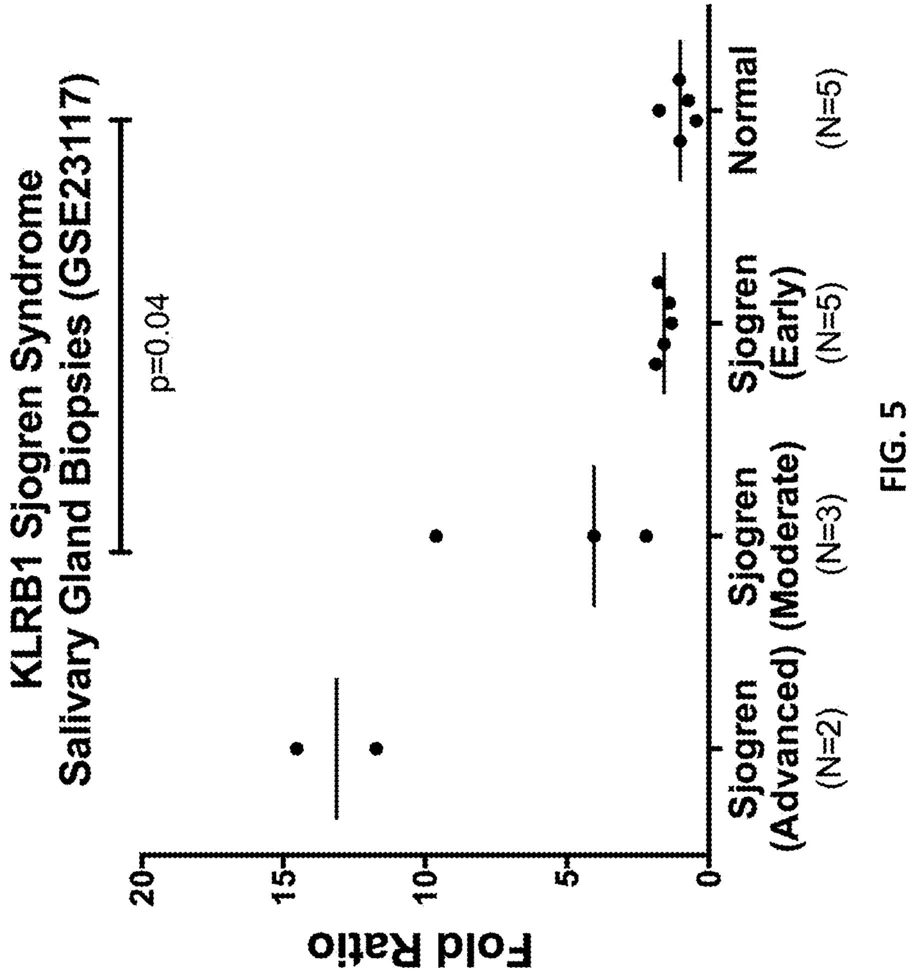
FIG. 5 shows KLRB1 is overexpressed in advanced and moderate Sjogren's syndrome salivary gland compared to normal.

Sjögren's syndrome: Analysis of expression data (GSE23117) from salivary gland biopsies from patients with Sjogren's syndrome compared to normal shows increased expression of KLRB1 in advanced stage (13.1 fold ratio), moderate stage (5.3 fold ratio), and early stage (1.6 fold ratio) (FIG. 5). Accordingly, Sjogren's syndrome is a particularly attractive target for therapies according to the present disclosure.

Figure 6:
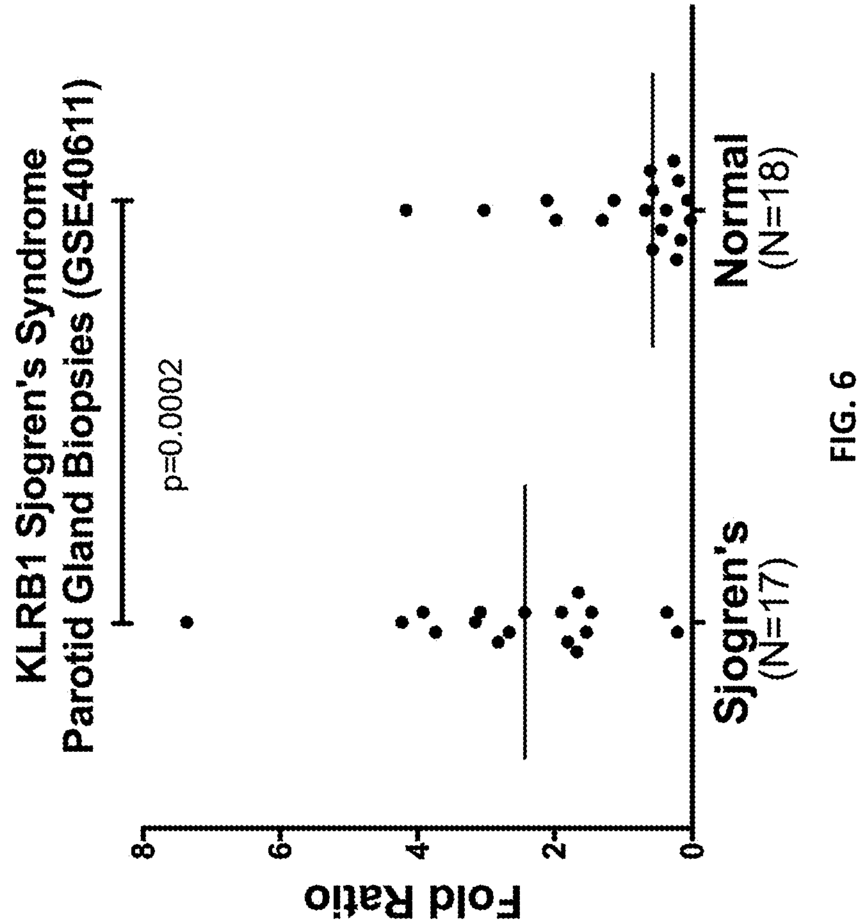
FIG. 6 shows KLRB1 is overexpressed in Sjogren's syndrome parotid gland compared to normal.

Analysis of expression data (GSE40611) from parotid gland biopsies from patients with Sjogren's syndrome compared to normal shows increased expression of KLRB1 (2.6 fold ratio) (FIG. 6). Accordingly, Sjogren's syndrome is a particularly attractive target for therapies according to the present disclosure.

Figure 7:
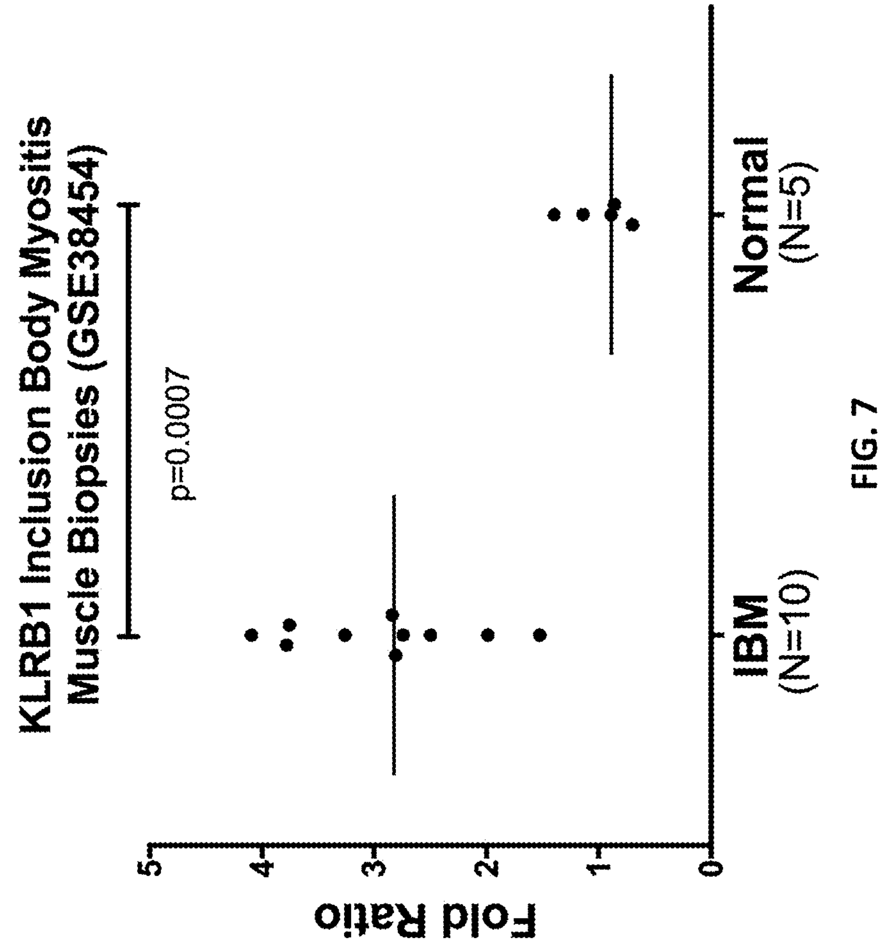
FIG. 7 shows KLRB1 is overexpressed in muscle tissue from patients with inclusion body myositis.

Inclusion body myositis: Analysis of expression data (GSE38454) from muscle biopsies from patients with inclusion body myositis compared to normal shows increased expression of KLRB1 (2.9 fold ratio) (FIG. 7). Accordingly, inclusion body myositis is a particularly attractive target for therapies according to the present disclosure.

Figure 8:
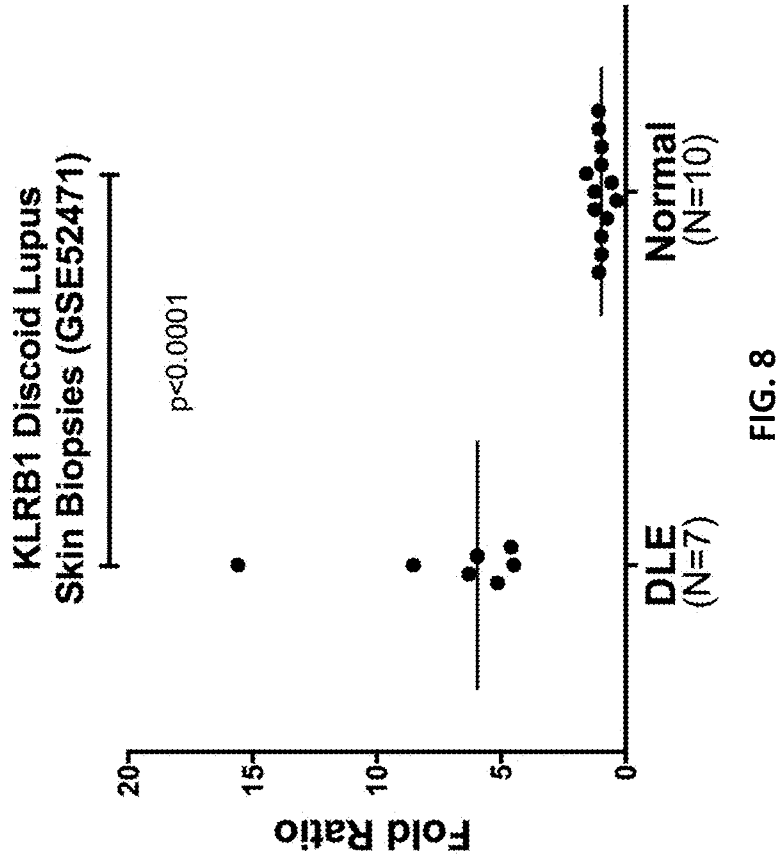
FIG. 8 shows KLRB1 is overexpressed in skin tissue from patients with discoid lupus.

Discoid lupus: Analysis of expression data (GSE52471) from skin biopsies from patients with discoid lupus compared to normal shows increased expression of KLRB1 (7.2 fold ratio) (FIG. 8). Accordingly, discoid lupus is a particularly attractive target for therapies according to the present disclosure.

Figure 9:
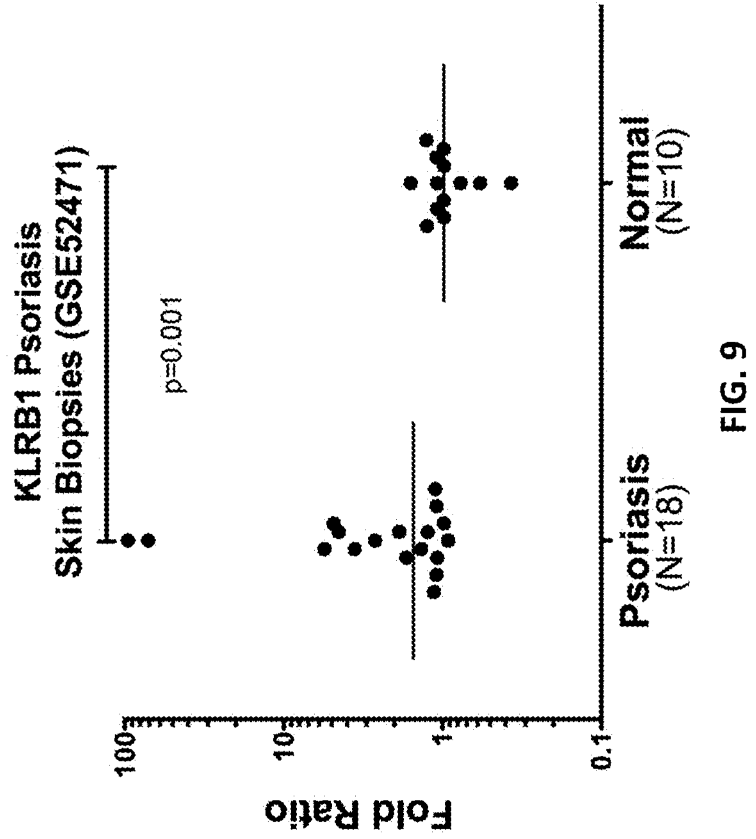
FIG. 9 shows KLRB1 is overexpressed in skin tissue from patients with psoriasis.

Psoriasis: Analysis of expression data (GSE52471) from skin biopsies from patients with psoriasis compared to normal shows increased expression of KLRB1 (11.2 fold ratio) (FIG. 9). Accordingly, discoid lupus is a particularly attractive target for therapies according to the present disclosure.

Figure 10:
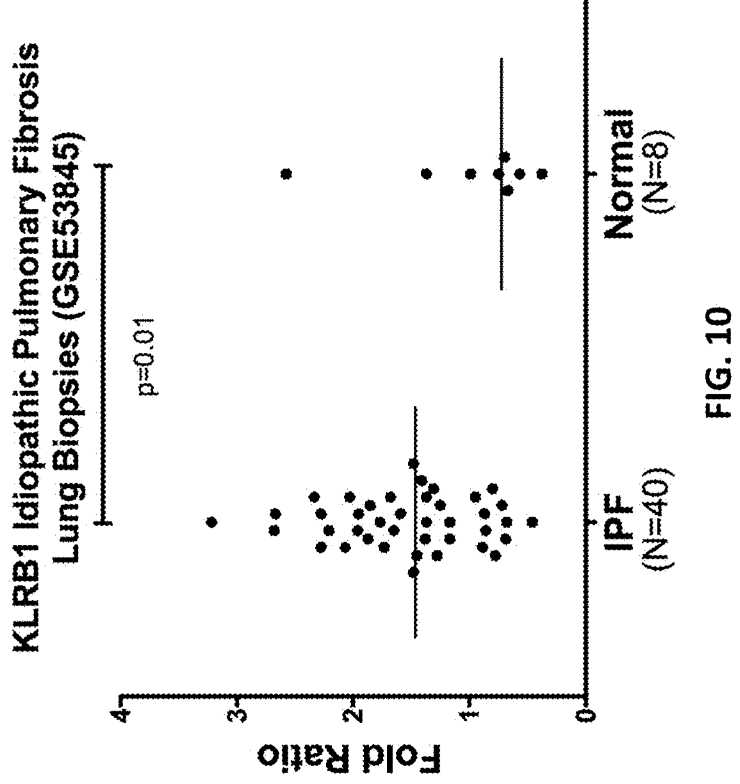
FIG. 10 shows KLRB1 is overexpressed in lung tissue from patients with idiopathic pulmonary fibrosis.

Idiopathic pulmonary fibrosis: Analysis of expression data (GSE53845) from lung biopsies from patients with idiopathic pulmonary fibrosis compared to normal shows increased expression of KLRB1 (1.5 fold ratio) (FIG. 10). Accordingly, idiopathic pulmonary fibrosis is a particularly attractive target for therapies according to the present disclosure.

Figure 11:
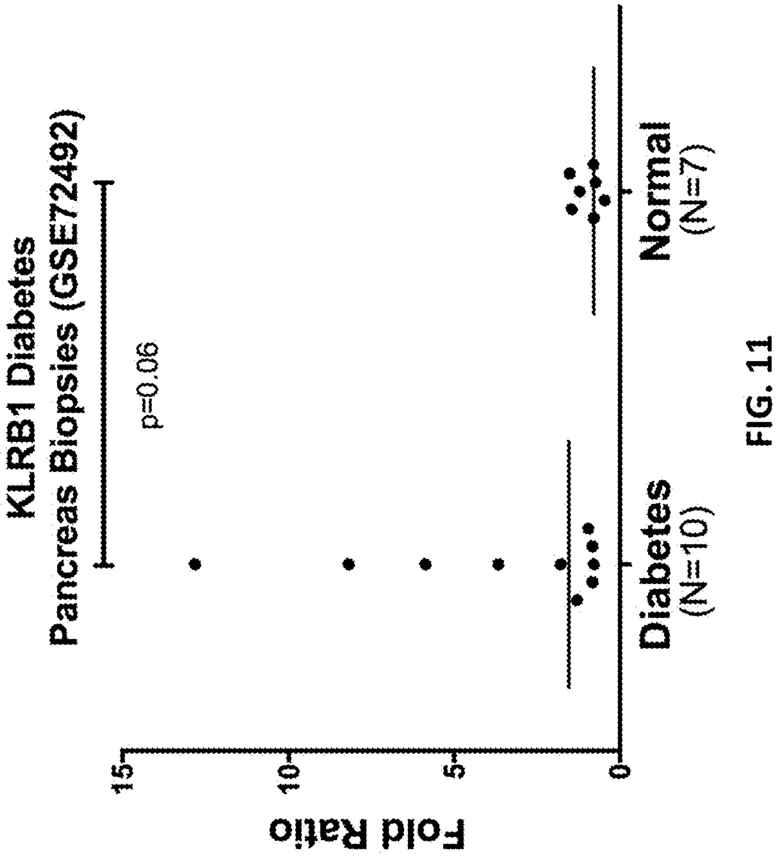
FIG. 11 shows KLRB1 is overexpressed in pancreas tissue from patients with diabetes.

Diabetes: Analysis of expression data (GSE72492) from pancreas biopsies from patients with diabetes compared to normal shows increased expression of KLRB1 (3.7 fold ratio) (FIG. 11). Accordingly, diabetes is a particularly attractive target for therapies according to the present disclosure.

Figure 12:
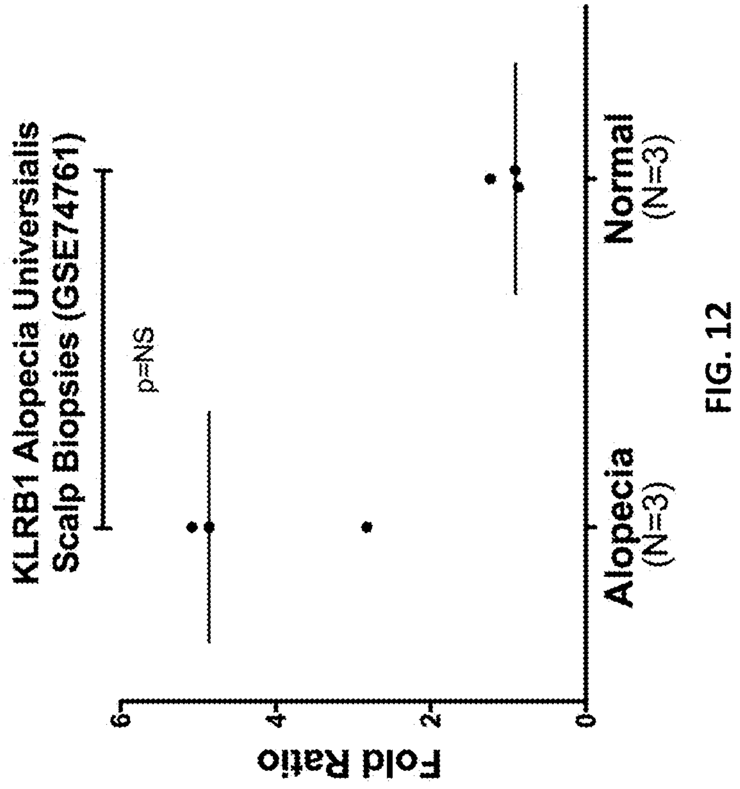
FIG. 12 shows KLRB1 is overexpressed in scalp tissue from patients with alopecia universalis.

Alopecia universalis: Analysis of expression data (GSE74761) from scalp biopsies from patients with idiopathic pulmonary fibrosis compared to normal shows increased expression of KLRB1 (4.3 fold ratio) (FIG. 12). Accordingly, alopecia universalis is a particularly attractive target for therapies according to the present disclosure.

Figure 13:
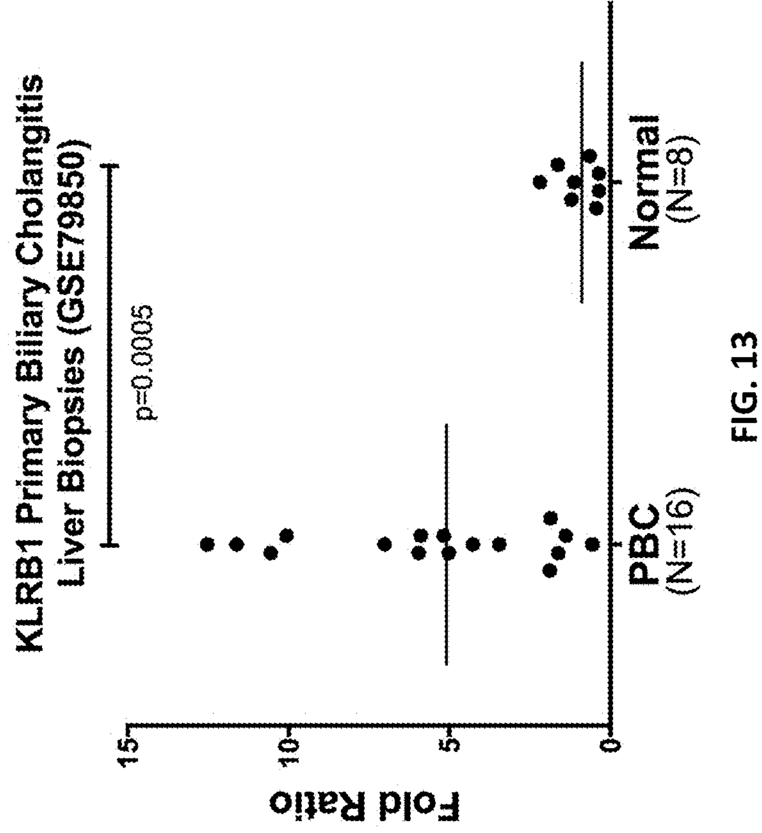
FIG. 13 shows KLRB1 is overexpressed in liver tissue from patients with primary biliary cholangitis.

Primary biliary cholangitis: Analysis of expression data (GSE79850) from liver biopsies from patients with primary biliary cholangitis eventually requiring liver transplantation compared to normal shows increased expression of KLRB1 (5.6 fold ratio) (FIG. 13). Accordingly, primary biliary cholangitis is a particularly attractive target for therapies according to the present disclosure.

Figure 14:
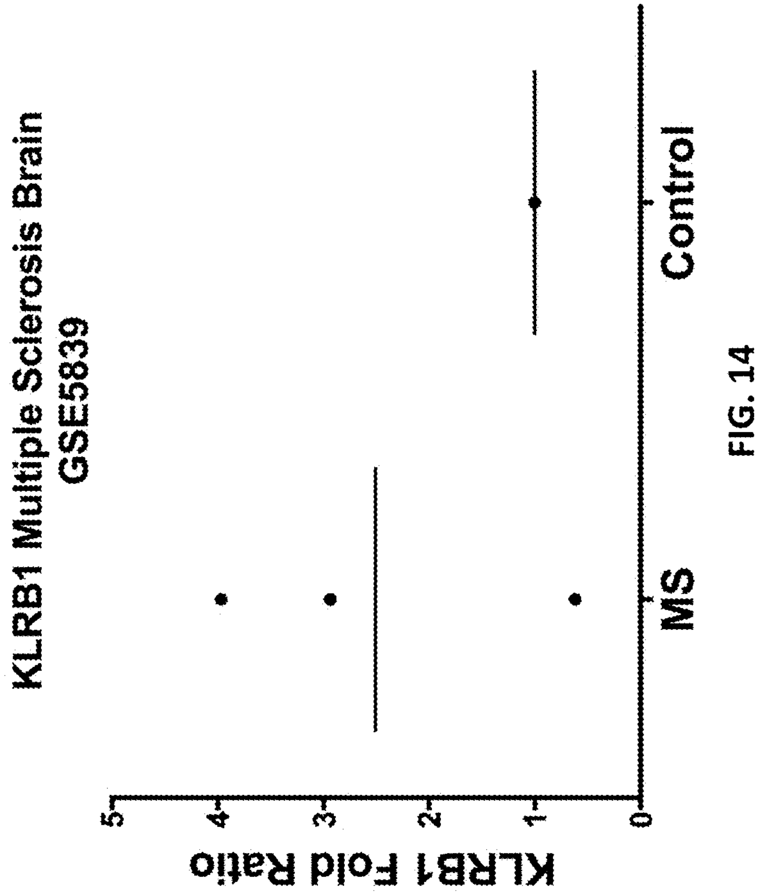
FIG. 14 shows KLRB1 is overexpressed in brain tissue from patients with multiple sclerosis.

Multiple Sclerosis: Analysis of expression data (GSE5839) from brain biopsies from patients with multiple sclerosis show elevated expression of KLRB1 compared to control brain (2.5-fold) (FIG. 14). Accordingly, multiple sclerosis is a particularly attractive target for therapies according to the present disclosure.

Figure 15:
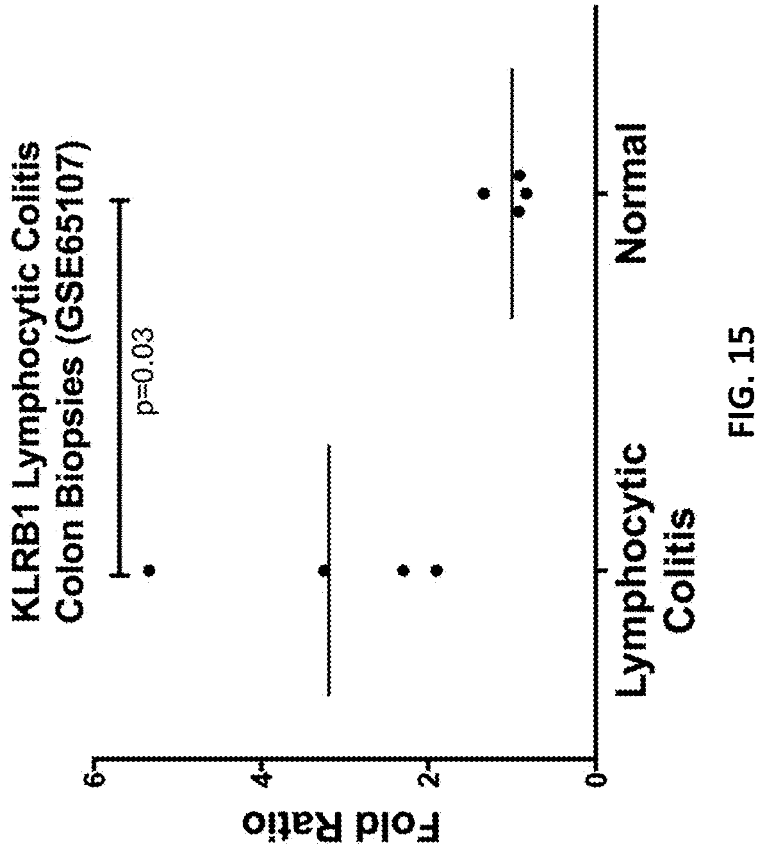
FIG. 15 shows KLRB1 is overexpressed in colon tissue from patients with lymphocytic colitis.

Lymphocytic colitis: Analysis of expression data (GSE65107) from colon biopsies from 4 patients with lymphocytic colitis compared to 4 healthy persons shows increased expression of KLRB1 (3.2 fold ratio) (FIG. 15). Accordingly, lymphocytic colitis is a particularly attractive target for therapies according to the present disclosure.

Figure 16:
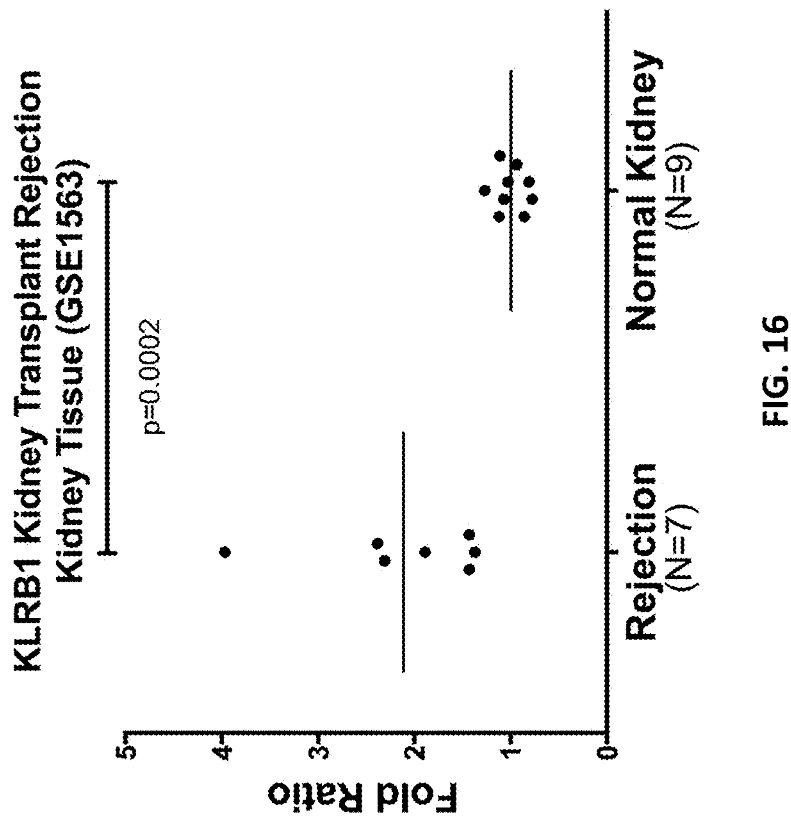
FIG. 16 shows KLRB1 is overexpressed in kidney tissue from patients with renal transplants.

Kidney transplant rejection: Analysis of expression data (GSE1563) from kidney biopsies from 7 patients with acute kidney rejection compared to 9 healthy persons shows increased expression of KLRB1 (2.1 fold ratio) (FIG. 16). Accordingly, kidney transplant rejection is a particularly attractive target for therapies according to the present disclosure.

Figure 17:
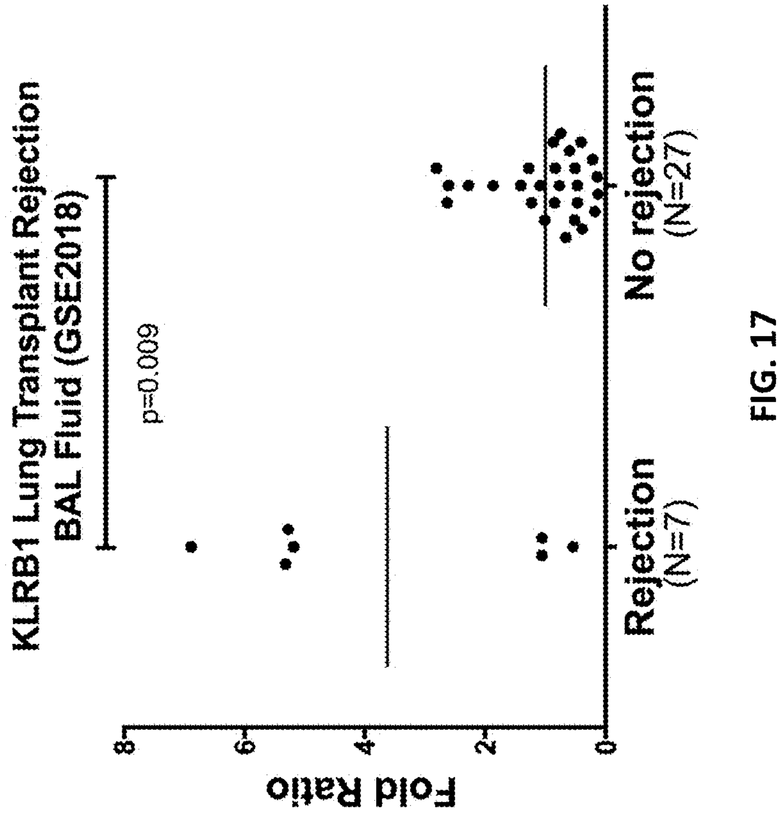
FIG. 17 shows KLRB1 is overexpressed in broncheoalveolar lavage fluid from patients with lung transplants.

Lung transplant: Analysis of expression data (GSE65107) from lung broncheoalveolar lavage (BAL) fluid from 7 patients with lung transplant rejection compared to 27 patients with lung transplants not undergoing rejection shows increased expression of KLRB1 (3.6 fold ratio) (FIG. 17). Accordingly, lung transplant rejection is a particularly attractive target for therapies according to the present disclosure.

Figure 18:
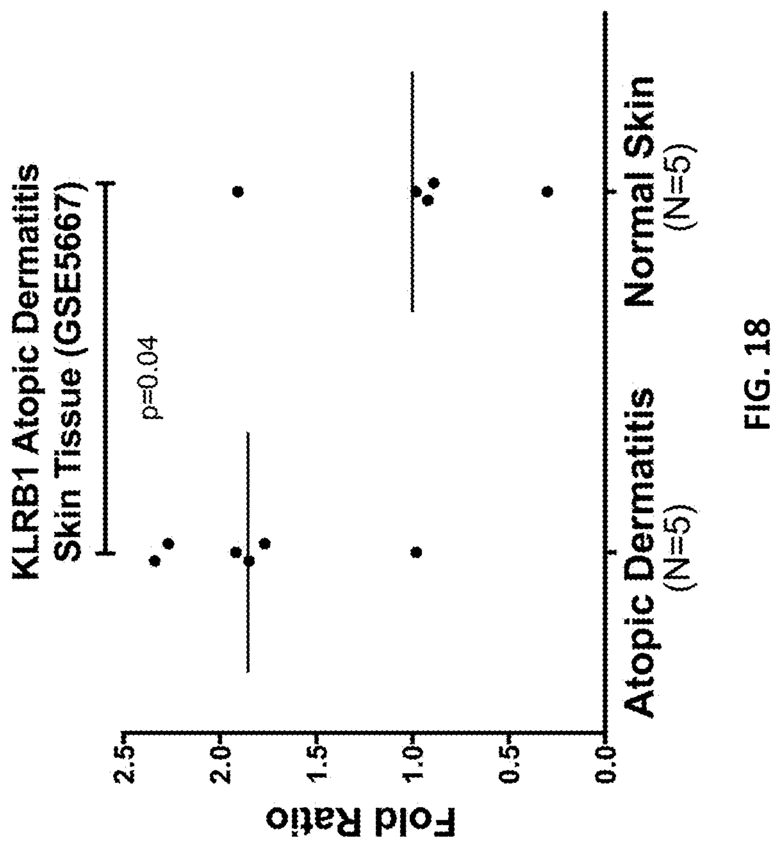
FIG. 18 shows KLRB1 is overexpressed in skin tissue from patients with atopic dermatitis.

Atopic dermatitis: Analysis of expression data (GSE65107) from skin biopsies from 5 patients with atopic dermatitis compared to 5 healthy persons shows increased expression of KLRB1 (1.9 fold ratio) (FIG. 18). Accordingly, atopic dermatitis is a particularly attractive target for therapies according to the present disclosure.

Figure 19:
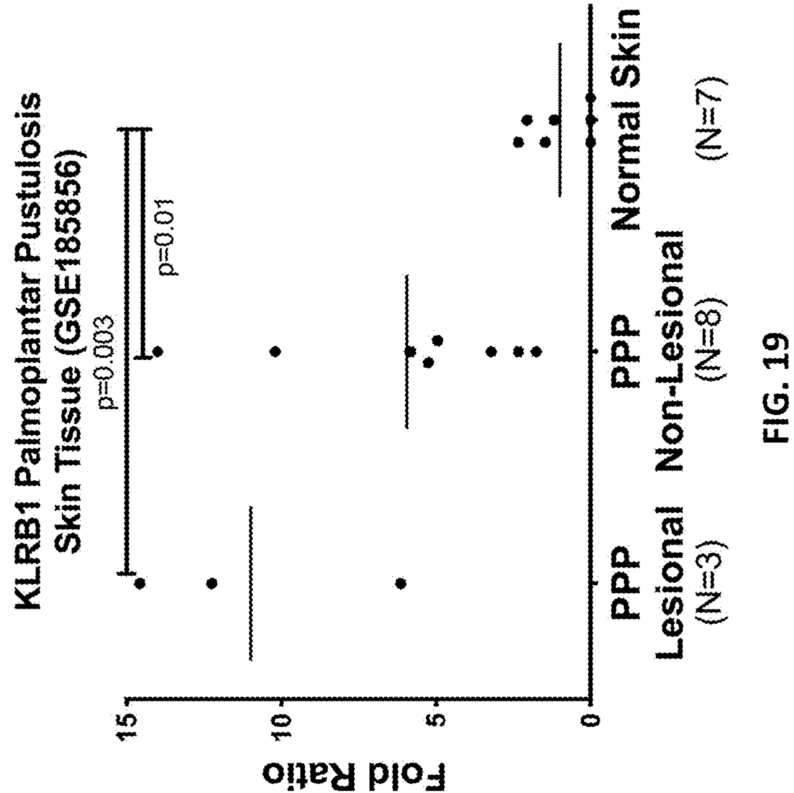
FIG. 19 shows KLRB1 is overexpressed in skin tissue from patients with palmoplantar pustulosis.

Palmoplantar pustulosis: Analysis of expression data (GSE185856) from skin biopsies from 3 patients with palmoplantar pustulosis lesional skin and 8 patients palmoplantar pustulosis non-lesional skin compared to 7 healthy persons shows increased expression of KLRB1 (11.0 fold ratio lesional to healthy; 5.9 fold ratio non-lesional to healthy) (FIG. 19). Accordingly, palmoplantar pustulosis is a particularly attractive target for therapies according to the present disclosure.

Figure 20:
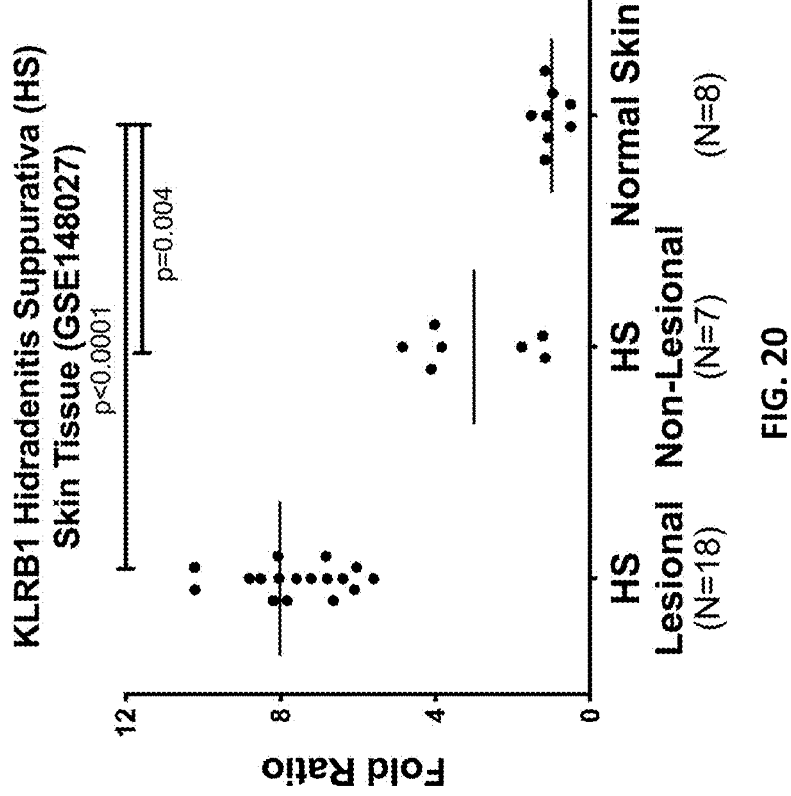
FIG. 20 shows KLRB1 is overexpressed in skin tissue from patients with hidradenitis suppurativa.

Hidradenitis suppurativa: Analysis of expression data (GSE148027) from skin biopsies from 18 patients with hidradenitis suppurativa lesional skin and 7 patients hidradenitis suppurativa non-lesional skin compared to 8 healthy persons shows increased expression of KLRB1 (8.0 fold ratio lesional to healthy; 3.0 fold ratio non-lesional to healthy) (FIG. 20). Accordingly, hidradenitis suppurativa is a particularly attractive target for therapies according to the present disclosure.

Figure 21:
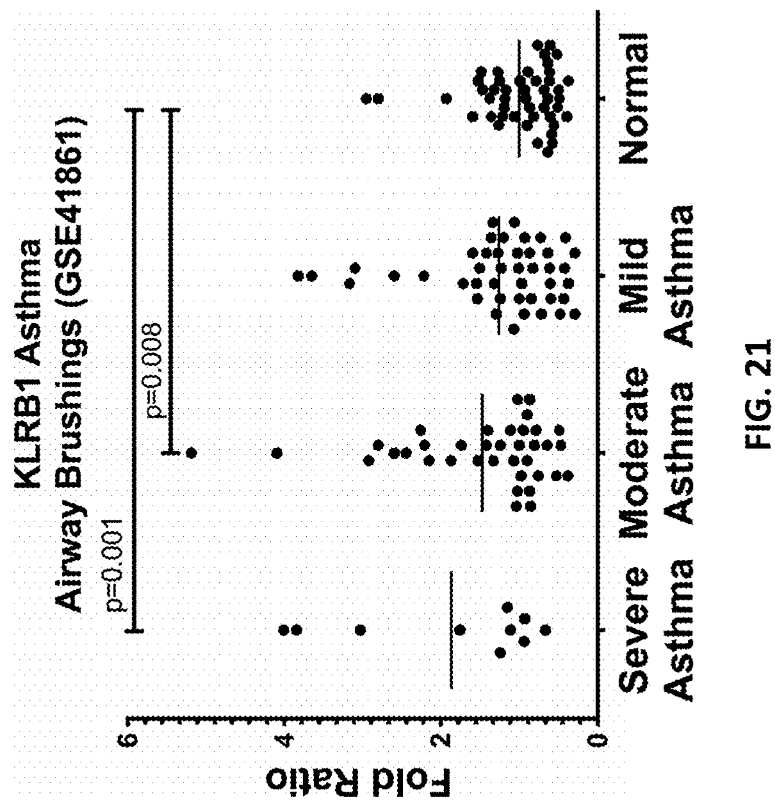
FIG. 21 shows KLRB1 is overexpressed in airway brushings from patients with asthma.
Figure 22A:
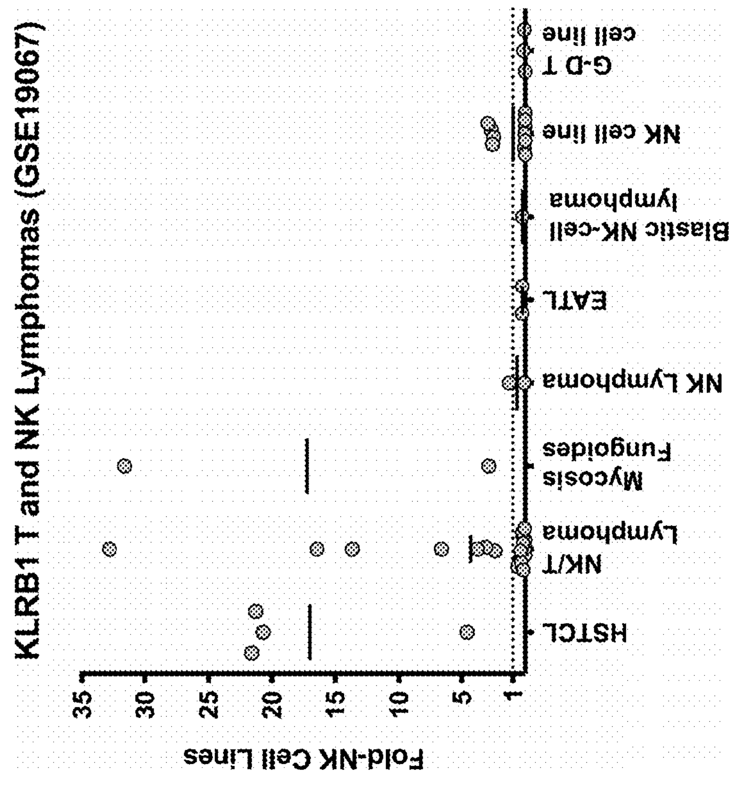
FIGS. 22A-D shows KLRB1 is expressed in various T and NK cell lymphomas and leukemias.
Figure 22B:
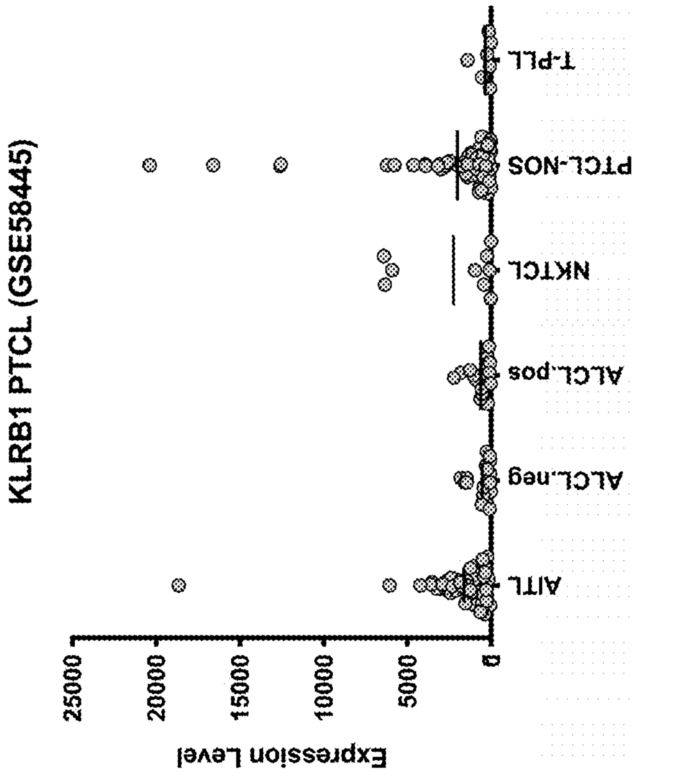
Figure 22C:
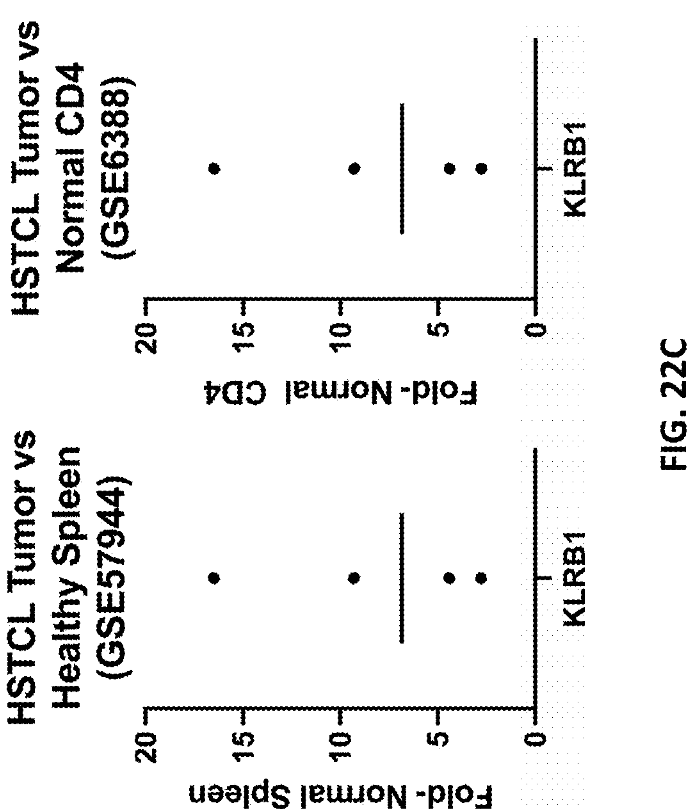
Figure 22D:
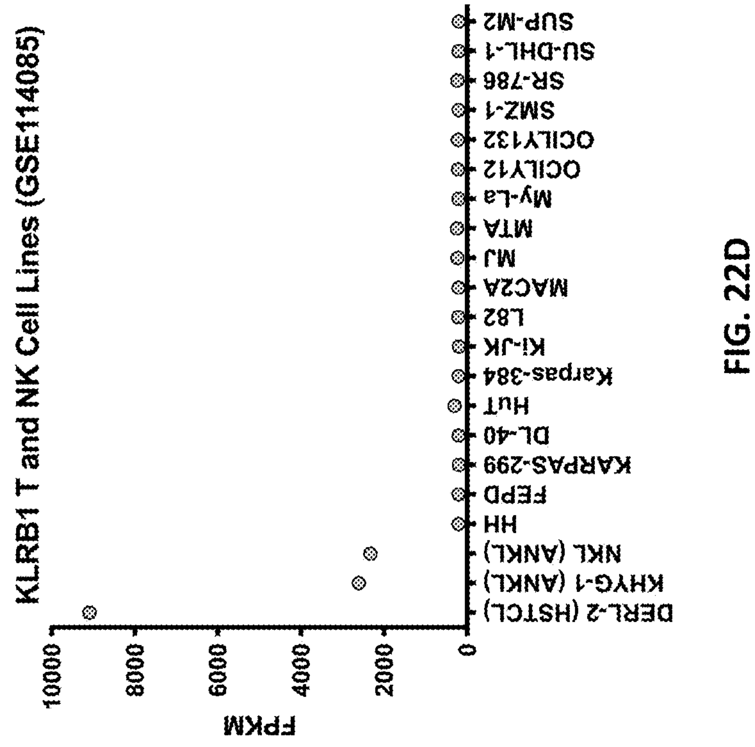

Asthma: Analysis of expression data (GSE41861) from lung airway brushings from 10 patients with severe asthma, 37 patients with moderate asthma, and 44 patients with mild asthma compared to 47 healthy persons shows increased expression of KLRB1 (1.9 fold ratio severe asthma to healthy; 1.5 fold ratio moderate asthma to healthy; and 1.3 fold ratio mild asthma to healthy) (FIG. 21). Accordingly, atopic dermatitis is a particularly attractive target for therapies according to the present disclosure.

Example 3: KLRB1 Expression is Enhanced in Various T and NK Cell Lymphomas and Leukemias Analysis of expression data (GSE19067) from tumor cells from patients with various T and NK cell lymphomas and leukemias compared to normal NK cell expression shows increased expression of KLRB1 (e.g., hepatosplenic T cell lymphoma has 17 fold ratio compared to normal NK cell line) (FIG. 22). Accordingly, various T and NK cell lymphomas are particularly attractive targets for therapies according to the present disclosure.

In particular, some patients with hepatosplenic T cell lymphoma (HSTCL), NK/T cell lymphomas (NKTCL), aggressive NK cell leukemia (ANKL), mycosis fungoides, Sezary syndrome, peripheral T cell lymphoma not otherwise specified (PTCL-NOS), T cell prolymphocytic leukemia (T-PLL), and peripheral T cell lymphoma (PTCL) have increased expression of KLRB1 or similar expression of KLRB1 to CD4+ T cells (FIG. 22). Accordingly, hepatosplenic T cell lymphoma (HSTCL), NK/T cell lymphomas (NKTCL), aggressive NK cell leukemia (ANKL), mycosis fungoides, Sezary syndrome, peripheral T cell lymphoma not otherwise specified (PTCL-NOS), T cell prolymphocytic leukemia (T-PLL), and peripheral T cell lymphoma (PTCL) are particularly attractive targets for therapies according to the present disclosure.

Example 4: Improved Anti-KLRB1 Antibodies

In order to increase humanness and/or remove potential deamidation and isomerization sites, various anti-KLRB1 variants were derived from anti-KLRB1 antibodies whose sequences are listed in Table 18. These variants (antibodies 11.12, 11.27, 11.29, 11.41.1, 11.44.1, 11.45, 11.54, 11.55, 11.57, 12.0, 12.1.3, 12.2, 12.3, 13.2, 13.4, 13.5, and 13.6), the new sequences they contain, and their humanness as calculated using the BioPhi Humanness Report are shown in Table 19. Humanness evaluation settings were chosen as Kabat numbering, Kabat CDR definition, and relaxed OASis prevalence threshold.

TABLE 18

| Initial antibody variants | | | |
|---|---|---|---|
| Name | Humanness | Heavy Chain Variable Sequence | Light Chain Variable Sequence |
| 10A3D6hum2.2 | 19% | QVQLVQSGAEVKKPGASVKVSCKASGYSFTGYTMNWVRQAPGQNLEWIGLINPNTGGTYYNQKFKDRVTLTVDTSISTAYMELSRLRSDDTAVYYCARLGDNYRGYFDSWGQGTTVTVSS (SEQ ID NO: 111) | DIQLTQSPSFLSASVGDRVTITCKASQDVGTAVVWYQQKPGKAPKLLIDWASIRHTGVPSRFSGSGSGTEFTLTISSLQPEDFADYFCQQYSTYLYTFGGGTKLEIK (SEQ ID NO: 114) |
| 10A3D6hum8.2 | 14% | QVQLVQSGAEVKKPGASVKVSCKASGYSFTGYTMNWVRQAPGONLEWIGLINPATGGTYYNQKFKDRVTLTVDTSISTAYMELSRLRSDDTAVYYCARLGDNYRGYFDVWGQGTTVTVSS (SEQ ID NO: 112) | DIQLTQSPSFLSASVGDRVTITCKASQDVGTAVVWYQQKPGKAPKLLIDWASIRHTGVPSRFSGSGSGTEFTLTISSLQPEDFADYFCQQYSTYLYTFGGGTKLEIK (SEQ ID NO: 114) |

TABLE 18-continued

| Initial antibody variants | | | |
|---|---|---|---|
| Name | Human-ness | Heavy Chain Variable Sequence | Light Chain Variable Sequence |
| 10A3D6hum1.2 | 42% | QVQLVQSGAEVKKPGASVKVSCKASGYSF TGYTMNWVRQAPGQGLEWMGLINPNTGG TYYNQKFKDRVTMTRDTSISTAYMELSRL RSDDTAVYYCARLGDNYRGYFDSWGQGT TVTVSS (SEQ ID NO: 113) | DIQLTQSPSFLSASVGDRVTITCKASQD VGTAVVWYQQKPGKAPKLLIDWASIR HTGVPSRFSGSGSGTEFTLTISSLQPEDF ADYFCQQYSTYLYTFGGGTKLEIK (SEQ ID NO: 114) |
| 10A3D6hum1.5 | 46% | QVQLVQSGAEVKKPGASVKVSCKASGYSF TGYTMNWVRQAPGQGLEWMGLINPNTGG TYYNQKFKDRVTMTRDTSISTAYMELSRL RSDDTAVYYCARLGDNYRGYFDSWGQGT TVTVSS (SEQ ID NO: 113) | EIVMTQSPATLSVSPGERATLSCKASQ DVGTAVVWYQQKPGQAPRLLIDWASI RHTGIPARFSGSGSGTEFTLTISSLQSED FAVYYCQQYSTYLYTFGGGTKVEIK (SEQ ID NO: 115) |

TABLE 19

| Antibodies with improved humanness or removed deamidation or isomerization sites. | | | | | | |
|---|---|---|---|---|---|---|
| Antibody | Humanness | New CDRHs | New CDRLs | New FRs | New VH | New VL |
| 11.12 | 45% | CDRH3 DS->DY SEQ ID NO: 22 SEQ ID NO: 24 | No | No | SEQ ID NO: 33 | No |
| 11.27 | 35% | CDRH2 NT->ST SEQ ID NO: 35 SEQ ID NO: 36 SEQ ID NO: 37 SEQ ID NO: 38 SEQ ID NO: 39 | No | No | SEQ ID NO: 44 | No |
| 11.29 | 42% | CDRH2 NT->SS SEQ ID NO: 44 SEQ ID NO: 45 SEQ ID NO: 46 SEQ ID NO: 47 | No | No | SEQ ID NO: 48 | No |
| 11.41.1 | 39% | CDRH2 NT->ST SEQ ID NO: 35 SEQ ID NO: 36 SEQ ID NO: 37 SEQ ID NO: 38 SEQ ID NO: 39 | No | FRL3 DYF->TYY | SEQ ID NO: 51 | SEQ ID NO: 52 |
| 11.44.1 | 46% | CDRH2 NT->SS SEQ ID NO: 44 SEQ ID NO: 45 SEQ ID NO: 46 SEQ ID NO: 47 | No | FRL3 DYF->TYY | SEQ ID NO: 53 | SEQ ID NO: 52 |
| 11.45 | 53% | CDRH2 NT->SS SEQ ID NO: 44 SEQ ID NO: 45 SEQ ID NO: 46 SEQ ID NO: 47 CDRH3 DS->DY SEQ ID NO: 22 SEQ ID NO: 24 | No | FRH1 YSF->YTF FRL3 DYF->TYY | SEQ ID NO: 57 | SEQ ID NO: 52 |
| 11.54 | 50% | CDRH2 NT->SS SEQ ID NO: 44 SEQ ID NO: 45 SEQ ID NO: 46 SEQ ID NO: 47 CDRH3 DS->DY SEQ ID NO: 22 SEQ ID NO: 24 | CDRL1 T->S SEQ ID NO: 58 SEQ ID NO: 59 SEQ ID NO: 60 CDRL2 T->S SEQ ID NO: 61 | FRL3 DYF->TYY | SEQ ID NO: 62 | SEQ ID NO: 63 |
| 11.55 | 53% | CDRH2 NT->SS SEQ ID NO: 44 SEQ ID NO: 45 SEQ ID NO: 46 SEQ ID NO: 47 CDRH3 DS->DY SEQ ID NO: 22 SEQ ID NO: 24 | CDRL1 K->R SEQ ID NO: 64 | FRL3 DYF->TYY | SEQ ID NO: 62 | SEQ ID NO: 65 |
| 11.57 | 56% | CDRH2 NT->SS SEQ ID NO: 44 SEQ ID NO: 45 SEQ ID NO: 46 SEQ ID NO: 47 | CDRL1 K->R SEQ ID NO: 64 CDRL1 T->S SEQ ID NO: 58 SEQ ID NO: 59 | FRH1 YSF->YTF FRL3 DYF->TYY | SEQ ID NO: 57 | SEQ ID NO: 67 |

TABLE 19-continued

Antibodies with improved humanness or removed deamidation or isomerization sites.

| Antibody | Humanness | New CDRHs | New CDRLs | New FRs | New VH | New VL |
|---|---|---|---|---|---|---|
| | | CDRH3 DS->DY SEQ ID NO: 22 SEQ ID NO: 24 | SEQ ID NO: 60 CDRL2 T->S SEQ ID NO: 61 | | | |
| 12.0 | 52% | CDRH2 NT->ST SEQ ID NO: 35 SEQ ID NO: 36 SEQ ID NO: 37 SEQ ID NO: 38 SEQ ID NO: 39 CDRH3 DS->DY SEQ ID NO: 22 SEQ ID NO: 24 | CDRL1 K->R SEQ ID NO: 64 | FRH1 YSF->YTF FRL3 DYF->TYY | SEQ ID NO: 68 | SEQ ID NO: 65 |
| 12.1.3 | 53% | CDRH2 NT->ST SEQ ID NO: 35 SEQ ID NO: 36 SEQ ID NO: 37 SEQ ID NO: 38 SEQ ID NO: 39 CDRH3 DS->DY SEQ ID NO: 22 SEQ ID NO: 24 | CDRL1 K->R CDRL1 DVGT->GIGS SEQ ID NO: 59 SEQ ID NO: 69 SEQ ID NO: 70 | FRH1 YSF->YTF FRL3 DYF->TYY | SEQ ID NO: 68 | SEQ ID NO: 71 |
| 12.2 | 59% | CDRH2 NT->ST SEQ ID NO: 35 SEQ ID NO: 36 SEQ ID NO: 37 SEQ ID NO: 38 SEQ ID NO: 39 CDRH3 DS->DY SEQ ID NO: 22 SEQ ID NO: 24 | CDRL1 Major SEQ ID NO: 72 SEQ ID NO: 73 SEQ ID NO: 74 | FRH1 YSF->YTF FRL3 DYF->TYY | SEQ ID NO: 68 | SEQ ID NO: 75 |
| 12.3 | 61% | CDRH2 NT->ST SEQ ID NO: 35 SEQ ID NO: 36 SEQ ID NO: 37 SEQ ID NO: 38 SEQ ID NO: 39 CDRH3 DS->DY SEQ ID NO: 22 SEQ ID NO: 24 | CDRL1 Major SEQ ID NO: 72 SEQ ID NO: 73 SEQ ID NO: 74 CDRL2 D->Y SEQ ID NO: 76 CDRL3 Y->L, L->P SEQ ID NO: 77 SEQ ID NO: 78 | FRH1 YSF->YTF FRL2 D->Y FRL3 DYF->TYY | SEQ ID NO: 68 | SEQ ID NO: 79 |
| 13.2 | 51% | CDRH2 NT->ST SEQ ID NO: 35 SEQ ID NO: 36 SEQ ID NO: 37 SEQ ID NO: 38 SEQ ID NO: 39 CDRH3 DS->DY SEQ ID NO: 22 SEQ ID NO: 24 | CDRL1 K->R SEQ ID NO: 64 | FRH1 YSF->YTF | SEQ ID NO: 68 | SEQ ID NO: 80 |
| 13.4 | 56% | CDRH2 NT->ST SEQ ID NO: 35 SEQ ID NO: 36 SEQ ID NO: 37 SEQ ID NO: 38 SEQ ID NO: 39 CDRH3 DS->DY SEQ ID NO: 22 SEQ ID NO: 24 | CDRL1 K->R SEQ ID NO: 64 CDRL2 YLY->WPL SEQ ID NO: 81 SEQ ID NO: 82 | FRH1 YSF->YTF | SEQ ID NO: 68 | SEQ ID NO: 83 |
| 13.5 | 57% | CDRH2 NT->ST SEQ ID NO: 35 SEQ ID NO: 36 SEQ ID NO: 37 SEQ ID NO: 38 SEQ ID NO: 39 CDRH3 DS->DY SEQ ID NO: 22 SEQ ID NO: 24 | CDRL1 K->R, D->S SEQ ID NO: 84 SEQ ID NO: 85 CDRL2 YLY->WPL SEQ ID NO: 81 SEQ ID NO: 82 | FRH1 YSF->YTF | SEQ ID NO: 68 | SEQ ID NO: 86 |

TABLE 19-continued

| Antibodies with improved humanness or removed deamidation or isomerization sites. | | | | | | |
|---|---|---|---|---|---|---|
| Antibody | Humanness | New CDRHs | New CDRLs | New FRs | New VH | New VL |
| 13.6 | 63% | CDRH2 NT->ST<br>SEQ ID NO: 35<br>SEQ ID NO: 36<br>SEQ ID NO: 37<br>SEQ ID NO: 38<br>SEQ ID NO: 39<br>CDRH3 DS->DY<br>SEQ ID NO: 22<br>SEQ ID NO: 24 | CDRL1 Major<br>SEQ ID NO: 87<br>SEQ ID NO: 88<br>SEQ ID NO: 89<br>CDRL2<br>YLY->WPL<br>SEQ ID NO: 81<br>SEQ ID NO: 82 | FRH1<br>YSF->YTF | SEQ ID NO: 68 | SEQ ID NO: 90 |

Amino acid changes as indicated (e.g., DS-->DY indicates replacement of DS with DY).

Example 5: Anti-KLRB1 Antibodies 10A3D6hum2.2, 10A3D6hum8.2, 10A3D6hum1.2, 11.12, 11.27, 11.29, 11.41.1, 11.44.1, 11.45, 11.54, 11.55, 11.57, 12.0, 12.1.3, 12.2, 12.3, 13.2, 13.4, 13.5, and 13.6 Bind to Human KLRB1

Various humanized antibodies derived from humanized variants of antibody 10A3D6 with human IgG1-kappa were produced in CHO cells and then assayed for binding against human KLRB1 extracellular domain (ECD) via surface plasma resonance (SPR). Human KLRB1 extracellular domain was amino acids 67-225 from human KLRB1 protein (SEQ ID NO: 1). A Biacore 8K instrument was used with multiple cycle kinetics and affinity capture in 96-well microplates, and single antibody concentration of 20 nM. Antibody was fixed to the chip and analyte of human KLRB1 extracellular domain (ECD) was flowed over the surface at 30 ul/min, with contact time 120 seconds and dissociation time 360 seconds. The results are shown from two separate experiments in Tables 20 and 21. Collectively, these show retention of binding by some variants (e.g., 11.27, 12.0, and 13.2) and loss of binding by other variants (e.g., 12.3 and 13.5).

TABLE 20

Binding kinetics by SPR and production yields for anti-KLRB1 antibodies

| | Biacore SPR Full Range | | | | | Production Purified Ab Yields | | | |
|---|---|---|---|---|---|---|---|---|---|
| Antibody | Chi$^2$ (RU$^2$) | ka (1/Ms) | kd (1/s) | KD (M) | Rmax (RU) | Purified Ab Conc. (mg/mL) | Purified Ab volume (mL) | Purified Ab quantity (mg) | Scale (mL) |
| 10A3D6hum2.2 | 7.99E−02 | 3.11E+05 | 8.18E−05 | 2.63E−10 | 60.7 | 3.28 | 2.6 | 8.53 | 20 |
| 10A3D6hum8.2 | 1.29E−02 | 3.35E+05 | 1.71E−04 | 5.12E−10 | 62.8 | 2.52 | 2.5 | 6.3 | 20 |
| 10A3D6hum1.2 | 1.14E−01 | 4.85E+05 | 1.35E−04 | 2.79E−10 | 44.4 | 1.573 | 2.45 | 3.85 | 20 |
| 11.12 | 1.31E−01 | 4.34E+05 | 1.20E−04 | 2.75E−10 | 57.7 | 3.90 | 2.45 | 9.56 | 20 |
| 11.27 | 5.35E−02 | 3.91E+05 | 1.23E−04 | 3.14E−10 | 48.8 | 2.94 | 2.60 | 7.65 | 20 |
| 11.29 | 6.73E−02 | 2.78E+05 | 2.07E−04 | 7.43E−10 | 50.3 | 3.49 | 2.50 | 8.71 | 20 |
| 11.41.1 | 6.30E−02 | 4.03E+05 | 1.67E−04 | 4.14E−10 | 44.7 | 3.04 | 2.70 | 8.19 | 20 |
| 11.44.1 | 1.82E−02 | 2.15E+05 | 2.34E−04 | 1.09E−09 | 47.4 | 4.10 | 2.50 | 10.24 | 20 |
| 11.45 | 3.54E−02 | 1.81E+05 | 2.27E−04 | 1.26E−09 | 42.7 | 3.42 | 2.55 | 8.71 | 20 |
| 11.54 | 1.76E−02 | 1.41E+05 | 3.15E−04 | 2.24E−09 | 58.6 | 2.43 | 2.50 | 6.08 | 20 |
| 11.55 | 1.21E−02 | 1.80E+05 | 2.20E−04 | 1.23E−09 | 58.6 | 3.16 | 2.55 | 8.05 | 20 |
| 11.57 | 8.78E−03 | 1.48E+05 | 3.08E−04 | 2.08E−09 | 43.8 | 2.48 | 2.50 | 6.20 | 20 |

TABLE 21

Binding kinetics by SPR and production yields for anti-KLRB1 antibodies

| | Biacore SPR Full Range | | | | | Production Purified Ab Yields | | | |
|---|---|---|---|---|---|---|---|---|---|
| Antibody | Chi$^2$ (RU$^2$) | ka (1/Ms) | kd (1/s) | KD (M) | Rmax (RU) | Purified Ab Conc. (mg/mL) | Purified Ab volume (mL) | Purified Ab quantity (mg) | Scale (mL) |
| 10A3D6hum1.2 | 4.72E−02 | 3.10E+05 | 1.07E−04 | 3.44E−10 | 61.2 | N/A | N/A | N/A | N/A |
| 11.57 | 8.72E−02 | 1.22E+05 | 3.08E−04 | 2.52E−09 | 85.8 | N/A | N/A | N/A | N/A |
| 12.0 | 5.65E−02 | 2.43E+05 | 1.45E−04 | 5.97E−10 | 69.2 | 4.54 | 1.85 | 8.41 | 30 |
| 12.1.3 | 4.32E−02 | 1.41E+05 | 2.48E−04 | 1.75E−09 | 86.5 | 4.44 | 1.95 | 8.65 | 30 |
| 12.2 | 3.75E−02 | 1.53E+05 | 2.36E−04 | 1.54E−09 | 76.5 | 3.08 | 1.90 | 5.86 | 30 |
| 12.3 | 2.77E−02 | 1.97E+04 | 1.35E−03 | 6.88E−08 | 16.5 | 2.81 | 2.00 | 5.61 | 30 |

TABLE 21-continued

Binding kinetics by SPR and production yields for anti-KLRB1 antibodies

| Antibody | Biacore SPR Full Range Chi$^2$ (RU$^2$) | ka (1/Ms) | kd (1/s) | KD (M) | Rmax (RU) | Production Purified Ab Yields Purified Ab Conc. (mg/mL) | Purified Ab volume (mL) | Purified Ab quantity (mg) | Scale (mL) |
|---|---|---|---|---|---|---|---|---|---|
| 13.2 | 4.09E−02 | 3.00E+05 | 1.33E−04 | 4.44E−10 | 63 | 1.19 | 1.95 | 2.33 | 30 |
| 13.4 | 5.75E−02 | 1.49E+05 | 2.17E−03 | 1.46E−08 | 92.4 | 3.29 | 1.80 | 5.92 | 30 |
| 13.5 | 9.00E−03 | 8.73E+04 | 1.77E−03 | 2.03E−08 | 31.1 | 3.70 | 1.80 | 6.66 | 30 |
| 13.6 | 6.27E−03 | 6.00E+04 | 2.69E−03 | 4.48E−08 | 65.3 | 3.93 | 1.90 | 7.46 | 30 |

Example 6: Anti-KLRB1 Antibodies 12.0, 13.2, 10A3D6hum2.2, and 10A3D6hum1.2 can Elicit Antibody-Dependent Cell-Mediated Cytotoxicity (ADCC)

Figure 23:
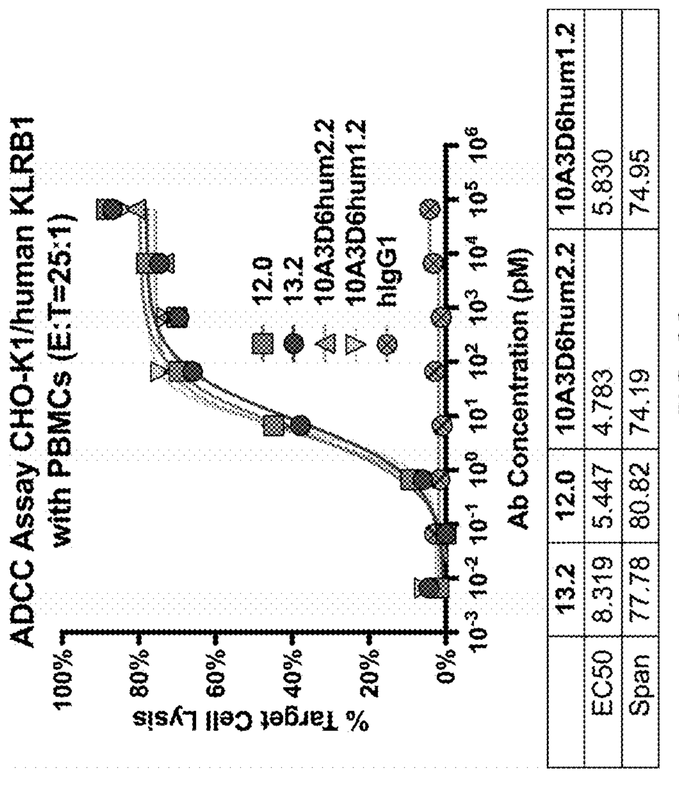
FIG. 23 shows an antibody dependent cell-mediated cytotoxicity (ADCC) assay measuring target cell lysis of CHO-K1 target cells expressing human KLRB1 (CHO-hum-KLRB1) incubated with human peripheral blood mononuclear cells (PBMCs) and the indicated antibodies 12.0, 13.2, 2.2, 11, and human IgG1 (negative control) in an ADCC cell lysis assay. The % target cell lysis for each test antibody at the various concentrations indicated is shown. The assay uses LDH release and detection of formazan salt (Genscript, SC1544).

ADCC elicited by anti-KLRB1 antibodies 12.0, 13.2, 10A3D6hum2.2, and 10A3D6hum1.2 was evaluated using a cell lysis assay involving LDH release and detection of formazan salt (Genscript, SC1544). CHO-hum-KLRB1 (a stable CHO cell line expressing human KLRB1 SEQ ID NO: 1) were incubated with human peripheral blood mononuclear cells (PBMCs) and these antibodies, along with control human IgG1. The EC50 for ADCC for antibody 12.0 was 5.4 pM, for antibody 13.2 was 8.3 pM, for antibody 10A3D6hum2.2 was 4.8 pM, and for antibody 10A3D6hum1.2 was 5.8 pM. The results are shown in FIG. 23.

Example 7: Other Anti-KLRB1 Humanized Antibody Sequences

Table D shows various other humanized anti-KLRB1 antibody complete HC and LC sequences. In some embodiments, the antibodies or antigen binding portions thereof comprise a constant region heavy chain and light chain, wherein the constant region heavy chain and/or light chain comprises or consists of an amino acid sequence set forth in Table D.

TABLE D

Various Other Anti-KLRB1 Antibody Complete Heavy Chain (HC) and Light Chain (LC) Regions

| Name | Heavy Chain Sequence | Light Chain Sequence |
|---|---|---|
| Hu47 A5H2-01-EN | QVQLVQSGAEVKKPGASVKVSCKASGYSFTGYWMHWVRQAPGQ GLEWMGMIHPSDSETRLNQKFKDRVTMTRDTSTSTVYMELSSLRS EDTAVYYCASEGLRRGSFAYWGQGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKKVEPKSCDK THTCPPCPAPEAAGAPSVFLFPPKPKDTLMISRTPEVTCVVVDVSH EDPEVKFNWYVDGVEVHNAKTKPREEQYNSTYRVVSVLTVLHQ DWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG K (SEQ ID NO: 122) | DIVMTQSPDSLAVSLGERATINCRA SESVDNYGMTFMSWYQQKPGQPP KLLIYAASNQGSGVPDRFSGSGSGT DFTLTISSLQAEDVAVYYCQQSKEV PYTFGQGTKLEIKRTVAAPSVFIFPP SDEQLKSGTASVVCLLNNFYPREA KVQWKVDNALQSGNSQESVTEQD SKDSTYSLSSTLTLSKADYEKHKVY ACEVTHQGLSSPVTKSFNRGEC (SEQ ID NO: 130) |
| Hu47 A5H2-02-EN | QVQLVQSGAEVKKPGASVKVSCKASGYSFTGYWMHWVRQAPGQ GLEWMGMIHPSDSETRLNQKFKDRVTMTRDTSTSTVYMELSSLRS EDTAVYYCASEGLRRGSFAYWGQGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKKVEPKSCDK THTCPPCPAPEAAGAPSVFLFPPKPKDTLMISRTPEVTCVVVDVSH EDPEVKFNWYVDGVEVHNAKTKPREEQYNSTYRVVSVLTVLHQ DWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG K (SEQ ID NO: 122) | DIVLTQSPDSLAVSLGERATINCRA SESVDNYGMTFMSWYQQKPGQPP KLLIYAASNQGSGVPDRFSGSGSGT DFTLTISSLQAEDVAVYYCQQSKEV PYTFGQGTKLEIKRTVAAPSVFIFPP SDEQLKSGTASVVCLLNNFYPREA KVQWKVDNALQSGNSQESVTEQD SKDSTYSLSSTLTLSKADYEKHKVY ACEVTHQGLSSPVTKSFNRGEC (SEQ ID NO: 131) |
| Hu47 A5H2-03-EN | QVQLVQSGAEVKKPGASVKVSCKASGYSFTGYWMHWVRQAPGQ GLEWMGMIHPSDSETRLNQKFKDRVTMTRDTSTSTVYMELSSLRS EDTAVYYCASEGLRRGSFAYWGQGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKKVEPKSCDK THTCPPCPAPEAAGAPSVFLFPPKPKDTLMISRTPEVTCVVVDVSH EDPEVKFNWYVDGVEVHNAKTKPREEQYNSTYRVVSVLTVLHQ DWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG K (SEQ ID NO: 122) | DIVLTQSPDSLAVSLGERATINCRA SESVDNYGMTFMSWFQQKPGQPP KLLIYAASNQGSGVPDRFSGSGSGT DFTLTISSLQAEDVAVYYCQQSKEV PYTFGQGTKLEIKRTVAAPSVFIFPP SDEQLKSGTASVVCLLNNFYPREA KVQWKVDNALQSGNSQESVTEQD SKDSTYSLSSTLTLSKADYEKHKVY ACEVTHQGLSSPVTKSFNRGEC (SEQ ID NO: 132) |

TABLE D-continued

Various Other Anti-KLRB1 Antibody Complete Heavy Chain (HC) and Light Chain (LC) Regions

| Name | Heavy Chain Sequence | Light Chain Sequence |
| --- | --- | --- |
| Hu47 A5H2-04-EN | QVQLVQSGAEVKKPGASVKVSCKASGYSFTGYWMHWVRQAPGQGLEWMGMIHPSDSETRLNQKFKDRVTMTRDTSTSTVYMELSSLRSEDTAVYYCASEGLRRGSFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 122) | EIVLTQSPATLSLSPGERATLSCRASESVDNYGMTFMSWYQQKPGQAPRLLIYAASNQGSGIPARFSGSGSGTDFTLTISSLEPEDFAVYYCQQSKEVPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 133) |
| Hu47 A5H2-05-EN | QVQLVQSGAEVKKPGASVKVSCKASGYSFTGYWMHWVRQAPGQGLEWMGMIHPSDSETRLNQKFKDRVTMTVDTSTSTVYMELSSLRSEDTAVYYCASEGLRRGSFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 123) | DIVMTQSPDSLAVSLGERATINCRASESVDNYGMTFMSWYQQKPGQPPKLLIYAASNQGSGVPDRFSGSGSGTDFTLTISSLQAEDVAVYYCQQSKEVPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 130) |
| Hu47 A5H2-06-EN | QVQLVQSGAEVKKPGASVKVSCKASGYSFTGYWMHWVRQAPGQGLEWMGMIHPSDSETRLNQKFKDRVTMTVDTSTSTVYMELSSLRSEDTAVYYCASEGLRRGSFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 123) | DIVLTQSPDSLAVSLGERATINCRASESVDNYGMTFMSWYQQKPGQPPKLLIYAASNQGSGVPDRFSGSGSGTDFTLTISSLQAEDVAVYYCQQSKEVPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 131) |
| Hu47 A5H2-07-EN | QVQLVQSGAEVKKPGASVKVSCKASGYSFTGYWMHWVRQAPGQGLEWMGMIHPSDSETRLNQKFKDRVTMTVDTSTSTVYMELSSLRSEDTAVYYCASEGLRRGSFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 123) | DIVLTQSPDSLAVSLGERATINCRASESVDNYGMTFMSWFQQKPGQPPKLLIYAASNQGSGVPDRFSGSGSGTDFTLTISSLQAEDVAVYYCQQSKEVPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 132) |
| Hu47 A5H2-08-EN | QVQLVQSGAEVKKPGASVKVSCKASGYSFTGYWMHWVRQAPGQGLEWMGMIHPSDSETRLNQKFKDRVTMTVDTSTSTVYMELSSLRSEDTAVYYCASEGLRRGSFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 123) | EIVLTQSPATLSLSPGERATLSCRASESVDNYGMTFMSWYQQKPGQAPRLLIYAASNQGSGIPARFSGSGSGTDFTLTISSLEPEDFAVYYCQQSKEVPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 133) |
| Hu47 A5H2-09-EN | QVQLVQSGAEVKKPGASVKVSCKASGYSFTGYWMHWVRQAPGQGLEWMGMIHPSDSETRLNQKFKDRVTMTVDKSTSTVYMELSSLRSEDTAVYYCASEGLRRGSFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 124) | DIVMTQSPDSLAVSLGERATINCRASESVDNYGMTFMSWYQQKPGQPPKLLIYAASNQGSGVPDRFSGSGSGTDFTLTISSLQAEDVAVYYCQQSKEVPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 130) |
| Hu47 A5H2-10- | QVQLVQSGAEVKKPGASVKVSCKASGYSFTGYWMHWVRQAPGQGLEWMGMIHPSDSETRLNQKFKDRVTMTVDKSTSTVYMELSSLRSEDTAVYYCASEGLRRGSFAYWGQGTLVTVSSASTKGPSVFPLAP | DIVLTQSPDSLAVSLGERATINCRASESVDNYGMTFMSWYQQKPGQPPKLLIYAASNQGSGVPDRFSGSGSGT |

TABLE D-continued

Various Other Anti-KLRB1 Antibody Complete Heavy Chain (HC) and Light Chain (LC) Regions

| Name | Heavy Chain Sequence | Light Chain Sequence |
|---|---|---|
| EN | SSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCD<br>KTHTCPPCPAPEAAGAPSVFLFPPKPKDTLMISRTPEVTCVVVDVS<br>HEDPEVKFNWYVDGVEVHNAKTKPREEQYNSTYRVVSVLTVLH<br>QDWLNGKEYKCKVSNKALPAPIEKTISKAKGQPREPQVYTLPPSR<br>DELTKNQVSLTCLVKGFYPSDIAVEWESNGQPENNYKTTPPVLDS<br>DGSFFLYSKLTVDKSRWQQGNVFSCSVMHEALHNHYTQKSLSLSP<br>GK (SEQ ID NO: 124) | DFTLTISSLQAEDVAVYYCQQSKEV<br>PYTFGQGTKLEIKRTVAAPSVFIFPP<br>SDEQLKSGTASVVCLLNNFYPREA<br>KVQWKVDNALQSGNSQESVTEQD<br>SKDSTYSLSSTLTLSKADYEKHKVY<br>ACEVTHQGLSSPVTKSFNRGEC<br>(SEQ ID NO: 131) |
| Hu47<br>A5H2<br>-11-<br>EN | QVQLVQSGAEVKKPGASVKVSCKASGYSFTGYWMHWVRQAPGQ<br>GLEWMGMIHPSDSETRLNQKFKDRVTMTVDKSTSTVYMELSSLR<br>SEDTAVYYCASEGLRRGSFAYWGQGTLVTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCD<br>KTHTCPPCPAPEAAGAPSVFLFPPKPKDTLMISRTPEVTCVVVDVS<br>HEDPEVKFNWYVDGVEVHNAKTKPREEQYNSTYRVVSVLTVLH<br>QDWLNGKEYKCKVSNKALPAPIEKTISKAKGQPREPQVYTLPPSR<br>DELTKNQVSLTCLVKGFYPSDIAVEWESNGQPENNYKTTPPVLDS<br>DGSFFLYSKLTVDKSRWQQGNVFSCSVMHEALHNHYTQKSLSLSP<br>GK (SEQ ID NO: 124) | DIVLTQSPDSLAVSLGERATINCRA<br>SESVDNYGMTFMSWFQQKPGQPP<br>KLLIYAASNQGSGVPDRFSGSGSGT<br>DFTLTISSLQAEDVAVYYCQQSKEV<br>PYTFGQGTKLEIKRTVAAPSVFIFPP<br>SDEQLKSGTASVVCLLNNFYPREA<br>KVQWKVDNALQSGNSQESVTEQD<br>SKDSTYSLSSTLTLSKADYEKHKVY<br>ACEVTHQGLSSPVTKSFNRGEC<br>(SEQ ID NO: 132) |
| Hu47<br>A5H2-<br>12-<br>EN | QVQLVQSGAEVKKPGASVKVSCKASGYSFTGYWMHWVRQAPGQ<br>GLEWMGMIHPSDSETRLNQKFKDRVTMTVDKSTSTVYMELSSLR<br>SEDTAVYYCASEGLRRGSFAYWGQGTLVTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCD<br>KTHTCPPCPAPEAAGAPSVFLFPPKPKDTLMISRTPEVTCVVVDVS<br>HEDPEVKFNWYVDGVEVHNAKTKPREEQYNSTYRVVSVLTVLH<br>QDWLNGKEYKCKVSNKALPAPIEKTISKAKGQPREPQVYTLPPSR<br>DELTKNQVSLTCLVKGFYPSDIAVEWESNGQPENNYKTTPPVLDS<br>DGSFFLYSKLTVDKSRWQQGNVFSCSVMHEALHNHYTQKSLSLSP<br>GK (SEQ ID NO: 124) | EIVLTQSPATLSLSPGERATLSCRAS<br>ESVDNYGMTFMSWYQQKPGQAPR<br>LLIYAASNQGSGIPARFSGSGSGTDF<br>TLTISSLEPEDFAVYYCQQSKEVPY<br>TFGQGTKLEIKRTVAAPSVFIFPPSD<br>EQLKSGTASVVCLLNNFYPREAKV<br>QWKVDNALQSGNSQESVTEQDSK<br>DSTYSLSSTLTLSKADYEKHKVYA<br>CEVTHQGLSSPVTKSFNRGEC (SEQ<br>ID NO: 133) |
| Hu47<br>A5H2<br>-13-<br>EN | QVQLVQSGAEVKKPGASVKVSCKGSGYSFTGYWMHWVRQAPGQ<br>GLEWMGMIHPSDSETRLNQKFKDKVTMTVDKSTSTVYMELSSLR<br>SEDTAVYYCASEGLRRGSFAYWGQGTLVTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCD<br>KTHTCPPCPAPEAAGAPSVFLFPPKPKDTLMISRTPEVTCVVVDVS<br>HEDPEVKFNWYVDGVEVHNAKTKPREEQYNSTYRVVSVLTVLH<br>QDWLNGKEYKCKVSNKALPAPIEKTISKAKGQPREPQVYTLPPSR<br>DELTKNQVSLTCLVKGFYPSDIAVEWESNGQPENNYKTTPPVLDS<br>DGSFFLYSKLTVDKSRWQQGNVFSCSVMHEALHNHYTQKSLSLSP<br>GK (SEQ ID NO: 125) | DIVMTQSPDSLAVSLGERATINCRA<br>SESVDNYGMTFMSWYQQKPGQPP<br>KLLIYAASNQGSGVPDRFSGSGSGT<br>DFTLTISSLQAEDVAVYYCQQSKEV<br>PYTFGQGTKLEIKRTVAAPSVFIFPP<br>SDEQLKSGTASVVCLLNNFYPREA<br>KVQWKVDNALQSGNSQESVTEQD<br>SKDSTYSLSSTLTLSKADYEKHKVY<br>ACEVTHQGLSSPVTKSFNRGEC<br>(SEQ ID NO: 130) |
| Hu47<br>A5H2-<br>14-<br>EN | QVQLVQSGAEVKKPGASVKVSCKGSGYSFTGYWMHWVRQAPGQ<br>GLEWMGMIHPSDSETRLNQKFKDKVTMTVDKSTSTVYMELSSLR<br>SEDTAVYYCASEGLRRGSFAYWGQGTLVTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCD<br>KTHTCPPCPAPEAAGAPSVFLFPPKPKDTLMISRTPEVTCVVVDVS<br>HEDPEVKFNWYVDGVEVHNAKTKPREEQYNSTYRVVSVLTVLH<br>QDWLNGKEYKCKVSNKALPAPIEKTISKAKGQPREPQVYTLPPSR<br>DELTKNQVSLTCLVKGFYPSDIAVEWESNGQPENNYKTTPPVLDS<br>DGSFFLYSKLTVDKSRWQQGNVFSCSVMHEALHNHYTQKSLSLSP<br>GK (SEQ ID NO: 125) | DIVLTQSPDSLAVSLGERATINCRA<br>SESVDNYGMTFMSWYQQKPGQPP<br>KLLIYAASNQGSGVPDRFSGSGSGT<br>DFTLTISSLQAEDVAVYYCQQSKEV<br>PYTFGQGTKLEIKRTVAAPSVFIFPP<br>SDEQLKSGTASVVCLLNNFYPREA<br>KVQWKVDNALQSGNSQESVTEQD<br>SKDSTYSLSSTLTLSKADYEKHKVY<br>ACEVTHQGLSSPVTKSFNRGEC<br>(SEQ ID NO: 131) |
| Hu47<br>A5H2-<br>15-<br>EN | QVQLVQSGAEVKKPGASVKVSCKGSGYSFTGYWMHWVRQAPGQ<br>GLEWMGMIHPSDSETRLNQKFKDKVTMTVDKSTSTVYMELSSLR<br>SEDTAVYYCASEGLRRGSFAYWGQGTLVTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCD<br>KTHTCPPCPAPEAAGAPSVFLFPPKPKDTLMISRTPEVTCVVVDVS<br>HEDPEVKFNWYVDGVEVHNAKTKPREEQYNSTYRVVSVLTVLH<br>QDWLNGKEYKCKVSNKALPAPIEKTISKAKGQPREPQVYTLPPSR<br>DELTKNQVSLTCLVKGFYPSDIAVEWESNGQPENNYKTTPPVLDS<br>DGSFFLYSKLTVDKSRWQQGNVFSCSVMHEALHNHYTQKSLSLSP<br>GK (SEQ ID NO: 125) | DIVLTQSPDSLAVSLGERATINCRA<br>SESVDNYGMTFMSWFQQKPGQPP<br>KLLIYAASNQGSGVPDRFSGSGSGT<br>DFTLTISSLQAEDVAVYYCQQSKEV<br>PYTFGQGTKLEIKRTVAAPSVFIFPP<br>SDEQLKSGTASVVCLLNNFYPREA<br>KVQWKVDNALQSGNSQESVTEQD<br>SKDSTYSLSSTLTLSKADYEKHKVY<br>ACEVTHQGLSSPVTKSFNRGEC<br>(SEQ ID NO: 132) |
| Hu47<br>A5H2-<br>16-<br>EN | QVQLVQSGAEVKKPGASVKVSCKGSGYSFTGYWMHWVRQAPGQ<br>GLEWMGMIHPSDSETRLNQKFKDKVTMTVDKSTSTVYMELSSLR<br>SEDTAVYYCASEGLRRGSFAYWGQGTLVTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCD<br>KTHTCPPCPAPEAAGAPSVFLFPPKPKDTLMISRTPEVTCVVVDVS | EIVLTQSPATLSLSPGERATLSCRAS<br>ESVDNYGMTFMSWYQQKPGQAPR<br>LLIYAASNQGSGIPARFSGSGSGTDF<br>TLTISSLEPEDFAVYYCQQSKEVPY<br>TFGQGTKLEIKRTVAAPSVFIFPPSD<br>EQLKSGTASVVCLLNNFYPREAKV |

TABLE D-continued

Various Other Anti-KLRB1 Antibody Complete Heavy Chain (HC) and Light Chain (LC) Regions

| Name | Heavy Chain Sequence | Light Chain Sequence |
|---|---|---|
| | HEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 125) | QWKVDNALQSGNSQESVTEQDSKDSTYSLSSTLTLSKADYEKHKVYACEVTHQGLSSPVTKSFNRGEC (SEQ ID NO: 133) |
| Hu50 A8F2-01-EN | QVQLVQSGAEVKKPGASVKVSCKASGYTFIDYYINWVRQAPGQGLEWMGWIFPGSGHTKYNENFKGRVTMTRDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 126) | DIQMTQSPSSLSASVGDRVTITCTASSSVSSTYLHWYQQKPGKAPKLLIYSTSNLASGVPSRFSGSGSGTDFTLTISSLQPEDFATYYCHQYHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 134) |
| Hu50 A8F2-02-EN | QVQLVQSGAEVKKPGASVKVSCKASGYTFIDYYINWVRQAPGQGLEWMGWIFPGSGHTKYNENFKGRVTMTRDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO:126) | DIQMTQSPSSLSASVGDRVTITCTASSSVSSTYLHWYQQKPGKAPKLLIYSTSNLASGVPSRFSGSGSGTDYTLTISSLQPEDFATYYCHQYHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:135) |
| Hu50 A8F2-03-EN | QVQLVQSGAEVKKPGASVKVSCKASGYTFIDYYINWVRQAPGQGLEWMGWIFPGSGHTKYNENFKGRVTMTRDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 126) | DIQLTQSPSSLSASVGDRVTITCTASSSVSSTYLHWYQQKPGKSPKLLIYSTSNLASGVPSRFSGSGSGTDYTLTISSLQPEDFATYYCHQYHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 136) |
| Hu50 A8F2-04-EN | QVQLVQSGAEVKKPGASVKVSCKASGYTFIDYYINWVRQAPGQGLEWMGWIFPGSGHTKYNENFKGRVTMTRDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO:126) | DIQLTQSPSSLSASVGDRVTITCTASSSVSSTYLHWYQQKPGKSPKLLIYSTSNLASGVPSRFSGSGSGTDYTLTISSLQPEDAATYYCHQYHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:137) |
| Hu50 A8F2-05-EN | QVQLVQSGAEVKKPGASVKVSCKASGYTFIDYYINWVRQAPGQGLEWMGWIFPGSGHTKYNENFKGKVTMTVDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 127) | DIQMTQSPSSLSASVGDRVTITCTASSSVSSTYLHWYQQKPGKAPKLLIYSTSNLASGVPSRFSGSGSGTDFTLTISSLQPEDFATYYCHQYHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 134) |
| Hu50 A8F2-06-EN | QVQLVQSGAEVKKPGASVKVSCKASGYTFIDYYINWVRQAPGQGLEWMGWIFPGSGHTKYNENFKGRVTMTRDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDV | DIQMTQSPSSLSASVGDRVTITCTASSSVSSTYLHWYQQKPGKAPKLLIYSTSNLASGVPSRFSGSGSGTDYTLTISSLQPEDFATYYCHQYHRSPLTFGQGTKLEIKRTVAAPSVFIFPPSDEQLKSGTASVVCLLNNFYPREAKVQWK |

TABLE D-continued

Various Other Anti-KLRB1 Antibody Complete Heavy Chain (HC) and Light Chain (LC) Regions

| Name | Heavy Chain Sequence | Light Chain Sequence |
| --- | --- | --- |
| | SHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO:127) | VDNALQSGNSQESVTEQDSKDSTYSLSSTLTLSKADYEKHKVYACEVTHQGLSSPVTKSFNRGEC (SEQ ID NO:135) |
| Hu50 A8F2-07-EN | QVQLVQSGAEVKKPGASVKVSCKASGYTFIDYYINWVRQAPGQGLEWMGWIFPGSGHTKYNENFKGKVTMTVDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 127) | DIQLTQSPSSLSASVGDRVTITCTASSSVSSTYLHWYQQKPGKSPKLLIYSTSNLASGVPSRFSGSGSGTDYTLTISSLQPEDFATYYCHQYHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 136) |
| Hu50 A8F2-08-EN | QVQLVQSGAEVKKPGASVKVSCKASGYTFIDYYINWVRQAPGQGLEWMGWIFPGSGHTKYNENFKGKVTMTVDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 127) | DIQLTQSPSSLSASVGDRVTITCTASSSVSSTYLHWYQQKPGKSPKLLIYSTSNLASGVPSRFSGSGSGTDYTLTISSLQPEDAATYYCHQYHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 137) |
| Hu50 A8F2-09-EN | QVQLVQSGAEVKKPGASVKVSCKASGYTFIDYYINWVRQAPGQGLEWMGWIFPGSGHTKYNENFKGKVTLTVDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 128) | DIQMTQSPSSLSASVGDRVTITCTASSSVSSTYLHWYQQKPGKAPKLLIYSTSNLASGVPSRFSGSGSGTDFTLTISSLQPEDFATYYCHQYHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 134) |
| Hu50 A8F2-10-EN | QVQLVQSGAEVKKPGASVKVSCKASGYTFIDYYINWVRQAPGQGLEWMGWIFPGSGHTKYNENFKGKVTLTVDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 128) | DIQMTQSPSSLSASVGDRVTITCTASSSVSSTYLHWYQQKPGKAPKLLIYSTSNLASGVPSRFSGSGSGTDYTLTISSLQPEDFATYYCHQYHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 135) |
| Hu50 A8F2-11-EN | QVQLVQSGAEVKKPGASVKVSCKASGYTFIDYYINWVRQAPGQGLEWMGWIFPGSGHTKYNENFKGKVTLTVDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 128) | DIQLTQSPSSLSASVGDRVTITCTASSSVSSTYLHWYQQKPGKSPKLLIYSTSNLASGVPSRFSGSGSGTDYTLTISSLQPEDFATYYCHQYHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 136) |
| Hu50 A8F2-12-EN | QVQLVQSGAEVKKPGASVKVSCKASGYTFIDYYINWVRQAPGQGLEWMGWIFPGSGHTKYNENFKGKVTLTVDTSTSTVYMELSSLRSEDTAVYYCARGDRSALGYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDS | DIQLTQSPSSLSASVGDRVTITCTASSSVSSTYLHWYQQKPGKSPKLLIYSTSNLASGVPSRFSGSGSGTDYTLTISSLQPEDAATYYCHQYHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID |

TABLE D-continued

Various Other Anti-KLRB1 Antibody Complete Heavy Chain (HC) and Light Chain (LC) Regions

| Name | Heavy Chain Sequence | Light Chain Sequence |
|---|---|---|
| | DGSFFLYSKLTVDKSRWQQGNVFSCSVMHEALHNHYTQKSLSLSP<br>GK (SEQ ID NO: 128) | NO: 137) |
| Hu50<br>A8F2-<br>13-EN | QVQLVQSGAEVKKPGASVKVSCKASGYTFIDYYINWVRQAPGQG<br>LEWIGWIFPGSGHTKYNENFKGKVTLTVDTSTSTVYMELSSLRSE<br>DTAVYFCARGDRSALGYFDYWGQGTTVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKKVEPKSCDK<br>THTCPPCPAPEAAGAPSVFLFPPKPKDTLMISRTPEVTCVVVDVSH<br>EDPEVKFNWYVDGVEVHNAKTKPREEQYNSTYRVVSVLTVLHQ<br>DWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K (SEQ ID NO: 129) | DIQMTQSPSSLSASVGDRVTITCTA<br>SSSVSSTYLHWYQQKPGKAPKLLIY<br>STSNLASGVPSRFSGSGSGTDFTLTI<br>SSLQPEDFATYYCHQYHRSPLTFGQ<br>GTKLEIKRTVAAPSVFIFPPSDEQLK<br>SGTASVVCLLNNFYPREAKVQWK<br>VDNALQSGNSQESVTEQDSKDSTY<br>SLSSTLTLSKADYEKHKVYACEVT<br>HQGLSSPVTKSFNRGEC (SEQ ID<br>NO: 134) |
| Hu50<br>A8F2-<br>14-EN | QVQLVQSGAEVKKPGASVKVSCKASGYTFIDYYINWVRQAPGQG<br>LEWIGWIFPGSGHTKYNENFKGKVTLTVDTSTSTVYMELSSLRSE<br>DTAVYFCARGDRSALGYFDYWGQGTTVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKKVEPKSCDK<br>THTCPPCPAPEAAGAPSVFLFPPKPKDTLMISRTPEVTCVVVDVSH<br>EDPEVKFNWYVDGVEVHNAKTKPREEQYNSTYRVVSVLTVLHQ<br>DWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K (SEQ ID NO: 129) | DIQMTQSPSSLSASVGDRVTITCTA<br>SSSVSSTYLHWYQQKPGKAPKLLIY<br>STSNLASGVPSRFSGSGSGTDYTLTI<br>SSLQPEDFATYYCHQYHRSPLTFGQ<br>GTKLEIKRTVAAPSVFIFPPSDEQLK<br>SGTASVVCLLNNFYPREAKVQWK<br>VDNALQSGNSQESVTEQDSKDSTY<br>SLSSTLTLSKADYEKHKVYACEVT<br>HQGLSSPVTKSFNRGEC (SEQ ID<br>NO: 135) |
| Hu50<br>A8F2-<br>15-EN | QVQLVQSGAEVKKPGASVKVSCKASGYTFIDYYINWVRQAPGQG<br>LEWIGWIFPGSGHTKYNENFKGKVTLTVDTSTSTVYMELSSLRSE<br>DTAVYFCARGDRSALGYFDYWGQGTTVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKKVEPKSCDK<br>THTCPPCPAPEAAGAPSVFLFPPKPKDTLMISRTPEVTCVVVDVSH<br>EDPEVKFNWYVDGVEVHNAKTKPREEQYNSTYRVVSVLTVLHQ<br>DWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K (SEQ ID NO: 129) | DIQLTQSPSSLSASVGDRVTITCTAS<br>SSVSSTYLHWYQQKPGKSPKLLIYS<br>TSNLASGVPSRFSGSGSGTDYTLTIS<br>SLQPEDFATYYCHQYHRSPLTFGQ<br>GTKLEIKRTVAAPSVFIFPPSDEQLK<br>SGTASVVCLLNNFYPREAKVQWK<br>VDNALQSGNSQESVTEQDSKDSTY<br>SLSSTLTLSKADYEKHKVYACEVT<br>HQGLSSPVTKSFNRGEC (SEQ ID<br>NO: 136) |

REFERENCES

Almagro, J. C., et al. (2008). "Humanization of antibodies." Front Biosci 13:1619-1633.

Aldemir, H., et al. (2005). "Cutting edge: lectin-like transcript 1 is a ligand for the CD161 receptor." J Immunol 175(12): 7791-7795.

Basdeo, S. A., et al. (2017). "Ex-Th17 (Nonclassical Th1) Cells Are Functionally Distinct from Classical Th1 and Th17 Cells and Are Not Constrained by Regulatory T Cells." J Immunol 198(6): 2249-2259.

Fergusson, J. R., et al. (2014). "CD161 defines a transcriptional and functional phenotype across distinct human T cell lineages." Cell Rep 9(3): 1075-1088.

Maggi, L., et al. (2010). "CD161 is a marker of all human IL-17-producing T-cell subsets and is induced by RORC." Eur J Immunol 40(8): 2174-81.

Mathewson, N. D., et al. (2021). "Inhibitory CD161 receptor identified in glioma-infiltrating T cells by single-cell analysis." Cell 184(5): 1281-1298.

Prihoda D, et. Al (2022). "BioPhi: A platform for antibody design, humanization, and humanness evaluation based on natural antibody repertoires and deep learning." MAbs 14(1): 2020203

Satoh, M., et al. (2008). "Non-fucosylated therapeutic antibodies as next-generation therapeutic antibodies." Expert Opin Biol Ther 6(11): 1161-1173.

Yang, J., et al. (2014). "Targeting Th17 cells in autoimmune diseases." Trends Pharmacol Sci 35(10): 493-500.

Exemplary embodiments of the invention are described in the enumerated paragraphs below:

E1. An antibody or antigen-binding fragment thereof that specifically binds to killer cell lectin-like receptor subfamily B, member 1 (KLRB1), comprising:

c. a heavy chain variable region (VH) comprising three VH complementarity determining regions (CDR-H1, CDR-H2 and CDR-H3); and d. a light chain variable region (VL) comprising three VL complementarity determining regions (CDR-L1, CDR-L2 and CDR-L3), wherein the CDR-H1, CDR-H2, CDR-H3, CDR-L1, CDR-L2 and CDR-L3 are selected from one of the following:

i. CDR-H1 has the amino acid sequence of any one of SEQ ID NOs: 14, 15, 54, 55, and 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 26, 27, and 64; CDR-L2 has the amino acid sequence of any one of SEQ ID NOs: 28-29 or WA; and CDR-L3 has the amino acid sequence of SEQ ID NOs: 31 or 32; or ii. CDR-H1 has the amino acid sequence of any one of SEQ ID NOs: 12-16; CDR-H2 has the amino acid sequence of any one of SEQ ID NOs: 17-21; CDR-H3 has the amino acid sequence of any one of SEQ ID NOs: 22-24; CDR-L1 has the amino acid sequence of any one of SEQ ID NOs: 25-27; CDR-L2 has the amino acid sequence of any one of SEQ ID NOs: 28-29 or WA; and CDR-L3 has the amino acid sequence of SEQ ID NOs: 31 or 32; or iii. CDR-H1 has the amino acid sequence of any one of SEQ ID NOs: 12-16; CDR-H2 has the amino acid sequence of any one of SEQ ID NOs: 35-39; CDR-H3 has the amino acid sequence of any one of SEQ ID NOs: 23, 40, or 41; CDR-L1 has the amino acid sequence of any one of SEQ ID NOs: 25-27; CDR-L2 has the amino acid sequence of any one of SEQ ID NOs: 28-29 or WA; and CDR-L3 has the amino acid sequence of SEQ ID NOs: 31 or 32; or iv. CDR-H1 has the amino acid sequence of any one of SEQ ID NOs: 12-16; CDR-H2 has the amino acid sequence of any one of SEQ ID NOs: 43-47; CDR-H3 has the amino acid sequence of any one of SEQ ID NOs: 23, 40, or 41; CDR-L1 has the amino acid sequence of any one of SEQ ID NOs: 25-27; CDR-L2 has the amino acid sequence of any one of SEQ ID NOs: 28-29 or WA; and CDR-L3 has the amino acid sequence of SEQ ID NOs: 31 or 32; or v. CDR-H1 has the amino acid sequence of any one of SEQ ID NOs: 12-16; CDR-H2 has the amino acid sequence of any one of SEQ ID NOs: 35-39; CDR-H3 has the amino acid sequence of any one of SEQ ID NOs: 23, 49, or 50; CDR-L1 has the amino acid sequence of any one of SEQ ID NOs: 25-27; CDR-L2 has the amino acid sequence of any one of SEQ ID NOs: 28-29 or WA; and CDR-L3 has the amino acid sequence of SEQ ID NOs: 31 or 32; or vi. CDR-H1 has the amino acid sequence of any one of SEQ ID NOs: 12-16; CDR-H2 has the amino acid sequence of any one of SEQ ID NOs: 43-47; CDR-H3 has the amino acid sequence of any one of SEQ ID NOs: 23, 49, or 50; CDR-L1 has the amino acid sequence of any one of SEQ ID NOs: 25-27; CDR-L2 has the amino acid sequence of any one of SEQ ID NOs: 28-29 or WA; and CDR-L3 has the amino acid sequence of SEQ ID NOs: 31 or 32; or vii. CDR-H1 has the amino acid sequence of any one of SEQ ID NOs: 14, 15, 54, 55, or 56; CDR-H2 has the amino acid sequence of any one of SEQ ID NOs: 43-47; CDR-H3 has the amino acid sequence of any one of SEQ ID NOs: 22-24; CDR-L1 has the amino acid sequence of any one of SEQ ID NOs: 25-27; CDR-L2 has the amino acid sequence of any one of SEQ ID NOs: 28-29 or WA; and CDR-L3 has the amino acid sequence of SEQ ID NOs: 31 or 32; or viii. CDR-H1 has the amino acid sequence of any one of SEQ ID NOs: 12-16; CDR-H2 has the amino acid sequence of any one of SEQ ID NOs: 43-47; CDR-H3 has the amino acid sequence of any one of SEQ ID NOs: 22-24; CDR-L1 has the amino acid sequence of any one of SEQ ID NOs: 58-60; CDR-L2 has the amino acid sequence of any one of SEQ ID NO:29, SEQ ID NO:61 or WA; and CDR-L3 has the amino acid sequence of SEQ ID NOs: 31 or 32; or ix. CDR-H1 has the amino acid sequence of any one of SEQ ID NOs: 12-16; CDR-H2 has the amino acid sequence of any one of SEQ ID NOs: 43-47; CDR-H3 has the amino acid sequence of any one of SEQ ID NOs: 22-24; CDR-L1 has the amino acid sequence of any one of SEQ ID NOs: 26, 27, or 64; CDR-L2 has the amino acid sequence of any one of SEQ ID NOs: 28-29 or WA; and CDR-L3 has the amino acid sequence of SEQ ID NOs: 31 or 32; or x. CDR-H1 has the amino acid sequence of any one of SEQ ID NOs: 14, 15, 54, 55, or 56; CDR-H2 has the amino acid sequence of any one of SEQ ID NOs: 43-47; CDR-H3 has the amino acid sequence of any one of SEQ ID NOs: 22-24; CDR-L1 has the amino acid sequence of any one of SEQ ID NOs: 59, 60, or 66; CDR-L2 has the amino acid sequence of any one of SEQ ID NO:29, SEQ ID NO:61 or WA; and CDR-L3 has the amino acid sequence of SEQ ID NOs: 31 or 32; or xi. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 59, 69, or 70; CDR-L2 has the amino acid sequence of any one of SEQ ID NOs: 28-29 or WA; and CDR-L3 has the amino acid sequence of SEQ ID NOs: 31 or 32; or xii. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 72-74; CDR-L2 has the amino acid sequence of any one of SEQ ID NOs: 28-29 or WA; and CDR-L3 has the amino acid sequence of SEQ ID NOs: 31 or 32; or xiii. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 72-74; CDR-L2 has the amino acid sequence of any one of SEQ ID NO:28, SEQ ID NO:76 or WA; and CDR-L3 has the amino acid sequence of SEQ ID NOs: 77 or 78; or xiv. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 26, 27, or 64; CDR-L2 has the amino acid sequence of any one of SEQ ID NOs: 28-29 or WA; and CDR-L3 has the amino acid sequence of SEQ ID NOs: 31 or 32; or xv. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 26, 27, or 64; CDR-L2 has the amino acid sequence of any one of SEQ ID NOs: 28-29 or WA; and CDR-L3 has the amino acid sequence of SEQ ID NOs: 81 or 82; or xvi. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 26, 84, or 85; CDR-L2 has the amino acid sequence of any one of SEQ ID NOs: 28-29 or WA; and CDR-L3 has the amino acid sequence of SEQ ID NOs: 81 or 82; or xvii. CDR-H1 has the amino acid sequence of any one of SEQ ID NOs: 14, 15, 54, 55, or 56; CDR-H2 has the amino acid sequence of any one of SEQ ID NOs: 35-39; CDR-H3 has the amino acid sequence of any one of SEQ ID NOs: 22-24; CDR-L1 has the amino acid sequence of any one of SEQ ID NOs: 87-89; CDR-L2 has the amino acid sequence of any one of SEQ ID NOs: 28-29 or WA; and CDR-L3 has the amino acid sequence of SEQ ID NOs: 81 or 82.

E2. The antibody or antigen-binding fragment thereof of embodiment E1, wherein the amino acid sequence of each grouping of CDR-H1, CDR-H2, CDR-H3, CDR-L1, CDR-L2 and CDR-L3 is selected from the same antibody numbering convention.

E3. The antibody or antigen-binding fragment thereof of embodiment E2, wherein the amino acid sequence of each grouping of CDR-H1, CDR-H2, CDR-H3, CDR-L1, CDR-L2 and CDR-L3 is selected from the Kabat antibody numbering convention.

E4. The antibody or antigen-binding fragment thereof of embodiment E3, wherein CDR-H1 has the amino acid sequence of SEQ ID NO: 14, CDR-H2 has the amino acid sequence of SEQ ID NO: 37, CDR-H3 has the amino acid sequence of SEQ ID NO: 22, CDR-L1 has the amino acid sequence of SEQ ID NO: 64, CDR-L2 has the amino acid sequence of SEQ ID NO: 28, and CDR-L3 has the amino acid sequence of SEQ ID NO: 31.

E5. The antibody or antigen-binding fragment thereof of any one of embodiments E1-E4, wherein the VH has the amino acid sequence of any one of SEQ ID NOs: 33, 42, 48, 51, 53, 57, 62, or 68, or an amino acid sequence having at least 90% sequence identity to any one of SEQ ID NOs: 33, 42, 48, 51, 53, 57, 62, or 68 and having the CDR-H1, CDR-H2, CDR-H3 amino acid sequences set forth in embodiment E1.

E6. The antibody or antigen-binding fragment thereof of embodiment E5, wherein the VH comprises the amino acid sequence of any one of SEQ ID NOs: 33, 42, 48, 51, 53, 57, 62, or 68.

E7. The antibody or antigen-binding fragment thereof of embodiment E6, wherein the VH comprises the amino acid sequence of SEQ ID NO: 68.

E8. The antibody or antigen-binding fragment thereof of any one of embodiments E1-E8, wherein the VL comprises the amino acid sequence of any one of SEQ ID NOs: 34, 52, 63, 65, 67, 71, 75, 79, 80, 83, 86, or 90, or an amino acid sequence having at least 90% sequence identity to any one of SEQ ID NOs: 34, 52, 63, 65, 67, 71, 75, 79, 80, 83, 86, or 90 and having the CDR-L1, CDR-L2, CDR-L3 amino acid sequences set forth in embodiment E1.

E9. The antibody or antigen-binding fragment thereof of embodiment E8, wherein the VL comprises the amino acid sequence of any one of SEQ ID NOs: 34, 52, 63, 65, 67, 71, 75, 79, 80, 83, 86, or 90.

E10. The antibody or antigen-binding fragment thereof of embodiment E9, wherein the VL comprises the amino acid sequence of SEQ ID NO:65.

E11. The antibody or antigen-binding fragment thereof of any one of embodiments E1-E10, wherein the VL and VH are selected from one of the following:

f. the VH comprises SEQ ID NO: 68; and the VL comprises any one of SEQ ID NOs: 65, 71, 75, 79, 80, 83, 86, or 90;
g. the VH comprises any one of SEQ ID NOs: 33, 42, or 48; and the VL comprises SEQ ID NO: 34;
h. the VH comprises any one of SEQ ID NO: 51, 53, or 57; and the VL comprises SEQ ID NO: 52;
i. the VH comprises SEQ ID NO: 62; and the VL comprises SEQ ID NO: 63, or SEQ ID NO: 65; or
j. the VH comprises SEQ ID NO: 57; and the VL comprises SEQ ID NO: 67

E12. The antibody or antigen-binding fragment thereof of embodiment E11, wherein the VH comprises SEQ ID NO:68; and the VL comprises SEQ ID NO:65.

E13. The antibody or antigen-binding fragment thereof of any one of embodiments E1-E12, wherein the VL is part of a light chain, wherein the light chain comprises the amino acid sequence of any one of SEQ ID NOs: 99-110, or an amino acid sequence having at least 90% sequence identity to any one of SEQ ID NOs: 99-110.

E14. The antibody or antigen-binding fragment thereof of embodiment E13, wherein the light chain comprises the amino acid sequence of any one of SEQ ID NOs: 99-110.

E15. The antibody or antigen-binding fragment thereof of embodiment E14, wherein the light chain comprises the amino acid sequence of SEQ ID NO: 102.

E16. The antibody or antigen binding portion thereof of any one of embodiments E1-E15, which is an antibody that comprises an Fc region that binds to Fc gamma receptors (FcγRs) and induces antibody dependent cell-mediated cytotoxicity (ADCC) to deplete cells expressing KLRB1, or that binds to C1q and induces complement dependent cytotoxicity (CDC).

E17. The antibody or antigen binding portion thereof of embodiment E16, wherein the Fc region is afucosylated.

E18. The antibody or antigen binding portion thereof of any one of embodiments E1-E17, wherein the antibody is an immunoglobulin G (IgG) subtype IgG1 antibody, an IgG2 antibody, or an IgG4 antibody.

E19. The antibody or antigen-binding fragment thereof of embodiment E18, wherein the VH is part of a heavy chain, wherein the heavy chain comprises the amino acid sequence of any one of SEQ ID NOs: 91-98, or an amino acid sequence having at least 90% sequence identity to any one of SEQ ID NOs: 91-98.

E20. The antibody or antigen-binding fragment thereof of embodiment E19, wherein the heavy chain comprises the amino acid sequence of any one of SEQ ID NOs: 91-98.

E21. The antibody or antigen-binding fragment thereof of embodiment E20, wherein the heavy chain comprises the amino acid sequence of SEQ ID NO:98.

E22. The antibody or antigen-binding fragment thereof of any one of embodiments E1-E21 comprising a heavy chain (HC) and a light chain (LC) selected from the one of the following:

f. the HC comprises SEQ ID NO: 98; and the LC comprises any one of SEQ ID NOS: 102, or 104-110;
g. the HC comprises any one of SEQ ID NOs: 91-93; and the LC comprises SEQ ID NO: 99;
h. the HC comprises any one of SEQ ID NOs: 94-96; and the LC comprises SEQ ID NO: 100;
i. the HC comprises SEQ ID NO: 97; and the LC comprises SEQ ID NO: 101, or SEQ ID NO: 102; or
j. the HC comprises SEQ ID NO: 96; and the LC comprises SEQ ID NO: 103.

E23. The antibody or antigen-binding fragment thereof of embodiment E22, wherein the HC comprises SEQ ID NO:98 and the LC comprises SEQ ID NO: 102.

E24. The antibody or antigen binding portion thereof of any one of embodiments E1-E22, which is conjugated to a cytotoxic agent.

E25. A set of polynucleotides comprising:

c. a first nucleic acid sequence encoding a VH or a heavy chain of an antibody or antigen binding portion thereof of embodiments E1 to E22; and d. a second nucleic acid sequence encoding a VL or a light chain of an antibody or antigen binding portion thereof of embodiments E1 to E22.

E26. The set of polynucleotides of embodiment E25, wherein the each of the first and second nucleic acid sequences is operably linked to a promoter.

E27. A vector comprising the set of polynucleotides of embodiment E25 or 26.

E28. A set of vectors comprising:

c. a first vector comprising the first nucleic acid sequence of embodiment E25 or 26; and d. a second vector comprising the second nucleic acid sequence of embodiment E25 or E26.

E29. A host cell comprising the set of polynucleotides of embodiment E25 or E26, or the vector of embodiment E27, or the set of vectors of embodiment E28, and optionally expressing the antibody or antigen binding portion thereof.

E30. A method of making the antibody or antigen binding portion thereof of any one of embodiments E1-E24, comprising the steps of:

c. culturing the host cell of embodiment E29 under conditions sufficient to express the antibody or antigen binding portion thereof; and d. isolating the antibody or antigen binding portion thereof.

E31. The method of embodiment E28, further comprising formulating the antibody as a pharmaceutical composition.

E32. A pharmaceutical composition comprising the antibody or antigen binding portion thereof of any one of embodiments E1-E24, and a pharmaceutically acceptable carrier or diluent.

E33. A method of treating one or more an autoimmune disease, an allergic disease, a transplant rejection, and a hematologic malignancy in a subject in need thereof, the method comprising administering to the subject an antibody or antigen binding portion thereof of any one of embodiments E1-E24, or the pharmaceutical composition of embodiment E32 in an amount effecting to treat.

E34. The method of embodiment E33, wherein the autoimmune disease is rheumatoid arthritis, Sjogren's syndrome, inclusion body myositis (IBM), discoid lupus, psoriasis, idiopathic pulmonary fibrosis, diabetes, alopecia universalis, primary biliary cholangitis, multiple sclerosis, lymphocytic colitis, palmoplantar pustulosis, or hidradenitis suppurativa.

E35. The method of embodiment E33, wherein the allergic disease is asthma, allergic eosinophilic asthma, allergy, atopic dermatitis, nasal polyposis, eosinophilic gastrointestinal disorder, or hypereosinophilic syndrome.

E36. The method of embodiment E33, wherein the transplant rejection can be a rejection of a kidney, lung, heart, liver, limb, skin, or multi-organ transplant.

E37. The method of embodiment E33, wherein the hematological malignancy is a lymphoma or leukemia.

E38. The method of embodiment E37, wherein the lymphoma NK/T cell lymphoma, mycosis fungoides, Sezary syndrome, peripheral T cell lymphoma, angioimmunoblastic T cell lymphoma (AITL), or peripheral T cell lymphoma not otherwise specified (PTCL-NOS) or mycosis fungoides.

E39. The method of embodiment E37, wherein the leukemia is T cell leukemia, aggressive NK cell leukemia, T cell prolymphocytic leukemia (T-PLL), or large granular lymphocytic leukemia (LGLL).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody that specifically binds to killer cell lectin-like receptor subfamily B, member 1 (KLRB1), the antibody comprising:

a heavy chain variable region (VH) comprising the amino acid sequence of SEQ ID NO: 62, and a light chain variable region (VL) comprising the amino acid sequence of SEQ ID NO: 65.

2. The antibody of claim 1, wherein the antibody comprises an afucosylated Fc region.

3. The antibody of claim 2, wherein the antibody binds to Fc gamma receptor (FcγR) and induces antibody dependent cell-mediated cytotoxicity.

4. The antibody of claim 2, wherein the antibody binds to C1q and induces complement dependent cytotoxicity.

5. The antibody of claim 1, wherein the antibody is a full-length antibody, a Fab fragment, or a single-chain variable fragment (scFv).

6. The antibody of claim 1, wherein the antibody is of the class IgG, IgA, IgM, or IgE.

7. The antibody of claim 1, wherein the antibody comprises a heavy chain (HC) constant region.

8. The antibody of claim 7, wherein the HC constant region is a constant region of human IgG1.

9. The antibody of claim 7, wherein the HC constant region comprises the amino acid sequence of SEQ ID NO: 4.

10. The antibody of claim 1, wherein the antibody comprises a light chain (LC) constant region.

11. The antibody of claim 10, wherein the LC constant region is a constant region of human Igκ.

12. The antibody of claim 10, wherein the LC constant region comprises the amino acid sequence of SEQ ID NO: 7.

13. The antibody of claim 1, wherein the antibody comprises a HC comprising the amino acid sequence of SEQ ID NO: 97, and a LC comprising the amino acid sequence of SEQ ID NO: 102.

14. The antibody of claim 1, wherein the antibody binds to and depletes Th17 cells, Th17.1 cells, ex-Th17 cells, Tc17 cells, mucosal-associated invariant T (MAIT) cells, innate lymphoid cells type 2 (ILC2), innate lymphoid cells type 3 (ILC3), pathogenic effector Th2 (peTh2) cells, or NK cells expressing KLRB1.

15. The antibody of claim 1, wherein the antibody binds to and depletes neoplastic T cells or neoplastic NK cells expressing KLRB1.

16. The antibody of claim 1, wherein the antibody binds to and depletes invariant NK-T (INKT) cells expressing KLRB1.

* * * * *